United States Patent
Wilson et al.

(10) Patent No.: US 11,414,384 B2
(45) Date of Patent: Aug. 16, 2022

(54) P300/CBP HAT INHIBITORS

(71) Applicant: Constellation Pharmaceuticals, Inc., Boston, MA (US)

(72) Inventors: Jonathan E. Wilson, Arlington, MA (US); Julian R. Levell, Arlington, MA (US)

(73) Assignee: Constellation Pharmaceuticals, Inc., Boston, MA (US)

(*) Notice: Subject to any disclaimer, the term of this patent is extended or adjusted under 35 U.S.C. 154(b) by 0 days.

(21) Appl. No.: 16/970,046

(22) PCT Filed: Feb. 15, 2019

(86) PCT No.: PCT/US2019/018150
§ 371 (c)(1),
(2) Date: Aug. 14, 2020

(87) PCT Pub. No.: WO2019/161157
PCT Pub. Date: Aug. 22, 2019

(65) Prior Publication Data
US 2021/0061762 A1   Mar. 4, 2021

Related U.S. Application Data

(60) Provisional application No. 62/758,867, filed on Nov. 12, 2018, provisional application No. 62/631,594, filed on Feb. 16, 2018.

(51) Int. Cl.
| | | |
|---|---|---|
| C07D 209/14 | (2006.01) |
| C07D 401/12 | (2006.01) |
| C07D 403/04 | (2006.01) |
| C07D 231/56 | (2006.01) |
| C07D 403/12 | (2006.01) |
| C07D 405/12 | (2006.01) |
| C07D 409/12 | (2006.01) |
| C07D 471/04 | (2006.01) |

(52) U.S. Cl.
CPC ......... *C07D 209/14* (2013.01); *C07D 231/56* (2013.01); *C07D 401/12* (2013.01); *C07D 403/04* (2013.01); *C07D 403/12* (2013.01); *C07D 405/12* (2013.01); *C07D 409/12* (2013.01); *C07D 471/04* (2013.01)

(58) Field of Classification Search
CPC ... C07D 209/14; C07D 401/12; C07D 403/04
See application file for complete search history.

(56) References Cited

U.S. PATENT DOCUMENTS

| | | | |
|---|---|---|---|
| 8,309,700 B2 | 11/2012 | Mizutani et al. | |
| 2014/0213586 A1* | 7/2014 | Bardiot ................ | C07D 513/04 514/235.2 |
| 2021/0115008 A1 | 4/2021 | Wilson et al. | |

FOREIGN PATENT DOCUMENTS

| | | |
|---|---|---|
| EP | 0415413 A1 | 3/1991 |
| WO | 2003/064397 A1 | 8/2003 |
| WO | 2010/021878 A1 | 2/2010 |
| WO | 2013/045516 A1 | 4/2013 |
| WO | 2015/054642 A2 | 4/2015 |
| WO | 2016/044770 A1 | 3/2016 |
| WO | 2016/044771 A1 | 3/2016 |
| WO | 2016/044777 A1 | 3/2016 |
| WO | 2016/196117 A1 | 12/2016 |
| WO | 2017/205536 A2 | 11/2017 |
| WO | 2019/161162 A1 | 8/2019 |

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Hubbs et al., Amino acid derivatives as histone deacetylase inhibitors. Bioorg Med Chem Lett. Jan. 1, 2008;18(1):34-8.
Tria et al., Discovery of LSZ102, a Potent, Orally Bioavailable Selective Estrogen Receptor Degrader (SERD) for the Treatment of Estrogen Receptor Positive Breast Cancer. J Med Chem. 2018;61:2837-64.
Copending U.S. Appl. No. 16/970,169, filed Aug. 14, 2020.
U.S. Appl. No. 16/970,169, filed Aug. 14, 2020, Pending.
U.S. Appl. No. 16/970,169, filed Aug. 14, 2020, Published.
U.S. Appl. No. 17/434,102, filed Aug. 26, 2021, Pending.
Winterton et al., Discovery of Cytochrome P450 4F11 Activated Inhibitors of Stearoyl Coenzyme A Desaturase. J Med Chem. Jun. 28, 2018;61(12):5199-5221.
Copending U.S. Appl. No. 17/434,102, filed Aug. 26, 2021.

* cited by examiner

*Primary Examiner* — Shawquia Jackson
(74) *Attorney, Agent, or Firm* — McCarter & English, LLP; Michael J. DeGrazia

(57) ABSTRACT

Provided are compounds of Formula (I): and pharmaceutically acceptable salts and compositions thereof, which are useful for treating a variety of conditions associated with histone acetyltransferase (HAT).

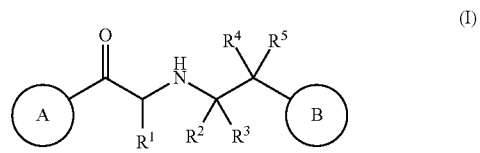

(I)

20 Claims, No Drawings

P300/CBP HAT INHIBITORS

RELATED APPLICATIONS

This application is a 35 U.S.C. § 371 national stage filing of International Application No. PCT/US2019/018150, filed Feb. 15, 2019, which claims the benefit of priority to U.S. Provisional Application No. 62/631,594, filed Feb. 16, 2018 and U.S. Provisional Application No. 62/758,867, filed Nov. 12, 2018, the entire contents of each of which are incorporated by reference herein.

BACKGROUND

Chromatin is a complex combination of DNA and protein that makes up chromosomes. It is found inside the nuclei of eukaryotic cells and is divided between heterochromatin (condensed) and euchromatin (extended) forms. The major components of chromatin are DNA and proteins. Histones are the chief protein components of chromatin, acting as spools around which DNA winds. The functions of chromatin are to package DNA into a smaller volume to fit in the cell, to strengthen the DNA to allow mitosis and meiosis, and to serve as a mechanism to control expression and DNA replication. The chromatin structure is controlled by a series of post-translational modifications to histone proteins, notably histones H3 and H4, and most commonly within the "histone tails" which extend beyond the core nucleosome structure. Histone tails tend to be free for protein-protein interaction and are also the portion of the histone most prone to post-translational modification (Goll and Bestor, 2002, Genes Dev. 16:1739-1742; Grant, 2001, Genome Biol. 2:). These modifications include acetylation, methylation, phosphorylation, ubiquitinylation, SUMOylation. These epigenetic marks are written and erased by specific enzymes that place the tags on specific residues within the histone tail, thereby forming an epigenetic code, which is then interpreted by the cell to allow gene specific regulation of chromatin structure and thereby transcription.

Covalent modification of histones is a fundamental mechanism of control of gene expression, and one of the major epigenetic mechanisms at play in eukaryotic cells (Kouzarides, Cell, 128, 693-705 (2007)). Because distinct transcriptional states define fundamental cellular processes, such as cell type specification, lineage commitment, cell activation and cell death, their aberrant regulation is at the core of a range of diseases (Medzhitov et al., Nat. Rev. Immunol., 9, 692-703 (2009); Portela et al., Nat. Biotech., 28, 1057-1068 (2010)). Distinct classes of enzymes, namely histone acetyltransferases (HATS) and histone deacetylases (HDACs), acetylate or de-acetylate specific histone lysine residues (Struhl K., Genes Dev., 1998, 12, 5, 599-606).

Histone acetyltransferases (HATs) catalyze the acetylation (transfer of an acetyl group) on a ε-amino group of a target lysine side chain within a substrate histone, and histone deacetylases (HDACs) catalyze the removal of acetyl groups from lysine residues. Subsequently, acetylated core histones were shown to preferentially associate with transcriptionally active chromatin. See Nucleic Acids Res. 5:1863-1876 (1978): Proc. Natl. Acad. Sci. 75:2239-2243 (1978); and EMBO J. 7:1395-1402 (1988). HATs are categorized into four major families based on primary sequence homology, shared structural features, and functional roles: Gen5/PCAF (General control nonrepressed protein 5 and p300 and CBP associated factor); MYST (named for the founding members MOZ, Ybf2/Sas3, Sas2, and Tip60); p300/CBP (protein of 300 kDa and CREB Binding Protein); and Rtt109 (Regulator of Ty1 Transposition gene production 109).

Paralogs p300 and CBP (CREB binding protein) were originally identified as binding partners of the adenovirus early-region 1A (E1A) protein (Yee and Branton, 1985, Virology 147:142-153; Harlow et al., 1986, Mol. Cell Biol. 6:1579-1589), and the cAMP-regulated enhancer (CRE) binding proteins (Chrivia et al, 1993, Nature 365:855-859), respectively. p300 and CBP HAT domains have >90% sequence identity and are conserved in metazoans with many overlapping functions. In addition to the HAT domain, p300/CBP contains other protein interaction domains including three cysteine-histidine rich domains (CH1, CH2 and CH3), a KIX domain, a bromodomain, and a steroid receptor coactivator interaction domain (SID, also the SRC-1 interaction domain) (Arany et al, Cell. 1994 Jun. 17; 77(6):799-800) p300/CBP was found to have intrinsic HAT activity (Ogryzko et al., 1996, Cell 87:953-959; Bannister and Kouzarides, 1996, Nature 384:641-643). In addition to acetylating multiple lysines on all four core histones (H2A, H2B, H3 and H4), p300/CBP has been shown to have acetyltransferase activity towards >70 substrates (Wang et al., 2008, Curr. Opin. Struct. Biol. 18:741-747), including, for example, p53 (Gu et al., 1997, Cell 90:595-606), MyoD (Polesskaya et al., 2002, J. Biol. Chem. 275:34359-64), STAT3 (Yuan et al., 2005, Science 307:269-73) and NFκβ (Chen et al., 2002, EMBO J. 21:6539-48). These two acetyltransferases are responsible for the majority of histone H3 lysine 18 acetylation (H3K18ac) and H3K27ac, modifications associated with active promoters and enhancers (Horwitz et al. 2008; Jin et al. 2011).

Besides acting as an acetyltransferase, p300 also acts as a scaffold for transcription factors or a bridge to connect the transcription factors and the basal transcriptional machinery to activate transcription (Chan and Thangue, 2001, J. Cell Sci. 114:2363-2373; Chen and Li, 2011, Epigenetics 6:957-961). P300/CBP proteins are involved in many cellular processes, including cell growth, proliferation, and differentiation (reviewed in Chan and Thangue, 2001, J. Cell Sci. 114:2363-2373). Mutations in p300/CBP have been observed in number of human diseases, particularly cancer with frequencies up to 30%. A higher frequency of these mutations occur within the HAT domain, suggesting a selective pressure to alter this activity in cancers. These mutations are mostly mono-allelic, with loss of heterozygosity of the second allele, consistent with Knudson's hypothesis of a classical tumor suppressor gene. See Nature 376, 348-351, 1995; Oncogene 12, 1565-1569, 1996; and Proc. Natl. Acad. Sci. USA 94, 8732-8737, 1997. Heterozygous mutations in CBP were first described in RTS, an autosomal-dominant disease, characterized by mental retardation, skeletal abnormalities and a high incidence of neoplasia (Nature 376, 348-351, 1995). This suggests that a full complement of CBP gene dosage is required for normal development. P300/CBP genes are also involved in various chromosomal translocations, particularly in hematological malignancies and possibly contribute to aberrant growth through gain of function (Kitabayashi et al. 2001; Panagopoulos et al. 2001)

High p300 expression, correlating with poor survival and aggressive phenotypes, has been observed in prostate cancer (Debes et al 2003; Cancer Res. 63: 7638-7640; Heemers et al., 2008, Adv. Exp. Med. Biol. 617:535-40; Isharwal et al., 2008, Prostate 68:1097-104), liver cancer (Yokomizo et al., 2011, Cancer Lett. 310:1407; Li et al., 2011, J. Transl. Med. 9:5), breast cancer (Fermento et al., 2010, Exp. Mol. Pathol. 88:256-64), esophageal carcinoma (Li et al, 2011, Ann Thorac Surg. 91: 1531-1538) and cutaneous squamous cell carcinoma (Chen et al, 2014, Br J Dermatol. 172: 111-119). Inhibition of p300/CBP has therapeutic potential in cancer (Iyer et al., 2004, Proc. Natl. Acad. Sci. USA 101:7386-7391; Stimson et al., 2005, Mol. Cancer Ther. 4:1521-1532; Zheng et al., 2004, Methods Enzymol. 376:188-199), cardiac disease (Davidson et al., 2005, Chembiochem. 6:162-170); diabetes mellitus (Zhou et al., 2004, Nat. Med. 10:633-637), and HIV (Varier and Kundu, 2006, Curr. Pharm. Des. 12:1975-1993). P300/CBP is also involved in regulating inflammatory mediators (Deng et al., 2004, Blood WO 2016/044770 PCT/US2015/051028 103:2135-42; Tumer-Brannen et al., 2011, J. Immunol. 186:7127-7135). P300/CBP has also been linked to other diseases, such as fibrosis (Ghosh and Varga, 2007, J. Cell. Physiol. 213:663-671), metabolic syndrome (Bricambert et al., 2010, J. Clin. Invest. 120:4316-4331), and progressive neurodegenerative diseases, such as Huntington Disease (Cong et al., 2005, Mol. Cell. Neurosci. 30:12-23), Kennedy's disease (Lieberman et al., 2002, Hum. Mol. Genet. 11:1967-76), and Alzheimer's disease (Francis et al., 2007, Neurosci. Lett. 413:137-140).

The association of p300/CBP activity in disease pathogenesis suggests potential utility of p300/CBP as a therapeutic target. However, the identification of potent, specific histone acetyltransferase inhibitors has been challenging (Cole, 2008, Nat. Chem. Biol. 4:590-97). P300 HAT inhibitors derived from natural compounds have moderate potency but lack specificity (Dekker and Haisma, 2009, Dmg Disc. Today 14:942-8). Lys-CoA, converted to a cell-permeable form with a Tat peptide attachment, is more selective, but has limited use in pharmacological studies due to its complexity. Recently, a selective p300 inhibitor C646 was identified using the Lys-CoA/p300 HAT structure in a virtual ligand screening approach (Bowers et al., 2010, Chemistry & Biology 17:471-482). While progress has been made in this field, there remains a need in the art for improved HAT inhibitors.

SUMMARY

Provided herein are compounds having the Formula I:

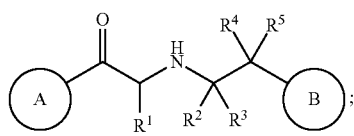

and pharmaceutically acceptable salts and compositions thereof, wherein A, B, $R^1$, $R^2$, $R^3$, $R^4$, and $R^5$ are as described herein. The disclosed compounds and compositions modulate histone acetyltranferases (see e.g., Table 10), and are useful in a variety of therapeutic applications such as, for example, in treating cancer.

DETAILED DESCRIPTION

1. General Description of Compounds

Provided herein is a compound of Formula I:

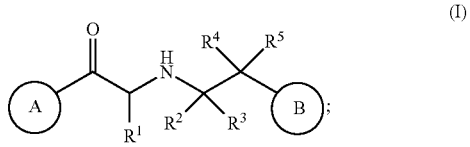

or a pharmaceutically acceptable salt thereof, wherein
Ring A is bicyclic heteroaryl optionally substituted with 1 to 4 groups selected from $R^a$;
Ring B is aryl, heterocyclyl, or heteroaryl each of which may be optionally substituted with 1 to 4 groups selected from $R^b$;
$R^1$ is $C_{1-6}$alkyl, $C_{1-6}$haloalkyl, $C_{2-6}$alkenyl, —$C_{1-6}$alkylOR$^c$, —$C_{1-6}$alkylN(R$^d$)$_2$, —$C_{1-6}$alkylC(O)OR$^d$, —$C_{1-6}$alkylOC$_{1-6}$alkylN(R$^d$)$_2$, —$C_{1-6}$alkylSOR$^d$, —$C_{1-6}$alkylS(O)$_2$R$^d$, —$C_{1-6}$alkylSON(R$^d$)$_2$, —$C_{1-6}$alkylSO$_2$N(R$^d$)$_2$, —$C_{1-6}$alkylcycloalkyl, —$C_{1-6}$alkylheterocyclyl, —$C_{1-6}$alkylheteroaryl, —$C_{1-6}$alkylaryl, cycloalkyl, aryl, heteroaryl, or heterocyclyl, wherein each of said cycloalkyl, heterocyclyl, aryl, and heteroaryl alone and in connection with —$C_{1-6}$alkylcycloalkyl, —$C_{1-6}$alkylaryl, —$C_{1-6}$alkylheteroaryl, and —$C_{1-6}$alkylheterocyclyl are optionally substituted with 1 to 3 groups selected from $R^c$;
each of $R^2$, $R^3$, $R^4$, and $R^5$ are independently hydrogen or $C_{1-6}$alkyl, wherein said $C_{1-6}$alkyl is optionally substituted with 1 or 2 groups selected from halo, —C(O)OR$^d$, —OC$_{1-6}$alkylN(R$^d$)$_2$, —C$_{1-6}$alkylN(R$^d$)$_2$, —N(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, cycloalkyl, heterocyclyl, heteroaryl, and aryl;
each of $R^a$, $R^b$, and $R^c$ are each independently halo, CN, oxo, NO$_2$, $C_{1-6}$alkyl, $C_{2-6}$alkenyl, $C_{1-6}$alkoxy, $C_{1-6}$haloalkoxy, $C_{1-6}$haloalkyl, —$C_{1-6}$alkylOR$^d$, —C(O)R$^d$, —C(O)OR$^d$, —$C_{1-6}$alkylC(O)OR$^d$, —C(O)N(R$^d$)$_2$, —C(O)NR$^d$C$_{1-6}$alkylOR$^d$, —OC$_{1-6}$alkylN(R$^d$)$_2$, —$C_{1-6}$alkylC(O)N(R$^d$)$_2$, —$C_{1-6}$alkylN(R$^d$)$_2$, —N(R$^d$)$_2$, —C(O)NR$^d$C$_{1-6}$alkylN(R$^d$)$_2$, —NR$^d$C$_{1-6}$alkylN(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, SF$_5$, —Ocycloalkyl, —Oheterocyclyl, —O—$C_{1-4}$alkylaryl, —$C_{1-6}$alkylcycloalkyl, —$C_{1-6}$alkylaryl, —$C_{1-6}$alkylheteroaryl, —$C_{1-6}$alkylheterocyclyl, cycloalkyl, heterocyclyl, heteroaryl, or aryl, wherein each of said cycloalkyl, heterocyclyl, aryl, and heteroaryl alone and in connection with —Ocycloalkyl, —$C_{1-6}$alkylcycloalkyl, —$C_{1-6}$alkylaryl, —$C_{1-6}$alkylheteroaryl, and —$C_{1-6}$alkylheterocyclyl are optionally substituted with 1 to 3 groups selected from halo, oxo, $C_{1-6}$alkyl, $C_{1-6}$haloalkyl, $C_{1-6}$alkoxy, $C_{1-6}$haloalkoxy, —N(R$^d$)$_2$, —C(O)R$^d$, and —$C_{1-6}$alkylOR$^d$; and each $R^d$ is independently hydrogen, heterocyclyl, $C_{1-6}$haloalkyl, or $C_{1-6}$alkyl, wherein said heterocyclyl is optionally substituted with 1 or 2 groups selected from $C_{1-4}$haloalkyl and $C_{1-4}$alkyl and said $C_{1-6}$alkyl is optionally substituted with —SO$_2$C$_{1-4}$alkyl or heterocyclyl optionally substituted with oxo;
provided the compound is not 4-(2-((2-(1H-indol-3-yl)-2-oxo-1-phenylethyl)amino)ethyl)benzenesulfonamide; 4-[2-[[2-(7-ethyl-1H-indol-3-yl)-2-oxo-1-phenylethyl]amino]ethyl]benzenesulfonamide; 2-[[2-(3,4-dimethoxyphenyl)ethyl]amino]-1-(1H-indol-3-yl)-2-phenylethanone, or a salt thereof.

2. Definitions

When used in connection to describe a chemical group that may have multiple points of attachment, a hyphen (-) designates the point of attachment of that group to the variable to which it is defined. For example, —N(R$^d$)$_2$ and —NR$^d$C$_{1-6}$alkylOR$^d$ mean that the point of attachment for this group occurs on the nitrogen atom.

The terms "halo" and "halogen" refer to an atom selected from fluorine (fluoro, —F), chlorine (chloro, —Cl), bromine (bromo, —Br), and iodine (iodo, —I).

The term "alkyl" when used alone or as part of a larger moiety, such as "haloalkyl", "alkylC$_{5-10}$heterocyclyl", and the like, means saturated straight-chain or branched monovalent hydrocarbon radical. Unless otherwise specified, an alkyl group typically has 1-6 carbon atoms, i.e., (C$_1$-C$_6$) alkyl.

"Alkoxy" means an alkyl radical attached through an oxygen linking atom, represented by —O-alkyl. For example, "(C$_1$-C$_4$)alkoxy" includes methoxy, ethoxy, proproxy, and butoxy.

The term "haloalkyl" includes mono, poly, and perhaloalkyl groups where the halogens are independently selected from fluorine, chlorine, bromine, and iodine.

"Haloalkoxy" is a haloalkyl group which is attached to another moiety via an oxygen atom such as, e.g., but are not limited to —OCHCF$_2$ or —OCF$_3$.

The term "oxo" refers to the diradical =O

The term "aryl" refers to an aromatic carbocyclic single ring or two fused ring system containing 6 to 10 carbon atoms. Examples include phenyl, indanyl, tetrahydronaphthalene, and naphthyl.

The term "carbocyclyl" means a monocyclic, bicyclic (e.g., a bridged or spiro bicyclic ring), polycyclic (e.g., tricyclic), or fused hydrocarbon ring system that is completely saturated or that contains one or more units of unsaturation, but where there is no aromatic ring. Cycloalkyl is a completely saturated carbocycle. Monocyclic cycloalkyl groups include, without limitation, cyclopropyl, cyclobutyl, cyclopentyl, cyclohexyl, cycloheptyl, and cyclooctyl. Bridged bicyclic cycloalkyl groups include, without limitation, bicyclo[3.2.1]octane, bicyclo[2.2.1]heptane, bicyclo[3.1.0]hexane, bicyclo[1.1.1]pentane, and the like. Spiro bicyclic cycloalkyl groups include, e.g., spiro[3.6]decane, spiro[4.5]decane, and the like. Fused cycloalkyl rings include, e.g., decahydronaphthalene, octahydropentalene, and the like. It will be understood that when specified, optional substituents on a carbocyclyl (e.g., in the case of an optionally substituted cycloalkyl) may be present on any substitutable position and, include, e.g., the position at which the carbocyclyl group is attached.

The term "heteroaryl" used alone or as part of a larger moiety refers to a 5- to 12-membered aromatic radical containing 1-4 heteroatoms selected from N, O, and S. A heteroaryl group may be mono- or bi-cyclic. Monocyclic heteroaryl includes, for example, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, etc. Bi-cyclic heteroaryls include groups in which a monocyclic heteroaryl ring is fused to one or more aryl or heteroaryl rings. Nonlimiting examples include indolyl, imidazopyridinyl, benzooxazolyl, benzooxodiazolyl, indazolyl, benzimidazolyl, benzthiazolyl, quinolyl, quinazolinyl, quinoxalinyl, pyrrolopyridinyl, pyrrolopyrimidinyl, pyrazolopyridinyl, thienopyridinyl, thienopyrimidinyl, indolizinyl, purinyl, naphthyridinyl, and pteridinyl. It will be understood that when specified, optional substituents on a heteroaryl group may be present on any substitutable position and, include, e.g., the position at which the heteroaryl is attached.

The term "heterocyclyl" means a 5- to 12-membered saturated or partially unsaturated heterocyclic ring containing 1 to 4 heteroatoms independently selected from N, O, and S. It can be mononcyclic, bicyclic (e.g., a bridged, fused, or spiro bicyclic ring), or tricyclic. A heterocyclyl ring can be attached to its pendant group at any heteroatom or carbon atom that results in a stable structure. Examples of such saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. A heterocyclyl group may be mono- or bicyclic. The term "heterocyclyl" also includes, e.g., unsaturated heterocyclic radicals fused to another unsaturated heterocyclic radical or aryl or heteroaryl ring, such as for example, tetrahydronaphthyridine, indolinone, dihydropyrrolotriazole, imidazopyrimidine, quinolinone, dioxaspirodecane. It will also be understood that when specified, optional substituents on a heterocyclyl group may be present on any substitutable position and, include, e.g., the position at which the heterocyclyl is attached (e.g., in the case of an optionally substituted heterocyclyl or heterocyclyl which is optionally substituted).

The term "spiro" refers to two rings that shares one ring atom (e.g., carbon).

The term "fused" refers to two rings that share two adjacent ring atoms with one another.

The term "bridged" refers to two rings that share three ring atoms with one another.

The disclosed compounds exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms.

"Racemate" or "racemic mixture" means a compound of equimolar quantities of two enantiomers, wherein such mixtures exhibit no optical activity, i.e., they do not rotate the plane of polarized light.

The compounds of the herein may be prepared as individual enantiomers by either enantio-specific synthesis or resolved from an enantiomerically enriched mixture. Conventional resolution techniques include forming the salt of a free base of each isomer of an enantiomeric pair using an optically active acid (followed by fractional crystallization and regeneration of the free base), forming the salt of the acid form of each enantiomer of an enantiomeric pair using an optically active amine (followed by fractional crystallization and regeneration of the free acid), forming an ester or amide of each of the enantiomers of an enantiomeric pair using an optically pure acid, amine or alcohol (followed by chromatographic separation and removal of the chiral auxiliary), or resolving an enantiomeric mixture of either a starting material or a final product using various well known chromatographic methods. Additionally, the compounds can be prepared as individual enantiomers by separating a racemic mixture using conventional chiral chromatography techniques.

When the stereochemistry of a disclosed compound is named or depicted by structure, the named or depicted stereoisomer is at least 60%, 70%, 80%, 90%, 99% or 99.9% by weight pure relative to all of the other stereoisomers. Percent by weight pure relative to all of the other stereoisomers is the ratio of the weight of one stereoisomer over the weight of the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When the stereochemistry of a disclosed compound is named or depicted by structure, and the named or depicted structure encompasses more than one stereoisomer (e.g., as in a diastereomeric pair), it is to be understood that one of the encompassed stereoisomers or any mixture of the encompassed stereoisomers are included. It is to be further understood that the stereoisomeric purity of the named or depicted stereoisomer is at least 60%, 70%, 80%, 90%, 99% or 99.9% by weight pure relative to all of the other stereoisomers. The stereoisomeric purity in this case is determined by dividing the total weight in the mixture of the stereoisomers encompassed by the name or structure by the total weight in the mixture of all of the stereoisomers.

When a disclosed compound is named or depicted by structure without indicating the stereochemistry, and the compound has one chiral center, it is to be understood that the name or structure encompasses one enantiomer of compound free from the corresponding optical isomer, a racemic mixture of the compound, or mixtures enriched in one enantiomer relative to its corresponding optical isomer.

When a disclosed compound is named or depicted by structure without indicating the stereochemistry and e.g., the compound has more than one chiral center (e.g., at least two chiral centers), it is to be understood that the name or structure encompasses one stereoisomer free of other stereoisomers, mixtures of stereoisomers, or mixtures of stereoisomers in which one or more stereoisomers is enriched relative to the other stereoisomer(s). For example, the name or structure may encompass one stereoisomer free of other diastereomers, mixtures of stereoisomers, or mixtures of stereoisomers in which one or more diastereomers is enriched relative to the other diastereomer(s).

Unless otherwise specified, when only some of the stereochemical centers in a disclosed compound are depicted or named by structure, the named or depicted configuration is enriched relative to the remaining configurations, for example, by a molar excess of at least 60%, 70%, 80%, 90%, 99% or 99.9%. For example, the structure:

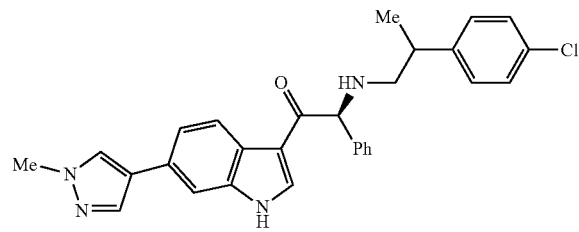 [SMILES: CC(CN[C@H](C(=O)c1c[nH]c2cc(-c3cnn(C)c3)ccc12)c1ccccc1)c1ccc(Cl)cc1]

means that that the configuration about the chiral carbon where the stereochemistry is depicted is stereochemically enriched as S (e.g., by a molar excess of at least 60%, 70%, 80%, 90%, 99% or 99.9%) and that the stereochemistry at the other chiral center, to which the stereochemistry is not identified, may be R or S, or a mixture thereof.

The terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

The term "inhibit," "inhibition" or "inhibiting" includes a decrease in the baseline activity of a biological activity or process.

As used herein, the terms "treatment," "treat," and "treating" refer to reversing, alleviating, delaying the onset of, or inhibiting the progress of a disease or disorder, or one or more symptoms thereof, as described herein. In some aspects, treatment may be administered after one or more symptoms have developed, i.e., therapeutic treatment. In other aspects, treatment may be administered in the absence of symptoms. For example, treatment may be administered to a susceptible individual prior to the onset of symptoms (e.g., in light of a history of symptoms and/or in light of exposure to a particular organism, or other susceptibility factors), i.e., prophylactic treatment. Treatment may also be continued after symptoms have resolved, for example to delay their recurrence.

The term "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The term "effective amount" or "therapeutically effective amount" refers to an amount of a compound described herein that will elicit a biological or medical response of a subject e.g., a dosage of between 0.01-100 mg/kg body weight/day.

3. Compounds

In a first embodiment, provided herein is a compound of Formula I:

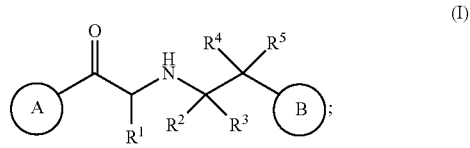

or a pharmaceutically acceptable salt thereof, wherein the variables are as described above.

In a second embodiment, $R^a$, $R^b$, and $R^c$ in the compound of Formula I are independently halo, CN, oxo, $NO_2$, $C_{1-6}$alkyl, $C_{2-6}$alkenyl, $C_{1-6}$alkoxy, $C_{1-6}$haloalkoxy, $C_{1-6}$haloalkyl, —$C_{1-6}$alkylO$R^d$, —C(O)$R^d$, —C(O)O$R^d$, —$C_{1-6}$alkylC(O) O$R^d$, —C(O)N($R^d$)$_2$, —C(O)N$R^d C_{1-6}$alkylO$R^d$, —O$C_{1-6}$alkylN($R^d$)$_2$, —$C_{1-6}$alkylC(O)N($R^d$)$_2$, —$C_{1-6}$alkylN($R^d$)$_2$, —N($R^d$)$_2$, —C(O)N$R^d C_{1-6}$alkylN($R^d$)$_2$, —N$R^d C_{1-6}$alkylN ($R^d$)$_2$, —N$R^d C_{1-6}$alkylO$R^d$, —SO$R^d$, —S(O)$_2R^d$, —SON ($R^d$)$_2$, —SO$_2$N($R^d$)$_2$, SF$_5$, —Ocycloalkyl, —O—$C_{1-4}$alkylaryl, —$C_{1-6}$alkylcycloalkyl, —$C_{1-6}$alkylaryl, —$C_{1-6}$alkylheteroaryl, —$C_{1-6}$alkylheterocyclyl, cycloalkyl, heterocyclyl, heteroaryl, or aryl, wherein each of said cycloalkyl, heterocyclyl, aryl, and heteroaryl alone and in connection with —Ocycloalkyl, —$C_{1-6}$alkylcycloalkyl, —$C_{1-6}$alkylaryl, —$C_{1-6}$alkylheteroaryl, and —$C_{1-6}$alkylheterocyclyl are optionally substituted with 1 to 3 groups selected from halo, $C_{1-6}$alkyl, $C_{1-6}$haloalkyl, $C_{1-6}$alkoxy, $C_{1-6}$haloalkoxy, —N($R^d$)$_2$, —C(O)$R^d$, and —$C_{1-6}$alkylO$R^d$; and each $R^d$ is independently hydrogen, $C_{1-6}$haloalkyl, or $C_{1-6}$alkyl, wherein the remaining variables are as described above for Formula I.

In a third embodiment, the compound of Formula I is of the Formula II or III:

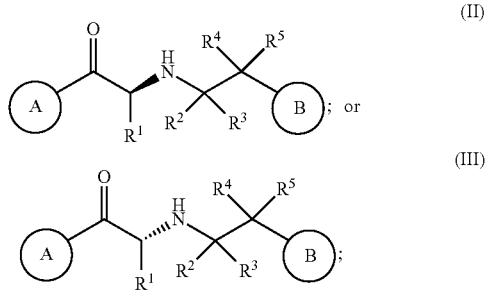

or a pharmaceutically acceptable salt thereof, wherein the remaining variables are as described for Formula I or the second embodiment.

In a fourth embodiment, Ring A in the compounds of Formula I, II, or III is a fused bicyclic heteroaryl optionally substituted with 1 to 3 groups selected from $R^a$, wherein the remaining variables are as described above for Formula I or the second embodiment. Alternatively, Ring A in the compounds of Formula I, II, or III is a 5,6-fused bicyclic heteroaryl comprising 1 or 2 nitrogen atoms and optionally substituted with 1 to 3 groups selected from $R^a$, wherein the remaining variables are as described above for Formula I or the second embodiment. In another alternative, Ring A in the compounds of Formula I, II, or III is selected from

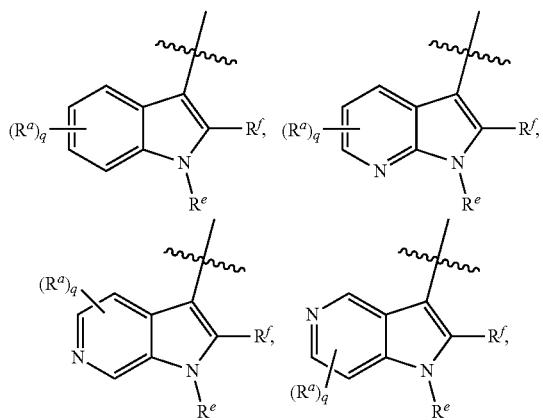

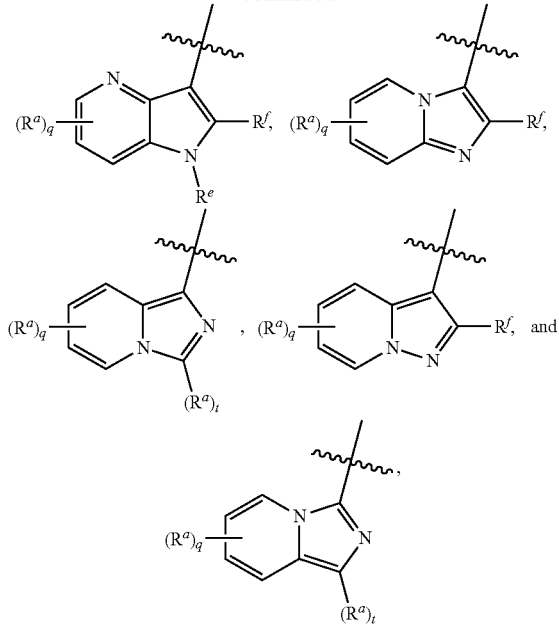

wherein each q is 0, 1, or 2; and $R^e$ and $R^f$ are each independently is hydrogen, $C_{1-6}$alkyl, and —$C_{1-6}$alkylO$R^d$, and wherein the remaining variables are as described above for Formula I or the second embodiment. In yet another alternative, Ring A in the compounds of Formula I, II, or III is

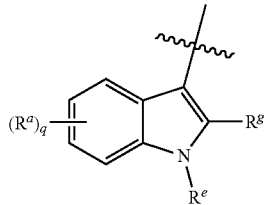

wherein q is 0, 1, or 2; and $R^e$ and $R^f$ are each independently is hydrogen, $C_{1-6}$alkyl, and —$C_{1-6}$alkylO$R^d$, and wherein the remaining variables are as described above for Formula I or the second embodiment.

In a fifth embodiment, $R^f$ in the compounds described herein is hydrogen or $C_{1-4}$alkyl, wherein the remaining variables are as described above for Formula I or the second, third, or fourth embodiment. Alternatively, $R^f$ in the compounds described herein is hydrogen, wherein the remaining variables are as described above for Formula I or the second, third, or fourth embodiment.

In a sixth embodiment, $R^e$ in the compounds described herein is hydrogen or $C_{1-4}$alkyl, wherein the remaining variables are as described above for Formula I or the second, third, fourth, or fifth embodiment. Alternatively, $R^e$ in the compounds described herein is hydrogen, wherein the remaining variables are as described above for Formula I or the second, third, fourth, or fifth embodiment.

In a seventh embodiment, Ring B in the compounds of Formula I, II, or III is phenyl, 5-6 membered heteroaryl, 9-10 membered heteroaryl, or 5-6 membered heterocyclyl, each optionally substituted with 1 to 3 groups selected from $R^b$, wherein the remaining variables are as described above for Formula I or the second, third, fourth, fifth, or sixth embodiment. Alternatively, Ring B in the compounds of Formula I, II, or III is phenyl, pyridinyl, morpholinyl, pyrazolyl, imidazolyl, or benzimidazolyl, each optionally substituted with 1 to 3 groups selected from $R^b$, wherein the remaining variables are as described above for Formula I or the second, third, fourth, fifth, or sixth embodiment.

In an eighth embodiment, $R^1$ in the compounds of Formula I, II, or III is $C_{1-6}$alkyl, aryl, cycloalkyl, or heteroaryl, wherein each of said aryl, cycloalkyl, and heteroaryl are optionally substituted with 1 to 3 groups selected from $R^c$, wherein the remaining variables are as described above for Formula I or the second, third, fourth, fifth, sixth, or seventh embodiment. Alternatively, $R^1$ in the compounds of Formula I, II, or III is $C_{1-4}$alkyl, phenyl, cyclopropyl, cyclopentyl, or pyridinyl, wherein each of said phenyl, cyclopropyl, cyclopentyl, and pyridinyl are optionally substituted with 1 to 3 groups selected from $R^c$, wherein the remaining variables are as described above for Formula I or the second, third, fourth, fifth, sixth, or seventh embodiment. In another alternative, $R^1$ in the compounds of Formula I, II, or III is phenyl optionally substituted with 1 to 3 groups selected from $R^c$, wherein the remaining variables are as described above for Formula I or the second, third, fourth, fifth, sixth, or seventh embodiment.

In an ninth embodiment, $R^3$ in the compounds of Formula I, II, or III is hydrogen, wherein the remaining variables are as described above for Formula I or the third, fourth, fifth, sixth, seventh, or eighth embodiment.

In a tenth embodiment, $R^5$ in the compounds of Formula I, II, or III is hydrogen, wherein the remaining variables are as described above for Formula I or the second, third, fourth, fifth, sixth, seventh, eighth, or ninth embodiment.

In an eleventh embodiment, $R^2$ in the compounds of Formula I, II, or III is hydrogen or $C_{1-4}$alkyl, wherein the remaining variables are as described above for Formula I or the second, third, fourth, fifth, sixth, seventh, eighth, ninth, or tenth embodiment. Alternatively, $R^2$ in the compounds of Formula I, II, or III is hydrogen or methyl, wherein the remaining variables are as described above for Formula I or the second, third, fourth, fifth, sixth, seventh, eighth, ninth, or tenth embodiment. In another alternative, $R^2$ in the compounds of Formula I, II, or III is hydrogen, wherein the remaining variables are as described above for Formula I or the second, third, fourth, fifth, sixth, seventh, eighth, ninth, or tenth embodiment.

In a twelfth embodiment, $R^4$ in the compounds of Formula I, II, or III is hydrogen or $C_{1-4}$alkyl, wherein the remaining variables are as described above for Formula I or the second, third, fourth, fifth, sixth, seventh, eighth, ninth, tenth, or eleventh embodiment. Alternatively, $R^4$ in the compounds of Formula I, II, or III is hydrogen, methyl, or ethyl, wherein the remaining variables are as described above for Formula I or the second, third, fourth, fifth, sixth, seventh, eighth, ninth, tenth, or eleventh embodiment. In another alternative, $R^4$ in the compounds of Formula I, II, or III is hydrogen, wherein the remaining variables are as described above for Formula I or the second, third, fourth, fifth, sixth, seventh, eighth, ninth, tenth, or eleventh embodiment.

In a thirteenth embodiment, the compound of Formula I is of the Formula IV or V:

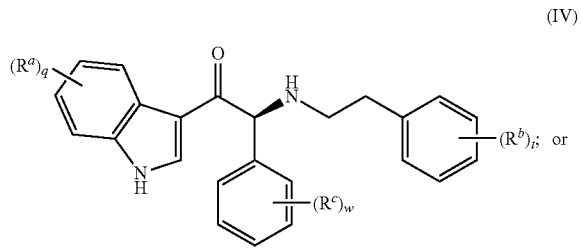

(IV)

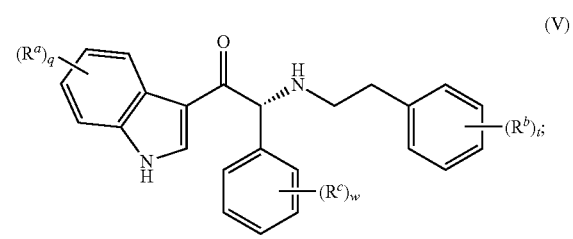

(V)

or a pharmaceutically acceptable salt thereof, wherein w and t are each independently 0, 1, or 2, and wherein the remaining variables are as described above for Formula I or the second, third, fourth, fifth, sixth, seventh, eighth, ninth, tenth, eleventh, or twelfth embodiment. Alternatively, the compound of Formula I is of the Formula VI or VII:

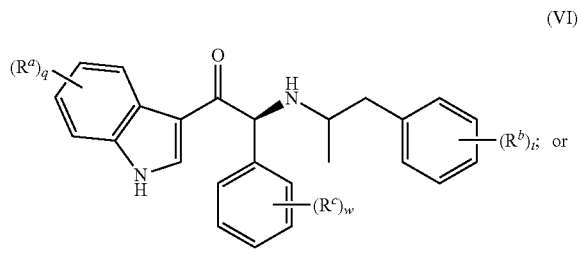

(VI)

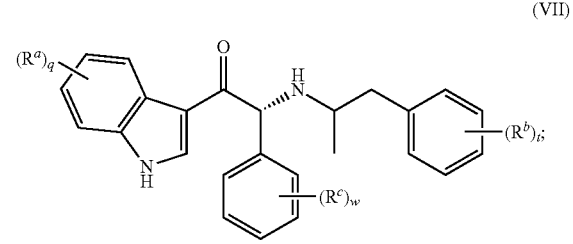

(VII)

or a pharmaceutically acceptable salt thereof, wherein w and t are each independently 0, 1, or 2, and wherein the remaining variables are as described above for Formula I or the second, third, fourth, fifth, sixth, seventh, eighth, ninth, tenth, eleventh, or twelfth embodiment. In another alternative, the compound of Formula I is of the Formula VIII or IX:

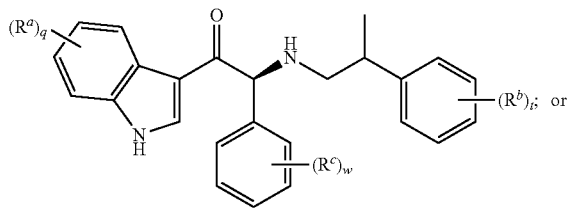

(VIII)

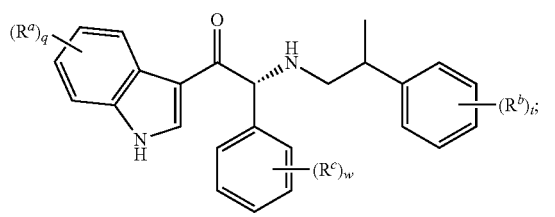

(IX)

or a pharmaceutically acceptable salt thereof, wherein w and t are each independently 0, 1, or 2, and wherein the remaining variables are as described above for Formula I or the second, third, fourth, fifth, sixth, seventh, eighth, ninth, tenth, eleventh, or twelfth embodiment.

In a fourteenth embodiment, $R^c$, if present, in the compounds of Formula I, II, III, IV, V, VI, VII, VIII, or IX is $C_{1-6}$alkyl, $C_{1-6}$alkoxy, $C_{1-6}$haloalkoxy, or $C_{1-6}$haloalkyl, wherein the remaining variables are as described above for Formula I or the second, third, fourth, fifth, sixth, seventh, eighth, ninth, tenth, eleventh, twelfth, or thirteenth embodiment.

In a fifteenth embodiment, the compound of Formula I is of the Formula X or XI:

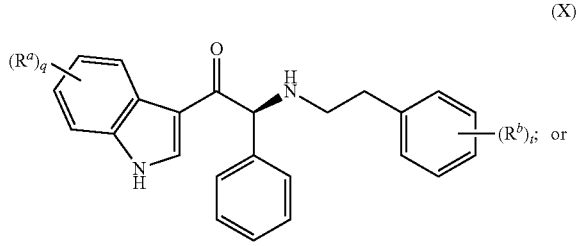

(X)

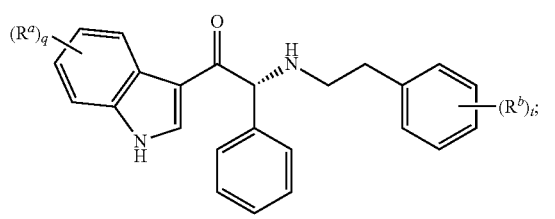

(XI)

or a pharmaceutically acceptable salt thereof, wherein the remaining variables are as described above for Formula I or the second, third, fourth, fifth, sixth, seventh, eighth, ninth, tenth, eleventh, twelfth, thirteenth, or fourteenth embodiment.

In a sixteenth embodiment, $R^a$ in the compounds of Formula I, II, III, IV, V, VI, VII, VIII, IX, X, or XI is selected from $C_{1-4}$alkyl, $C_{1-4}$haloalkyl, $C_{1-4}$alkoxy, halo, —$C_{1-4}$alkylC(O)N($R^d$)$_2$, —$C_{1-4}$alkylC(O)OR$^d$, —C(O)OR$^d$, —C(O)NR$^d$C$_{1-4}$alkylN(R$^d$)$_2$—C(O)NR$^d$C$_{1-4}$alkylOR$^d$, —C(O)N(R$^d$)$_2$, —OC$_{1-4}$alkylaryl, heterocyclyl, and heteroaryl, wherein said heterocyclyl is optionally substituted with $C_{1-4}$alkyl or —C(O)R$^d$ and wherein said heteroaryl is optionally substituted with $C_{1-4}$alkyl, —$C_{1-4}$alkylC(O)N(R$^d$)$_2$, —$C_{1-4}$alkylOR$^d$, wherein the remaining variables are as described above for Formula I or the second, third, fourth, fifth, sixth, seventh, eighth, ninth, tenth, eleventh, twelfth, thirteenth, fourteenth, or fifteenth embodiment. Alternatively, $R^a$ in the compounds of Formula I, II, III, IV, V, VI, VII, VIII, IX, X, or XI is selected from $C_{1-4}$alkyl, $C_{1-4}$haloalkyl, $C_{1-4}$alkoxy, halo, —$C_{1-4}$alkylC(O)N($C_{1-4}$alkyl)$_2$, —$C_{1-4}$alkylC(O)NHC$_{1-4}$alkyl, —O—$C_{1-4}$alkylphenyl, —C(O)$C_{1-4}$alkyl, —C(O)NHC$_{1-4}$alkyl, —C(O)N($C_{1-4}$alkyl)$_2$, —C(O)NHC$_{1-4}$alkylN($C_{1-4}$alkyl)$_2$, —C(O)NHC$_{1-4}$alkylOC$_{1-4}$alkyl, C(O)OH, —C(O)NHC$_{1-4}$haloalkyl, —$C_{1-4}$alkylC(O)OH, piperidinyl, piperazinyl, pyrazolyl, pyridinyl, oxadiazolyl, imidazolyl, pyrimidinyl, and triazolyl, wherein said piperidinyl and piperazinyl are each optionally substituted with $C_{1-4}$ alkyl or —C(O)$C_{1-4}$alkyl and wherein said pyrazolyl, pyridinyl, oxadiazolyl, imidazolyl, pyrimidinyl, and triazolyl are each optionally substituted with $C_{1-4}$alkyl, —$C_{1-4}$alkylC(O)N(R$^d$)$_2$, —$C_{1-4}$alkylOH, —$C_{1-4}$alkylOC$_{1-4}$alkyl, or —$C_{1-4}$alkylC(O)NHC$_{1-4}$alkyl, wherein the remaining variables are as described above for Formula I or the second, third, fourth, fifth, sixth, seventh, eighth, ninth, tenth, eleventh, twelfth, thirteenth, fourteenth, or fifteenth embodiment. In another alternative, $R^a$ in the compounds of Formula I, II, III, IV, V, VI, VII, VIII, IX, X, or XI is selected from CF$_3$, methyl, ethyl, isopropyl, chloro, —(CH$_2$)$_2$C(O)N(Me)$_2$, —CH$_2$C(O)N(Me)$_2$, —(CH$_2$)$_2$C(O)N(Me)$_2$, —CH$_2$C(O)NHMe, methoxy, —O(CH$_2$)phenyl, 1-methylpiperidin-4-yl, 1-acetylpiperidin-4-yl, 1-methyl-1H-pyrazol-4-yl, —C(O)NHMe, —C(O)N(Me)$_2$, 1-ethyl-1H-pyrazol-4-yl, compound 156, 2-methylpyridinyl, pyridinyl, (2-hydroxyethyl)-1H-pyrazol-4-yl, (2-methoxyethyl)-1H-pyrazol-4-yl, 5-methyl-1,3,4-oxadiazol-2-yl, N-methyl-2-(1H-pyrazol-1-yl)acetamide, 5-methyl-1H-imidazol-2-yl, 2-methyl-1H-imidazol-2-yl, pyrimidin-4-yl, pyridazin-3-yl, 1-methyl-1H-1,2,3-triazol-4-yl, 1H-imidazol-1-yl, 1H-pyrazol-1-yl, 4-methylpiperazin-1-yl, —C(O)NH(CH$_2$)$_2$N(Me)$_2$, —C(O)NH(CH$_2$)$_2$OMe, COOH, —C(O)NHCH$_2$CF$_3$, —CH$_2$COOH, —(CH$_2$)$_2$COOH, and —C(O)NHCH$_2$CH$_3$, wherein the remaining variables are as described above for Formula I or the second, third, fourth, fifth, sixth, seventh, eighth, ninth, tenth, eleventh, twelfth, thirteenth, fourteenth, or fifteenth embodiment.

In a seventeenth embodiment, $R^b$ in the compounds of Formula I, II, III, IV, V, VI, VII, VIII, IX, X, or XI is selected from —SON(R$^d$)$_2$, halo, $C_{1-4}$haloalkoxy, $C_{1-4}$alkoxy, $C_{1-4}$haloalkyl, $C_{1-4}$alkyl, —N(R$^d$)$_2$, oxo, —NR$^d$C$_{1-6}$alkylOR$^d$, CN, $C_{5-10}$heteroaryl, —C(O)N(R$^d$)$_2$, C(O)OR$^d$, and —$C_{1-4}$alkylC(O)N(R$^d$)$_2$, wherein the remaining variables are as described above for Formula I or the second, third, fourth, fifth, sixth, seventh, eighth, ninth, tenth, eleventh, twelfth, thirteenth, fourteenth, fifteenth, or sixteenth embodiment. Alternatively, $R^b$ in the compounds of Formula I, II, III, IV, V, VI, VII, VIII, IX, X, or XI is selected from —SON(R$^d$)$_2$, halo, $C_{1-4}$haloalkoxy, $C_{1-4}$alkoxy, $C_{1-4}$haloalkyl, $C_{1-4}$alkyl, —N(R$^d$)$_2$, oxo, —NR$^d$C$_{1-6}$alkylOR$^d$, CN, $C_{6-10}$heteroaryl, —C(O)N(R$^d$)$_2$, C(O)OR$^d$, and —$C_{1-4}$alkylC(O)N(R$^d$)$_2$; and $R^d$ is hydrogen or $C_{1-4}$alkyl, wherein the remaining variables are as described above for Formula I or the second, third, fourth, fifth, sixth, seventh, eighth, ninth, tenth, eleventh, twelfth, thirteenth, fourteenth, fifteenth, or sixteenth embodiment. In another alternative, $R^b$ in the compounds of Formula I, II, III, IV, V, VI, VII, VIII, IX, X, or XI is selected from SO$_2$, NH$_2$, —OMe, CF$_3$, Cl, F, Me, —NMe$_2$, —OCF$_3$, oxo, —NHEt, —NH(CH$_2$)$_2$OMe, CN, —C(O)NH$_2$, COOH, —CONH$_2$, —CONHMe, —CONMe$_2$, —CH$_2$C(O)NHMe, —CH$_2$C(O)N(Me)$_2$, 2H-tetrazol-5-yl, and 4H-1,2,4-triazol-3-yl, wherein the remaining variables are as described above for Formula I or the second, third, fourth, fifth, sixth, seventh, eighth, ninth, tenth, eleventh, twelfth, thirteenth, fourteenth, fifteenth, or sixteenth embodiment.

In an eighteenth embodiment, the compound of Formula I is of the Formula XII or XIII:

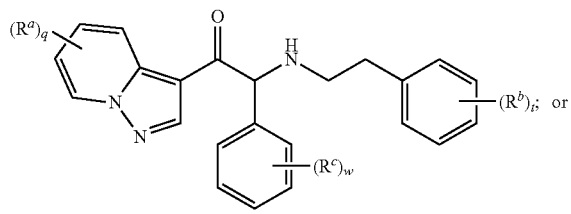

(XII)

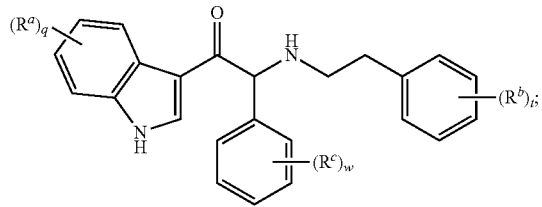

(XIII)

or a pharmaceutically acceptable salt thereof, wherein q, w, and t are each independently 0, 1, or 2, and wherein the remaining variables are as described above for Formula I.

In a nineteenth embodiment, the compound of Formula I is of the Formula XIV or XV:

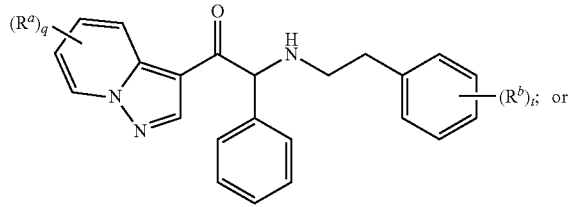

(XIV)

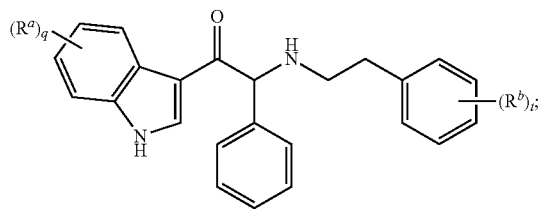

(XV)

or a pharmaceutically acceptable salt thereof, wherein q, and t are each 1, and wherein the remaining variables are as described above for Formula I.

In a twentieth embodiment, R$^b$ in the compound of Formula I, XII, XIII, XIV, or XV is CN, wherein the remaining variables are as described above for Formula I.

In a twenty-first embodiment, R$^a$ in the compound of Formula I, XII, XIII, XIV, or XV is selected from C$_{1-4}$alkyl, —C(O)NR$^d$C$_{1-4}$alkylOR$^d$, —C(O)N(R$^d$)$_2$, heterocyclyl, —Oheterocyclyl, and heteroaryl, wherein said heterocyclyl and —Oheterocyclyl are each optionally substituted with oxo and wherein said heteroaryl is optionally substituted with C$_{1-4}$alkyl, wherein the remaining variables are as described above for Formula I or the twentieth embodiment. Alternatively, R$^a$ in the compound of Formula I, XII, XIII, XIV, or XV is selected from C$_{1-4}$alkyl, —C(O)NR$^d$C$_{1-4}$alkylOR$^d$, —C(O)N(R$^d$)$_2$, pyrrolidinyl, —Opiperidinyl, and pyrazolyl, wherein said pyrrolidinyl and —Opiperidinyl are each optionally substituted with oxo and wherein said pyrazolyl is optionally substituted with C$_{1-4}$alkyl, wherein the remaining variables are as described above for Formula I or the twentieth embodiment.

In a twenty-second embodiment, each R$^d$ in the compound of Formula I, XII, XIII, XIV, or XV is independently hydrogen, heterocyclyl, C$_{1-6}$haloalkyl, or C$_{1-6}$alkyl, wherein said heterocyclyl is optionally substituted with 1 or 2 groups selected from C$_{1-4}$haloalkyl, oxo, and C$_{1-4}$alkyl and said C$_{1-6}$alkyl is optionally substituted with —SO$_2$C$_{1-4}$alkyl or heterocyclyl optionally substituted with oxo, wherein the remaining variables are as described above for Formula I or the twentieth or twenty-first embodiment. Alternatively, each R$^d$ in the compound of Formula I, XII, XIII, XIV, or XV is independently hydrogen, azetidinyl, thietanyl, oxetanyl, pyrrolidinyl, C$_{1-6}$haloalkyl, or C$_{1-6}$alkyl, wherein said azetidinyl, thietanyl, oxetanyl, and pyrrolidinyl are each optionally and independently substituted with 1 or 2 groups selected from C$_{1-4}$haloalkyl, oxo, and C$_{1-4}$alkyl and said C$_{1-6}$alkyl is optionally substituted with —SO$_2$C$_{1-4}$alkyl or pyrrolidinyl optionally substituted with oxo, wherein the remaining variables are as described above for Formula I or the twentieth or twenty-first embodiment.

In a twenty-third embodiment, the compounds of Formula I are selected from the following formula:



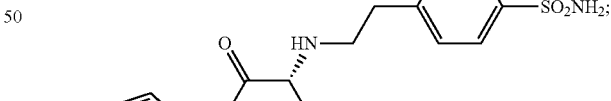

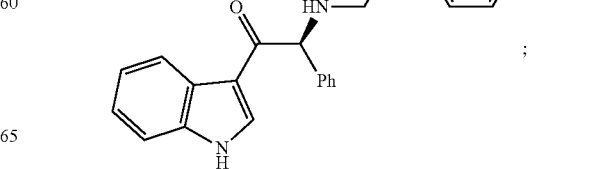

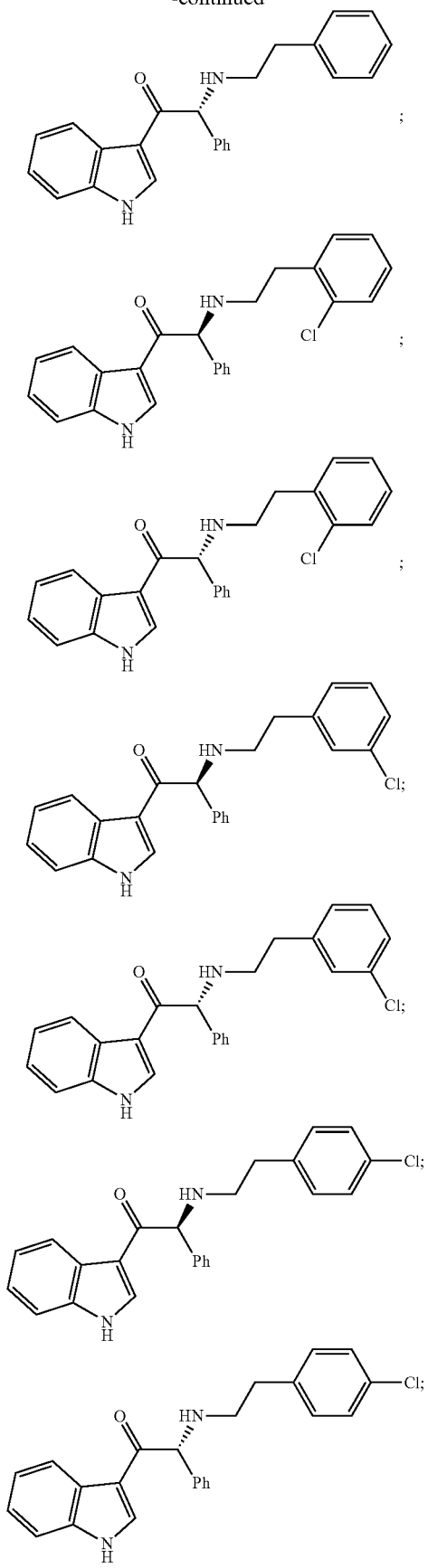
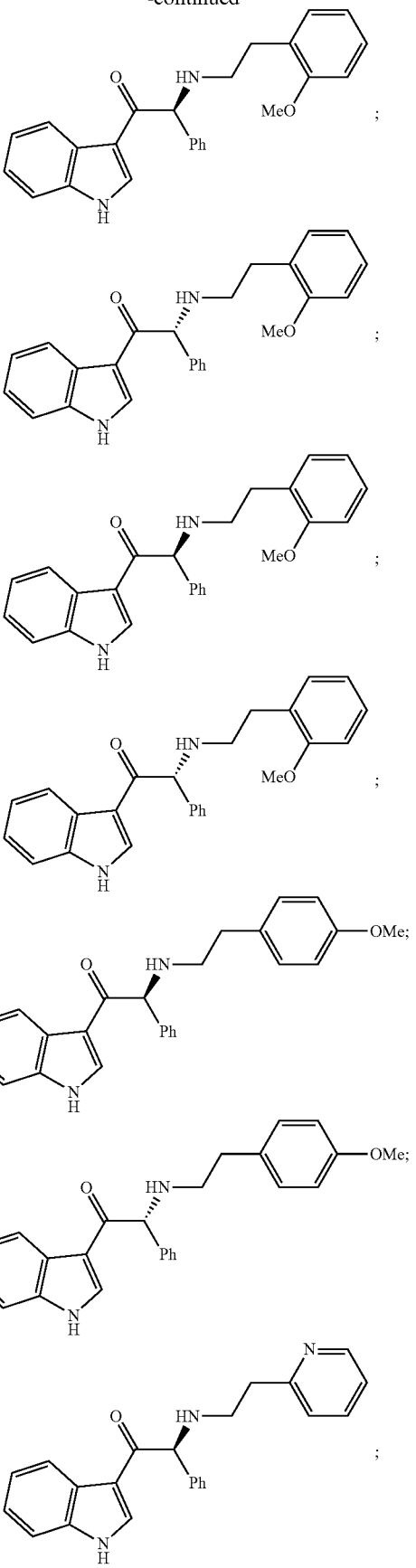

-continued
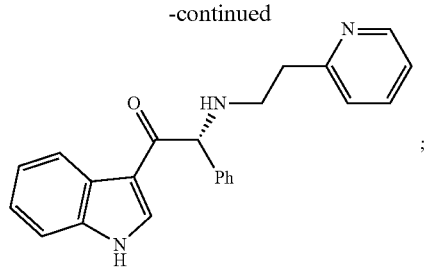
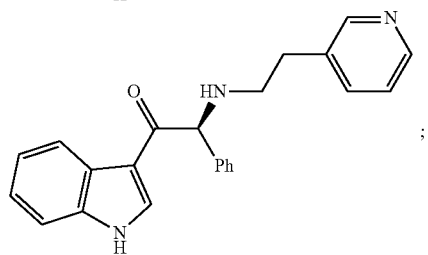
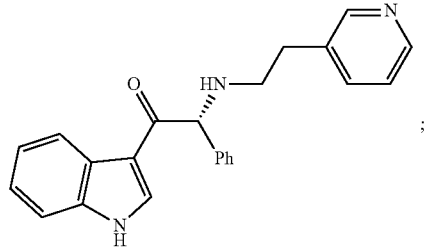
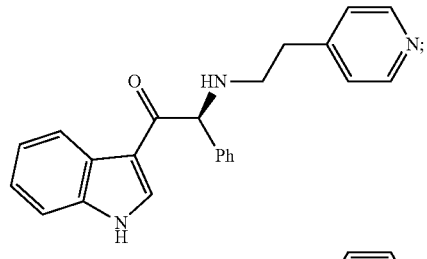
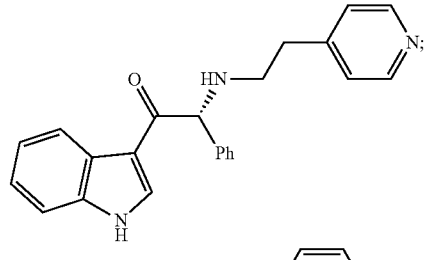
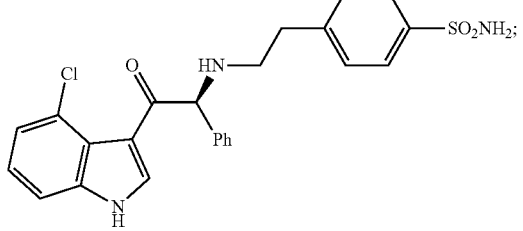
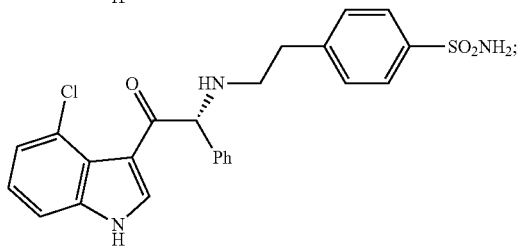
-continued
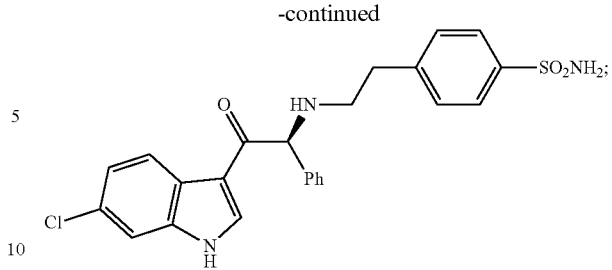
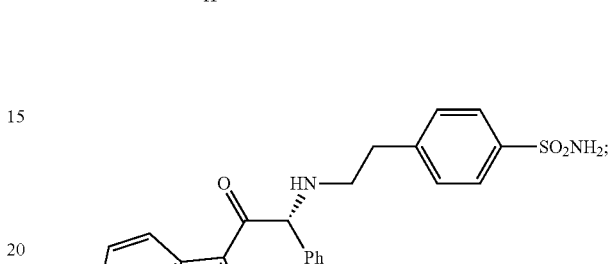

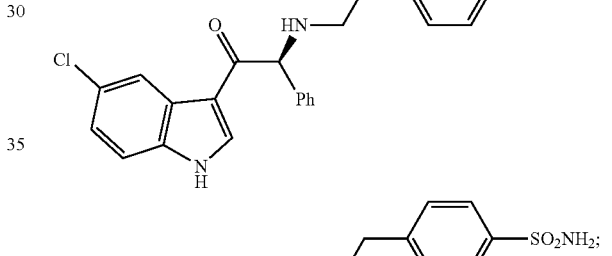
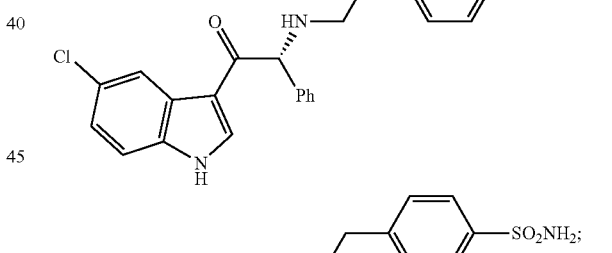
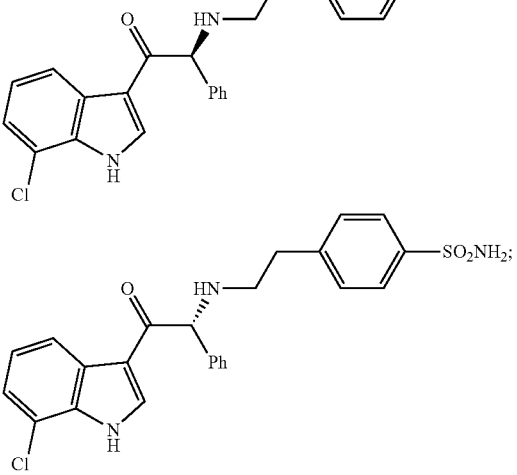

-continued
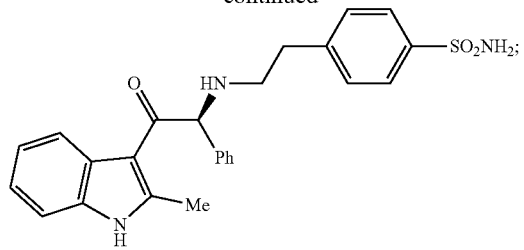
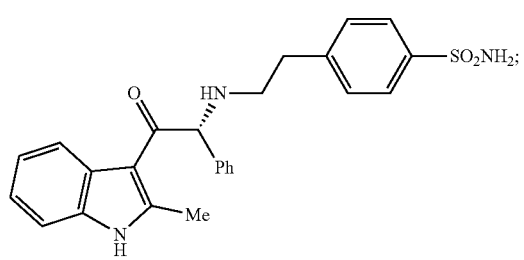
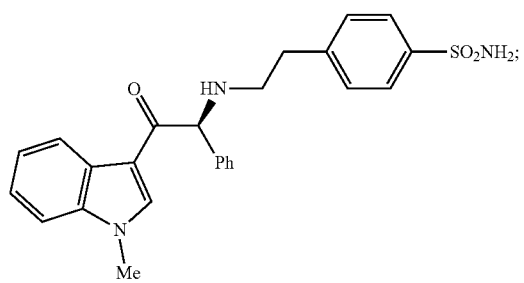
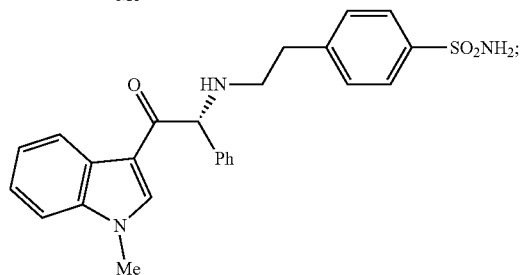
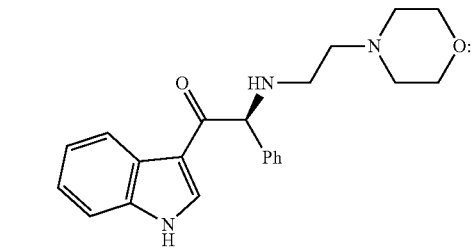
-continued
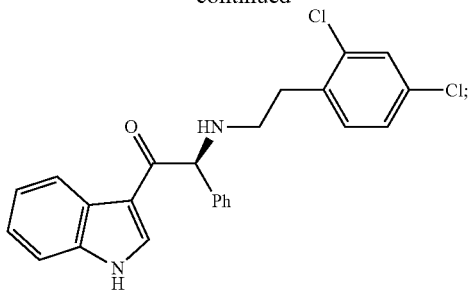
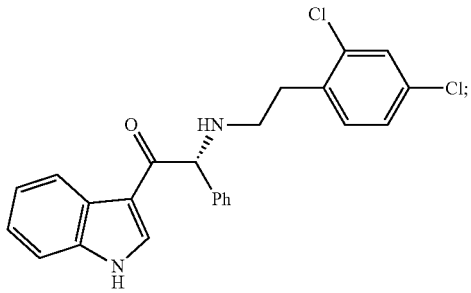
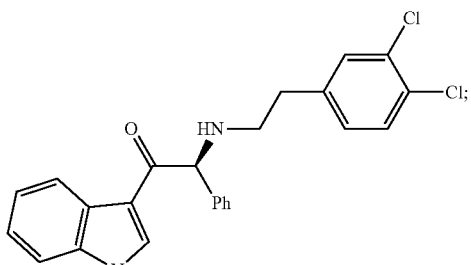
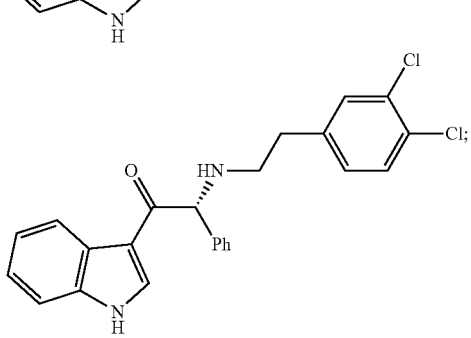
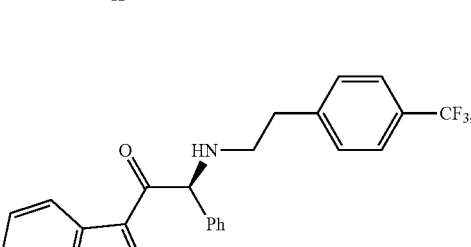
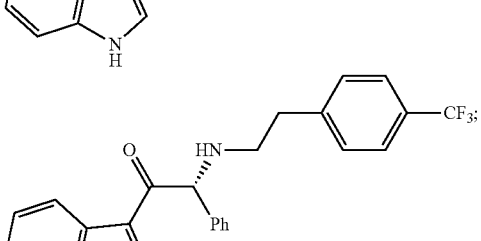

-continued
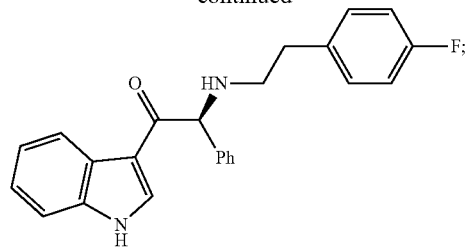
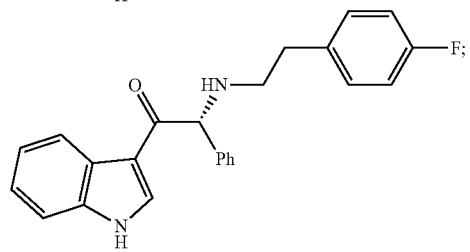
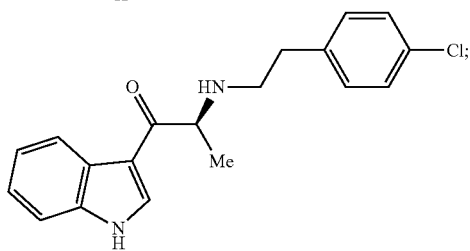
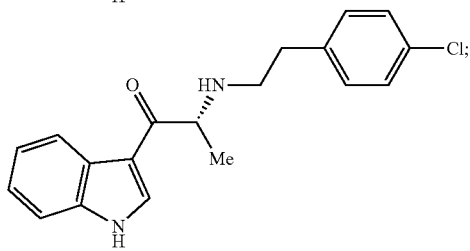
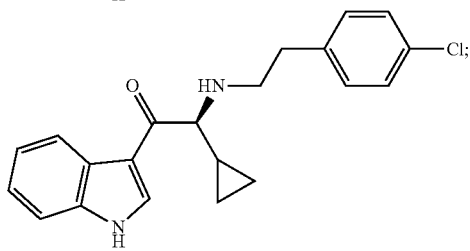
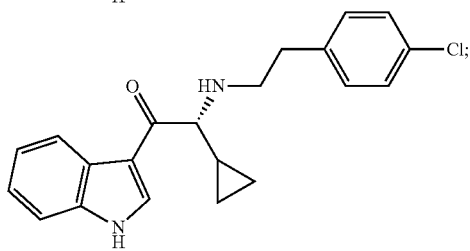
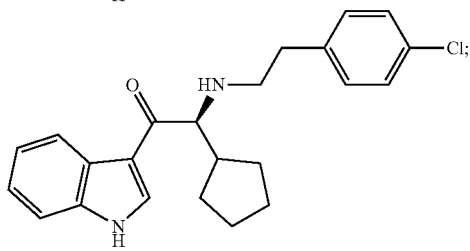
-continued
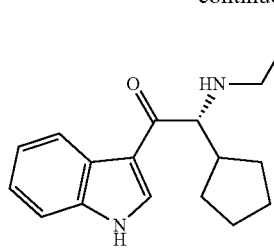
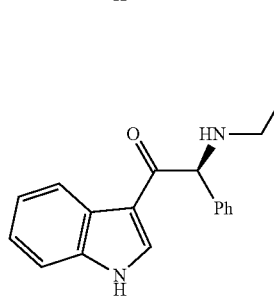
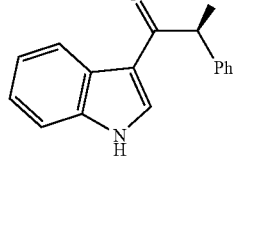
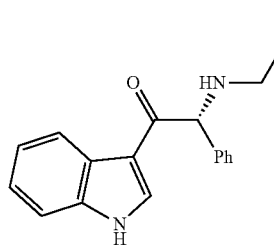
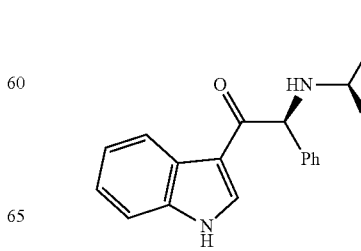
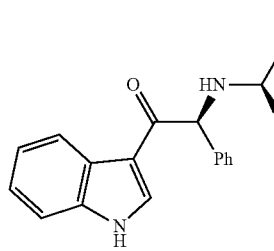

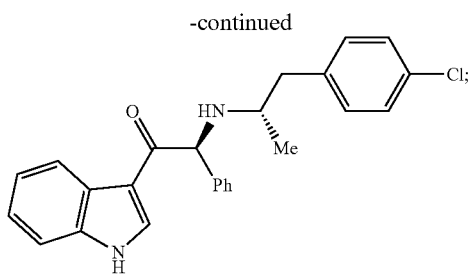
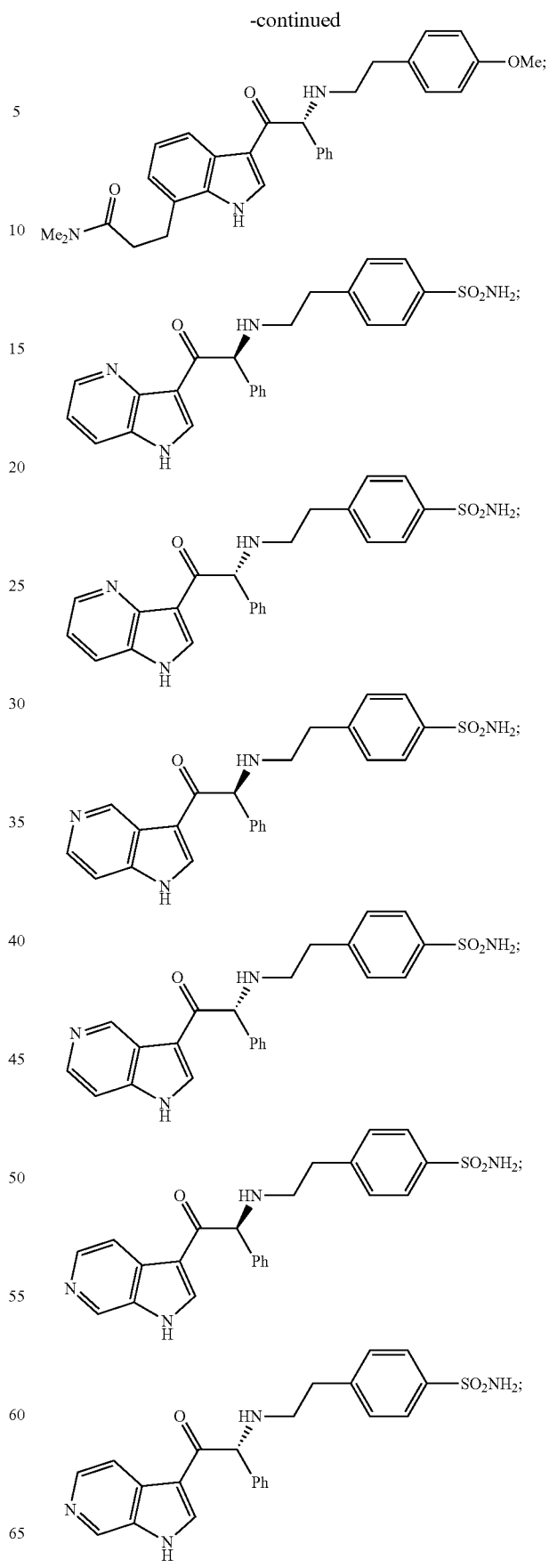

27
-continued
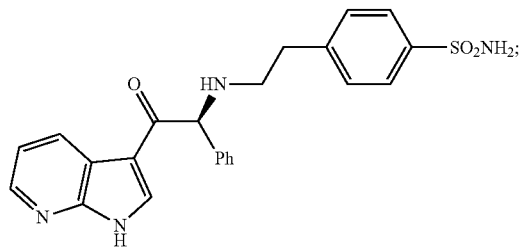
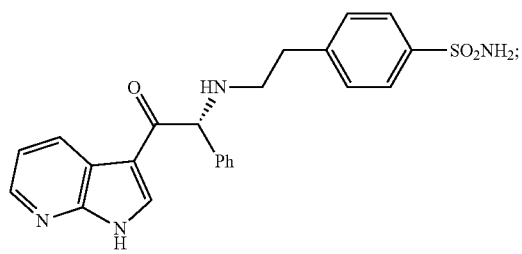
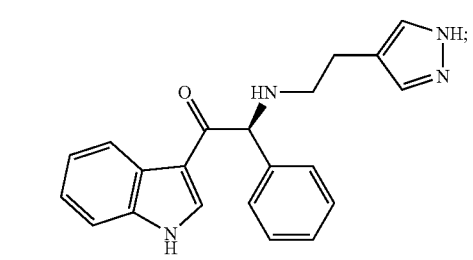
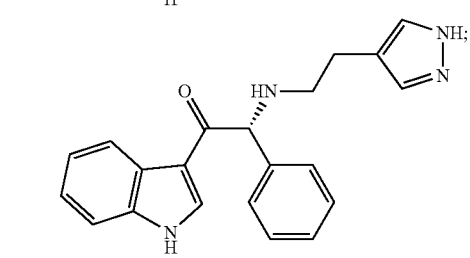
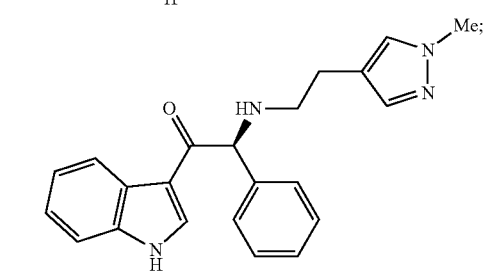
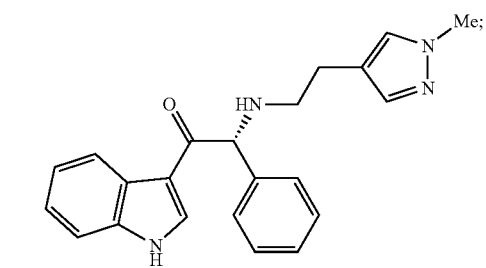
28
-continued
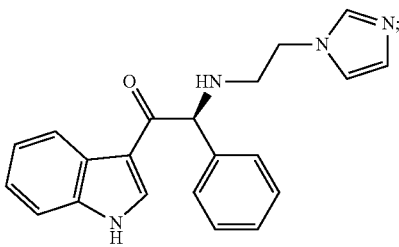
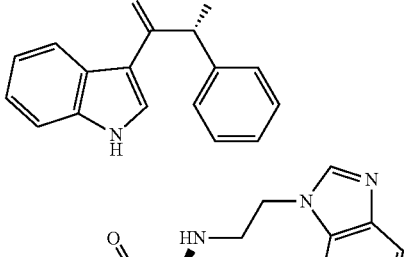
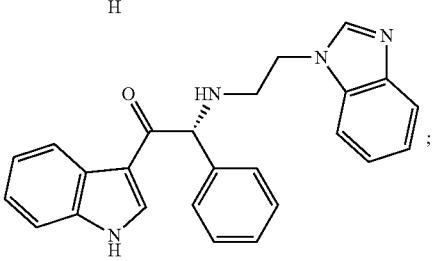
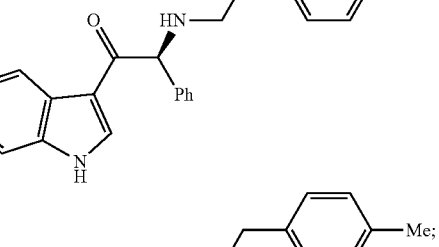
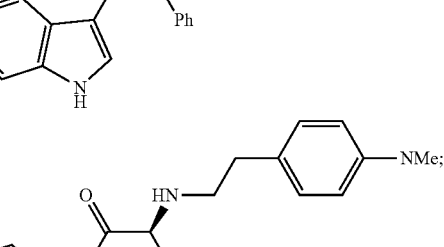

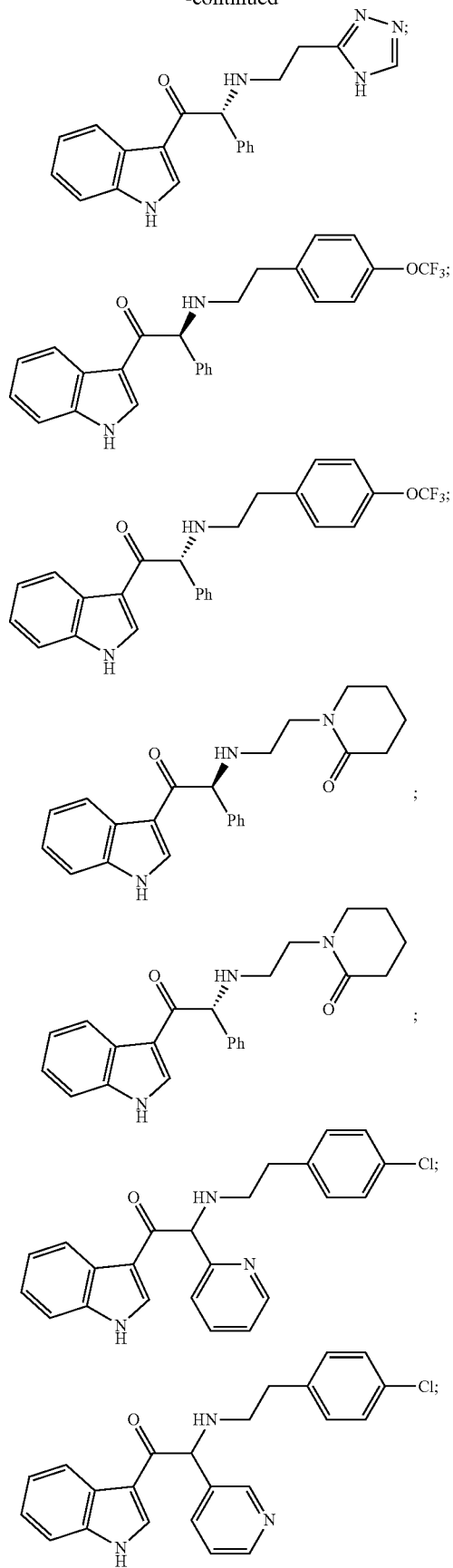
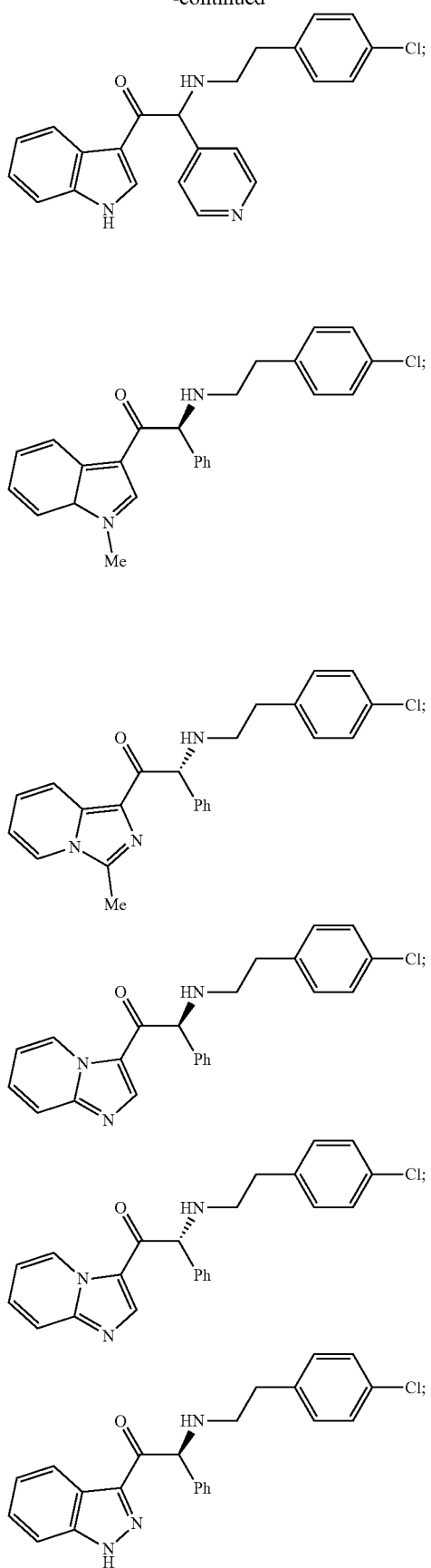

| 31 -continued | 32 -continued |
|---|---|
| 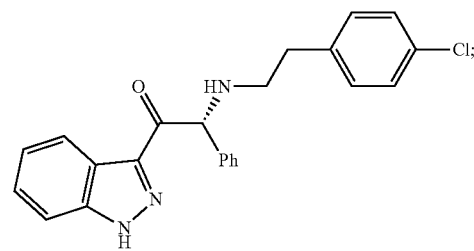 | 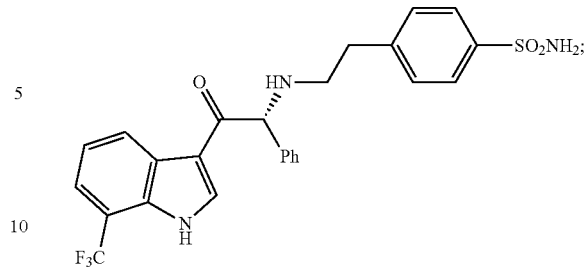 |
| 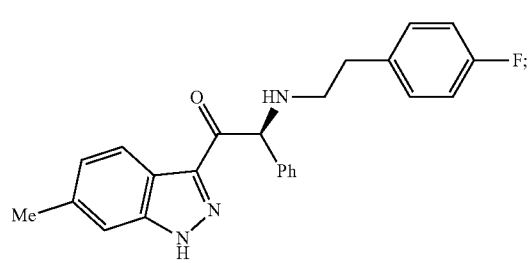 | 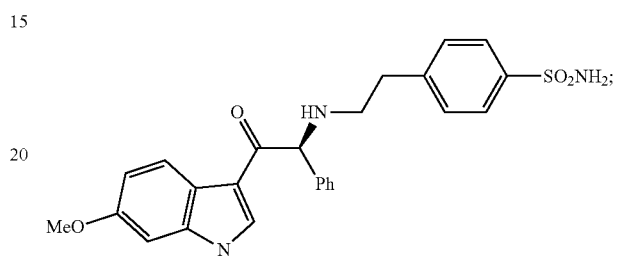 |
| 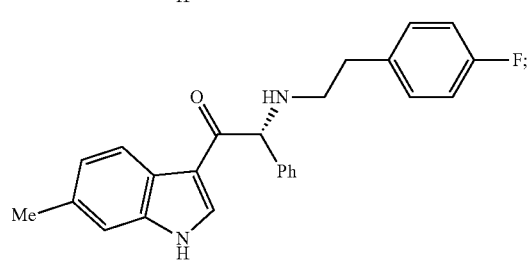 | 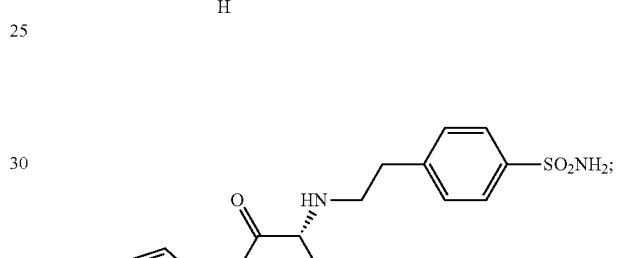 |
| 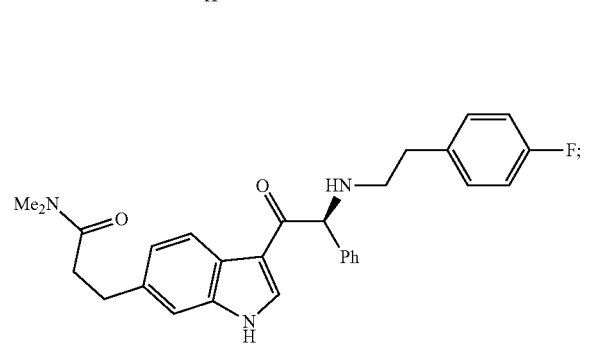 | 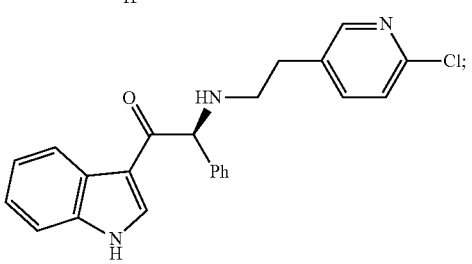 |
| 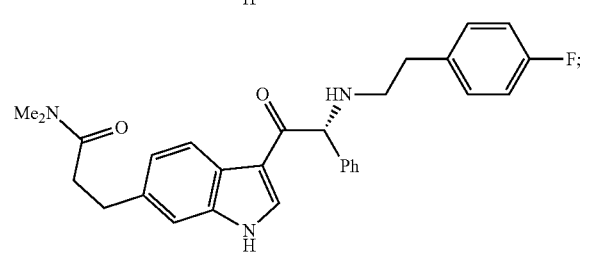 | 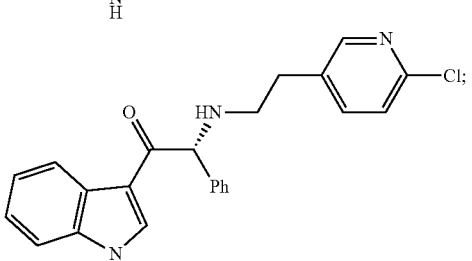 |
| 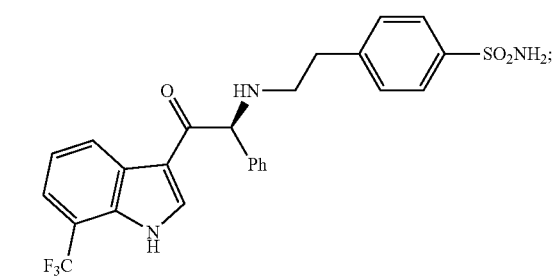 | 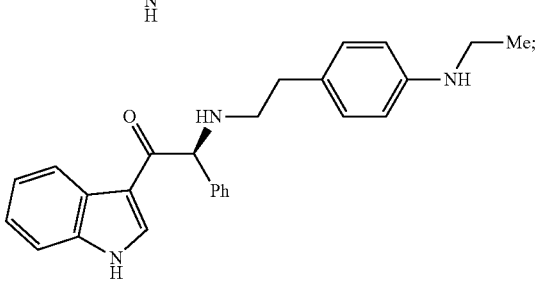 |

33
-continued
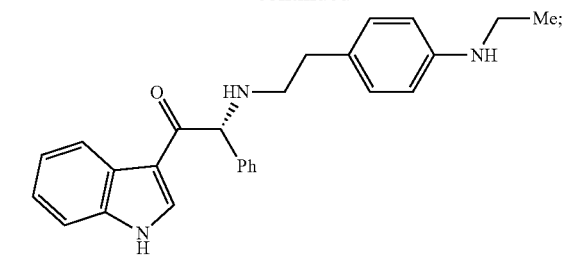
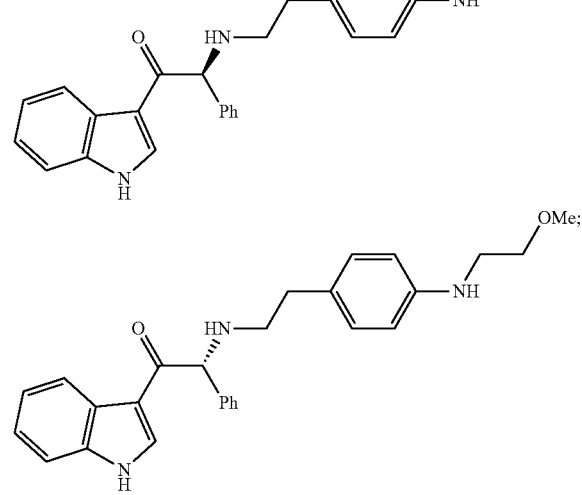
34
-continued
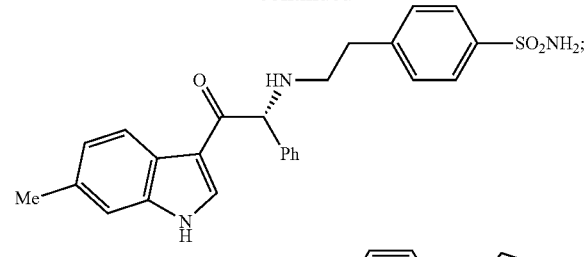
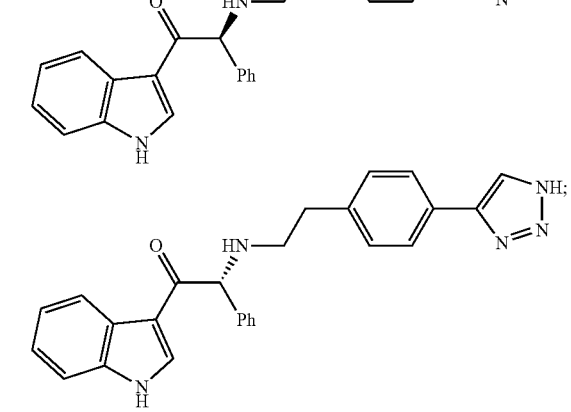
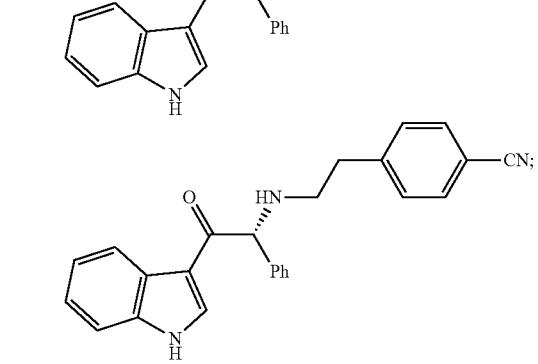
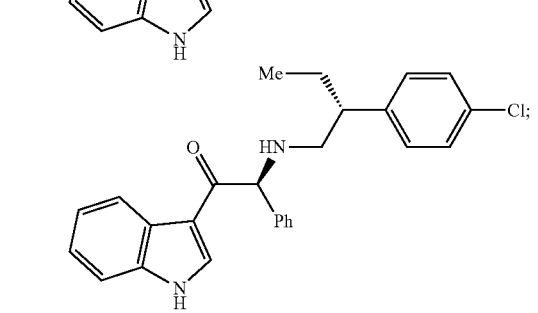

-continued
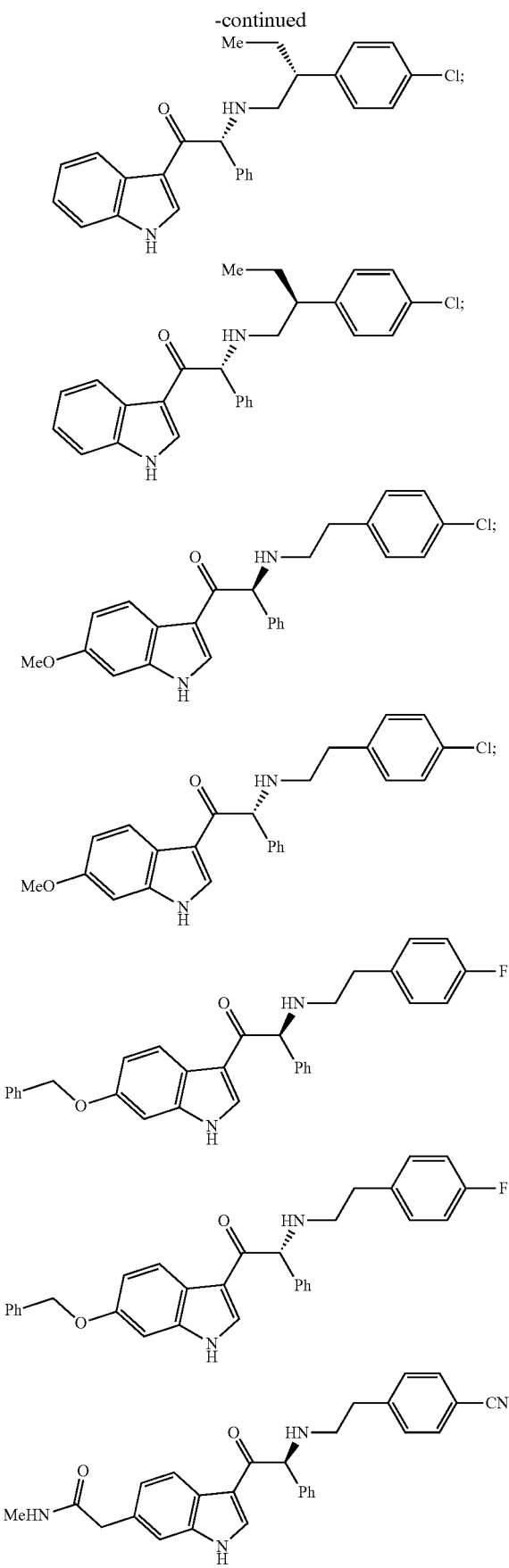
-continued
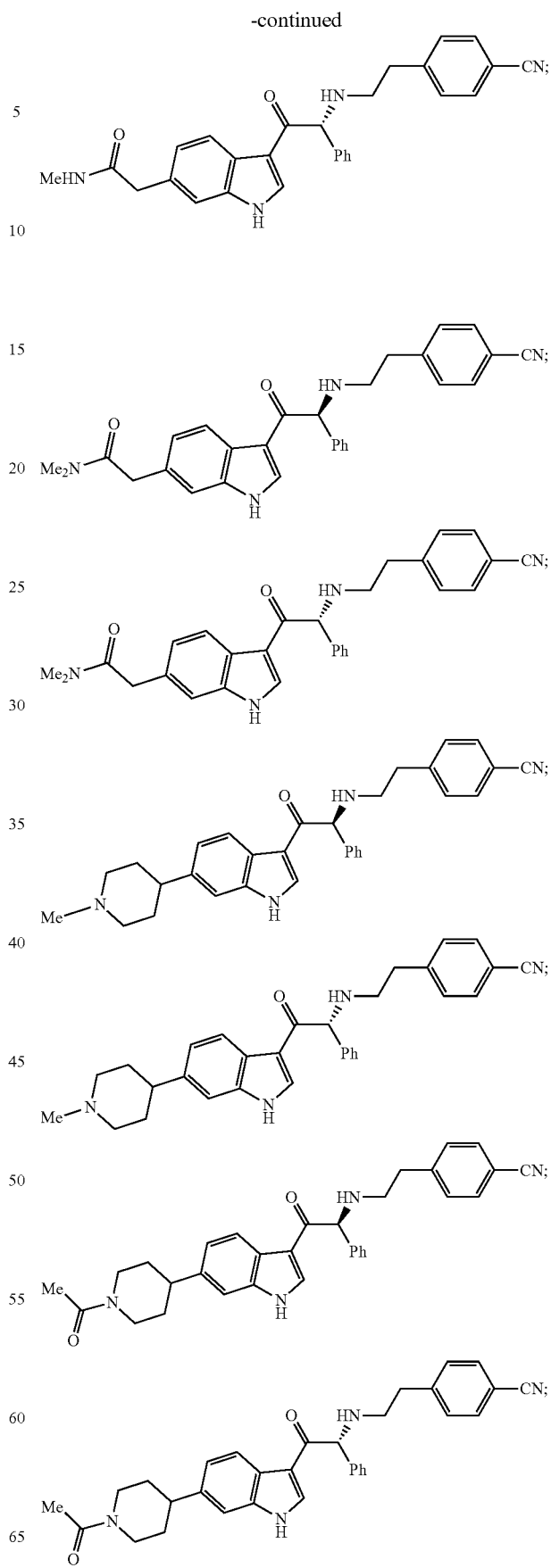

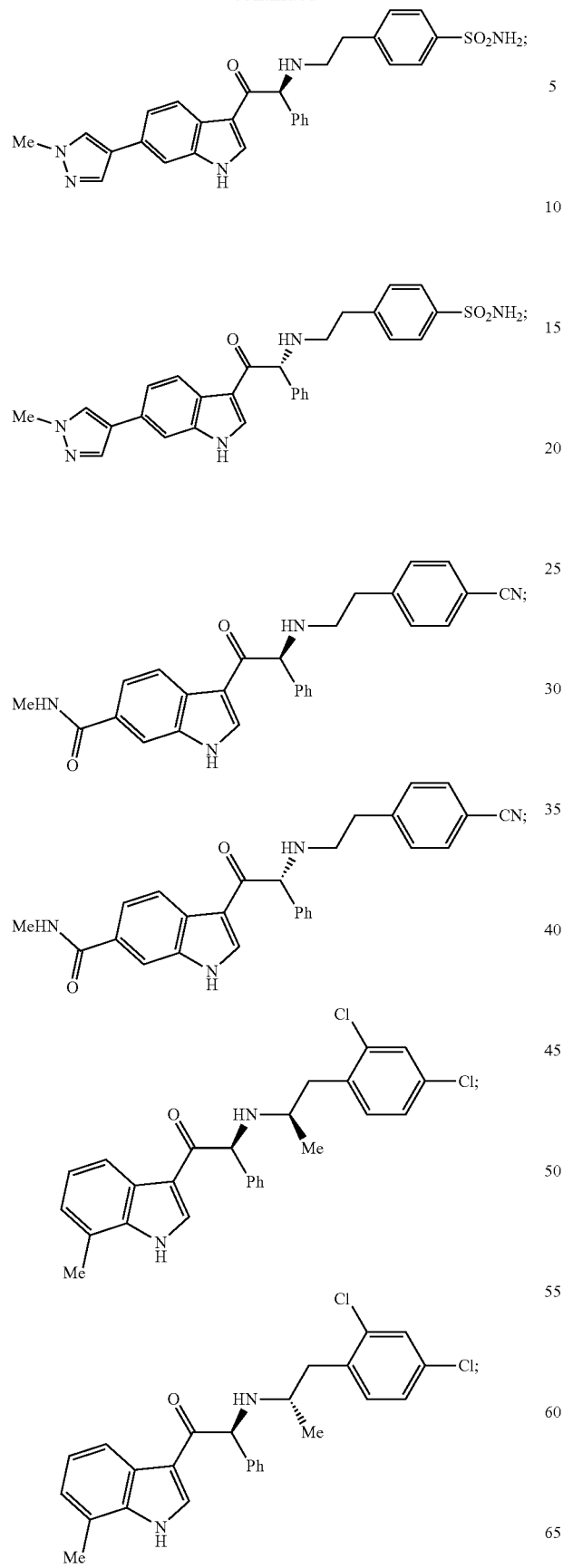
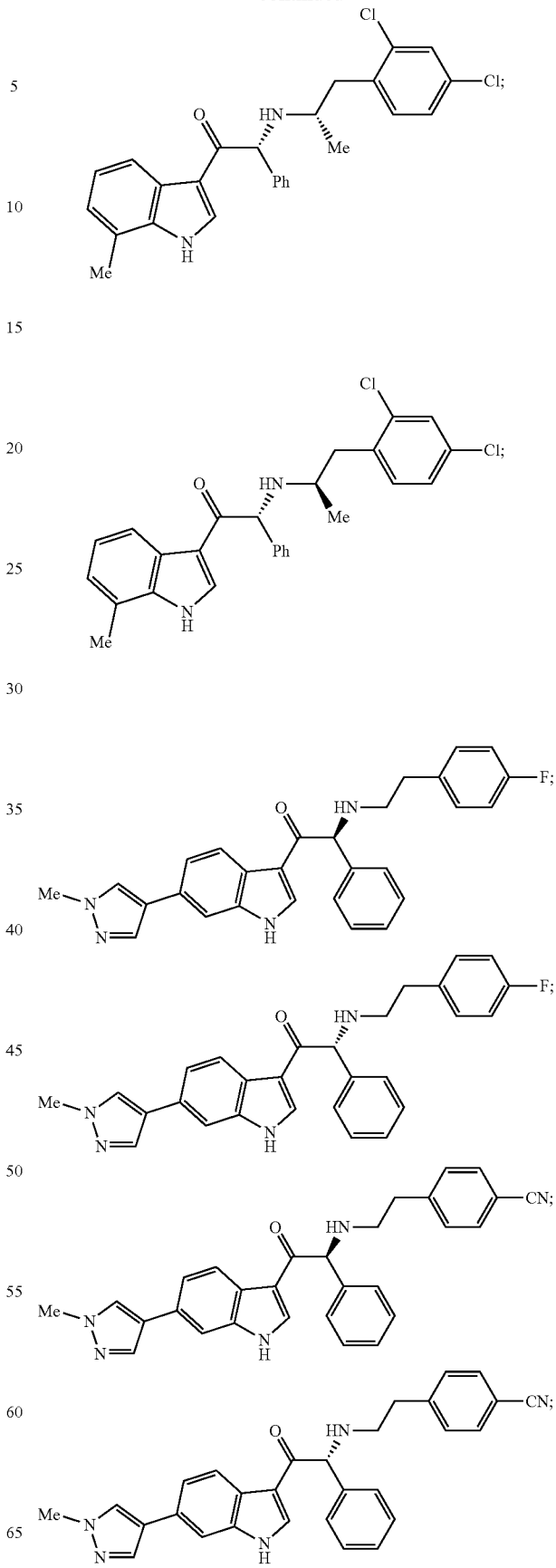

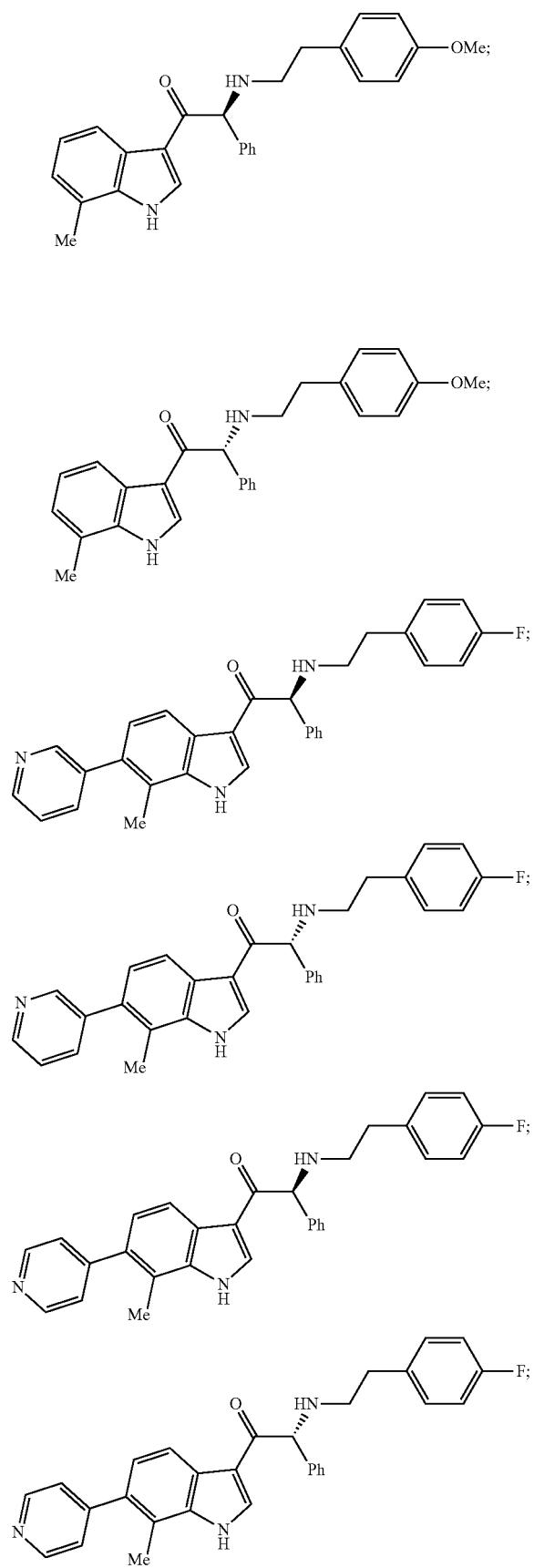
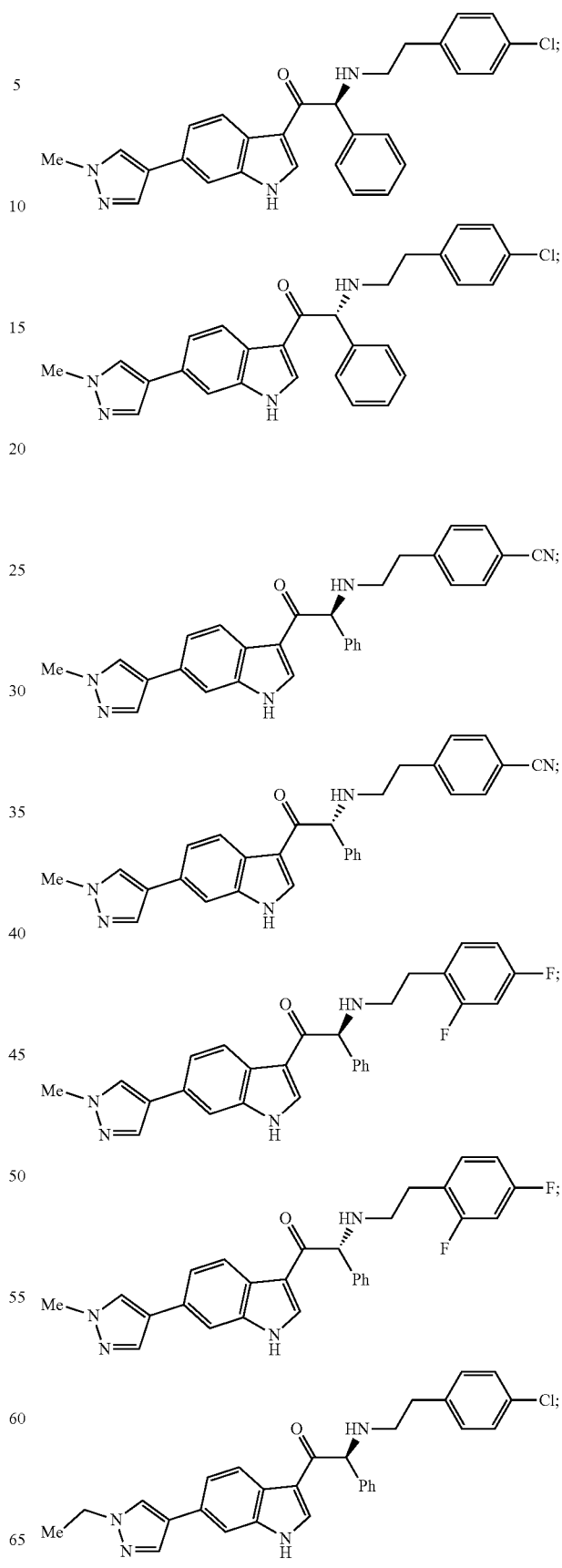

41
-continued
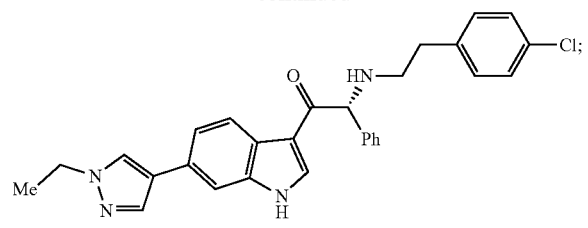
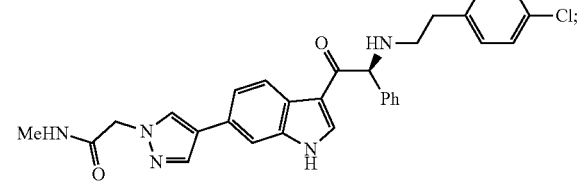
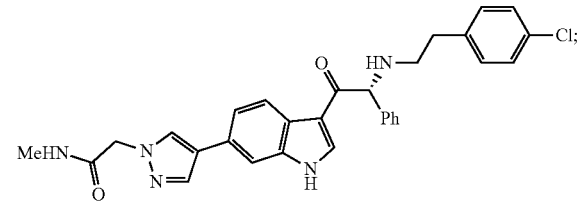
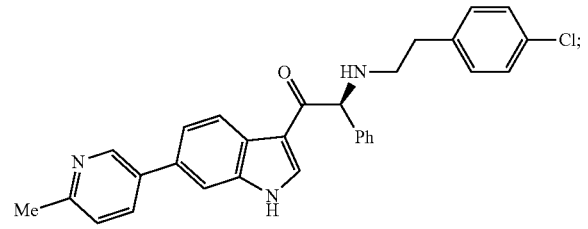

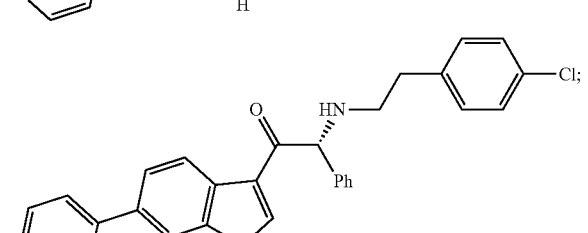
42
-continued
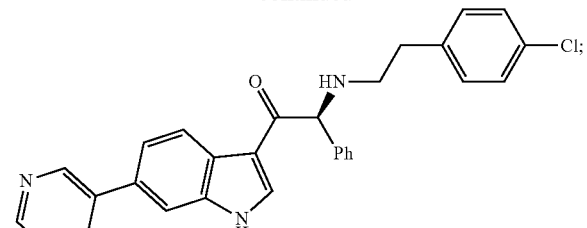
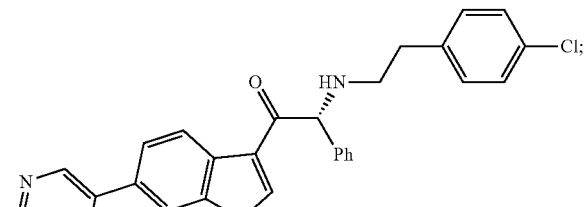
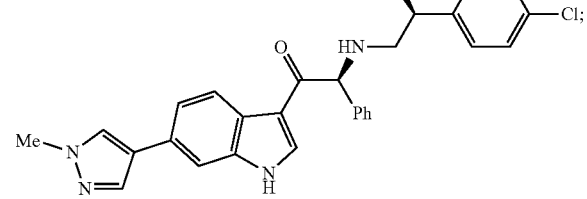
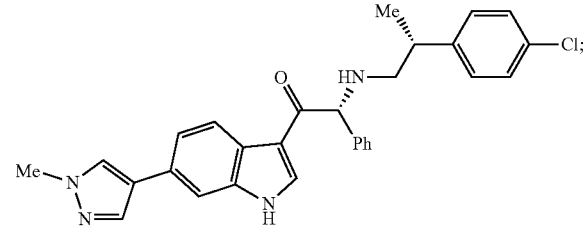
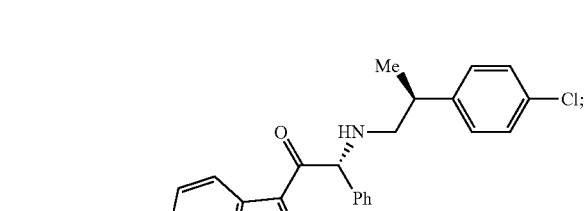
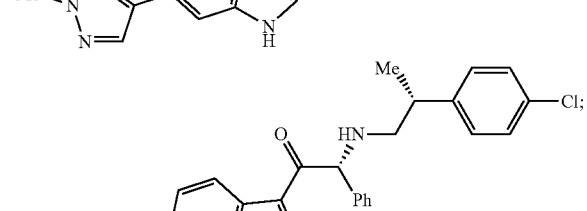
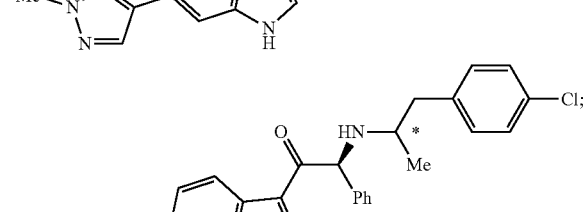

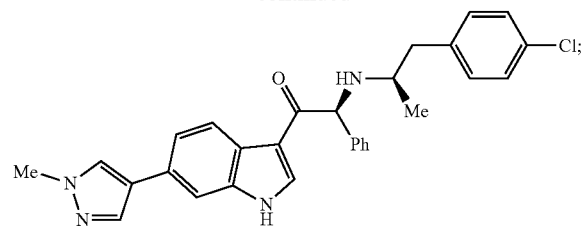
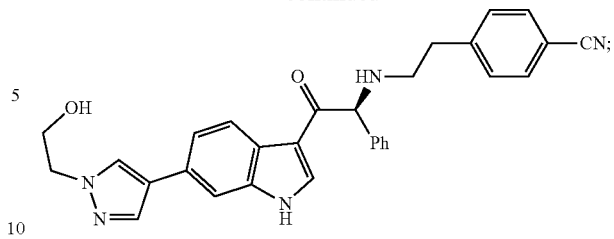
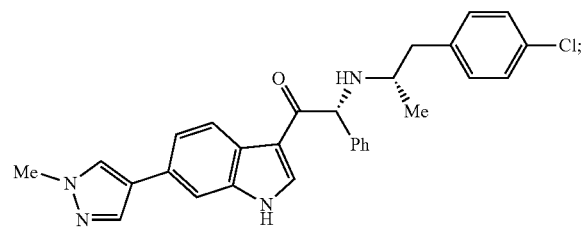
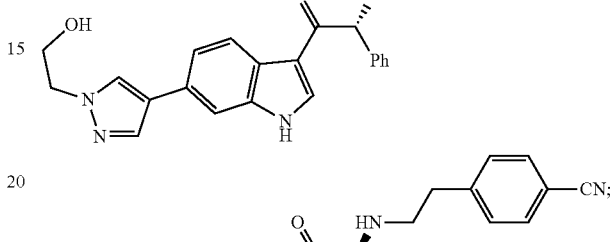
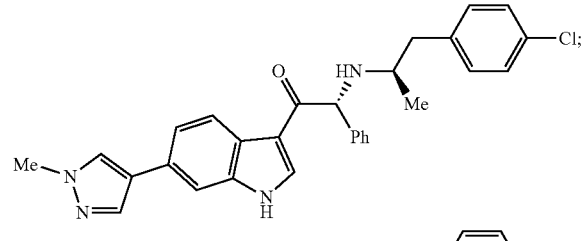
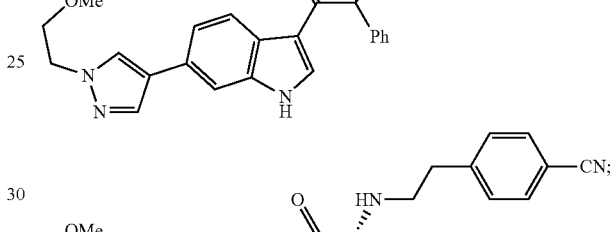
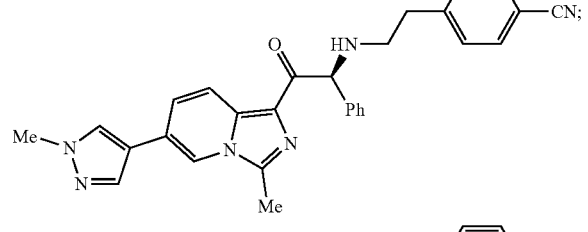
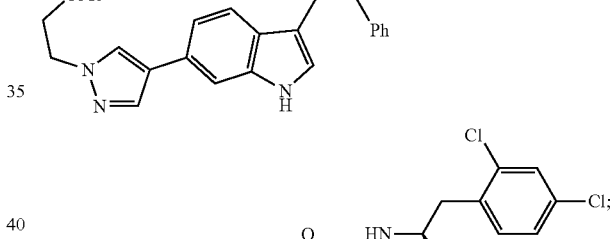
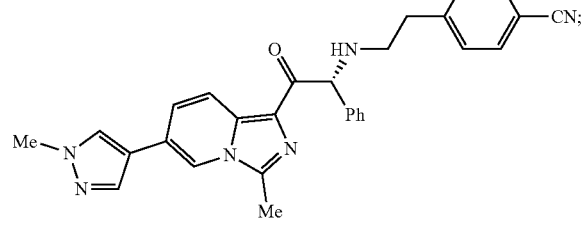
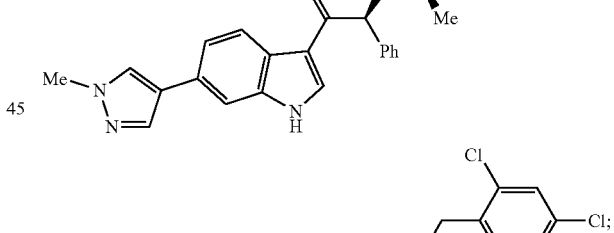
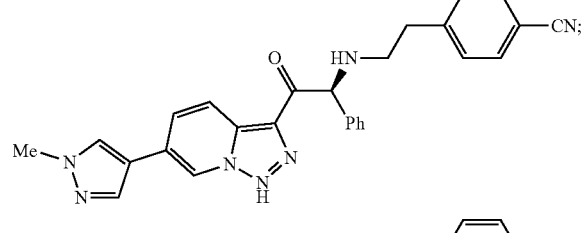
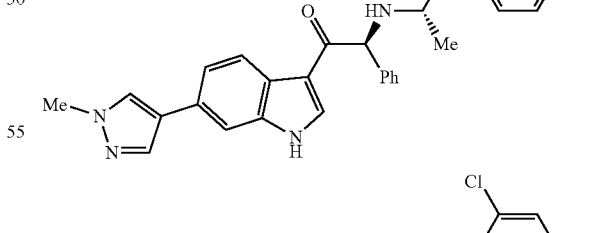
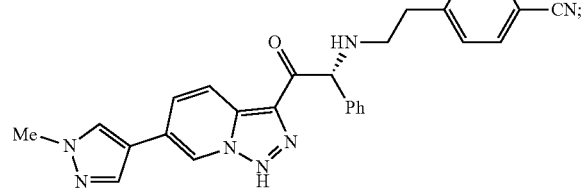
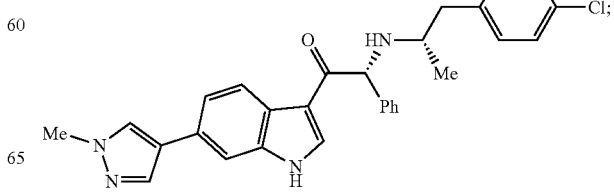

-continued
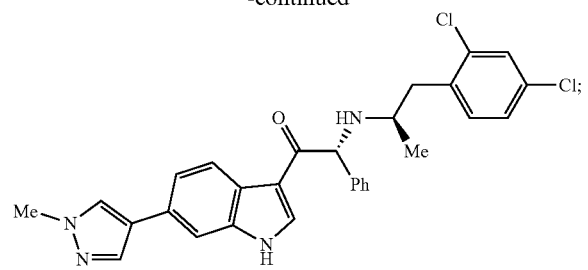
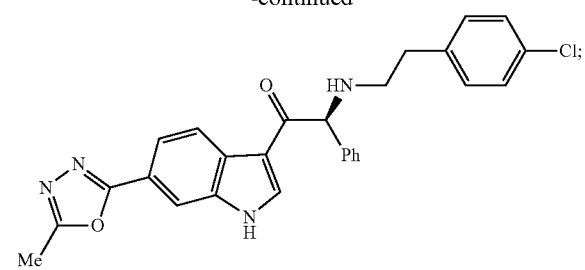
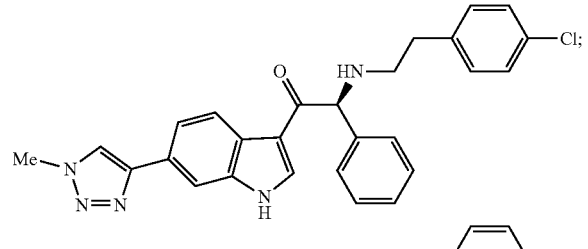
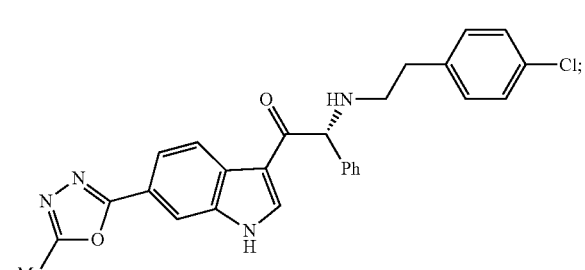
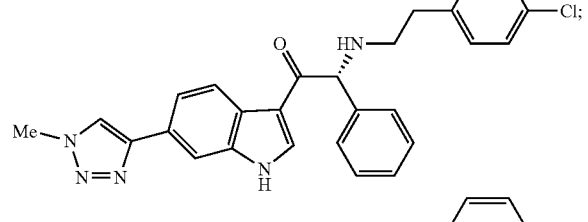
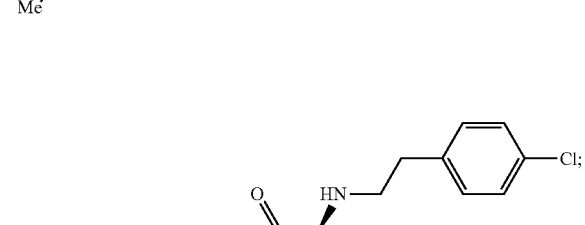
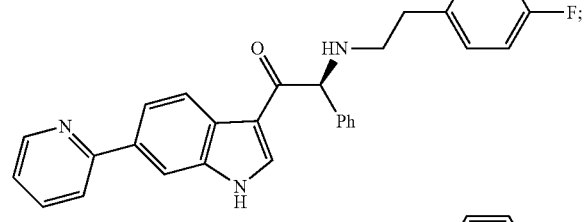
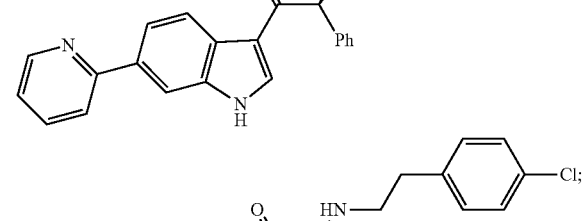
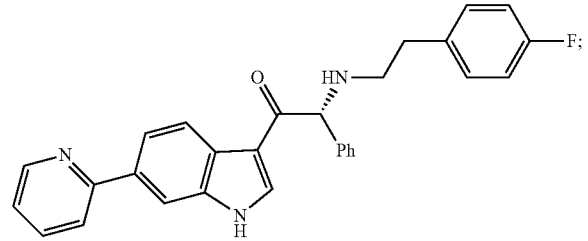
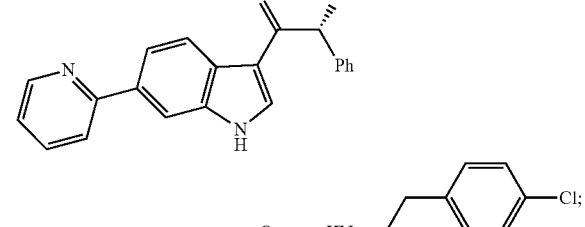
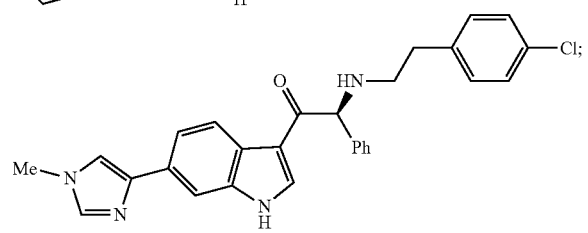
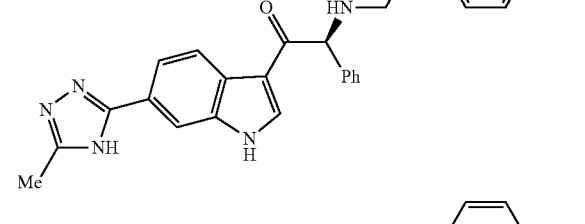
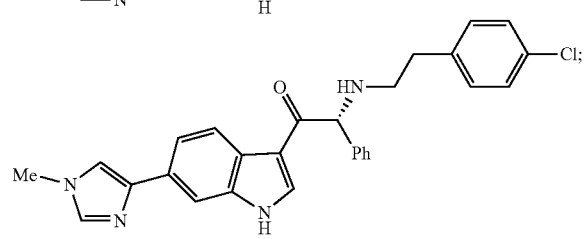
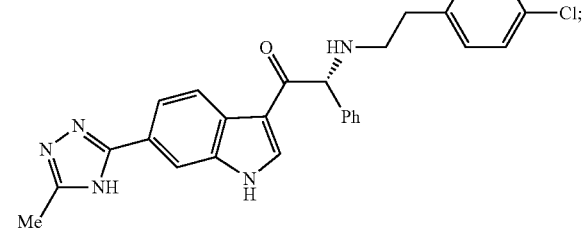

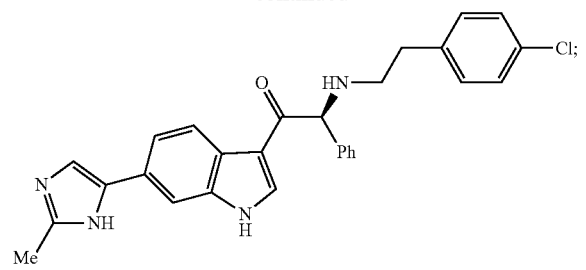
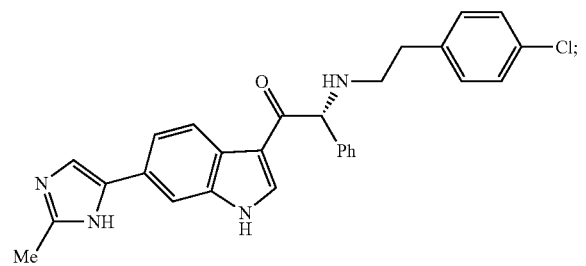
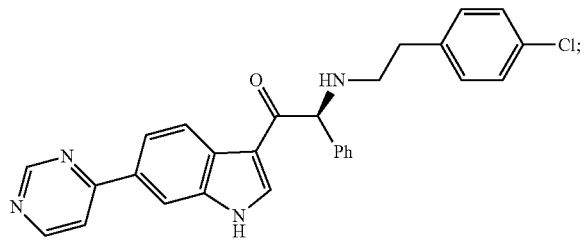
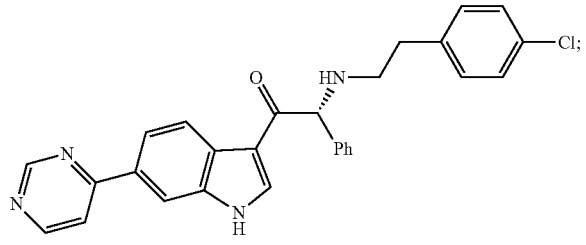

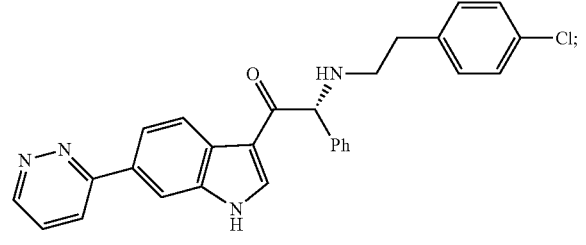
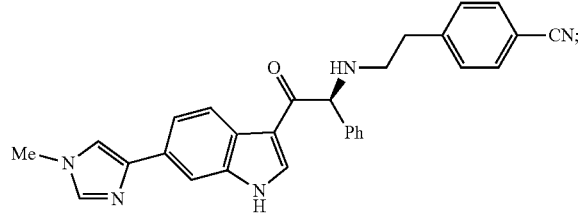
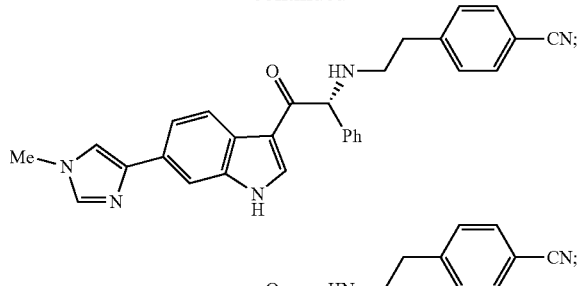

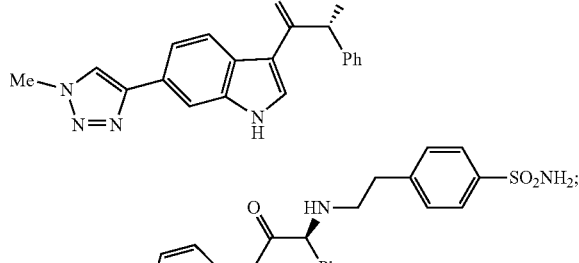

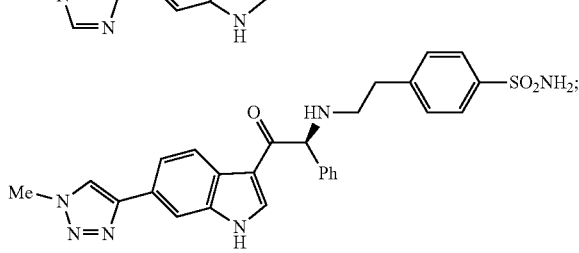
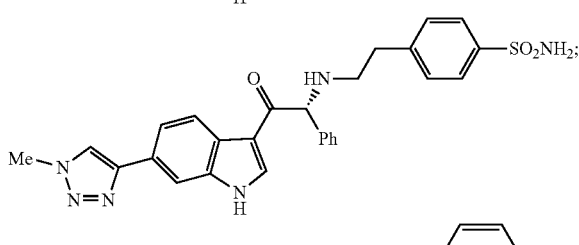
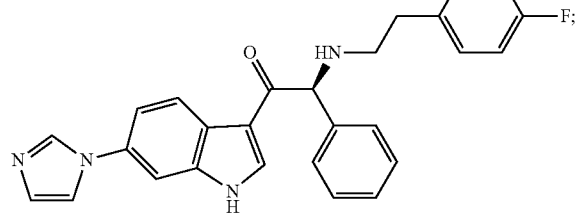

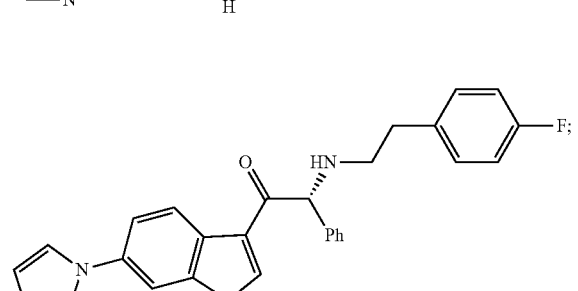
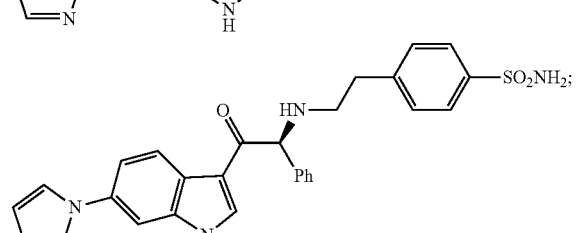
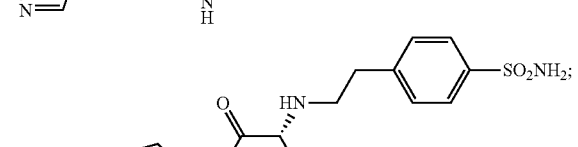

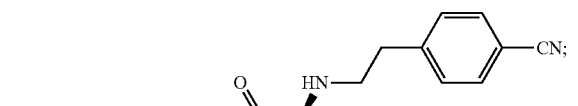
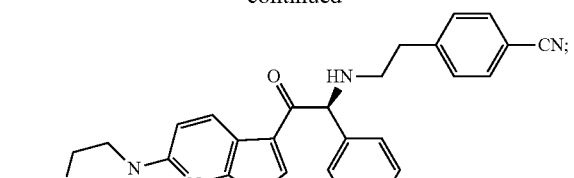
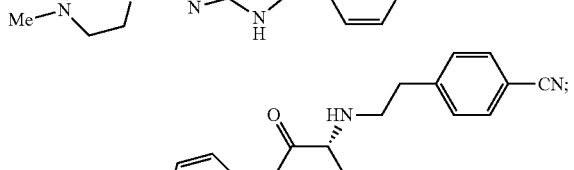
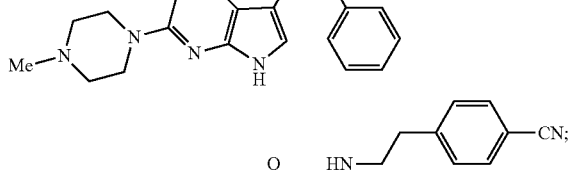
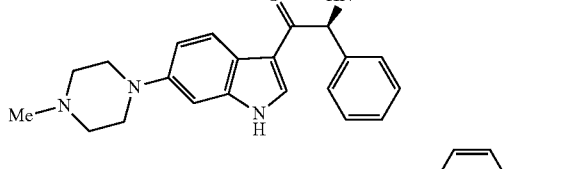
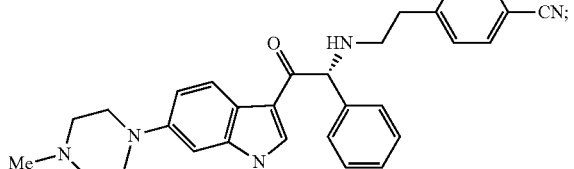
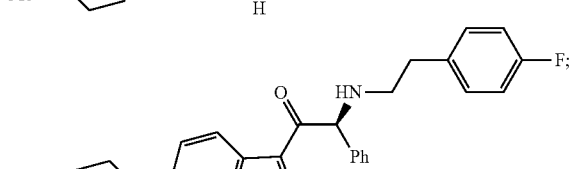
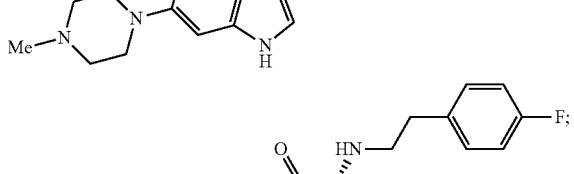
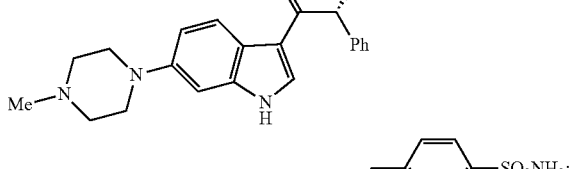

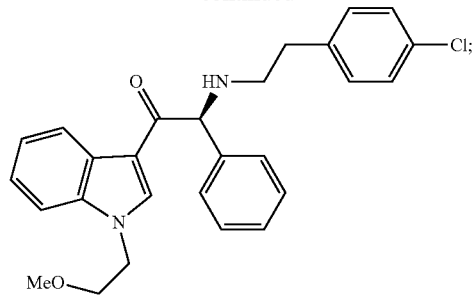
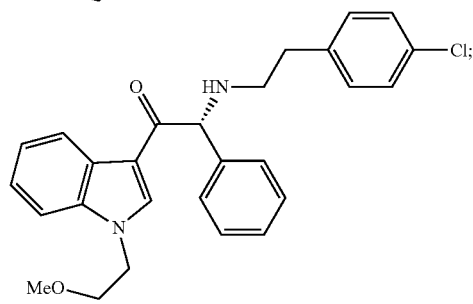
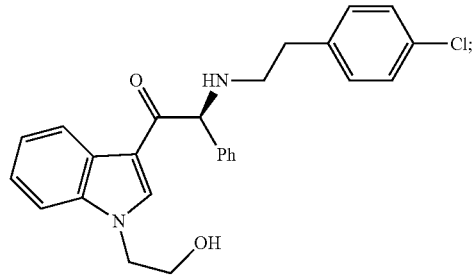
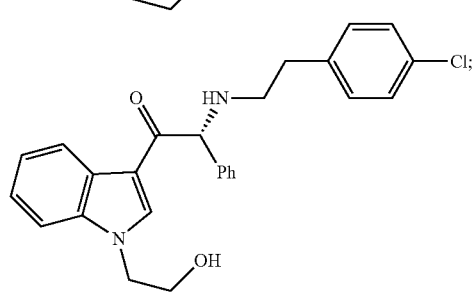
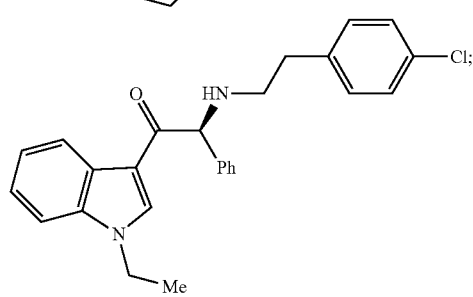
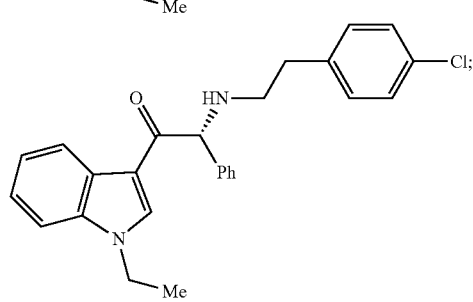
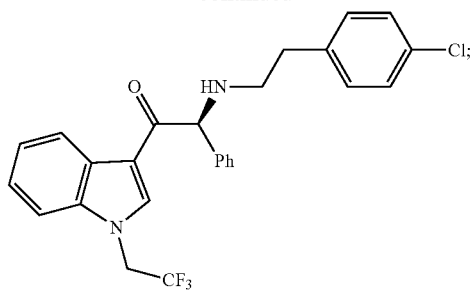
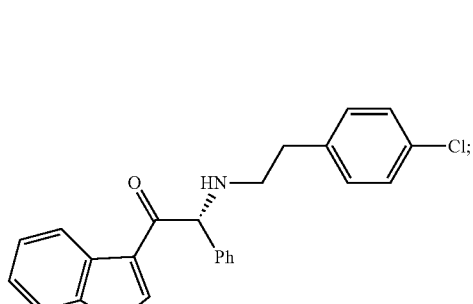
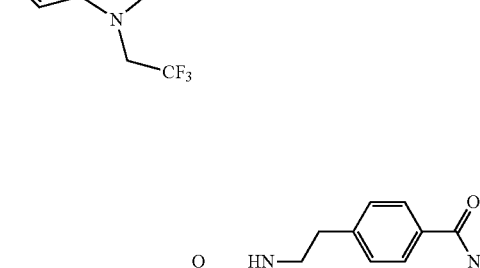
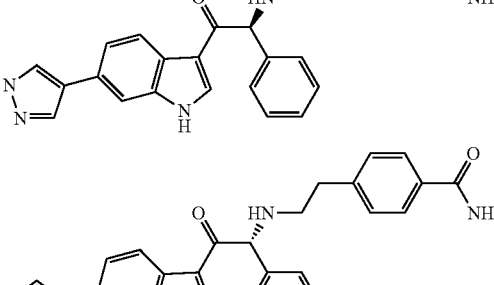
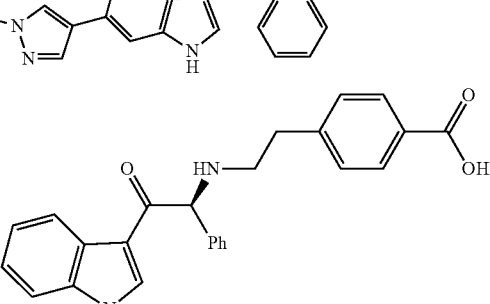
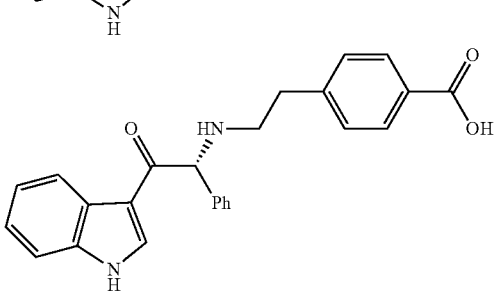

53
-continued
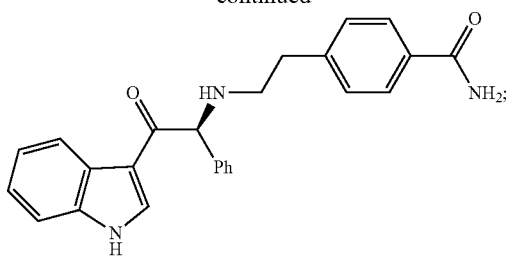
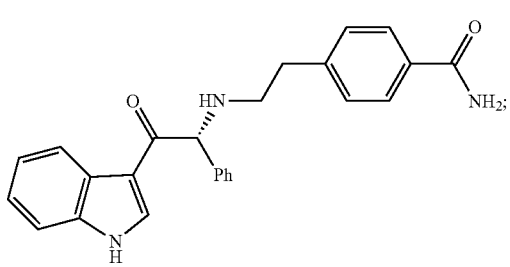
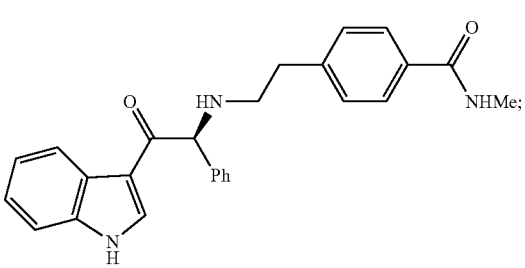
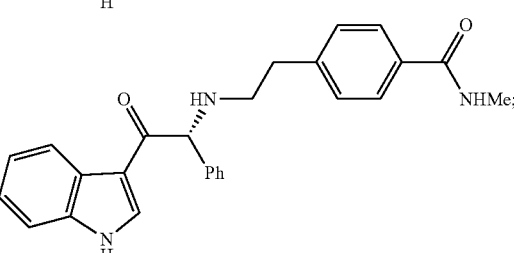
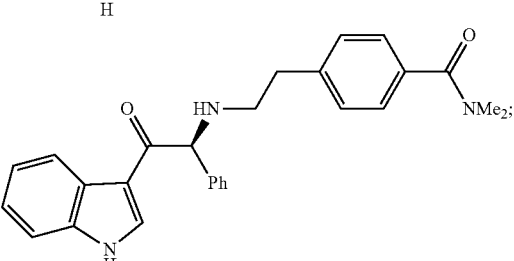
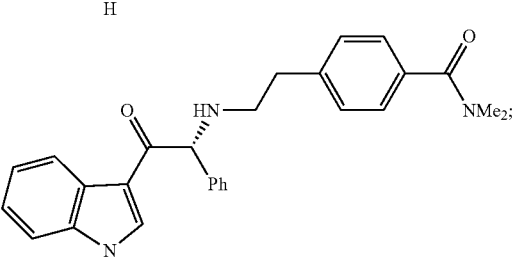
54
-continued
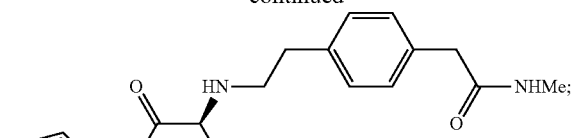

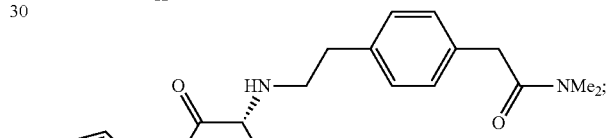

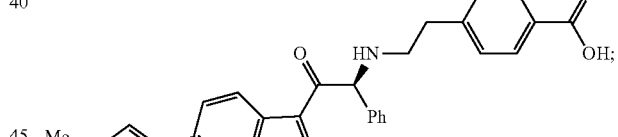

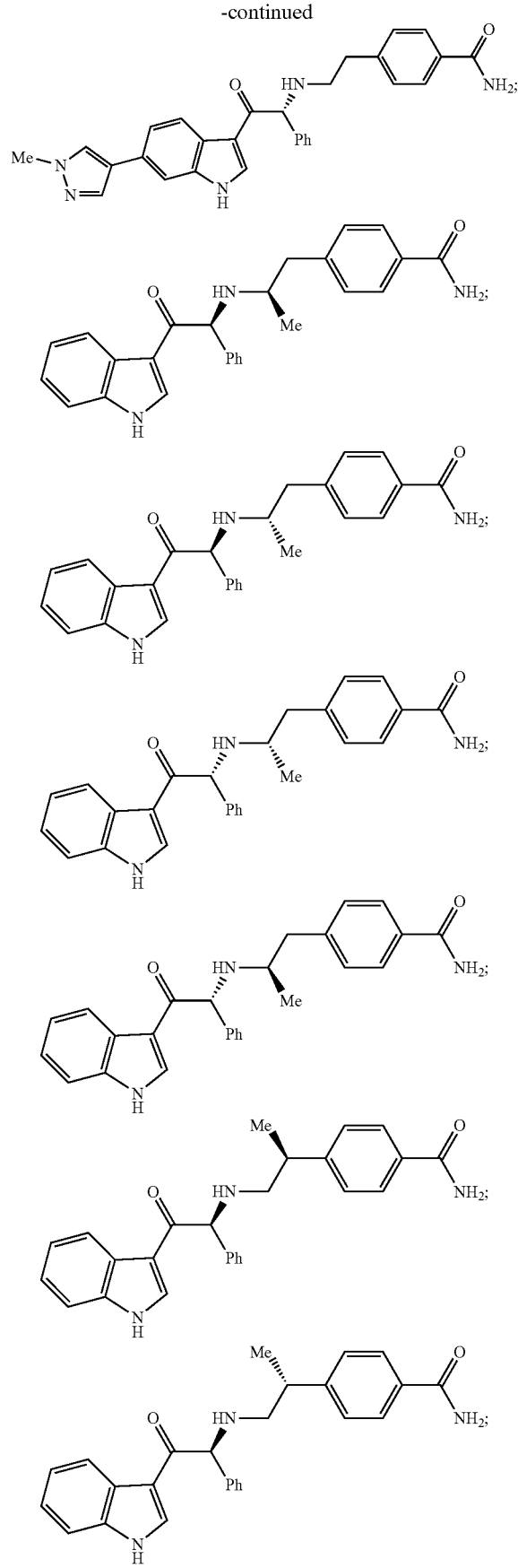
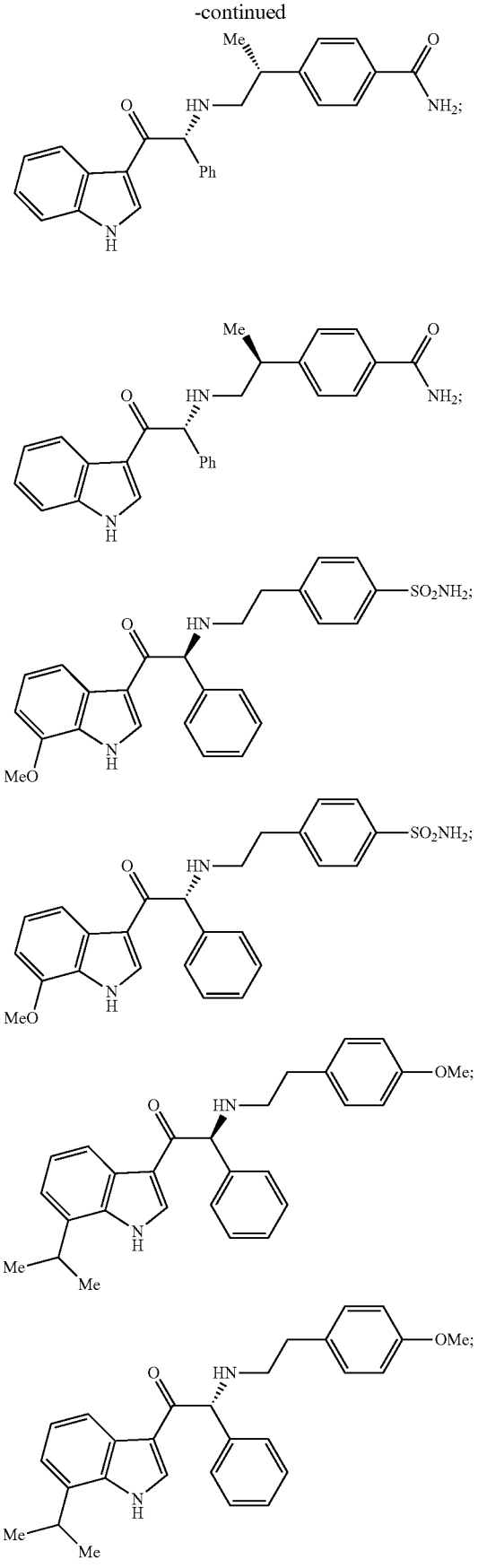

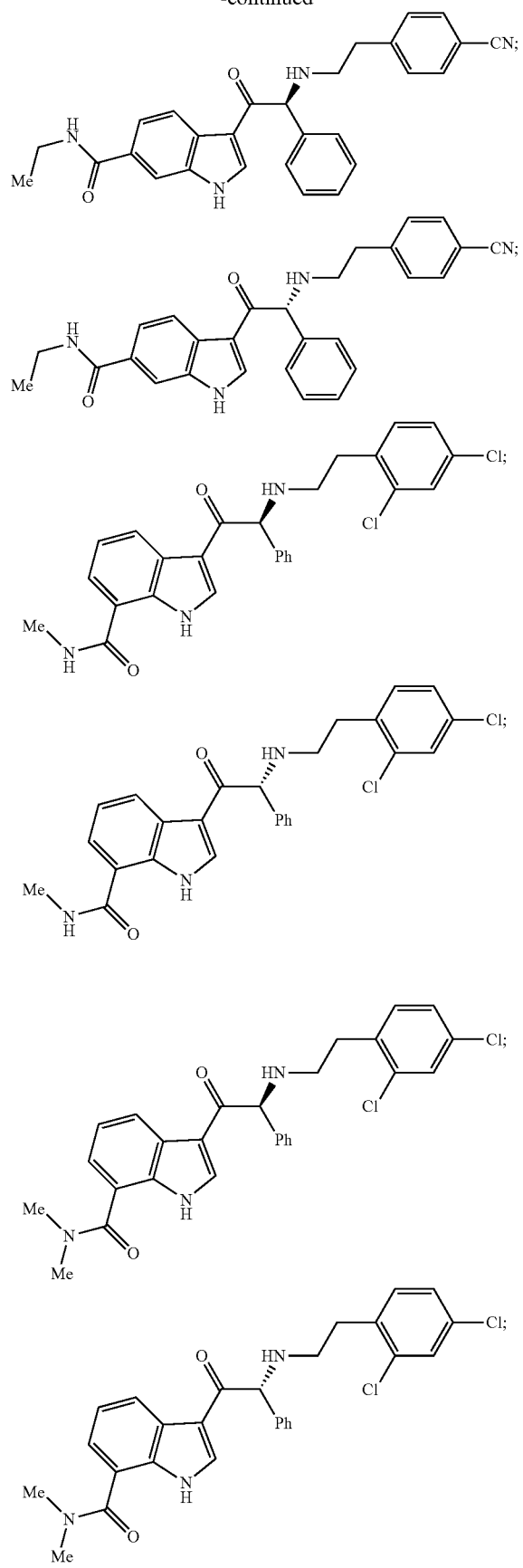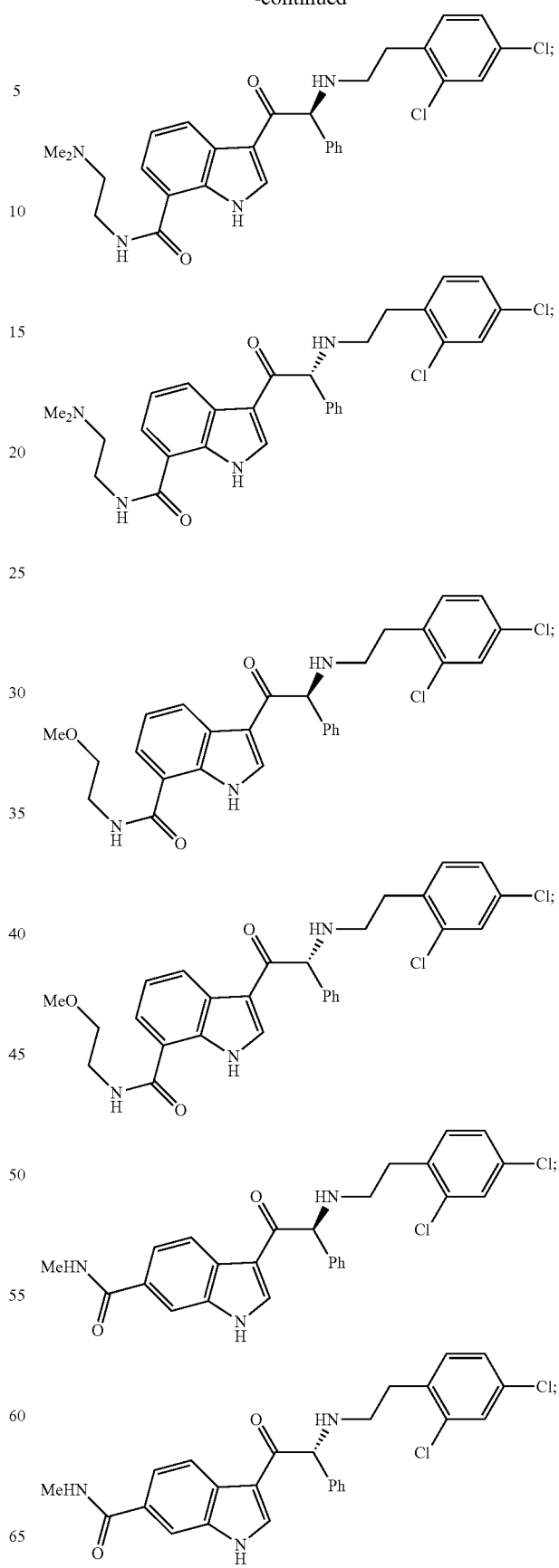

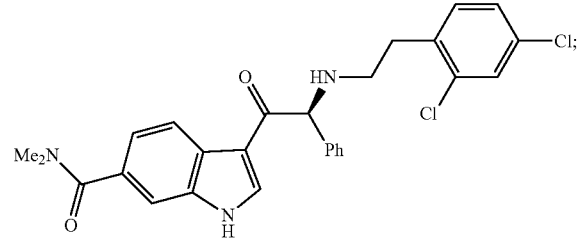
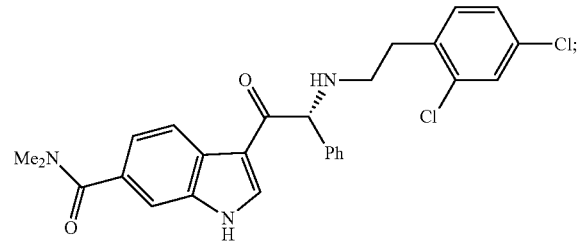
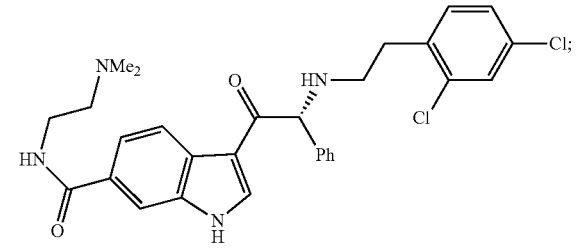
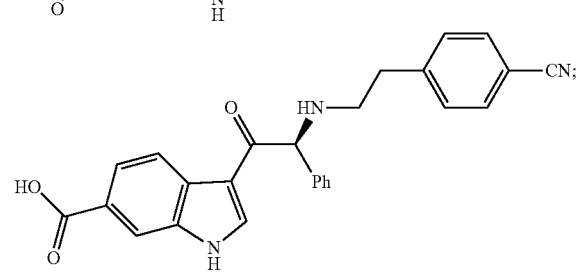
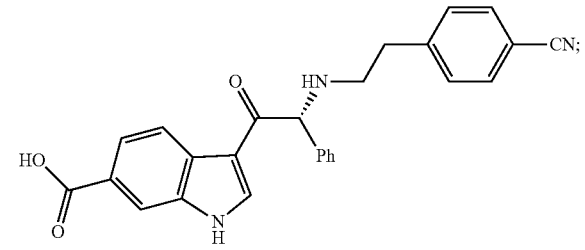
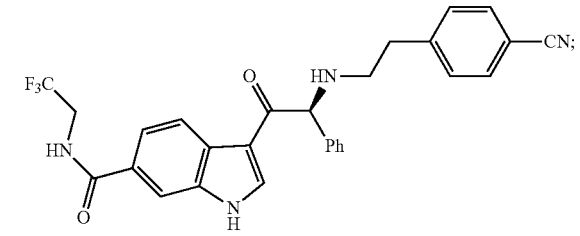
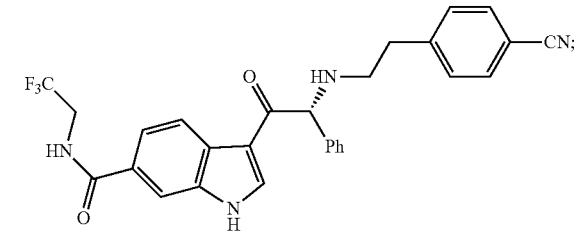
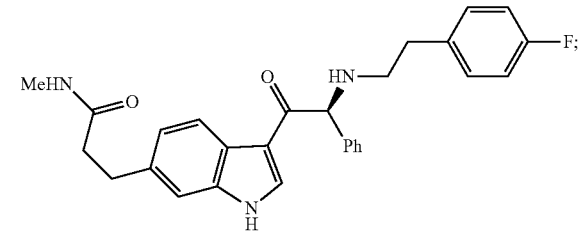
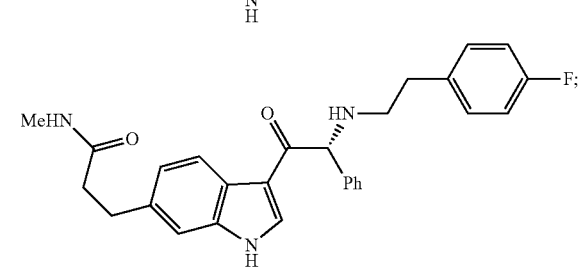

-continued
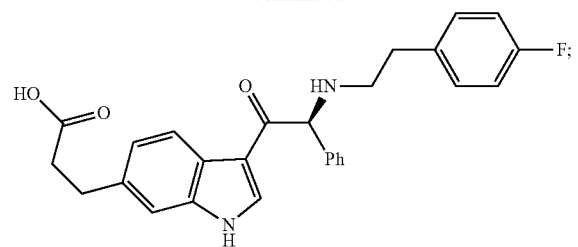
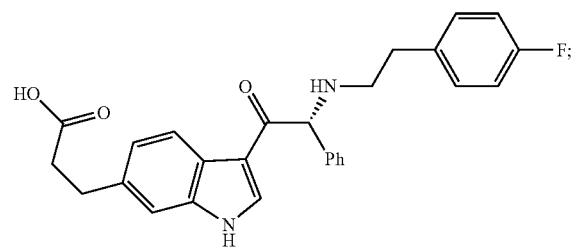
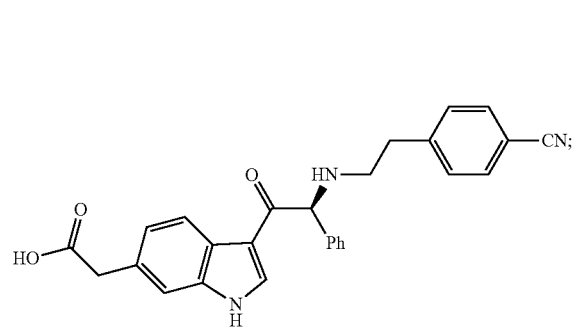
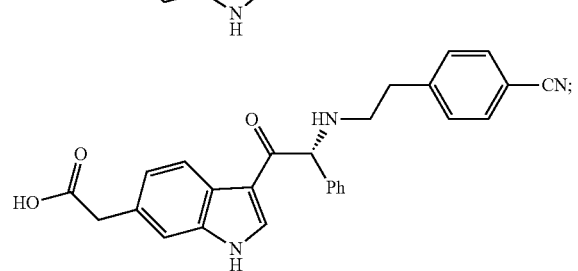
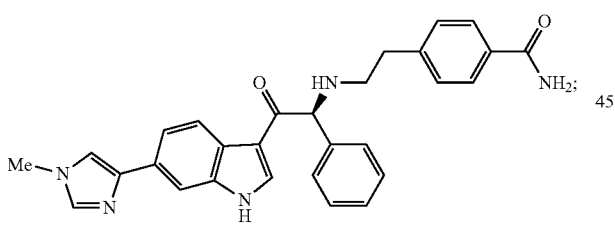
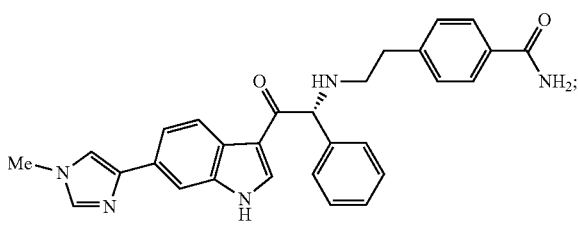
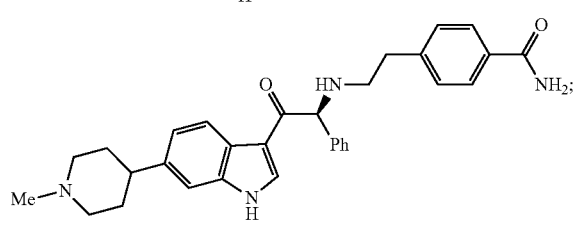
-continued
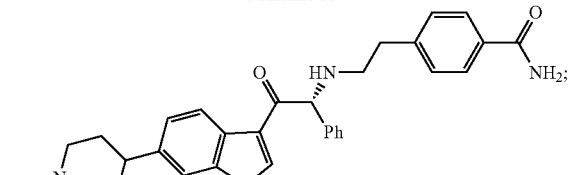
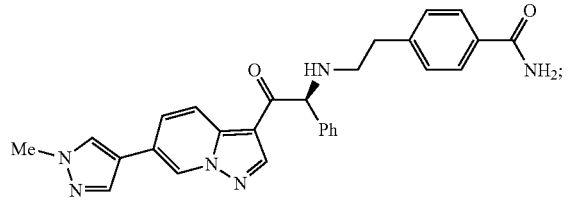
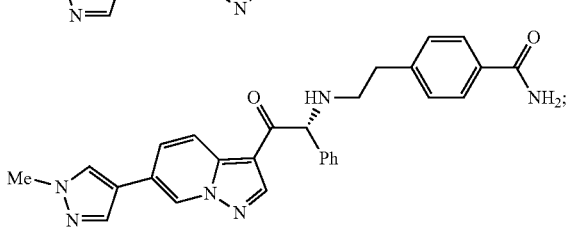
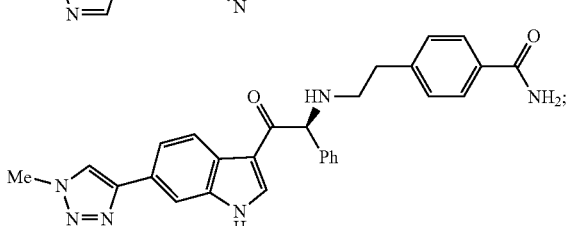
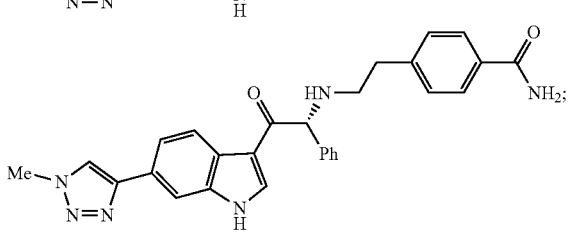

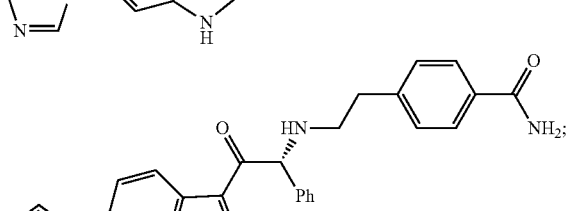

-continued
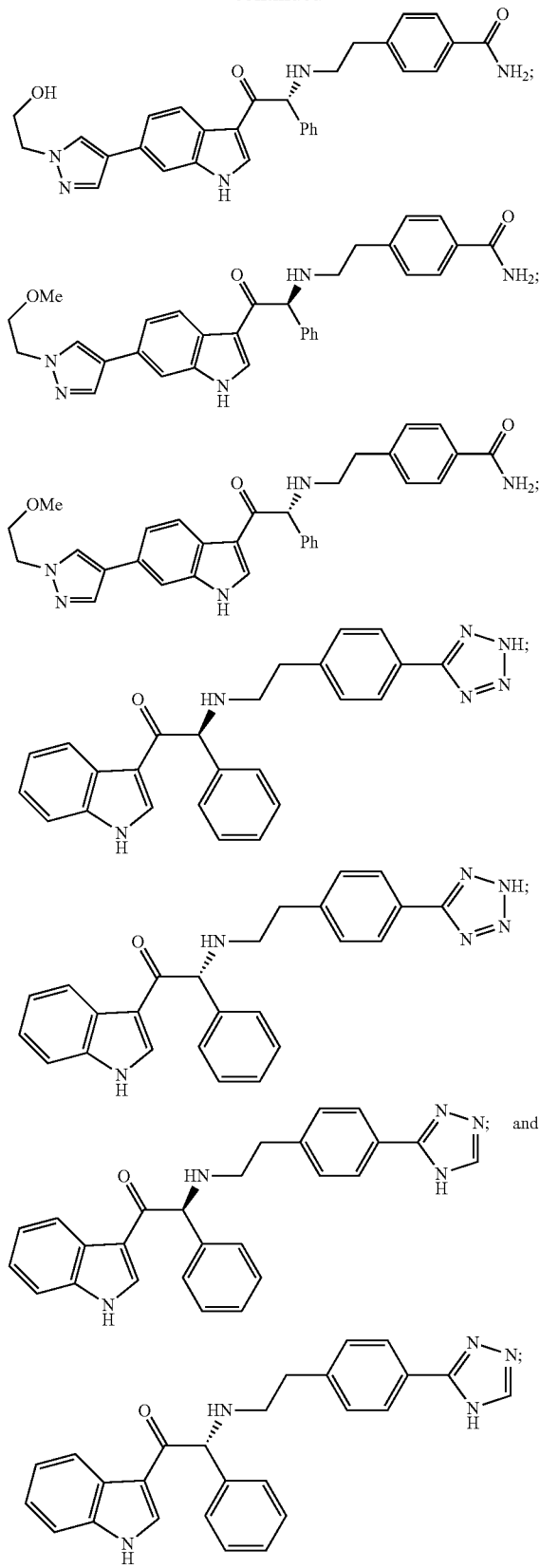
or a pharmaceutically acceptable salt thereof of any of the foregoing.
In a twenty-fourth embodiment, the compounds of Formula I are selected from the following formula:
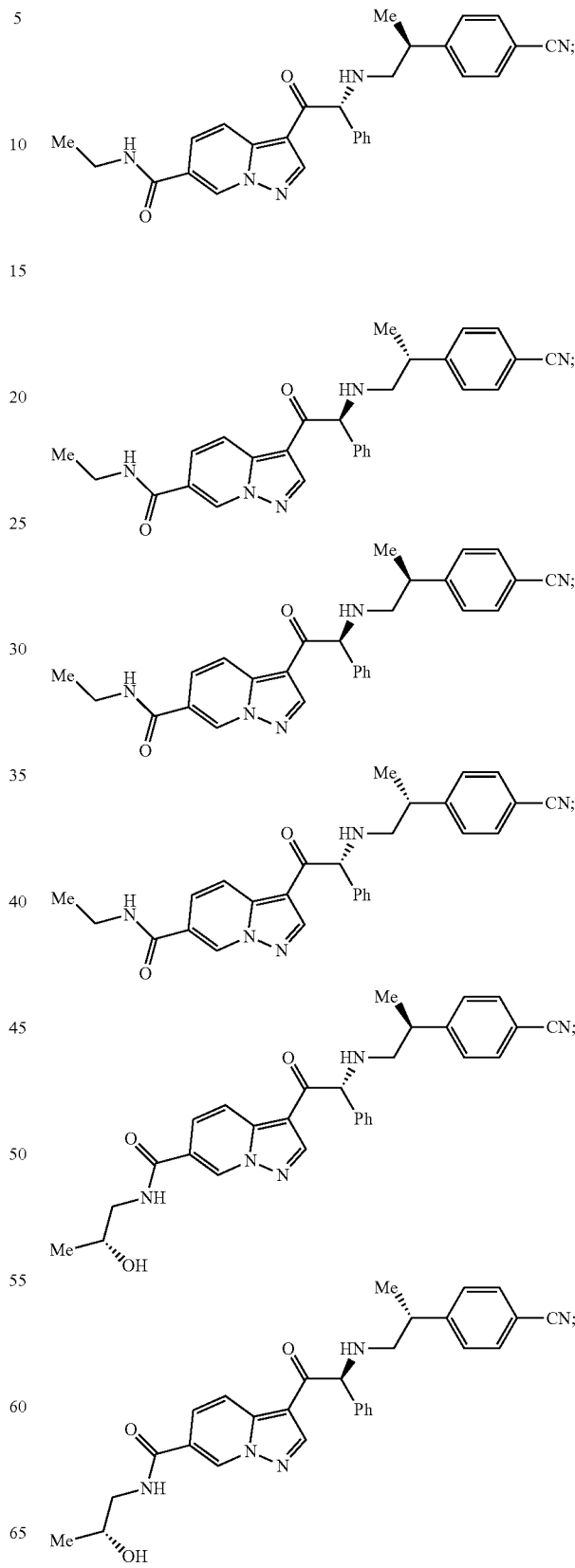

65
-continued
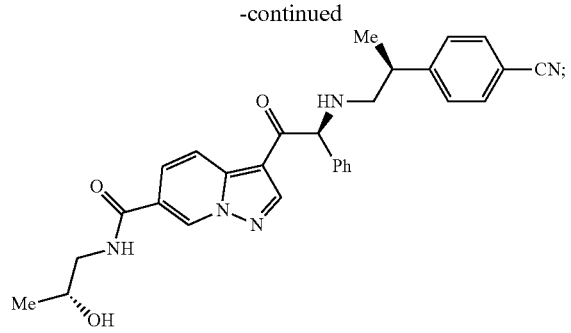
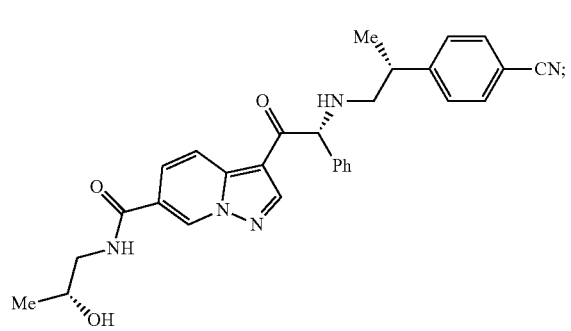
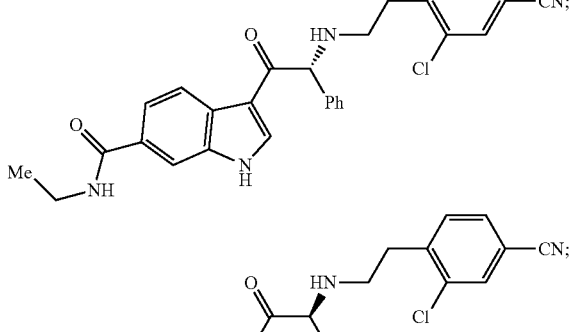
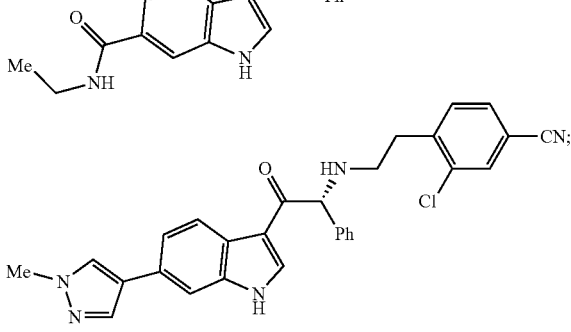
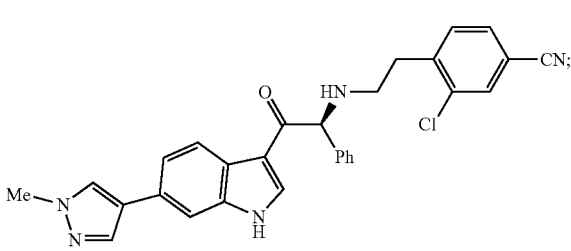
66
-continued
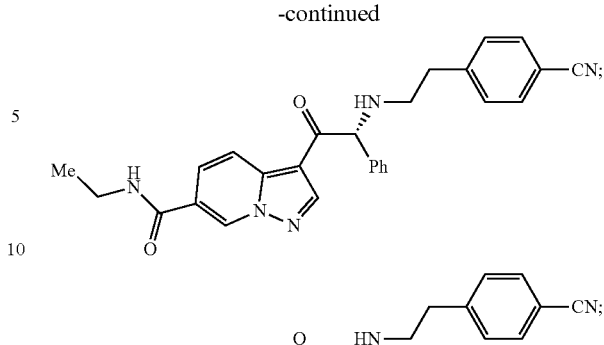
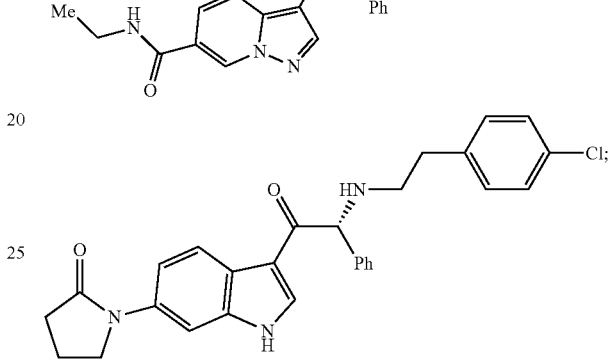
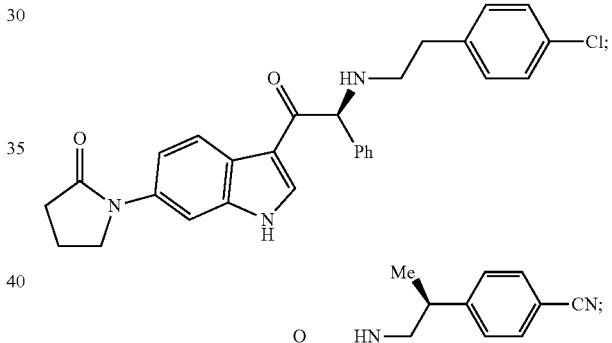
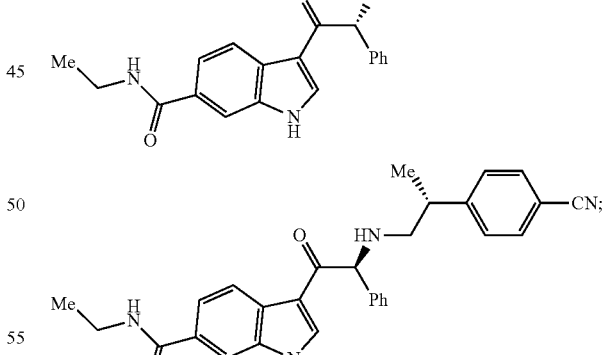
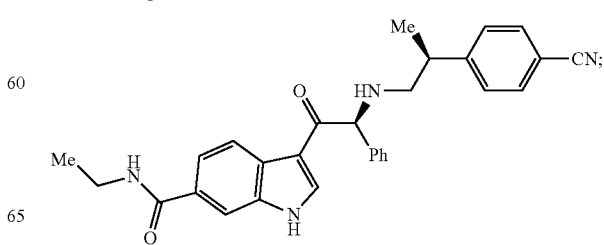

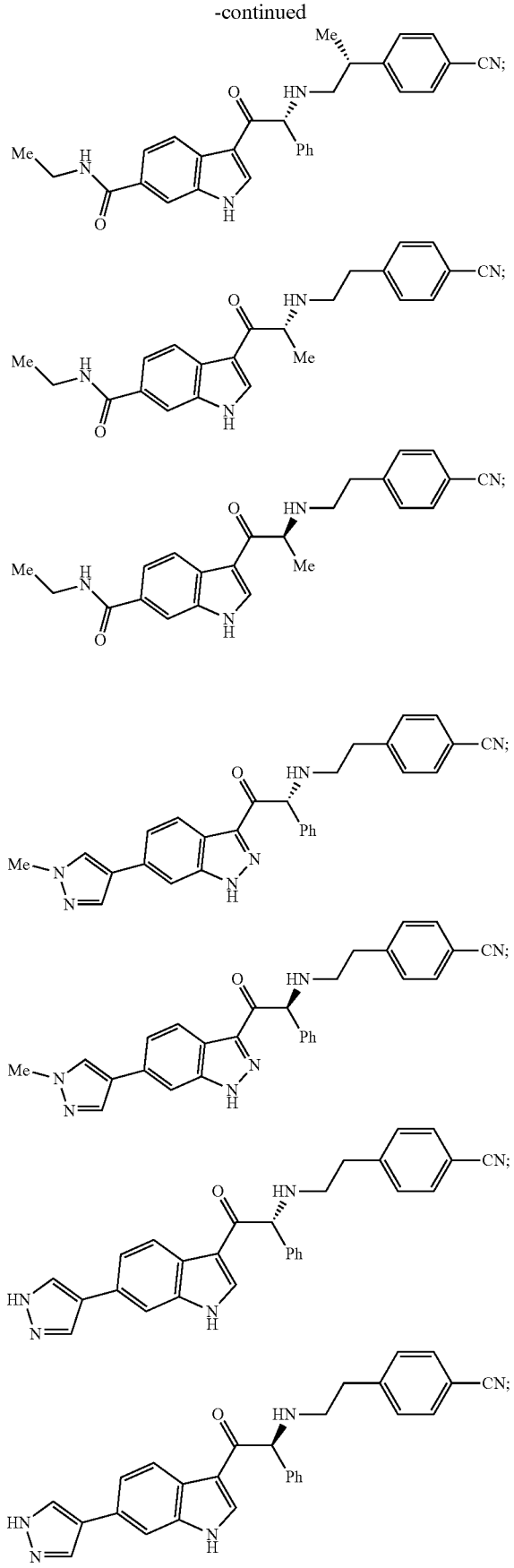
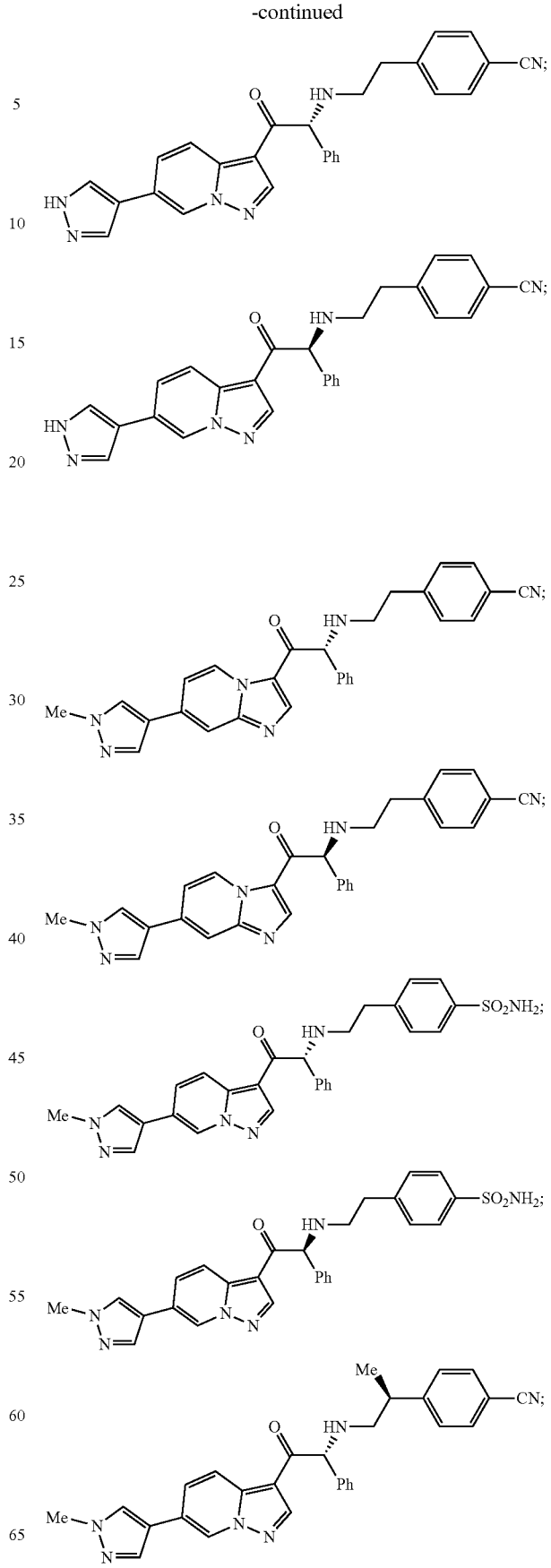

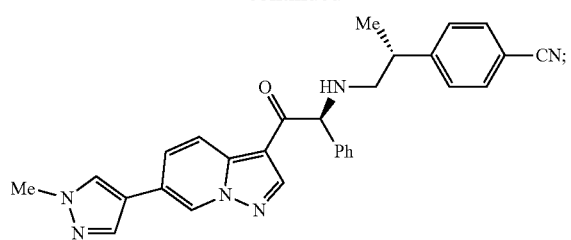
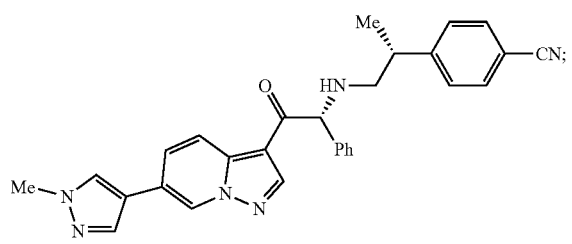
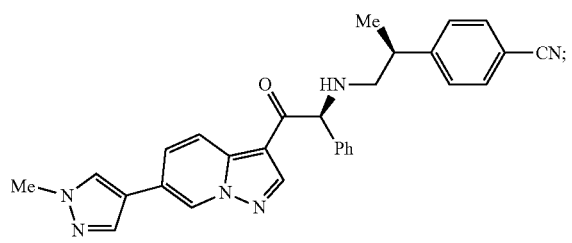
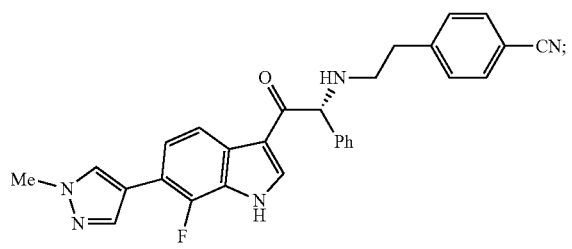
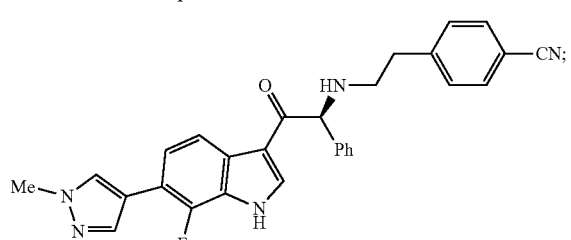
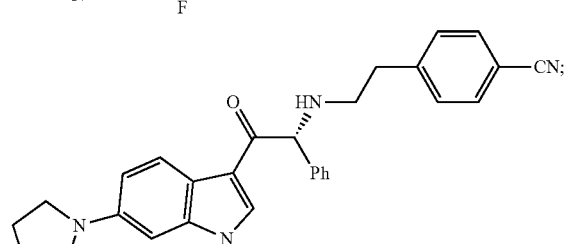
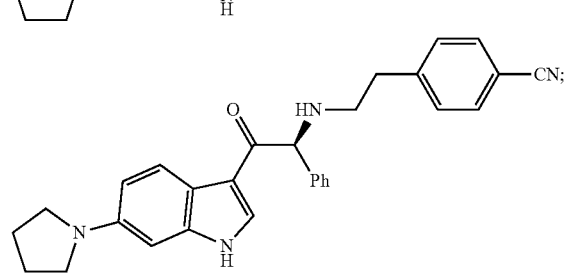
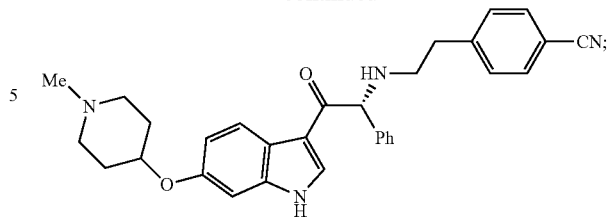
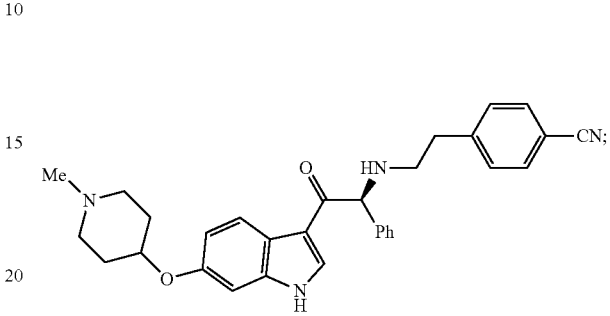
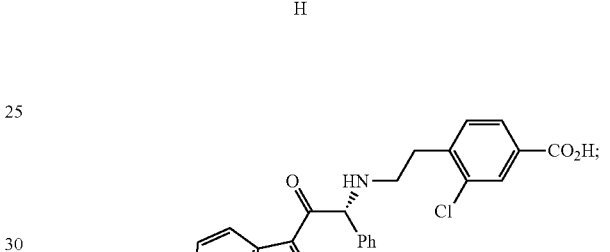

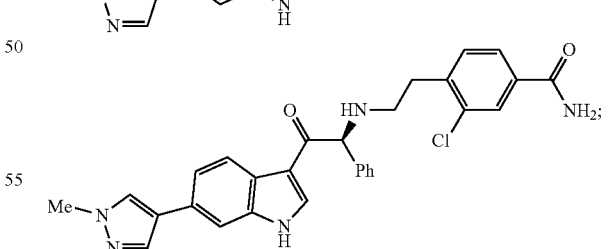
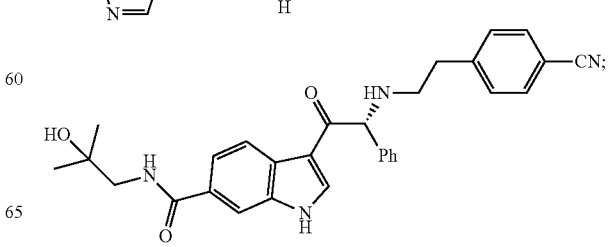

71
-continued
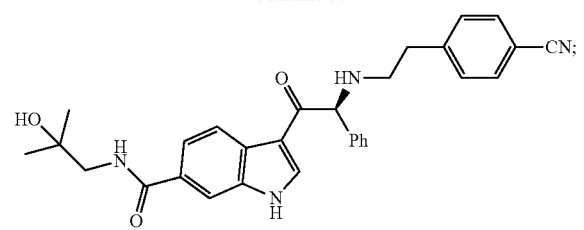
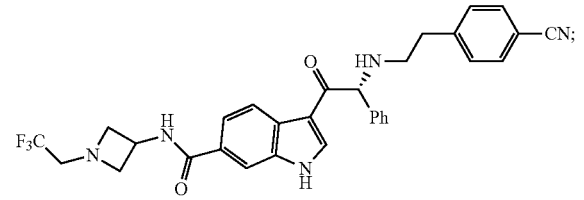
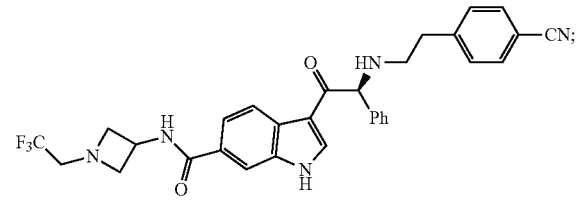
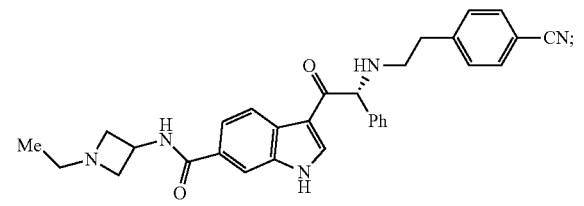
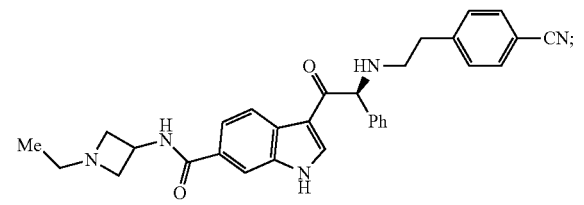
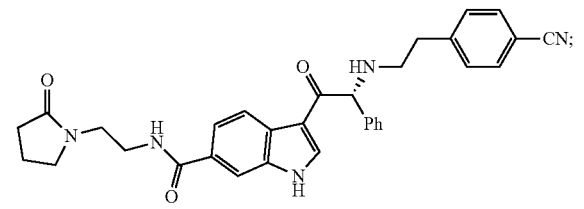
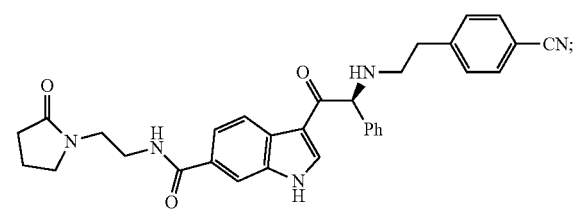
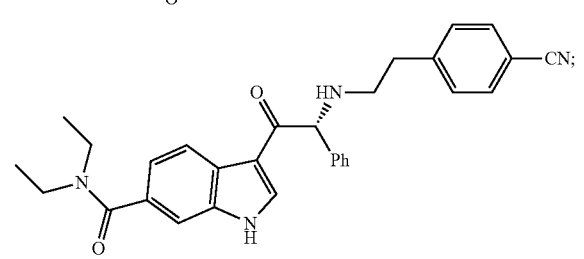
72
-continued
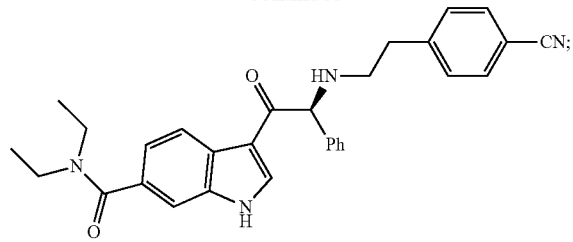
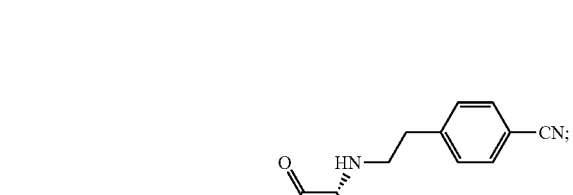
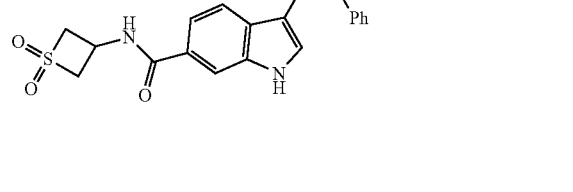
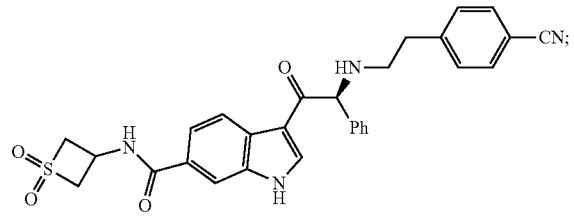
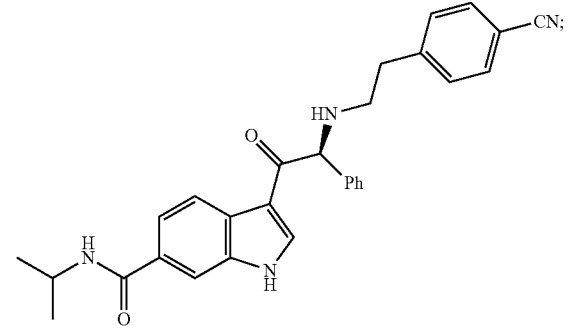
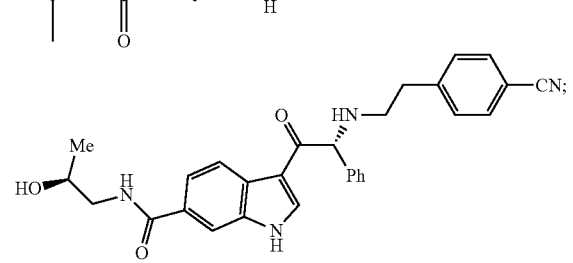

73
-continued
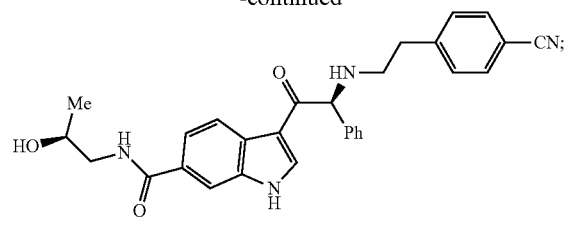
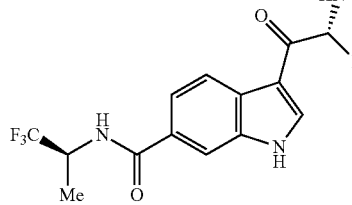
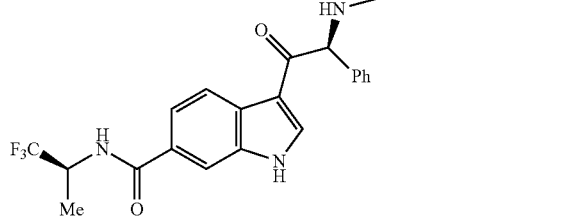
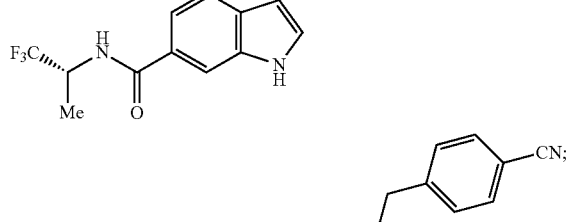
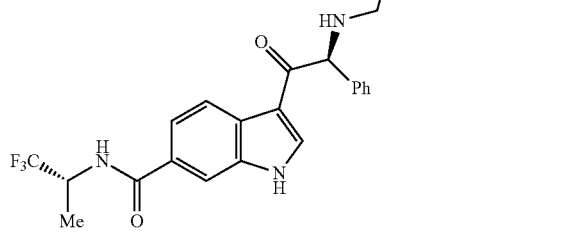
74
-continued
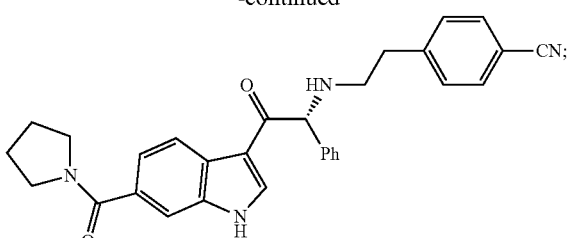
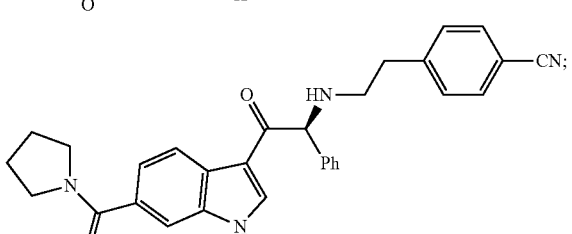
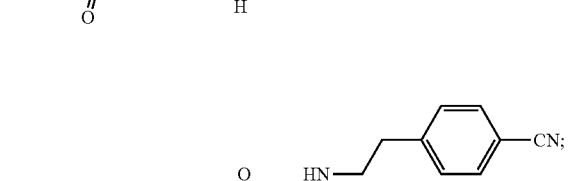
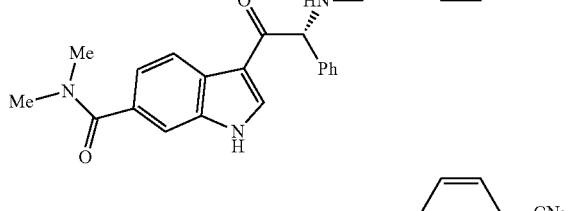
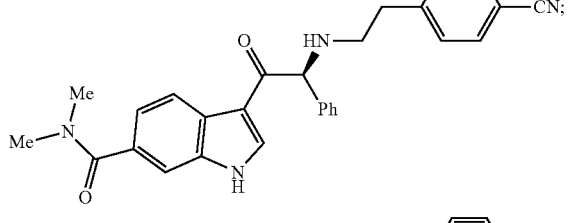
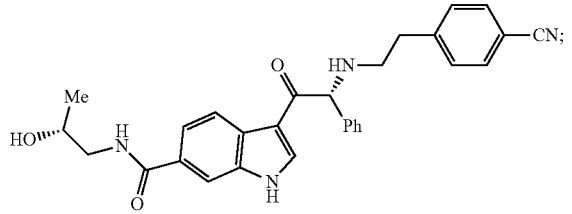
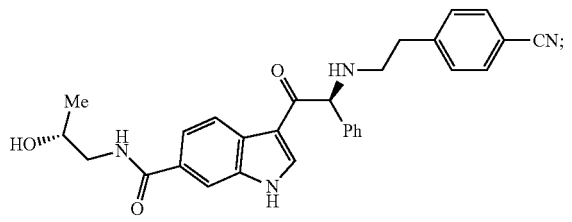
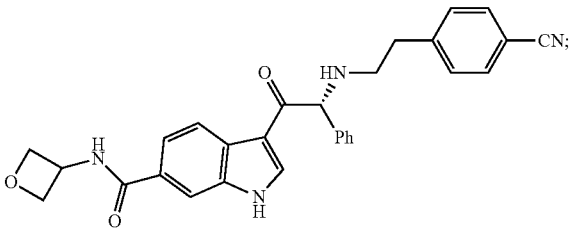

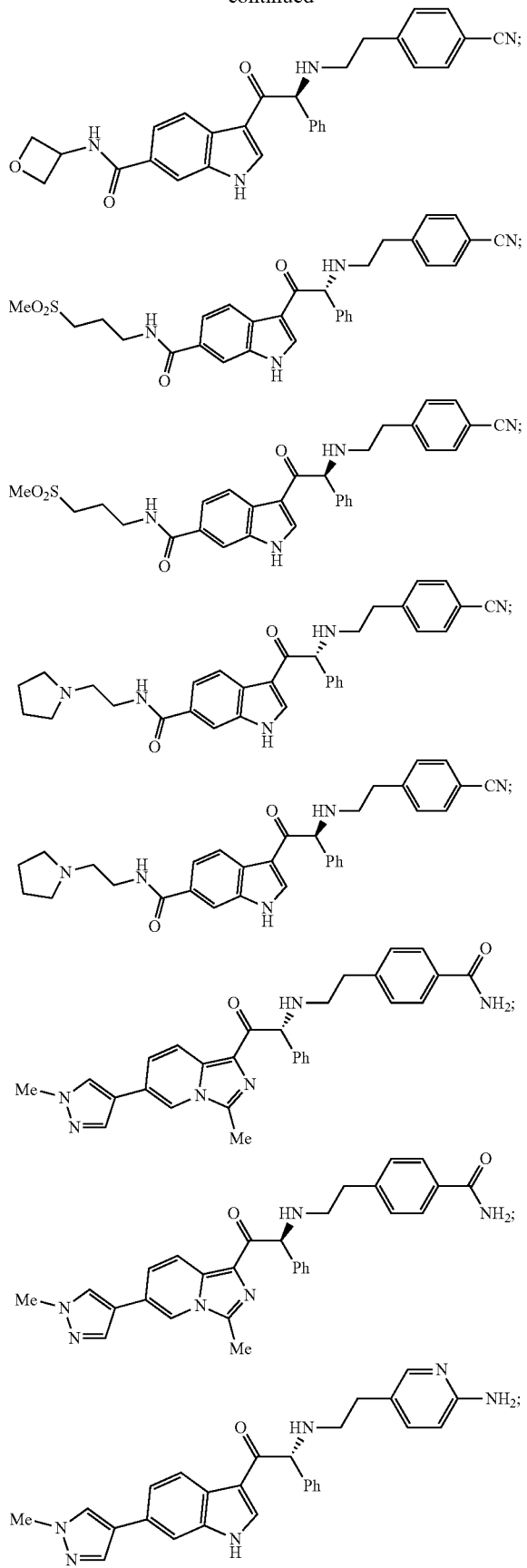

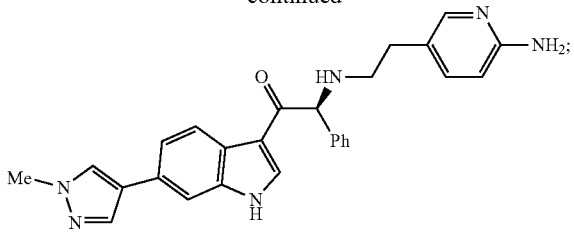

or a pharmaceutically acceptable salt thereof of any of the foregoing.

Specific examples of compounds are provided in the EXEMPLIFICATION section and are included as part of a twenty-fifth embodiment herein. Pharmaceutically acceptable salts as well as the neutral forms of these compounds are also included.

Also provided herein are pharmaceutical compositions comprising
1) a compound having the Formula I:

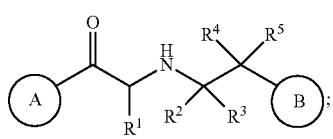

or a pharmaceutically acceptable salt thereof, wherein

Ring A is bicyclic heteroaryl optionally substituted with 1 to 4 groups selected from $R^a$;

Ring B is aryl, heterocyclyl, or heteroaryl each of which may be optionally substituted with 1 to 4 groups selected from $R^b$;

$R^1$ is $C_{1-6}$alkyl, $C_{1-6}$haloalkyl, $C_{2-6}$alkenyl, —$C_{1-6}$alkylOR$^c$, —$C_{1-6}$alkylN(R$^d$)$_2$, —$C_{1-6}$alkylC(O)OR$^d$, —$C_{1-6}$alkylOC$_{1-6}$alkylN(R$^d$)$_2$, —$C_{1-6}$alkylSOR$^d$, —$C_{1-6}$alkylS(O)$_2$R$^d$, —$C_{1-6}$alkylSON(R$^d$)$_2$, —$C_{1-6}$alkylSO$_2$N(R$^d$)$_2$, —$C_{1-6}$alkylcycloalkyl, —$C_{1-6}$alkylheterocyclyl, —$C_{1-6}$alkylheteroaryl, —$C_{1-6}$alkylaryl, cycloalkyl, aryl, heteroaryl, or heterocyclyl, wherein each of said cycloalkyl, heterocyclyl, aryl, and heteroaryl alone and in connection with —$C_{1-6}$alkylcycloalkyl, —$C_{1-6}$alkylaryl, —$C_{1-6}$alkylheteroaryl, and —$C_{1-6}$alkylheterocyclyl are optionally substituted with 1 to 3 groups selected from $R^c$;

each of $R^2$, $R^3$, $R^4$, and $R^5$ are independently hydrogen or $C_{1-6}$alkyl, wherein said $C_{1-6}$alkyl is optionally substituted with 1 or 2 groups selected from halo, —C(O)OR$^d$, —OC$_{1-6}$alkylN(R$^d$)$_2$, —$C_{1-6}$alkylN(R$^d$)$_2$, —N(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, cycloalkyl, heterocyclyl, heteroaryl, and aryl;

each of $R^a$, $R^b$, and $R^c$ are each independently halo, CN, oxo, NO$_2$, $C_{1-6}$alkyl, $C_{2-6}$alkenyl, $C_{1-6}$alkoxy, $C_{1-6}$haloalkoxy, $C_{1-6}$haloalkyl, —$C_{1-6}$alkylOR$^d$, —C(O)R$^d$, —C(O)OR$^d$, —$C_{1-6}$alkylC(O)OR$^d$, —C(O)N(R$^d$)$_2$, —C(O)NR$^d$C$_{1-6}$alkylOR$^d$, —OC$_{1-6}$alkylN(R$^d$)$_2$, —$C_{1-6}$alkylC(O)N(R$^d$)$_2$, —$C_{1-6}$alkylN(R$^d$)$_2$, —N(R$^d$)$_2$, —C(O)NR$^d$C$_{1-6}$alkylN(R$^d$)$_2$, —NR$^d$C$_{1-6}$alkylN(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, SF$_5$, —Ocycloalkyl, —OC$_{1-4}$alkylaryl, —$C_{1-6}$alkylcycloalkyl, —$C_{1-6}$alkylaryl, —$C_{1-6}$alkylheteroaryl, —$C_{1-6}$alkylheterocyclyl, cycloalkyl, heterocyclyl, heteroaryl, or aryl, wherein each of said cycloalkyl, heterocyclyl, aryl, and heteroaryl alone and in connection with —Ocycloalkyl, —$C_{1-6}$alkylcycloalkyl, —$C_{1-6}$alkylaryl, —$C_{1-6}$alkylheteroaryl, and —$C_{1-6}$alkylheterocyclyl are optionally substituted with 1 to 3 groups selected from halo, $C_{1-6}$alkyl, $C_{1-6}$haloalkyl, $C_{1-6}$alkoxy, $C_{1-6}$haloalkoxy, —$N(R^d)_2$, —$C(O)R^d$, and —$C_{1-6}$alkyl$OR^d$; and each $R^d$ is independently hydrogen, $C_{1-6}$haloalkyl, or $C_{1-6}$alkyl, or a pharmaceutically acceptable salt thereof; and 2) a pharmaceutically acceptable carrier.

In one aspect, the compound(s) and variable(s) of Formula I in the disclosed compositions are selected from any one of those described in the first, second, third, fourth, fifth, sixth, seventh, eighth, ninth, tenth, eleventh, twelfth, thirteenth, fourteenth, fifteenth, sixteenth, seventeenth, eighteenth, nineteenth, twentieth, twenty-first, twenty-second, twenty-third, twenty-fourth, and twenty-fifth embodiments.

4. Uses, Formulation and Administration

Compounds and compositions described herein are generally useful for modulating the activity of p300 and/or CBP HAT. In some aspects, the compounds and compositions described herein inhibit the activity of p300 and/or CBP HAT.

In some aspects, compounds and compositions described herein are useful in treating a disorder associated with p300 and/or CBP HAT function. Thus, provided herein are methods of treating a disorder associated with p300 and/or CBP HAT function, comprising administering to a subject in need thereof, a therapeutically effective amount of a compound described herein, or a pharmaceutically acceptable salt thereof, or a composition comprising a disclosed compound or pharmaceutically acceptable salt thereof. Also provided is the use of a compound described herein, or a pharmaceutically acceptable salt thereof, or a composition comprising a disclosed compound or pharmaceutically acceptable salt thereof, for the manufacture of a medicament for treating a disorder associated with p300 and/or CBP HAT function. Also provided is a compound described herein, or a pharmaceutically acceptable salt thereof, or a composition comprising a disclosed compound or pharmaceutically acceptable salt thereof, for use in treating a disorder associated with p300 and/or CBP HAT.

In some aspects, compounds and compositions described herein are useful in treating a disorder associated with chromatin acetylation at H3K27, H3K18, and other acetylation sites on the basic residues of chromatin acted upon by the p300 and/or CBP enzyme. Thus, provided herein are methods of treating a disorder associated with chromatin acetylation at H3K27, H3K18, and other acetylation sites on the basic residues of chromatin acted upon by the p300 and/or CBP enzyme, comprising administering to a subject in need thereof, a therapeutically effective amount of a compound described herein, or a pharmaceutically acceptable salt thereof, or a composition comprising a disclosed compound or pharmaceutically acceptable salt thereof. Also provided is the use of a compound described herein, or a pharmaceutically acceptable salt thereof, or a composition comprising a disclosed compound or pharmaceutically acceptable salt thereof, for the manufacture of a medicament for treating a disorder associated with chromatin acetylation at H3K27, H3K18, and other acetylation sites on the basic residues of chromatin acted upon by the p300 and/or CBP enzyme. Also provided is a compound described herein, or a pharmaceutically acceptable salt thereof, or a composition comprising a disclosed compound or pharmaceutically acceptable salt thereof, for use in treating a disorder associated with chromatin acetylation at H3K27, H3K18, and other acetylation sites on the basic residues of chromatin acted upon by the p300 and/or CBP enzyme.

In some aspects, compounds and compositions described herein are useful in treating a disorder associated with hyperacetylation of chromatin and/or hyperacetylation of proteins that are known to be acetylated by p300 and/or CBP. Thus, provided herein are methods of treating a disorder associated with hyperacetylation of chromatin and/or hyperacetylation of proteins that are known to be acetylated by p300 and/or CBP, comprising administering to a subject in need thereof, a therapeutically effective amount of a compound described herein, or a pharmaceutically acceptable salt thereof, or a composition comprising a disclosed compound or pharmaceutically acceptable salt thereof. Also provided is the use of a compound described herein, or a pharmaceutically acceptable salt thereof, or a composition comprising a disclosed compound or pharmaceutically acceptable salt thereof, for the manufacture of a medicament for treating a disorder associated with hyperacetylation of chromatin and/or hyperacetylation of proteins that are known to be acetylated by p300 and/or CBP. Also provided is a compound described herein, or a pharmaceutically acceptable salt thereof, or a composition comprising a disclosed compound or pharmaceutically acceptable salt thereof, for use in treating a disorder associated with hyperacetylation of chromatin and/or hyperacetylation of proteins that are known to be acetylated by p300 and/or CBP.

In some aspects, the compounds and compositions described herein are useful in treating cancer, cardiac disease, metabolic disease, fibrotic disease, inflammatory disease, or viral infections.

In some aspects, the cancer treated by the compounds and compositions described herein is selected from adenocarcinoma of the breast, prostate, and colon; bronchogenic carcinoma of the lung; myeloid; melanoma; hepatoma; neuroblastoma; papilloma; apudoma; choristoma; branchioma; malignant carcinoid syndrome; carcinoid heart disease; carcinoma (e.g., Walker, basal cell, basosquamous, Brown-Pearce, ductal, Ehrlich tumor, Krebs 2, merkel cell, mucinous, non-small cell lung, oat cell, papillary, scirrhous, bronchiolar, bronchogenic, squamous cell, and transitional cell); histiocytic disorders; leukemia; histiocytosis malignant; Hodgkin's disease; immunoproliferative small; non-Hodgkin's lymphoma; plasmacytoma; reticuloendotheliosis; melanoma; chondroblastoma; chondroma; chondrosarcoma; fibroma; fibrosarcoma; giant cell tumors; histiocytoma; lipoma; liposarcoma; mesothelioma; myxoma; myxosarcoma; osteoma; osteosarcoma; chordoma; craniopharyngioma; dysgerminoma; hamartoma; mesenchymoma; mesonephroma; myosarcoma; ameloblastoma; cementoma; odontoma; teratoma; thymoma; trophoblastic tumor; adenoma; cholangioma; cholesteatoma; cyclindroma; cystadenocarcinoma; cystadenoma; granulosa cell tumor; gynandroblastoma; hepatoma; hidradenoma; islet cell tumor; Leydig cell tumor; papilloma; sertoli cell tumor; theca cell tumor; leimyoma; leiomyosarcoma; myoblastoma; myomma; myosarcoma; rhabdomyoma; rhabdomyosarcoma; ependymoma; ganglioneuroma; glioma; medulloblastoma; meningioma; neurilemmoma; neuroblastoma; neuroepithelioma; neurofibroma; neuroma; paraganglioma; paraganglioma nonchromaffin; angiokeratoma; angiolymphoid hyperplasia with eosinophilia; angioma sclerosing; angiomatosis; glomangioma; hemangioendothelioma; hemangioma; hemangiopericytoma; hemangiosarcoma; lymphangioma; lymphangiomyoma; lymphangiosarcoma; pinealoma; carcinosarcoma; chondrosarcoma; cystosarcoma phyllodes; fibrosarcoma; hemangiosarcoma; leiomyosarcoma; leukosarcoma; liposarcoma; lymphangiosarcoma; myosarcoma; myxosarcoma; ovarian carcinoma; rhabdomyosarcoma; sarcoma; neoplasms; nerofibromatosis; and cervical dysplasia.

In other aspects, the cancer treated by the compounds and compositions described herein is selected from acoustic neuroma, acute leukemia, acute lymphocytic leukemia, acute myelocytic leukemia, acute T-cell leukemia, basal cell carcinoma, bile duct carcinoma, bladder cancer, brain cancer, breast cancer, bronchogenic carcinoma, cervical cancer, chondrosarcoma, chordoma, choriocarcinoma, chronic leukemia, chronic lymphocytic leukemia, chronic myelocytic leukemia, chronic myelogenous leukemia, colon cancer, colorectal cancer, craniopharyngioma, cystadenocarcinoma, diffuse large B-cell lymphoma, dysproliferative changes, embryonal carcinoma, endometrial cancer, endotheliosarcoma, ependymoma, epithelial carcinoma, erythroleukemia, esophageal cancer, estrogen-receptor positive breast cancer, essential thrombocythemia, Ewing's tumor, fibrosarcoma, follicular lymphoma, germ cell testicular cancer, glioma, glioblastoma, gliosarcoma, heavy chain disease, head and neck cancer, hemangioblastoma, hepatoma, hepatocellular cancer, hormone insensitive prostate cancer, leiomyosarcoma, leukemia, liposarcoma, lung cancer, lymphagioendotheliosarcoma, lymphangiosarcoma, lymphoblastic leukemia, lymphoma, lymphoid malignancies of T-cell or B-cell origin, medullary carcinoma, medulloblastoma, melanoma, meningioma, mesothelioma, multiple myeloma, myelogenous leukemia, myeloma, myxosarcoma, neuroblastoma, NUT midline carcinoma (NMC), non-small cell lung cancer, oligodendroglioma, oral cancer, osteogenic sarcoma, ovarian cancer, pancreatic cancer, papillary adenocarcinomas, papillary carcinoma, pinealoma, polycythemia vera, prostate cancer, rectal cancer, renal cell carcinoma, retinoblastoma, rhabdomyosarcoma, sarcoma, sebaceous gland carcinoma, seminoma, skin cancer, small cell lung carcinoma, solid tumors (carcinomas and sarcomas), small cell lung cancer, stomach cancer, squamous cell carcinoma, synovioma, sweat gland carcinoma, thyroid cancer, Waldenstrom's macroglobulinemia, testicular tumors, uterine cancer, and Wilms' tumor.

In some aspects, the cancer treated by the compounds and compositions described herein is selected from colon cancer, gastric cancer, thyroid cancer, lung cancer, leukemia, pancreatic cancer, melanoma, multiple melanoma, brain cancer, CNS cancer, renal cancer, prostate cancer, ovarian cancer, leukemia, and breast cancer.

In some aspects, the cancer treated by the compounds and compositions described herein is selected from lung cancer, breast cancer, pancreatic cancer, colorectal cancer, and melanoma.

In some aspects, the cancer treated by the compounds and compositions described herein is selected from prostate cancer, enhancer drive cancers, multiple myeloma, and lymphoma (e.g., mantle cell lymphoma). See e.g., Santer et al 2011, Mol Cancer Ther. 10: 1644-1655; Lasko et al, 2017, Nature. Oct 5; 550(7674):128-132; Tie F, et al. 2009 Development 136:3131-3141; Bergsagel P L, Kuehl W M 2001, Oncogene, 20(40):5611-22; Chesi and Bergsagel 2013, Int J Hematol. 97(3): 313-323; and Jares P et al 2007, Nat Rev Cancer. 7(10):750-762.

In one aspect, the cardiac disease treated by the compound and compositions described herein is selected from cardiac hypertrophy and heart failure.

In one aspect, the metabolic disease treated by the compound and compositions described herein is selected from obesity, hepatic steatosis, dyslipidemia, hypertension, coronary heart disease, hepatic inflammation, and diabetes mellitus type 2.

In one aspect, the fibrotic disease treated by the compound and compositions described herein is selected from radiation-induced pneumonitis, radiation fibrosis, acute respiratory distress syndrome, chronic obstructive pulmonary disease, idiopathic pulmonary fibrosis, interstitial lung disease, myocardial infarction, ischemic stroke, ischemic kidney disease, transplant rejection, Leishmaniasis, type I diabetes, rheumatoid arthritis, chronic hepatitis, cirrhosis, inflammatory bowel disease, Crohn's disease, scleroderma, keloid, post-operative fibrosis, chemotherapy induced fibrosis (e.g., chemotherapy induced pulmonary fibrosis or ovarian cortical fibrosis), nephrogenic systemic fibrosis, retroperitoneal fibrosis, myelofibrosis, mediastinal fibrosis, cystic fibrosis, asbestosis, asthma, and pulmonary hypertension.

In one aspect, the inflammatory disease treated by the compound and compositions described herein is selected from asthma, inflammatory bowel disease (Crohn's disease or ulcerative colitis), chronic obstructive pulmonary disease, rheumatoid arthritis, and psoriasis. In another aspect, the inflammatory disease treated by the compound and compositions described herein is selected from Addison's disease, acute gout, ankylosing spondylitis, asthma, atherosclerosis, Behcet's disease, bullous skin diseases, chronic obstructive pulmonary disease, Crohn's disease, dermatitis, eczema, giant cell arteritis, fibrosis, glomerulonephritis, hepatic vascular occlusion, hepatitis, hypophysitis, immunodeficiency syndrome, inflammatory bowel disease, Kawasaki disease, lupus nephritis, multiple sclerosis, myocarditis, myositis, nephritis, organ transplant rejection, osteoarthritis, pancreatitis, pericarditis, Polyarteritis nodosa, pneumonitis, primary biliary cirrhosis, psoriasis, psoriatic arthritis, rheumatoid arthritis, scleritis, sclerosing cholangitis, sepsis, systemic lupus erythematosus, Takayasu's Arteritis, toxic shock, thyroiditis, type I diabetes, ulcerative colitis, uveitis, vitiligo, vasculitis, and Wegener's granulomatosis.

In one aspect, the viral infection treated by the compound and compositions described herein is selected from human immunodeficiency virus, hepatitis C virus, and human papilloma virus.

In certain aspects, a composition described herein is formulated for administration to a patient in need of such composition. Compositions described herein may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. In some embodiments, the compositions are administered orally, intraperitoneally or intravenously. Sterile injectable forms of the compositions described herein may be aqueous or oleaginous suspension. These suspensions may be formulated according to techniques known in the art using suitable dispersing or wetting agents and suspending agents.

In some aspects, the compositions are administered orally.

A specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound described herein in the composition will also depend upon the particular compound in the composition.

The compounds described herein may be present in the form of pharmaceutically acceptable salts. For use in medicines, the salts of the compounds described herein refer to non-toxic "pharmaceutically acceptable salts." Pharmaceutically acceptable salt forms include pharmaceutically acceptable acidic/anionic or basic/cationic salts. Suitable pharmaceutically acceptable acid addition salts of the compounds described herein include e.g., salts of inorganic acids (such as hydrochloric acid, hydrobromic, phosphoric, nitric, and sulfuric acids) and of organic acids (such as, acetic acid, benzenesulfonic, benzoic, methanesulfonic, and p-toluenesulfonic acids). Compounds of the present teachings with acidic groups such as carboxylic acids can form pharmaceutically acceptable salts with pharmaceutically acceptable base(s). Suitable pharmaceutically acceptable basic salts include e.g., ammonium salts, alkali metal salts (such as sodium and potassium salts) and alkaline earth metal salts (such as magnesium and calcium salts). Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, benzoates and salts with amino acids such as glutamic acid.

Combination therapies using a therapeutically effective amount of a compound of Formula I, or a pharmaceutically acceptable salt thereof, and an effective amount of one or more additional pharmaceutically active agents are also included herein. Additional active agents that can be combined with a compound of Formula I, or a pharmaceutically acceptable salt thereof, include e.g., those which target the estrogen receptor (ER). These include, but are not limited to selective estrogen receptor degraders (SERDs), ER antagonists, selective estrogen receptor modulators (SERMs), and aromatase inhibitors (AIs). Examples of SERDs and ER antagonists include, but are not limited to, fulvestrant, RAD-1901 (elacestrant), GDC-0927 ((2S)-2-(4-{2-[3-(fluoromethyl)-1-azetidinyl]ethoxy}phenyl)-3-(3-hydroxyphenyl)-4-methyl-2H-chromen-6-ol), GDC-0810 (brilanestrant), AZD-9496 ((2E)-3-[3,5-difluoro-4-[(1R,3R)-2-(2-fluoro-2-methylpropyl)-2,3,4,9-tetrahydro-3-methyl-1H-pyrido[3,4-b]indol-1-yl]phenyl]-2-propenoic acid), OP-1250 (a prodrug of (S)-3-(4-hydroxyphenyl)-4-methyl-2-(4-(2-((R)-3-methylpyrrolidin-1-yl)ethoxy)phenyl)-2H-chromen-7-ol found in U.S. Pat. No. 9,018,244, the contents of which are incorporated herein by reference), (S)-3-(4-hydroxyphenyl)-4-methyl-2-(4-(2-((R)-3-methylpyrrolidin-1-yl)ethoxy)phenyl)-2H-chromen-7-ol, also found in U.S. Pat. No. 9,018,244, the contents of which are incorporated herein by reference), LSZ102 ((E)-3-(4-((2-(2-(1,1-difluoroethyl)-4-fluorophenyl)-6-hydroxybenzo[b]thiophen-3-yl)oxy)phenyl)acrylic acid), and H3B-6545 ((E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide). Examples of SERMs include, but are not limited to, tamoxifen, toremifene, raloxifene, bazedoxifene, ospemifene, and nafoxidene. Examples of AIs include, but are not limited to, anastrozole, letrozole, exemestane, vorozole, formestane and fadrozole. In one aspect, provided is a compound of Formula I, or a pharmaceutically acceptable salt thereof, and an additional therapeutic agent selected from fulvestrant, RAD-1901, GDC-0927, GDC-0810, AZD-9496, OP-1250, LSZ102, H3B-6545, tamoxifen, toremifene, raloxifene, bazedoxifene, ospemifene, nafoxidene, anastrozole, letrozole, exemestane, vorozole, formestane and fadrozole. In one aspect, the additional therapeutic agent is fulvestrant. The use of one or more of the combination therapies discussed above for treating a condition recited herein is also included within the scope of the present disclosure. For example, in one aspect, the combination treatments meantion above are useful in the treatment of cancer e.g., breast cancer.

Exemplification

Representative examples of the disclosed compounds are illustrated in the following non-limiting methods, schemes, and examples.

General starting materials used were obtained from commercial sources or prepared in other examples, unless otherwise noted.

The following abbreviations have the indicated meanings: Ac=acetyl; ACN=acetonitrile; AcO acetate; BOC=t-butyloxycarbonyl; CBZ=carbobenzoxy; CDI=carbonyldiimidazole; DBU=1,8-Diazabicycloundec-7-ene; DCC=1,3-dicyclohexylcarbodiimide; DCE=1,2-dichloroethane; DI=de-ionized; DIAD=Diisopropyl azodicarboxylate; DIBAL=diisobutyl aluminum hydride; DIPA=diisopropylamine; DIPEA or DIEA=N,N-diisoproylethylamine, also known as Hunig's base; DMA=dimethylacetamide; DMAP=4-(dimethylamino)pyridine; DMF=dimethylformamide; DMP=Dess-Martin periodinane; DPPA=Diphenylphosphoryl azide; DPPP=1,3-bis(diphenylphosphino)propane; Dtbbpy=4,4'-di-/e/7-butyl-2,2'-dipyridyl; EDC or EDCI=1-(3-dimethylaminopropyl)-3-ethylcarbodiimide hydrochloride; EDTA=ethylenediaminetetraacetic acid, tetrasodium salt; EtOAc=ethyl acetate; FAB=fast atom bombardment; FMOC=9-fluorenylmethoxycarbonyl; HMPA=hexamethylphosphoramide; HATU=(9-(7-Azabenzotriazol-1-yl)-N, N, N, N-tetramethyluroniumhexafluorophosphate; HOAt=1-Hydroxy-7-azabenzotriazole or 3H-[1,2,3]triazolo[4,5-b]pyridin-3-ol; HOBt=1-hydroxybenzotriazole; HRMS=high resolution mass spectrometry; KHMDS=potassium hexamethyldisilazane; LC-MS=Liquid chromatography-mass spectrometry; LDA=lithium diisopropylamide; LiHMDS=lithium hexamethyldisilazane; MCPBA=meta-chloroperbenzoic acid; MMPP=magnesium monoperoxyphthlate hexahydrate; Ms=methanesulfonyl=mesyl; MsO=methanefulfonate=mesylate; MTBE=Methyl t-butyl ether; NBS=N-bromosuccinimide; NMM=4-methylmorpholine; NMP=N-methylpyrrolidinone; NMR=Nuclear magnetic resonance; PCC=pyridinium chlorochromate; PDC=pyridinium dichromate; Ph=phenyl; PPTS=pyridinium p-toluene sulfonate; pTSA=p-toluene sulfonic acid; r.t./RT=room temperature; rac.=racemic; T3P=2,4,6-Tripropyl-1,3,5,2,4,6-trioxatriphosphinane 2,4,6-trioxide; TEA=triethylamine; TFA=trifluoroacetic acid; TfO=trifluoromethanesulfonate=triflate; THF=tetrahydrofuran; TLC=thin layer chromatography; TMSCl=trimethylsilyl chloride.

Unless otherwise stated, the absolute configuration of each eluting stereoisomer in the following examples was not identified.

The progress of reactions was often monitored by TLC or LC-MS. The LC-MS was recorded using one of the following methods.

Method-C3

| Mobile Phase | (A) | 2 mM Ammonium acetate + 0.1% Formic Acid in Water |  |
|---|---|---|---|
|  | (B) | 0.1% Formic Acid in Acetonitrile |  |
| Column | : | BEH C18 (50*2.1 mm) 1.7 um |  |
| Column Flow | : | 0.55 ml/min |  |
| Gradient | : | Time (min) | % A | % B |

| Time (min) | % A | % B |
|---|---|---|
| 0.01 | 98 | 2 |
| 0.30 | 98 | 2 |
| 0.60 | 50 | 50 |
| 1.10 | 25 | 75 |
| 2.00 | 0 | 100 |
| 2.70 | 0 | 100 |
| 2.71 | 98 | 2 |
| 3.00 | 98 | 2 |

PDS Method-J

| Mobile Phase | (A) | 5 mM Ammonium Acetate + 0.1% Formic Acid in Water |
|---|---|---|
|  | (B) | 0.1% Formic Acid in Acetonitrile |
| Column | : | BEH C18 (50*2.1 mm), 1.7 um or Equivalent |
| Column Flow | : | 0.45 ml/min |

| Time (min) | % A | % B |
|---|---|---|
| 0.01 | 98 | 2 |
| 0.50 | 98 | 2 |
| 5.00 | 10 | 90 |
| 6.00 | 5 | 95 |
| 7.00 | 5 | 95 |
| 7.01 | 98 | 2 |
| 8.00 | 98 | 2 |

Method-H

| Mobile Phase | (A) | 5 mM Ammonium bicarbonate in water |
|---|---|---|
|  | (B) | Acetonitrile |
| Column | : | X-Bridge C18 (50*4.6 mm), 3.5 um |
| Column Flow | : | 1.0 ml/min |

| Time (min) | % A | % B |
|---|---|---|
| 0.01 | 95 | 5 |
| 5.00 | 10 | 90 |
| 5.80 | 5 | 95 |
| 7.20 | 5 | 95 |
| 7.21 | 95 | 5 |
| 10.00 | 95 | 5 |

Method-F

| Mobile Phase | (A) | 10 mM Ammonium Acetate in WATER |
|---|---|---|
|  | (B) | 100% Acetonitrile |
| Column | : | X-Bridge C18 (150*4.6 mm), 5 um or Equivalent |
| Column Flow | : | 1.0 ml/min |

| Time (min) | % A | % B |
|---|---|---|
| 0.01 | 90 | 10 |
| 5.00 | 10 | 90 |
| 7.00 | 0 | 100 |
| 11.00 | 0 | 100 |
| 11.01 | 90 | 10 |
| 12.00 | 90 | 10 |

Method-G

| Mobile Phase | (A) | 10 mM Ammonium Acetate in Water |
|---|---|---|
|  | (B) | 100% Acetonitrile |
| Column | : | X-Bridge C18 (150*4.6 mm), 5 um or Equivalent |
| Column Flow | : | 1.0 ml/min |

| Time (min) | % A | % B |
|---|---|---|
| 0.01 | 100 | 0 |
| 7.00 | 50 | 50 |
| 9.00 | 0 | 100 |
| 11.00 | 0 | 100 |
| 11.01 | 100 | 0 |
| 12.00 | 100 | 0 |

NMR was recorded at room temperature unless noted otherwise on Varian Inova 400 or 500 MHz spectrometers with the solvent peak used as the reference or on Bruker 300 or 400 MHz spectrometers with the TMS peak used as internal reference.

Methods 1, 2, and 3

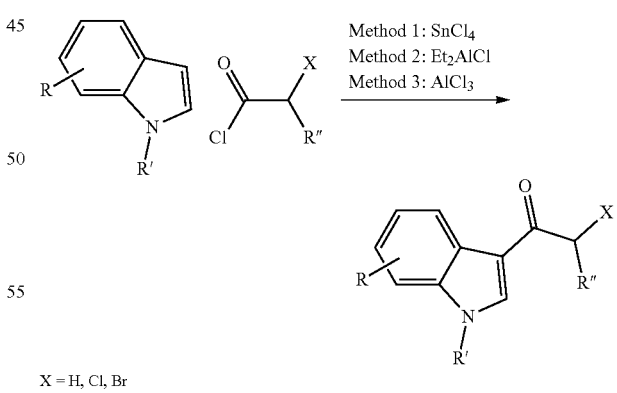

X = H, Cl, Br

Methods 1, 2, and 3 are protocols for the preparation of 3-ketoindoles, from indoles and various acylchlorides, that are useful for the synthesis of intermediates en route to the compounds described herein. Other related bromoketones useful for the synthesis of compounds described herein may be prepared with similar methodology.

Method 4

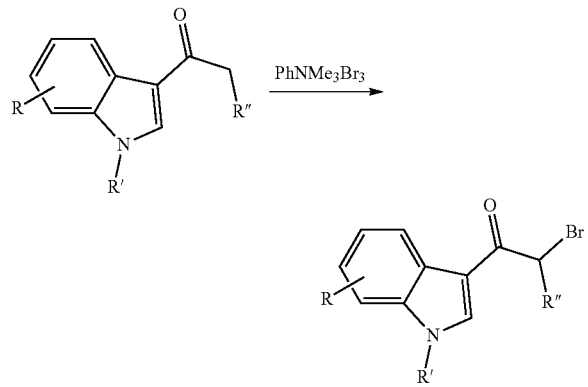

Method 4 is a protocol for the preparation of 2-bromo-1-(1H-indol-3-yl)-2-substituted ethan-1-ones, from 3-ketoindoles and trimethylphenylammonium tribromide, that is useful for the synthesis of intermediates en route to the compounds described herein. Other related bromoketones useful for the synthesis of compounds described herein may be prepared with similar methodology.

Method 5

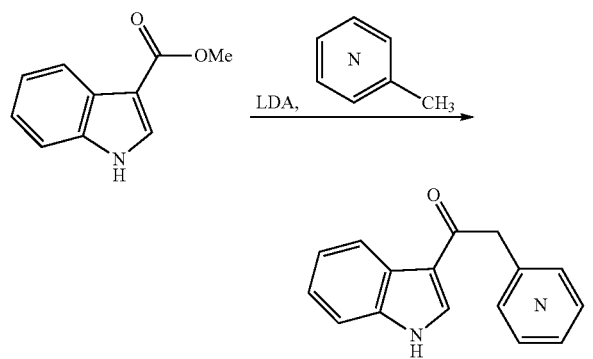

Method 5 is a protocol for the preparation of 1-(1H-indol-3-yl)-2-(pyridinyl)ethan-1-ones, from methyl-1H-indole-3-carboxylate and methylpyridines, that is useful for the synthesis of intermediates en route to the compounds described herein.

Method 6

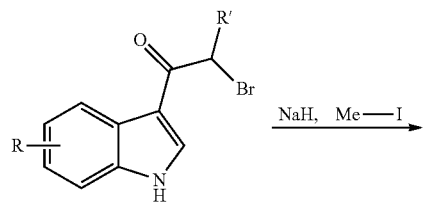

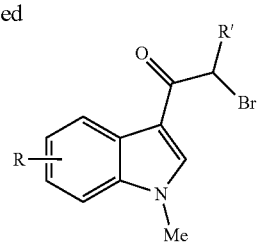

Method 6 is a protocol for the preparation of 2-bromo-1-(N-methyl-indol-3-yl)-2-substituted ethan-1-ones, from alkylation of an N-unsubstituted indole, that is useful for the synthesis of intermediates en route to the compounds described herein. Other related 2-bromo-1-(N-alkyl-indol-3-yl)-2-substituted ethan-1-ones useful for the synthesis of compounds described herein may be prepared with similar methodology.

Method 7

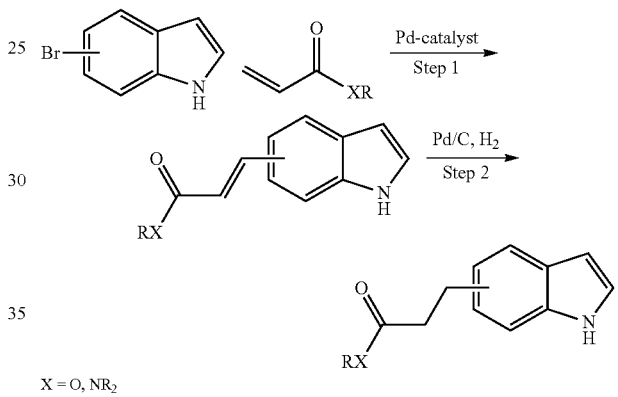

X = O, NR$_2$

Method 7 is a 2-step protocol, which consists of a Heck reaction and a palladium-catalyzed hydrogenation reaction, for the preparation of 3-(1H-indol-6-yl)propanoate esters and 3-(1H-indol-6-yl)-propanamides, from bromoindoles and acrylates or acrylamides, that is useful for the synthesis of intermediates en route to the compounds described herein.

Method 8

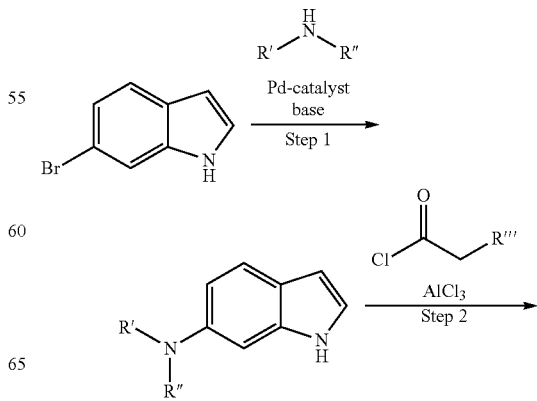

Method 10

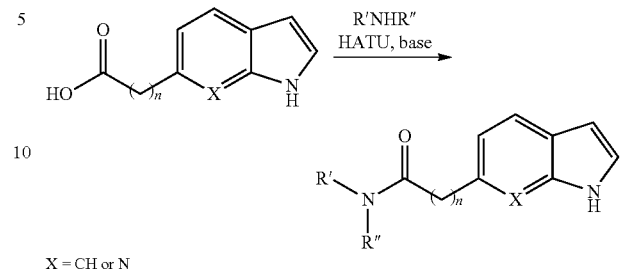

X = CH or N

Method 10 is a protocol for the preparation of amide-substituted indoles, from their acid precursors and amines, that is useful for the synthesis of intermediates en route to the compounds described herein.

Method 11

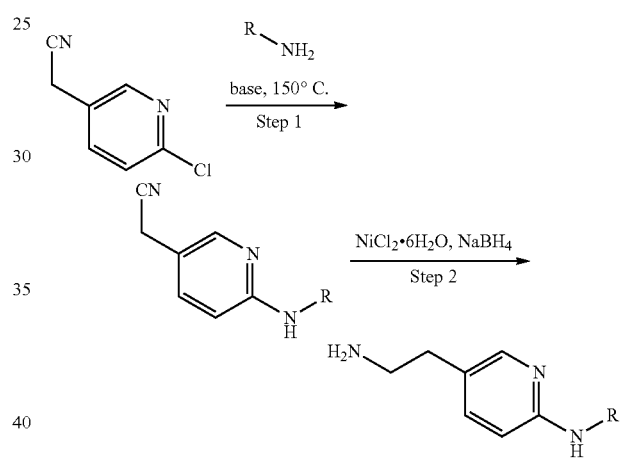

Method 11 is a 2-step protocol, which consists of a $S_NAr$ reaction and a nickel-mediated nitrile reduction, for the preparation of 5-(2-aminoethyl)-N-alkylpyridin-2-amines starting from 2-(6-chloropyridin-3-yl)acetonitrile and various amines that is useful for the synthesis of intermediates en route to the compounds described herein.

Method 12

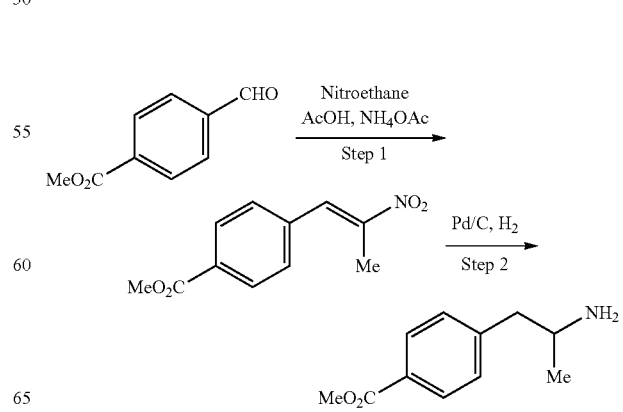

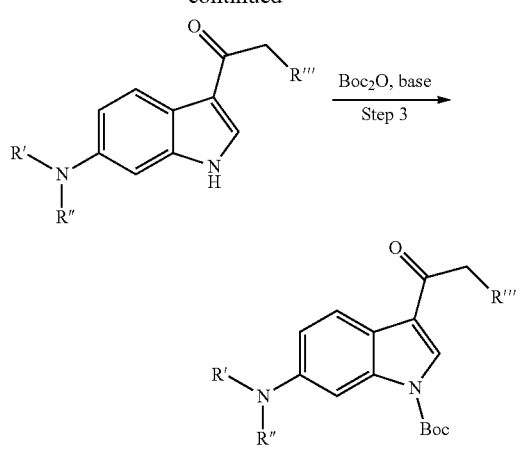

Method 8 is a 3-step protocol, which consists of a C—N coupling, Friedel-Crafts reaction, and the introduction of t-butoxycarbonyl protecting group, for the preparation of 1-(6-(amino)-1H-indol-3-yl)-2-substituted-1-ones starting from bromoindoles and amines that is useful for the synthesis of intermediates en route to the compounds described herein.

Method 9

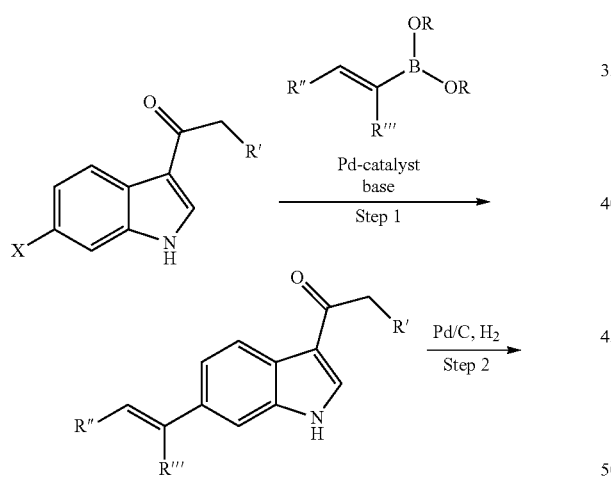

Method 9 is a 2-step protocol, which consists of a Suzuki cross-coupling reaction and a palladium-catalyzed hydrogenation reaction, for the preparation of 1-(6-(amino)-1H-indol-3-yl)-2-substituted-1-ones starting from 1-(6-bromo-1H-indol-3-yl)-2-substituted-ethan-1-ones and alkenylboronic esters that is useful for the synthesis of intermediates en route to the compounds described herein.

Method 12 is a 2-step protocol, which consists of a condensation reaction of aldehydes with nitroalkanes and a palladium-catalyzed hydrogenation reaction, for the preparation of methyl 4-(2-aminoalkyl)benzoates starting from methyl 4-formylbenzoate and nitroalkanes that is useful for the synthesis of intermediates en route to the compounds described herein.

Method 13

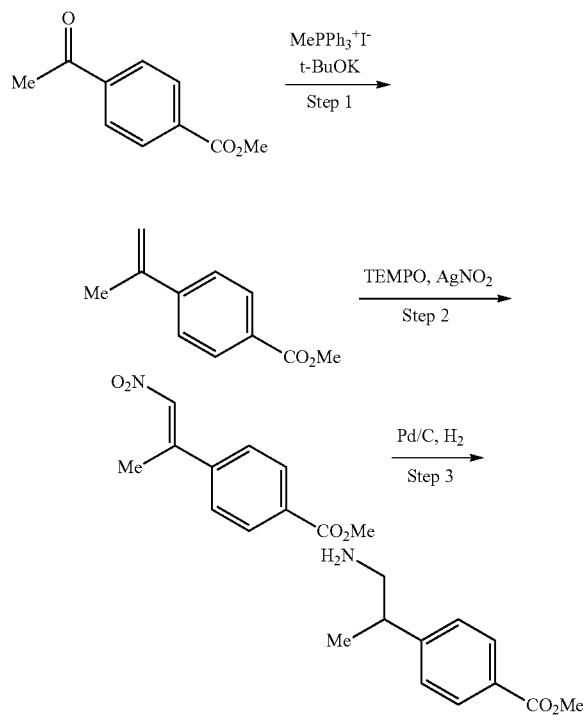

Method 13 is a 3-step protocol, which consists of a Wittig olefination, a TEMPO-mediated nitration, and a palladium-catalyzed hydrogenation reaction, for the preparation of methyl 4-(1-aminoalk-2-yl)benzoates starting from methyl 4-ketobenzoates that is useful for the synthesis of intermediates en route to the compounds described herein.

Method 14

Method 14 is a 5-step protocol for the preparation of methyl 2-(4-(1H-1,2,3-triazol-4-yl)phenyl)ethan-1-amines starting from 2-(4-bromophenyl)ethan-1-amines that is useful for the synthesis of intermediates en route to the compounds described herein.

Method 15

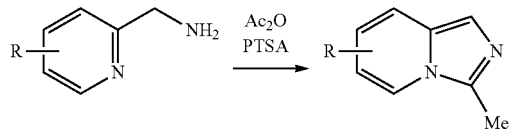

Method 15 is a protocol for the preparation of imidazopyridines synthesis from 2-aminomethylpyridines that is useful for the synthesis of intermediates en route to the compounds described herein.

Method 16

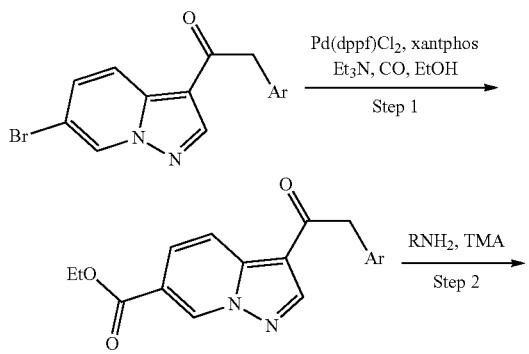

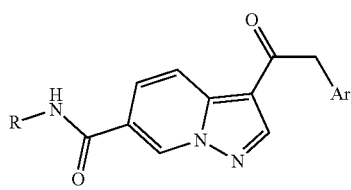

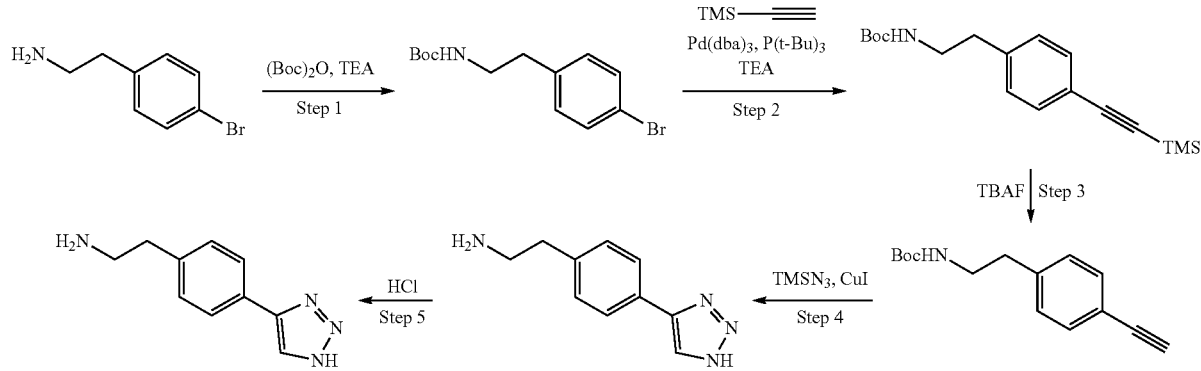

Method 16 is a two-step protocol for the preparation of N-ethyl-3-(2-phenylacetyl)pyrazolo[1,5-a]pyridine-6-carboxamides starting from 1-(6-bromopyrazolo[1,5-a]pyridin-3-yl)-2-arylethan-1-ones that is useful for the synthesis of intermediates en route to the compounds described herein.

Method 17

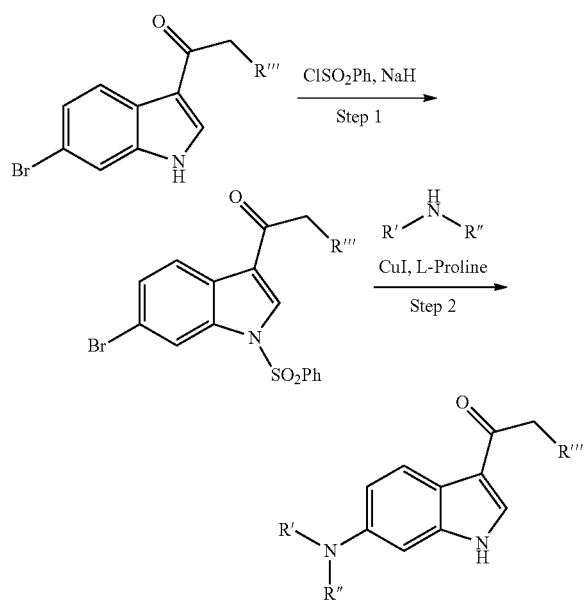

Method 17 is a protocol for the preparation of 3-(2-arylacetyl)pyrazolo[1,5-a]pyridine-6-carboxylic acid derivatives starting from ethyl 3-(2-arylacetyl)pyrazolo[1,5-a]pyridine-6-carboxylates that is useful for the synthesis of intermediates en route to the compounds described herein.

Method 18

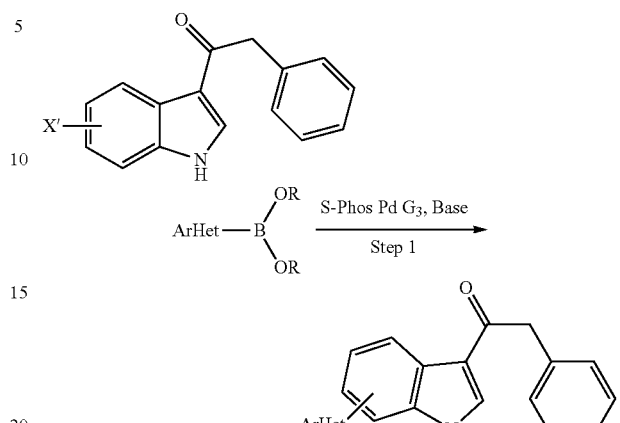

Method 18 is a two-step protocol for the preparation of 1-(6-(amino)-1H-indol-3-yl)-2-substituted-1-ones starting from 3-keto-6-bromoindole derivatives that is useful for the synthesis of intermediates en route to the compounds described herein.

Method 19

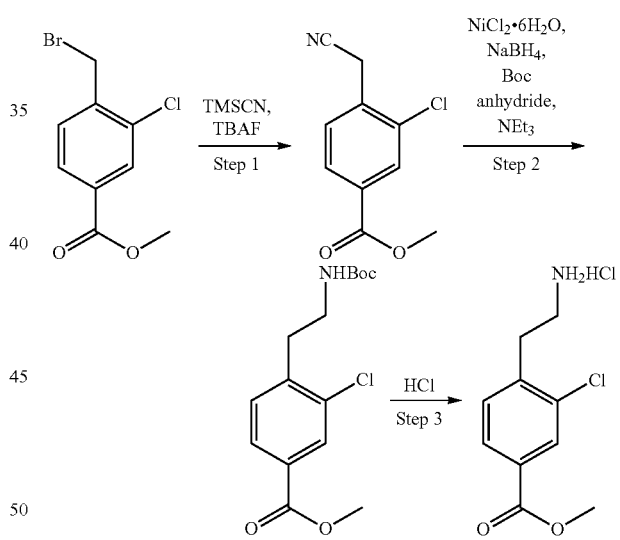

Method 19 is a protocol for the preparation of substituted-3-ketoindole derivatives from halo-3-ketoindoles via a Suzuki reaction that is useful for the synthesis of intermediates en route to the compounds described herein.

Method 20

Method 20 is three-step protocol for the preparation of methyl 4-(2-aminoethyl)-3-chlorobenzoate hydrochloride from methyl 4-(bromomethyl)-3-chlorobenzoate that is useful for the synthesis of intermediates en route to the compounds described herein.

Method 21

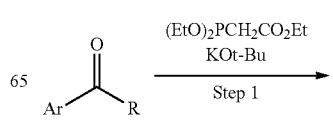

-continued

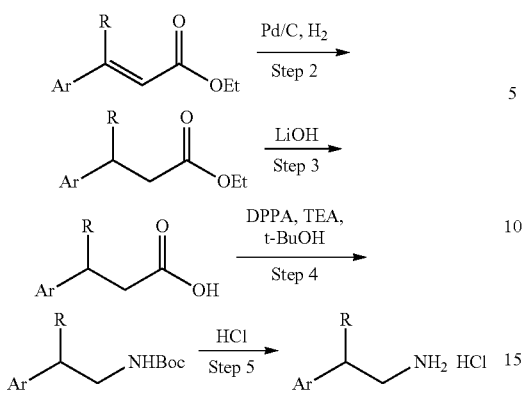

Method 21 is a five-step protocol for the preparation of substituted 2-aryl-ethylamines starting from substituted benzaldehydes or ketones that is useful for the synthesis of intermediates en route to the compounds described herein.

Method 22

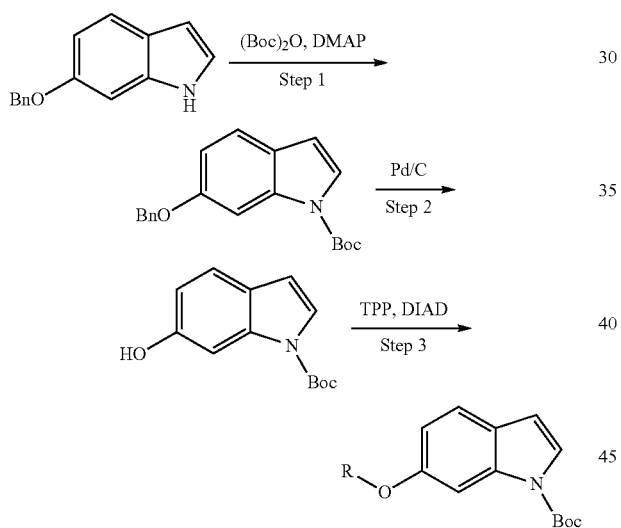

Method 22 is a three-step protocol for the preparation of N-Boc-6-alkoxy-1H-indole derivatives starting from 6-(benzyloxy)-1H-indole that is useful for the synthesis of intermediates en route to the compounds described herein.

Method 23

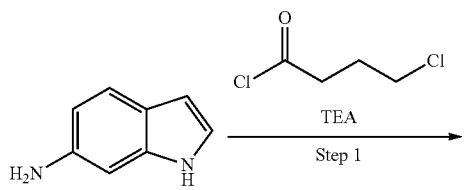

-continued

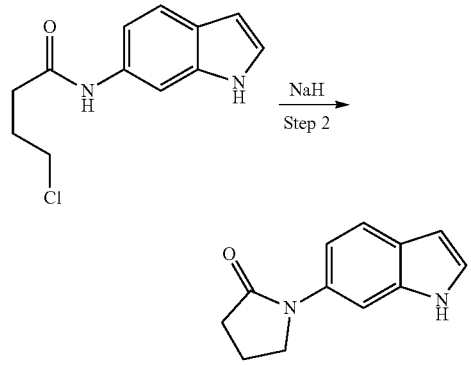

Method 23 is a two-step protocol for the preparation of 1-(1H-indol-6-yl)pyrrolidin-2-ones from starting from 1H-indol-6-amine that is useful for the synthesis of intermediates en route to the compound described herein.

Method 24

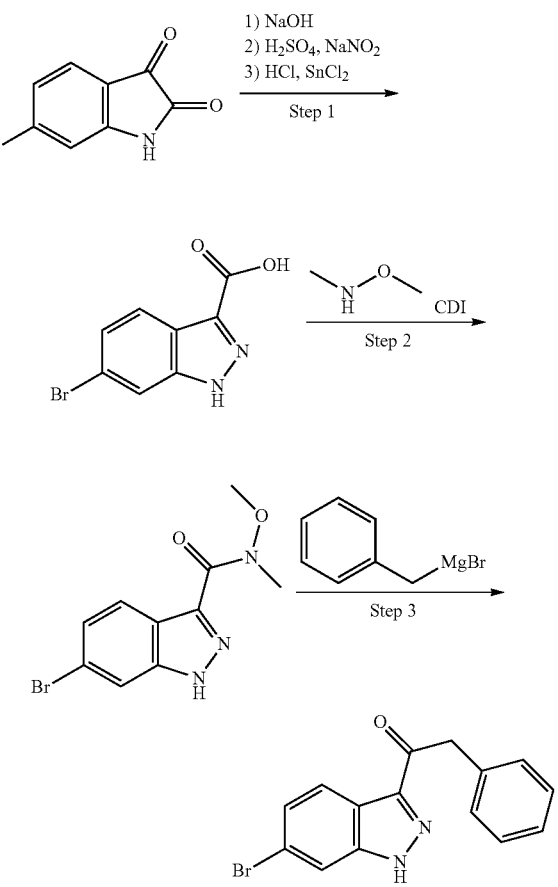

Method 24 is a three-step protocol for the preparation of 1-(6-bromo-1H-indazol-3-yl)-2-phenylethan-1-one starting from 6-bromoindoline-2,3-dione that is useful for the synthesis of intermediates en route to the compound described herein.

Scheme 1

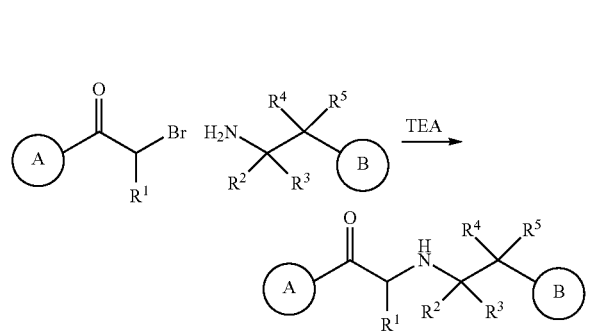

Scheme 1 illustrates a general method for the synthesis of the compounds described herein via alkylation of amine with an α-bromoketone or α-bromoamide where A, B, $R^1$, $R^2$, $R^3$, $R^4$, and $R^5$ are as defined herein.

Scheme 2

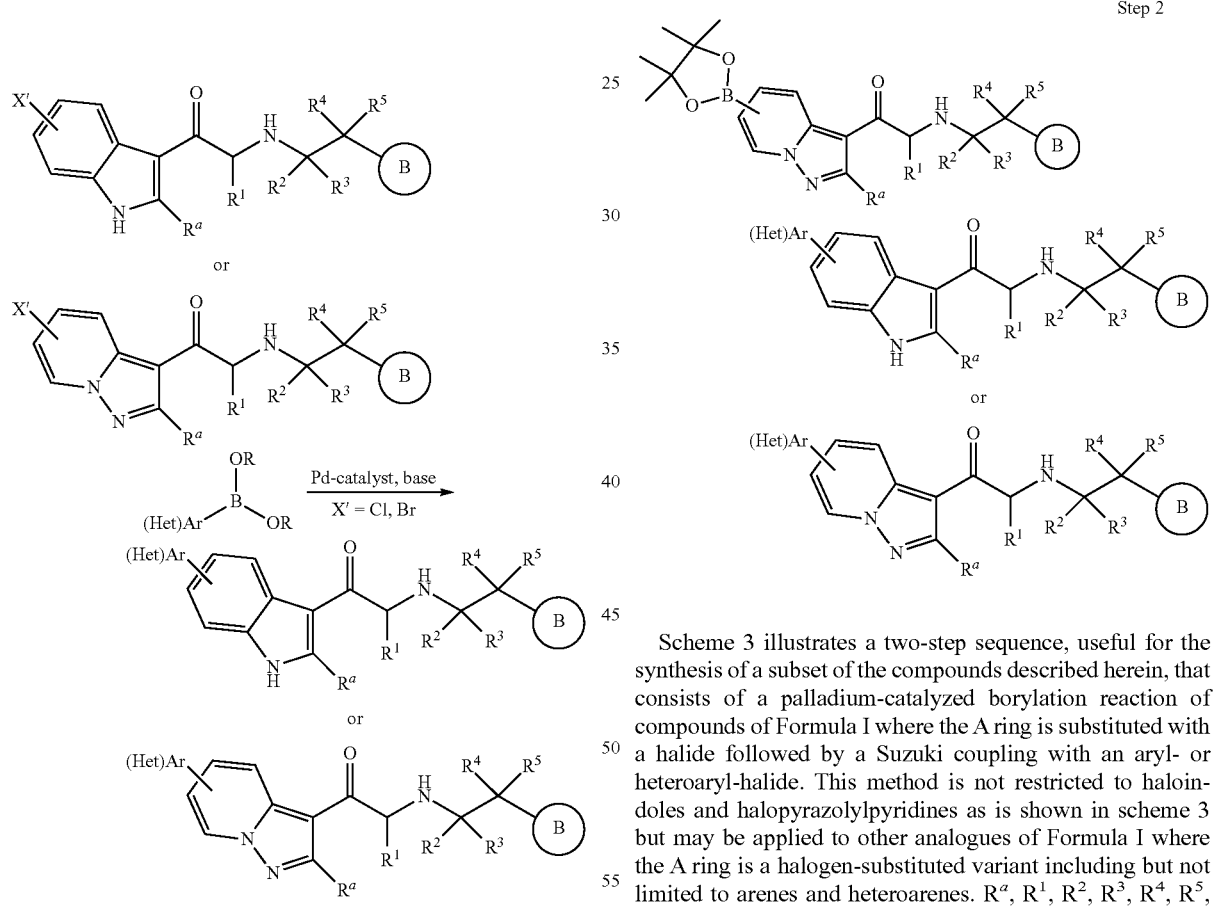

Scheme 2 illustrates a general method for the synthesis of a subset of the compounds described herein via a Suzuki reaction of a variety aryl- or heteroarylboronic esters and acids with a subset substituted compounds of Formula I where the A ring is substituted with a halide. This method is not restricted to haloindoles and halopyrazolylpyridines as is shown in scheme 2 but may be applied to other analogues of Formula I where the A ring is a halogen-substituted variant including but not limited to arenes and heterorenes. $R^a$, $R^1$, $R^2$, $R^3$, $R^4$, $R^5$, $R^6$, and B are as defined herein.

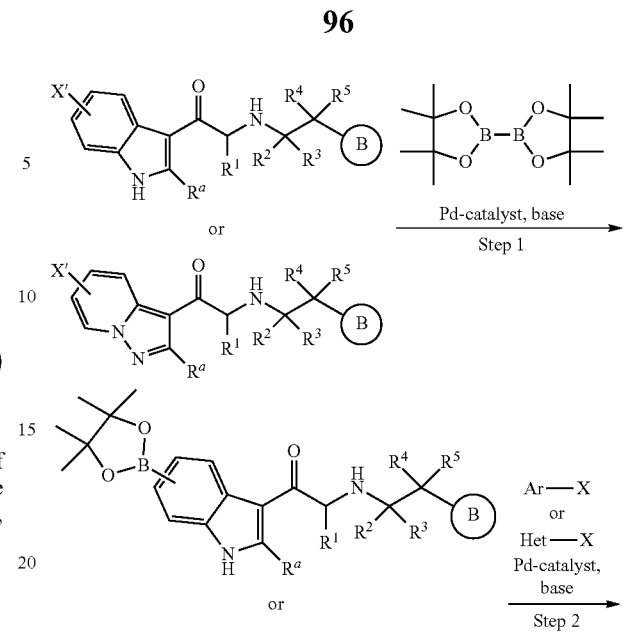

Scheme 3 illustrates a two-step sequence, useful for the synthesis of a subset of the compounds described herein, that consists of a palladium-catalyzed borylation reaction of compounds of Formula I where the A ring is substituted with a halide followed by a Suzuki coupling with an aryl- or heteroaryl-halide. This method is not restricted to haloindoles and halopyrazolylpyridines as is shown in scheme 3 but may be applied to other analogues of Formula I where the A ring is a halogen-substituted variant including but not limited to arenes and heteroarenes. $R^a$, $R^1$, $R^2$, $R^3$, $R^4$, $R^5$, and B are as defined herein.

Scheme 4

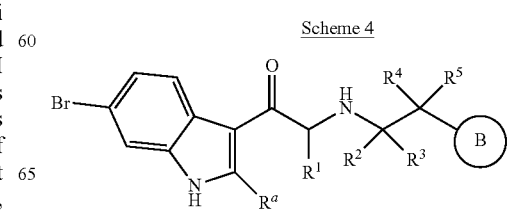

-continued

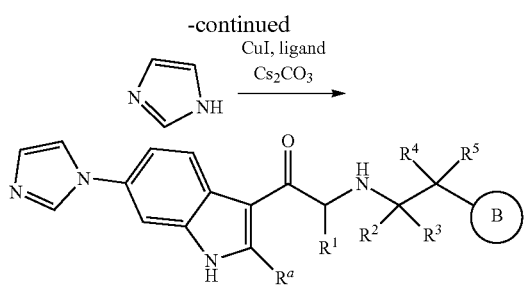

Scheme 4 illustrates a general method for the synthesis of a subset of the compounds described herein via a copper-catalyzed coupling reaction of a variety of azoles with a family of substituted compounds of Formula I where the A ring is substituted with a halide. This method is not restricted to haloindoles and halopyrazolylpyridines as is shown in scheme 3 but may be applied to other analogues of Formula I where the A ring is a halogen-substituted variant including but not limited to arenes and heteroarenes. $R^a$, $R^1$, $R^2$, $R^3$, $R^4$, $R^5$, and B are as defined herein.

Scheme 5

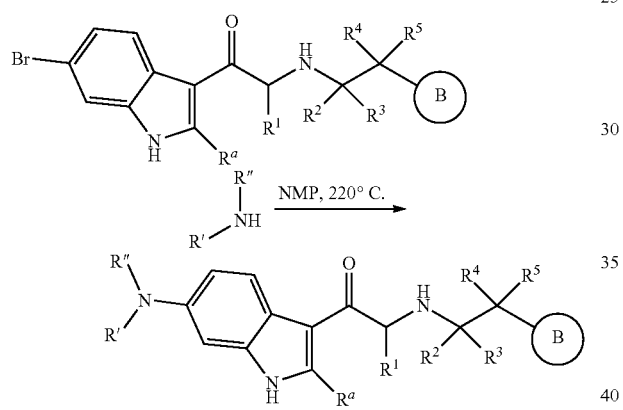

Scheme 5 illustrates a method for the conversion of 6-bromo-1H-pyrrolo[2,3-b]pyridines into 6-amino-1H-pyrrolo[2,3-b]pyridines via a $S_NAr$ reaction where $R^a$, $R^1$, $R^2$, $R^3$, $R^4$, $R^5$, and B are as defined herein.

Scheme 6

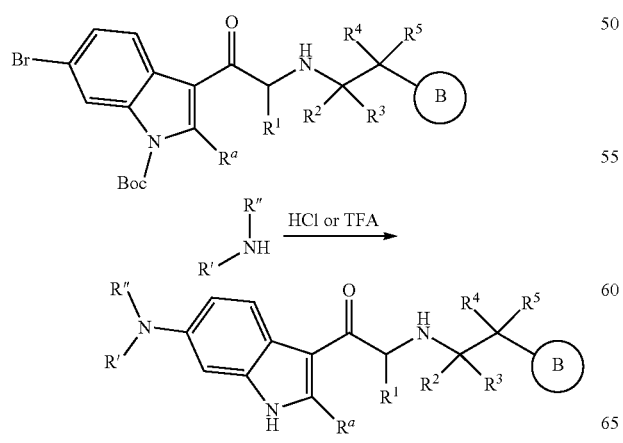

Scheme 6 illustrates a method for the conversion of an N-Boc indole derivative to an N—H indole derivative that is useful for the synthesis of a subset of the compounds of Formula I where $R^a$, $R^1$, $R^2$, $R^3$, $R^4$, $R^5$, and B are as defined herein.

Scheme 7

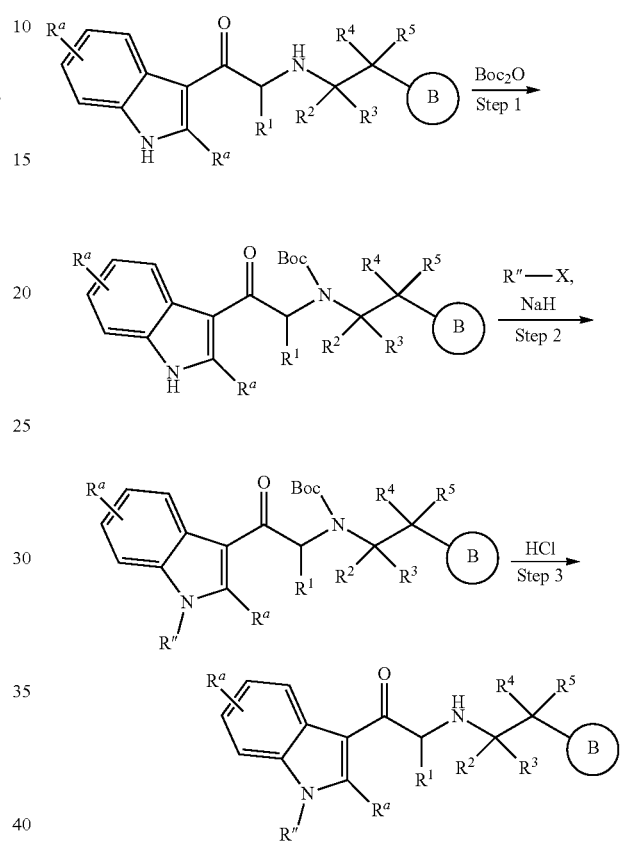

Scheme 7 illustrates a three-step sequence for the conversion of an N—H indole derivative to an N-alkylated indole derivative that is useful for the synthesis of a subset of the compounds of Formula I where $R^a$, $R^1$, $R^2$, $R^3$, $R^4$, $R^5$, and B are as defined herein.

Scheme 8

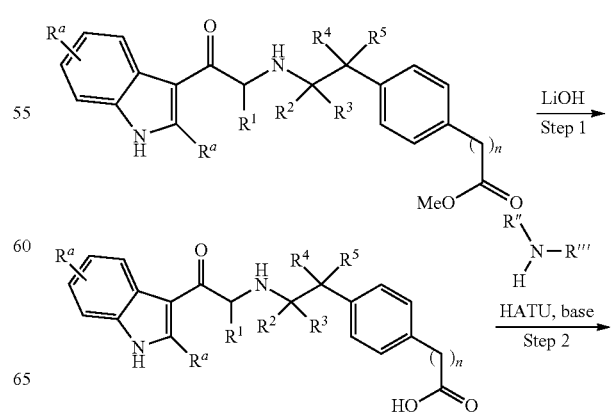

-continued

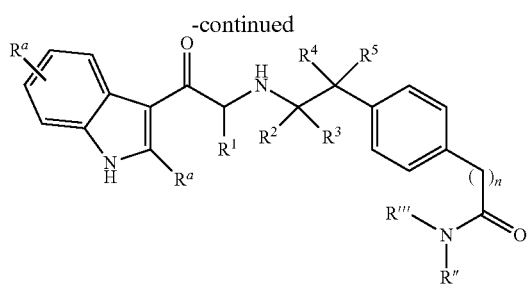

Scheme 8 illustrates a two-step sequence that is useful for the synthesis of a subset of the compounds of Formula I where the B ring is an aryl group functionalized with an amide side-chain. This method is not restricted to compounds where ring A is an indole as shown in scheme 8 but may be applied to other analogues of Formula I. $R^a$, $R^1$, $R^2$, $R^3$, $R^4$, $R^5$, and B are as defined herein.

Scheme 9

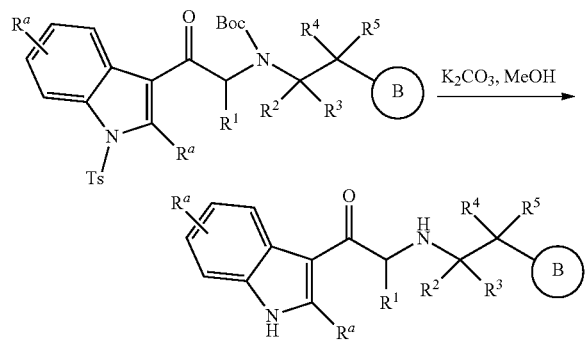

Scheme 9 illustrates a method for the conversion of an N-tosyl indole derivative to an N—H indole derivative that is useful for the synthesis of a subset of the compounds of Formula I where ring A is an indole and $R^a$, $R^1$, $R^2$, $R^3$, $R^4$, $R^5$, and B are as defined herein.

Scheme 10

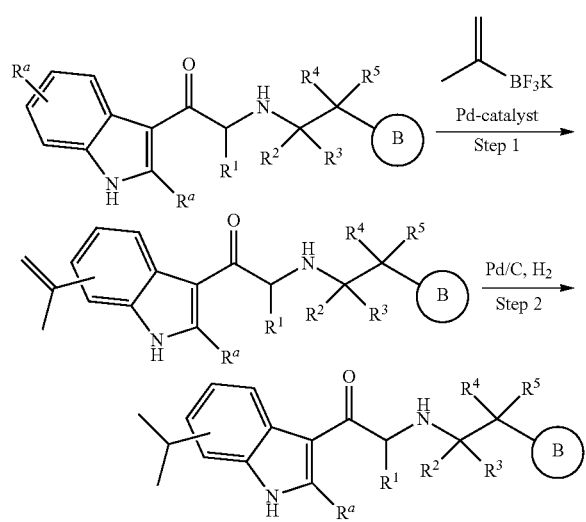

Scheme 10 illustrates a two-step sequence, that consists of a Suzuki reaction of halogen-substituted A groups followed by a Suzuki coupling with an aryl- or heteroaryl-halide, that is useful for the synthesis of a subset of the compounds described herein. This method is not restricted to haloindoles as is shown in scheme 10 but may be applied to other analogues of Formula I where the A ring is a halogen-substituted variant including but not limited to arenes and heteroarenes. $R^a$, $R^1$, $R^2$, $R^3$, $R^4$, $R^5$, and B are as defined herein.

Scheme 11

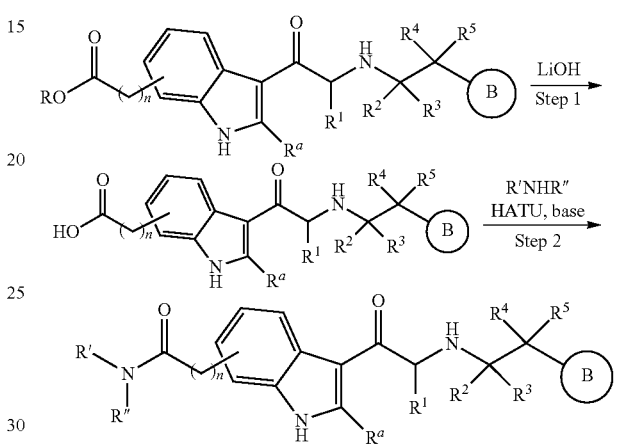

Scheme 11 illustrates a two-step sequence that is useful for the synthesis of a subset of the compounds described herein where the A ring of Formula I is functionalized with an amide side-chain. This method is not restricted to compounds where A is an indole as shown in scheme 11 but may be applied to other analogues of Formula I where the A ring is an amide-substituted variant including but not limited to arenes and heteroarenes. $R^a$, $R^1$, $R^2$, $R^3$, $R^4$, $R^5$, and B are as defined herein.

Scheme 12

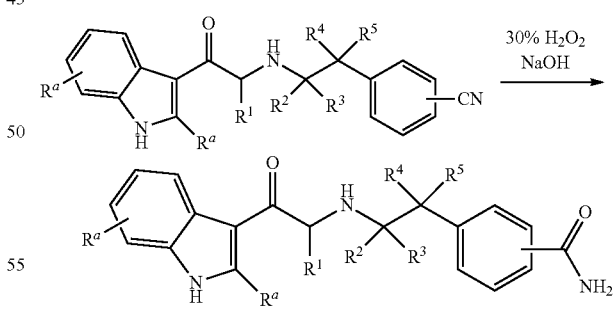

Scheme 12 illustrates a method for conversion of a nitrile to a primary amide that is useful for the synthesis of a subset of the compounds of Formula I where the B ring is an arene functionalized with a primary amide. This method is not restricted to compounds where the A ring is an indole as shown in scheme 12 but may be applied to other analogues of Formula I where the A ring is another variant including but not limited to arenes and heteroarenes. $R^a$, $R^1$, $R^2$, $R^3$, $R^4$, $R^5$, and B are as defined herein.

Scheme 13

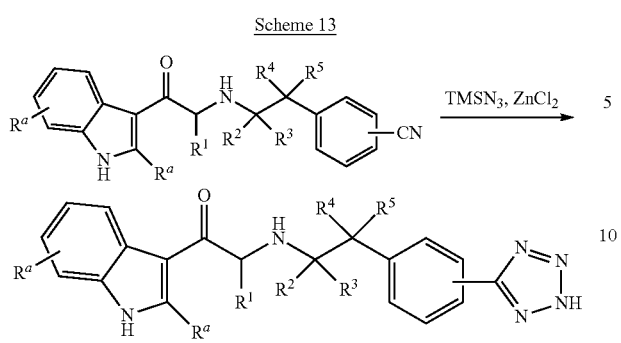

Scheme 13 illustrates a method for conversion of a nitrile to a tetrazole that is useful for the synthesis of a subset of the compounds of Formula I where the B ring is an arene functionalized with a tetrazole. This method is not restricted to compounds where the A ring is an indole as shown in scheme 13 but may be applied to other analogues of Formula I where the A ring is another variant including but not limited to arenes and heteroarenes. $R^a$, $R^1$, $R^2$, $R^3$, $R^4$, $R^5$, and B are as defined herein.

Scheme 14

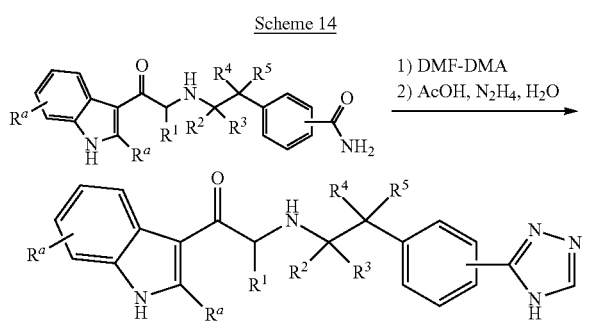

Scheme 14 illustrates a method for conversion of a nitrile to a triazole that is useful for the synthesis of a subset of the compounds of Formula I where the A ring is an arene functionalized with a triazole. This method is not restricted to compounds where A ring is an indole as shown in scheme 14 but may be applied to other analogues of Formula I where the A ring is another variant including but not limited to arenes and heteroarenes. $R^a$, $R^1$, $R^2$, $R^3$, $R^4$, $R^5$, and B are as defined herein.

Scheme 15

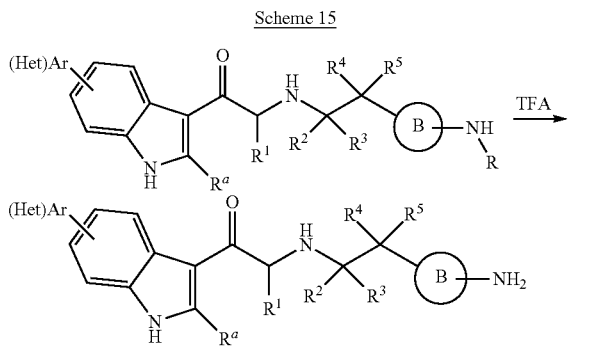

Scheme 15 illustrates a general method for the synthesis of a subset of the compounds described herein via deprotection of R group with a subset substituted compounds of Formula I where the B ring is an aryl group functionalized with an amine group. Formula I where the A ring is substituted variant including but not limited to arenes and heteroarenes. $R^a$, R, $R^1$, $R^2$, $R^3$, $R^4$, $R^5$, and B are as defined herein.

Methods 1, 2, and 3

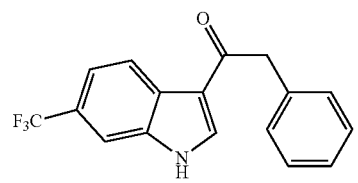 [SMILES: O=C(Cc1ccccc1)c1c[nH]c2cc(C(F)(F)F)ccc12]

2-phenyl-1-(6-(trifluoromethyl)-1H-indol-3-yl)ethan-1-one

Method 1. 2-phenyl-1-(6-(trifluoromethyl)-1H-indol-3-yl)ethan-1-one:

To a stirred solution of 6-(trifluoromethyl)-1H-indole (0.5 g, 2.70 mmol) in dry DCM (12.5 ml) under an atmosphere of nitrogen was added $SnCl_4$ (1.05 g, 1.0 M in DCM, 4.05 mmol) at room temperature. The resulting reaction mixture was stirred for 30 minutes at room temperature and phenylacetyl chloride (0.5 g, 3.24 mmol) was added dropwise. To this nitromethane (5 ml) was added and the reaction mixture was stirred at room temperature for 1.5 hours. Saturated sodium bicarbonate solution (10 ml) was added and the reaction mixture was extracted with ethyl acetate (2×10 ml). The combined organic layers were washed with brine, dried over anhydrous $Na_2SO_4$ and concentrated under reduced pressure. The crude product was triturated with n-pentane to give the title compound as brown solid (quantitative yield) which was used the next step without further purification. LCMS: m/z=304.3 [M+1].

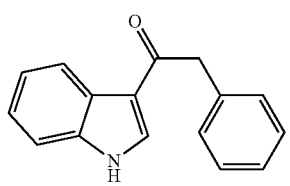

1-(1H-indol-3-yl)-2-phenylethan-1-one

Method 2. 1-(1H-indol-3-yl)-2-phenylethan-1-one:

To a stirred solution of 1-H-indole (10 g, 85.36 mmol) in dry DCM (260 ml) was added diethylaluminum chloride (128 ml, 1.0 M solution in hexane, 128 mmol) drop wise at 0° C. and the reaction mixture was stirred at 0° C. for 2 hours. To this mixture phenyl acetyl chloride (19.79 g, 128 mmol) was added dropwise at 0° C. and the resulting reaction mixture was stirred for 4 hours at 0° C. Saturated sodium bicarbonate solution was added slowly. The organic layer was separated and the aqueous layer was extracted with DCM (2×100 ml). The precipitate that was generated during the workup was filtered through a Buchner funnel and the resulting solid was stirred in DCM (200 ml) for 30 minutes. This suspension was then filtered again with a Buchner funnel. The combined organic extracts were washed with brine, dried over anhydrous Na₂SO₄ and concentrated under reduced pressure. The crude solid was triturated with 80:20 ethyl acetate:hexanes. The precipitate was collected by filtration and dried to obtain the title compound as brown solid (7.0 g, 34%). ¹H NMR (400 MHz, DMSO-d6): δ 4.16 (s, 2H), 7.15-7.22 (m, 3H), 7.29-7.37 (m, 4H), 7.48 (d, J=7.6 Hz, 1H), 8.17 (d, J=7.2 Hz, 1H), 8.55 (d, J=2.4 Hz, 1H), 12.02 (s, —NH). LCMS: m/z=236.2 [M+1].

was extracted with ethyl acetate (2×150 ml). The combined organic layers were washed with brine, dried over anhydrous Na₂SO₄ and concentrated under reduced pressure. The resulting residue was triturated with an 80:20 mixture of ethyl acetate:hexanes (2×50 ml). The solid was collected by filtration through Buchner funnel and dried to obtain the title compound as off white solid (7.0 g, 74%). ¹H NMR (400 MHz, DMSO-d6): δ 6.85 (s, 1H), 7.21-7.33 (m, 3H), 7.38 (t, J=7.6 Hz, 2H), 7.49 (d, J=8.4 Hz, 1H), 7.69 (d, J=7.2 Hz, 2H), 8.19 (d, J=8.8 Hz, 1H), 8.66 (d, J=3.2 Hz, 1H), 12.22 (s, —NH). LCMS: m/z=314.2.3 [M+1] and 316.2 [M+2].

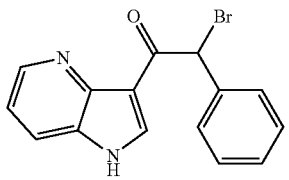 [SMILES: O=C(c1c[nH]c2cccnc12)C(Br)c1ccccc1]

2-bromo-2-phenyl-1-(1H-pyrrolo[3,2-b]pyridin-3-yl)ethan-1-one

Method 3. 2-bromo-2-phenyl-1-(1H-pyrrolo[3,2-b]pyridin-3-yl)ethan-1-one:

To a stirred solution of 2-bromo-2-phenylacetyl chloride (0.3 g, 25.42 mmol) in dry DCM (10 ml) under an atmosphere of nitrogen was added AlCl₃ (0.67 g, 50.84 mmol) at room temperature. The resulting reaction mixture was allowed to stir for 30 minutes at room temperature and 2-bromo-2-phenylacetyl chloride (0.89 g, 38.89 mmol) was added dropwise. The reaction mixture was stirred at room temperature for 1.5 hours. Saturated sodium bicarbonate solution (15 ml) was added and reaction mixture was extracted with ethyl acetate (2×15 ml). The combined organic layers were washed with brine (15 ml), dried over anhydrous Na₂SO₄ and concentrated under reduced pressure. The resulting residue was triturated with pentane (2×10 ml) to afford the title compound as solid (0.5 g, 62%) which was used in the next step without further purification. LCMS: m/z=315.3 [M+1].

Method 4

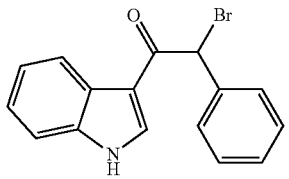 [SMILES: O=C(c1c[nH]c2ccccc12)C(Br)c1ccccc1]

2-bromo-1-(1H-indol-3-yl)-2-phenylethan-1-one

Method 4. 2-bromo-1-(1H-indol-3-yl)-2-phenylethan-1-one:

To a solution of 1-(1H-indol-3-yl)-2-phenylethan-1-one (7.0 g, 29.78 mmol) in dry THF (260 ml) under an atmosphere of nitrogen was added a solution of trimethylphenyl ammoniumtribromide (12.28 g, 32.76 mmol) dropwise in THF (125 ml) at 0° C. and the resulting reaction mixture was stirred for another 3 hours. Saturated sodium bicarbonate solution (150 ml) was added slowly and the reaction mixture

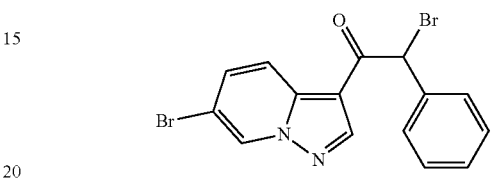

2-bromo-1-(6-bromopyrazolo[1,5-a]pyridin-3-yl)-2-phenylethan-1-one

Method 4. 2-bromo-1-(6-bromopyrazolo[1,5-a]pyridin-3-yl)-2-phenylethan-1-one:

To a solution of 1-(6-bromopyrazolo[1,5-a]pyridin-3-yl)-2-phenylethan-1-one (1 g, 3.20 mmol) in dry THF (12 ml) under an atmosphere of nitrogen was added a solution of trimethylphenylammonium tribromide (1.313 g, 3.50 mmol) in THF (6 ml) drop wise at room temperature and the resulting reaction mixture was stirred for another 12 hours. Water (35 ml) was added and reaction mixture was extracted with ethyl acetate (2×35 ml). The combined organic layers were washed with brine (35 ml), dried over anhydrous Na₂SO₄ and concentrated under reduced pressure. The resulting residue was purified by column chromatography to afford the title compound (1 g, 79%). LCMS: m/z=395.2 [M+1] and 397.0 [M+2].

Method 5

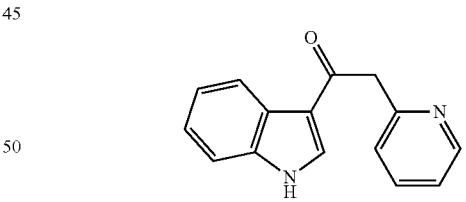

1-(1H-indol-3-yl)-2-(pyridin-2-yl)ethan-1-one

Method 5. 1-(1H-indol-3-yl)-2-(pyridin-2-yl)ethan-1-one:

To a stirred solution of diisopropylamine (0.816 g, 8.00 mmol) in THF (7 ml) was added n-BuLi (3.2 ml, 2.5 M solution in hexanes, 8.00 mmol) drop wise over 4 minutes under an atmosphere of argon gas at −78° C. Then the reaction was stirred at −78° C. for 30 minutes. To this reaction mixture, 2-methyl pyridine (0.76 g, 8.00 mmol) was added. Then the reaction mixture was warmed to −60° C. and stirred for 30 minutes. After 30 minutes, the reaction was warmed to 0° C. and stirred for 30 minutes. To the above reaction mixture was added methyl 1H-indole-3-carboxylate (0.35 g, 2.00 mmol) as a solution in THF (2 ml) and stirred at room temperature for 18 hours. After completion of the reaction ice cold water (10 ml) was added slowly at 0° C. and the aqueous layer was extracted with DCM (3×30 ml). The combined organic layers were washed with brine (30 ml), dried over anhydrous $Na_2SO_4$ and concentrated under reduced pressure. The resulting residue was purified by column chromatography to afford the title compound (0.380 g, 77%). LCMS: m/z=237.29 [M+1].

Method 6

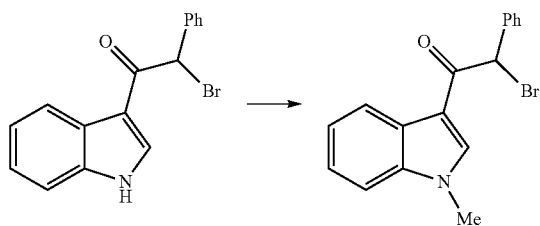 [SMILES: O=C(c1c[nH]c2ccccc12)C(Br)c1ccccc1 ; Cn1cc(C(=O)C(Br)c2ccccc2)c2ccccc21]

2-bromo-1-(1-methyl-1H-indol-3-yl)-2-phenylethan-1-one

Method 6. 2-bromo-1-(1-methyl-1H-indol-3-yl)-2-phenylethan-1-one:

To a solution of 2-bromo-1-(1H-indol-3-yl)-2-phenylethan-1-one (0.4 g, 1.28 mmol) in dry DMF (8 ml) under nitrogen atmosphere was added sodium hydride (0.034 g, 95%, 1.41 mmol) portion wise at 0° C. After 30 minutes, methyl iodide (0.096 ml, 1.54 mmol) was added at 0° C. and the resulting reaction mixture was stirred for 2 hours at room temperature. After completion of the reaction, ice cold water (15 ml) was added and reaction mixture was extracted with ethyl acetate (2×15 ml). The combined organic layers were washed with brine (15 ml), dried over anhydrous $Na_2SO_4$ and concentrated under reduced pressure. The resulting residue was purified by column chromatography to afford the title compound (0.2 g, 50%). LCMS: m/z=328.20 [M+1] and 330.20 [M+2].

Method 7

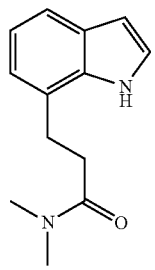

3-(1H-Indol-7-yl)-N,N-dimethylpropanamide

Method 7, step 1. (E)-3-(1H-Indol-7-yl)-N,N-dimethylacrylamide:

To a stirred solution of 7-bromo-1H-indole (0.46 g, 2.3 mmol) in dry DMF (2.6 ml) was added N,N-dimethylacrylamide (0.46 g, 4.6 mmol) at room temperature. To this mixture $Pd(OAc)_2$ (0.010 g, 0.04 mmol), triphenyl phosphine (0.024 g, 0.1 mmol), and diisopropylethyl amine (0.5 ml, 2.9 mmol) were added at room temperature. The reaction mixture was then purged with argon gas for 20 minutes. Then it was heated to 100° C. overnight. The reaction mixture was poured into ice cold water (50 ml) and extracted with ethyl acetate (3×50 ml). The combined organic layers were washed with brine (50 ml), dried over anhydrous $Na_2SO_4$ and concentrated under reduced pressure. The resulting residue was purified by silica gel chromatography to afford the title compound (0.43 g, 85%) as light brown solid. $^1$H NMR (400 MHz, DMSO-d6): δ 2.97 (s, 3H), 3.20 (s, 3H), 6.50 (s, 1H), 7.05 (t, J=7.6 Hz, 1H), 7.24 (d, J=15.2 Hz, 1H), 7.38 (t, J=2.8 Hz, 1H), 7.56-7.63 (m, 2H), 7.96 (d, J=8.0 Hz, 1H), 11.53 (s, 1H, —NH). LCMS: m/z=215.3 [M+1].

Method 7, step 2. 3-(1H-Indol-7-yl)-N,N-dimethylpropanamide:

(E)-3-(1H-indol-7-yl)-N,N-dimethyl acrylamide (0.43 g, 2.0 mmol) was taken up in ethanol (5 ml). To it 10% Pd/C (43 mg, 50% moisture) was added at room temperature. The reaction mixture was allowed to stir for 4 hours under an atmosphere of hydrogen gas. The reaction mixture was then diluted with methanol (25 ml) and DCM (25 ml) and filtered through a pad of celite washing with a mixture of methanol and DCM (1:1, 50 ml). The filtrate was concentrated under reduced pressure to afford the title compound as brown semi-solid (0.40 g, 92%). $^1$H NMR (400 MHz, DMSO-d6): 2.69 (t, J=7.6 Hz, 2H), 2.85 (s, 3H), 2.92 (s, 3H), 3.07 (t, J=8.4 Hz, 2H), 6.42 (t, J=2.4 Hz, 1H, —NH), 6.91-6.93 (m, 2H), 7.30 (t, J=2.4 Hz, 1H), 7.37-7.39 (m, 1H), 11.08 (s, 1H, —NH). LCMS: m/z=217.3 [M+1].

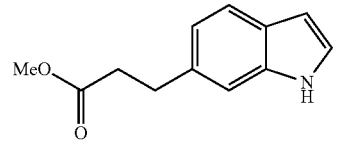 [SMILES: COC(=O)CCc1ccc2cc[nH]c2c1]

Methyl 3-(1H-indol-6-yl)propanoate

Method 7, step 1. Methyl (E)-3-(1H-indol-6-yl)acrylate:
To a stirred solution of 6-bromo-1H-indole (1.5 g, 7.6 mmol) in dry DMF (1.5 ml) was added methyl acrylate (0.79 g, 9.1 mmol) at room temperature. To this mixture $Pd(OAc)_2$ (0.085 g, 0.38 mmol), (o-tolyl)$_3$P (0.23 g, 0.76 mmol) and triethylamine (1.26 ml, 9.1 mmol) were added at room temperature. The reaction mixture was then purged with argon gas for 20 minutes. Then it was heated to 100° C. overnight. The reaction mixture was poured into ice cold water (50 ml) and extracted with ethyl acetate (3×50 ml). The combined organic layers were washed with brine (50 ml), dried over anhydrous $Na_2SO_4$ and concentrated under reduced pressure. The resulting residue was purified by silica gel column chromatography to afford the title compound (1.3 g, 84%) as light brown solid. $^1$H NMR (400 MHz, DMSO-d6): 3.73 (s, 3H), 6.48 (s, 1H), 6.55 (d, J=16.0

Hz, 1H), 7.41 (dd, J=0.8 Hz, 8.0 Hz, 1H), 7.47 (t, J=2.4 Hz, 1H), 7.58 (d, J=8.4 Hz, 1H), 7.70 (s, 1H), 7.79 (d, J=16.0 Hz, 1H), 11.38 (s, 1H, —NH).

Method 7, Step 2. Methyl 3-(1H-indol-6-yl)propanoate:

Methyl (E)-3-(1H-indol-6-yl)acrylate (1.7 g, 8.4 mmol) was taken in methanol (30 ml). To this solution 10% Pd/C (0. 170 g, 50% moisture) was added at room temperature. The mixture was allowed to stir for 4 hours under an atmosphere of hydrogen gas. The reaction mixture was then diluted with methanol (50 ml) and DCM (50 ml) and filtered through a pad of celite pad washing with mixture of methanol and DCM (1:1, 50 ml). The filtrate was concentrated under reduced pressure to afford the title compound as brown semi-solid (1.5 g, 89%). $^1$H NMR (400 MHz, DMSO-d6): 2.65 (t, J=7.6 Hz, 2H), 2.93 (t, J=7.6 Hz, 2H), 3.59 (s, 3H), 6.36 (s, 1H), 6.86 (dd, J=0.8 Hz, 8.0 Hz, 1H), 7.21 (s, 1H), 7.27 (t, J=2.8 Hz, 1H), 7.43 (d, J=8.0 Hz, 1H), 10.98 (s, 1H, —NH).

Method 8

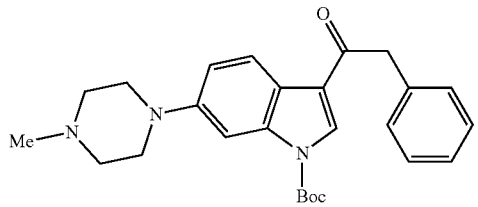 [SMILES: CN1CCN(c2ccc3c(C(=O)Cc4ccccc4)cn(C(=O)OC(C)(C)C)c3c2)CC1]

tert-Butyl 6-(4-methylpiperazin-1-yl)-3-(2-phenylacetyl)-1H-indole-1-carboxylate Method 8, step 1. 6-(4-Methylpiperazin-1-yl)-1H-indole:

A mixture of 6-bromo-1H-indole (2.0 g, 10.2 mmol) and N-methylpiperazine (1.2 g, 12.2 mmol) was taken in dry THF (20 ml). To the reaction mixture, Pd$_2$(dba)$_3$ (0.09 g, 0.10 mmol), X-Phos (0.14 g, 0.30 mmol) and LiHMDS (22.4 ml, 1M in THF, 22.4 mmol) was added at room temperature. The reaction mixture was purged with argon gas for 30 minutes and heated in a sealed tube at 65° C. overnight. After completion of reaction (monitored by TLC), the reaction mixture was treated with water (100 ml) and the mixture was extracted with ethyl acetate (2×150 ml). The combined organic layers were washed with brine (75 ml), dried over anhydrous Na$_2$SO$_4$ and concentrated under reduced pressure. The resulting residue was purified by silica gel chromatography to afford the title compound as an off-white solid (1.5 g, 68%). $^1$H NMR (400 MHz, DMSO-d6): δ 2.34 (s, 3H), 2.634 (bs, 4H), 3.12 (bs, 4H), 6.28 (s, 1H), 6.78 (d, J=8.4 Hz, 1H), 6.84 (s, 1H), 7.15 (t, J=2.8 Hz, 1H), 7.38 (d, J=8.8 Hz, 1H), 10.78 (s, 1H, —NH). LCMS: m/z=216.1 [M+1].

Method 8, step 2. 1-(6-(4-Methylpiperazin-1-yl)-1H-indol-3-yl)-2-phenylethan-1-one:

To a stirred solution of 6-(4-methylpiperazin-1-yl)-1H-indole (1.5 g, 6.9 mmol) in CS$_2$ (30 ml) under an atmosphere of nitrogen, AlCl$_3$ (1.86 g, 13.9 mmol) was added portion wise at 50° C. The reaction mixture was stirred for 30 minutes at 50° C. and phenyl acetyl chloride (1.61 g, 10.4 mmol) was added dropwise. The resulting reaction mixture was heated at 50° C. for 12 hours. Saturated sodium bicarbonate solution (100 ml) was added and reaction mixture was extracted with ethyl acetate (3×150 ml). The combined organic layers were washed with brine (75 ml), dried over anhydrous Na$_2$SO$_4$ and concentrated under reduced pressure. The resulting residue was purified by silica gel column chromatography to afford the title compound (0.6 g, 26%) as a light brown solid. $^1$H NMR (400 MHz, DMSO-d6): δ 2.24 (s, 3H), 2.51 (bs, 4H), 3.11 (t, J=4.8 Hz, 4H), 4.11 (s, 2H), 6.86 (d, J=1.6 Hz, 1H), 6.94 (dd, J=2 Hz, 8.8 Hz, 1H), 7.19-7.23 (m, 1H), 7.26-7.35 (m, 5H), 7.96 (d, J=8.8 Hz, 1H), 8.34 (d, J=2.8 Hz, 1H), 11.68 (s, 1H, —NH). LCMS: m/z=334.5 [M+1].

Method 8, step 3. tert-Butyl 6-(4-methylpiperazin-1-yl)-3-(2-phenylacetyl)-1H-indole-1-carboxylate:

To a solution of 1-(6-(4-methylpiperazin-1-yl)-1H-indol-3-yl)-2-phenylethan-1-one (0.6 g, 1.8 mmol) in DCM (6 ml) was added TEA (0.5 ml, 3.6 mmol) at room temperature. The mixture was then stirred for 30 minutes and before the addition of Boc-anhydride (0.47 g, 2.1 mmol). The reaction mixture was then stirred overnight at room temperature. After completion of reaction (monitored by TLC), the reaction mixture was treated with water (50 ml) and extracted with ethyl acetate (2×50 ml). The combined organic layers were washed with brine (50 ml), dried over anhydrous Na$_2$SO$_4$ and concentrated under reduced pressure. The resulting residue was purified by the silica gel chromatography to afford the title compound as light brown semi solid (0.61 g, 78%). $^1$H NMR (400 MHz, DMSO-d6): δ 1.68 (s, 9H), 2.24 (s, 3H), 2.51 (bs, 4H), 3.18 (bs, 4H), 4.29 (s, 2H), 7.10 (dd, J=2 Hz, 8.0 Hz, 1H), 7.24-7.27 (m, 1H), 7.32-7.35 (m, 4H), 7.59 (d, J=1.6 Hz, 1H), 8.01 (d, J=8.8 Hz, 1H), 8.55 (s, 1H). LCMS: m/z=434.7 [M+1].

Method 9

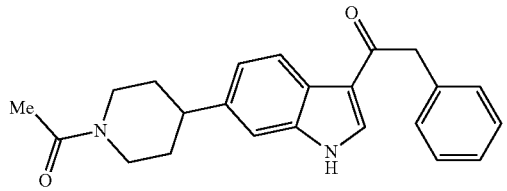 [SMILES: CC(=O)N1CCC(c2ccc3c(C(=O)Cc4ccccc4)c[nH]c3c2)CC1]

1-(6-(1-Acetylpiperidin-4-yl)-1H-indol-3-yl)-2-phenylethan-1-one

Method 9, step 1. 1-(6-(1-Acetyl-1,2,3,6-tetrahydropyridin-4-yl)-1H-indol-3-yl)-2-phenylethan-1-one:

A mixture of 1-(6-bromo-1H-indol-3-yl)-2-phenylethan-1-one (500 mg, 1.591 mmol), 1-(3,6-dihydropyridin-1(2H)-yl)ethan-1-one-4-boronate ester (401 mg, 1.591 mmol) and cesium carbonate (1.561 g, 4.774 mmol) in a mixture of 2:1 dioxane:water (10 ml) was purged for 20 minutes with argon. S-Phos Palladium G3 precatalyst (125 mg, 0.159 mmol) was added and purging was continued for another 10 minutes. The reaction mixture was heated in a sealed tube at 100° C. for 4 hours. After completion of the reaction (monitored by TLC), DCM (20 ml) was added to the reaction mixture and the solid was filtered and washed with 1:1 DCM:methanol (20 ml) to afford the title compound (400 mg 70%). $^1$H NMR (400 MHz, DMSO-d6): δ 2.04-2.08 (m, 3H), 2.50-2.60 (m, 2H), 3.63-3.69 (m, 2H), 4.09-4.11 (m, 1H), 4.15 (s, 3H), 6.18 (s, 1H), 7.21 (t, J=7.2 Hz, 1H), 7.28-7.37 (m, 5H), 7.45 (d, J=3.2 Hz, 2H), 8.09 (d, J=8.4 Hz, 1H), 8.52 (d, J=2.4 Hz, 1H), 12.01 (s, 1H, —NH). LCMS: in&=359.52 [M+1].

Method 9, step 2. 1-(6-(1-Acetylpiperidin-4-yl)-1H-indol-3-yl)-2-phenylethan-1-one:

To a clear solution of 1-(6-(1-acetyl-1,2,3,6-tetrahydropyridin-4-yl)-1H-indol-3-yl)-2-phenylethan-1-one (200 mg, 0.558 mmol) in 1:1:1 DCM:methanol:ethyl acetate (21 ml), 10% Pd/C (20 mg, 50% moisture) was added in an autoclave. The autoclave was closed and pressurized with hydrogen (75 psi) pressure and the reaction was stirred for 24 hours at room temperature. After completion of reaction (monitored by TLC), the reaction mixture was filtered through a pad of celite, washed with 1:1:1 DCM:methanol:ethyl acetate (51 ml). The filtrate was concentrated and dried to afford the title compound (190 mg, 94.5%). $^1$H NMR (400 MHz, DMSO-d6): δ 1.44-1.49 (m, 1H), 1.60-1.64 (m, 1H), 1.79-1.86 (m, 2H), 2.04 (s, 3H), 2.52-2.60 (m, 1H), 2.80-2.90 (m, 1H), 3.11-3.17 (m, 1H), 3.91-3.95 (m, 1H), 4.16 (s, 2H), 4.53-4.56 (m, 1H), 7.09 (d, J=8.0 Hz, 1H), 7.19-7.23 (m, 1H), 7.29-7.36 (m, 5H), 8.07 (d, J=8.0 Hz, 1H), 8.47 (d, J=3.2 Hz, 1H), 11.92 (s, —NH, 1H). LCMS: m/z=361.52 [M+1].

Method 10

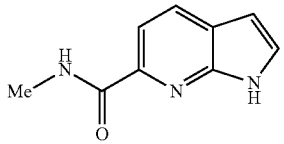 [SMILES: CNC(=O)c1ccc2cc[nH]c2n1]

N-Methyl-1H-pyrrolo[2,3-b]pyridine-6-carboxamide

Method 10. N-Methyl-1H-pyrrolo[2,3-b]pyridine-6-carboxamide:

To a stirred solution of 1H-pyrrolo[2,3-b]pyridine-6-carboxylic acid (1 g, 6.2 mmol) in dry DMF (10 ml) was added HATU (3.51 g, 9.3 mmol) portion wise at 0° C. Then methyl amine (3.7 ml, 2M in THF, 7.4 mmol) was added drop wise at 0° C. and the reaction was warmed to room temperature. The reaction mixture was stirred at room temperature for 15 minutes, then DIPEA (2.14 ml, 12.4 mmol) was added and the resulting mixture was stirred overnight. The reaction was quenched with ice cold water (40 ml) and the aqueous layer was extracted with ethyl acetate (2×40 ml). The combined organic layers were washed with brine (40 ml), dried over anhydrous Na$_2$SO$_4$ and concentrated under reduced pressure. The resulting residue was purified by silica gel chromatography to afford the title compound (0.6 g, 56%). LCMS: m/z=176.25 [M+1].

Method 11

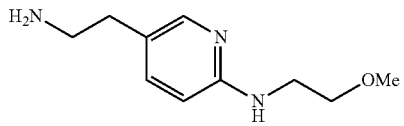 [SMILES: COCCNc1ccc(CCN)cn1]

5-(2-Aminoethyl)-N-(2-methoxyethyl)pyridin-2-amine

Method 11, step 1. 2-(6-((2-Methoxyethyl)amino)pyridin-3-yl)acetonitrile:

2-(6-Chloropyridin-3-yl) acetonitrile (1.0 g, 6.553 mmol), 2-methoxyethan-1-amine (0.984 g, 13.106 mmol) and DIPEA (1.69 g, 13.106 mmol) and DMSO (5 ml) were combined in a microwave tube. The tube was sealed and irradiated with microwaves at 150° C. for 8 hours. The reaction mixture was concentrated under reduced pressure and resulting residue was purified by silica gel chromatography to afford the title compound (0.160 g, 13%) as thick liquid. $^1$H NMR (400 MHz, DMSO-d6): 3.26 (s, 3H), 3.37-3.42 (m, 4H), 3.79 (s, 2H), 6.52 (d, J=8.8 Hz, 1H), 6.67 (t, J=5.2 Hz, 1H, —NH), 7.34 (dd, J=8.8, 2.4 Hz, 1H), 7.90 (d, J=1.6 Hz, 1H). LCMS: m/z=192.3 [M+1].

Method 11, step 2. 5-(2-Aminoethyl)-N-(2-methoxyethyl) pyridin-2-amine:

To a stirred solution 2-(6-(2-methoxyethylamino)pyridin-3-yl)acetonitrile (0.160 g, 0.836 mmol) and NiCl$_2$6H$_2$O (0.235 g, 0.083 mmol) in methanol (2 ml) was cooled to 0° C. Sodium borohydride (0.216 g, 5.859 mmol) was added in portions slowly at 0° C. After the addition was complete, the reaction mixture was stirred at room temperature for 8 hours. The reaction mixture was concentrated under reduced pressure and the resulting residue was purified by silica gel chromatography to afford the title compound (0.070 g, 43%) as thick liquid. $^1$H NMR (400 MHz, DMSO-d6): 2.44 (t, J=7.2 Hz, 2H), 2.67 (t, J=7.2 Hz, 2H), 3.26 (s, 3H), 3.37-3.40 (m, 2H), 3.43-3.45 (m, 2H), 6.30 (t, J=5.2 Hz, 1H, —NH), 6.45 (d, J=8.4 Hz, 1H), 7.23 (dd, J=8.4, 2.0 Hz, 1H), 7.79 (d, J=1.6 Hz, 1H); LCMS: m/z=196.3 [M+1].

Method 12

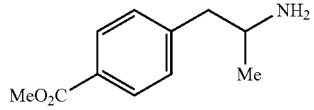 [SMILES: COC(=O)c1ccc(CC(C)N)cc1]

Methyl 4-(2-aminopropyl)benzoate

Method 12, step 1. Methyl (E)-4-(2-nitroprop-1-en-1-yl) benzoate:

To a stirred solution of methyl terephthalaldehyde (6.0 g, 36.55 mmol) in glacial acetic acid (16.8 ml), ammonium acetate (2.057 g, 26.68 mmol) and nitroethane (10.8 ml) were added at room temperature. The resulting reaction mixture was purged with nitrogen, sealed and heated at 105° C. for 4 hours. After completion of reaction (monitored by TLC), the reaction mixture was quenched with saturated sodium bicarbonate solution to adjust the pH to 7-8 and the mixture was extracted with ethyl acetate (2×50 ml). The combined organic layers were washed with brine (50 ml), dried over anhydrous Na$_2$SO$_4$ and concentrated under reduced pressure. The resulting residue was purified by silica gel chromatography to afford the title compound (4.5 g, 55%). $^1$H NMR (400 MHz, CDCl$_3$): δ 2.49 (s, 3H), 3.99 (s, 3H), 7.53 (d, J=8.4 Hz, 2H), 8.12 (s, 1H), 8.15 (d, J=8.4 Hz, 2H).

Method 12, step 2. Methyl 4-(2-aminopropyl)benzoate:

10% Pd/C (900 mg, 50% moisture) was added to a solution of methyl (E)-4-(2-nitroprop-1-en-1-yl)benzoate (4.5 g, 20.34 mmol) in 2:1 ethyl acetate:methanol (135 ml) in an autoclave. The reaction mixture was heated at 80° C. for 61 hours at 50 psi of hydrogen gas pressure. After completion of reaction (monitored by TLC), the reaction mixture was filtered through a pad of celite and washed with 1:1 ethyl acetate:methanol (100 ml). The filtrate was concentrated to give the crude product. The residue was purified by silica gel chromatography to afford the title compound (1.2 g, 30%). LCMS: m/z=194.31 [M+1].

Method 13

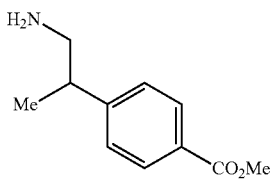 [SMILES: COC(=O)c1ccc(C(C)CN)cc1]

Methyl 4-(1-aminopropan-2-yl)benzoate

Method 13, step 1. Methyl 4-(prop-1-en-2-yl)benzoate:
Potassium-tert-butoxide (6.29 g, 56.11 mmol) was added in portions to a stirred solution of methyltriphenylphosphonium iodide (22.68 g, 56.11 mmol) in dry THF (35 ml) under an atmosphere of nitrogen at 0° C. The resulting reaction mixture was allowed to stir for 1 hour at 0° C. Then a solution of methyl 4-acetylbenzoate (5 g, 28.05 mmol) in THF (10 ml) was added at 0° C. The reaction mixture was stirred for 1 hour and then warmed to room temperature. The mixture was diluted with DCM (100 ml) and filtered through a pad of celite washing with DCM (50 ml). The filtrate was then concentrated under reduced pressure to give a residue which was purified by silica gel column chromatography to afford the title compound (4.2 g, 85%) as clear colorless liquid. $^1$H NMR (400 MHz, CDCl$_3$): δ 2.21 (s, 3H), 3.96 (s, 3H), 5.23 (s, 1H), 5.51 (s, 1H), 7.56 (d, J=8.8 Hz, 2H), 8.03 (d, J=8.4 Hz, 2H).

Method 13, step 2. Methyl (E)-4-(1-nitroprop-1-en-2-yl) benzoate:
To a stirred solution of methyl 4-(prop-1-en-2-yl)benzoate (1.0 g, 6.5 mmol) in dry DCE (10 ml) under nitrogen atmosphere was added AgNO$_2$ (3.0 g, 19.7 mmol), TEMPO (0.41 g, 2.6 mmol), and 4 Å Molecular Sieve (1.0 g) at room temperature. The resulting reaction mixture was stirred for 10 minutes at room temperature and then heated at 70° C. overnight. The reaction mixture was cooled to room temperature and diluted with DCM (50 ml). The reaction mixture was then filtered through a pad of celite and washed with DCM (50 ml). The filtrate was concentrated under reduced pressure and the resulting residue was purified by silica gel column chromatography to afford the title compound (0.99 g, 76%) as light yellow liquid. $^1$H NMR (400 MHz, CDCl$_3$): 2.69 (s, 3H), 3.96 (s, 3H), 7.36 (d, J=1.2 Hz, 1H), 7.56 (d, J=8.4 Hz, 2H), 8.14 (d, J=8.8 Hz, 2H).

Method 13, step 3. Methyl 4-(1-aminopropan-2-yl)benzoate:
To a solution of methyl-4-(1-nitroprop-1-en-2-yl)benzoate (0.99 g, 5.0 mmol) in dry THF (30 ml) cooled to 0° C. was added LiAlH$_4$ (10 ml, 1M in THF, 10 mmol) drop wise. The resulting reaction mixture was allowed to come to room temperature and stirred overnight. The reaction mixture was poured into saturated sodium bicarbonate solution (50 ml) and extracted with ethyl acetate (2×25 ml). The combined organic layers were washed with brine (20 ml), dried over anhydrous Na$_2$SO$_4$ and concentrated under reduced pressure. The resulting residue was purified by silica gel chromatography to afford the title compound (0.65 g, 76%) as yellow liquid. $^1$H NMR (400 MHz, DMSO-d6): 1.27 (m, 3H), 2.67-2.84 (m, 2H), 2.96-2.99 (m, 1H), 3.93 (s, 3H), 7.16-7.22 (m, 2H), 7.91 (d, J=7.2 Hz, 2H). LCMS: m/z=194.20 [M+1].

Method 14

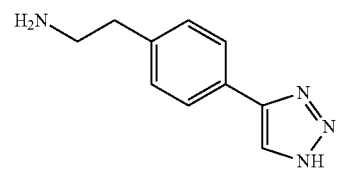 [SMILES: NCCc1ccc(-c2c[nH]nn2)cc1]

2-(4-(1H-1,2,3-Triazol-4-yl)phenyl)ethan-1-amine

Method 14, step 1. tert-Butyl (4-bromophenethyl)carbamate:
To a stirred solution of 2-(4-bromophenyl)ethan-1-amine (3.0 g, 14.99 mmol) in dry DCM (30 ml) was added TEA (4.55 g, 44.98 mmol) at 0° C. Boc anhydride (3.92 g, 17.98 mmol) was added dropwise at 0° C. and the resulting reaction mixture was allowed to come to room temperature over a period of 2 hours. The reaction mixture was poured into water (50 ml) and extracted with ethyl acetate (2×30 ml). The combined organic layers were washed with brine (50 ml), dried over anhydrous Na$_2$SO$_4$ and concentrated under reduced pressure. The resulting residue was purified by silica gel chromatography to afford the title compound (4.0 g, 89%) as off-white solid. $^1$H NMR (400 MHz, DMSO-d$_6$): 1.36 (s, 9H), 2.66 (t, J=7.2 Hz, 2H), 3.10-3.15 (m, 2H), 6.89 (S, 1H, —NH), 7.16 (d, J=8.4 Hz, 2H), 7.47 (d, J=8.4 Hz, 2H). LCMS: m/z=244.1 [M+1-56] and 246.1 [M+2-56].

Method 14, step 2. tert-Butyl (4-((trimethylsilyl)ethynyl) phenethyl)carbamate:
A mixture of tert-butyl (4-bromophenethyl) carbamate (4.0 g, 13.32 mmol), trimethylsilylacetylene (2.61 g, 26.64 mmol), Pd$_2$(dba)$_3$ (0.609 g, 0.67 mmol), P(t-Bu)$_3$ (0.135 g, 0.67 mmol) and TEA (2.69 g, 26.64 mmol) was dissolved in THF (40 ml) under nitrogen atmosphere. The reaction mixture was stirred at room temperature for 72 hours. The reaction mixture was poured in to water (75 ml) and extracted with ethyl acetate (2×40 ml). The combined organic layers were washed with brine (50 ml), dried over anhydrous Na$_2$SO$_4$ and concentrated under reduced pressure. The resulting residue was purified by silica gel chromatography to afford the title compound (2.0 g, 47%) as thick liquid. $^1$H NMR (400 MHz, DMSO-d$_6$): 0.23 (s, 9H), 1.36 (s, 9H), 2.70 (t, J=7.2 Hz, 2H), 3.12-3.16 (m, 2H), 6.89 (S, 1H, —NH), 7.20 (d, J=8.0 Hz, 2H), 7.37 (d, J=8.0 Hz, 2H); LCMS: m/z=262.4 [M+1-56].

Method 14, step 3. tert-Butyl (4-ethynylphenethyl)carbamate:
To a stirred solution of tert-butyl (4-((trimethylsilyl)ethynyl)phenethyl)carbamate (2.0 g, 6.29 mmol) in THF (20 ml) was added TBAF (3.28 g, 1 M in THF, 12.59 mmol) at 0° C. The resulting reaction mixture was allowed to warm to room temperature over a period of 2 hours. The reaction mixture was poured into saturated sodium bicarbonate solution (50 ml) and extracted with ethyl acetate (2×30 ml). The combined organic layers were washed with brine (30 ml), dried over anhydrous Na₂SO₄ and concentrated under reduced pressure. The resulting residue was purified by silica gel chromatography to afford the title compound (0.95 g, 61%) as thick liquid. ¹H NMR (400 MHz, DMSO-d₆): 1.36 (s, 9H), 2.70 (t, J=7.2 Hz, 2H), 3.11-3.17 (m, 2H), 4.12 (s, 1H), 6.89 (S, 1H, —NH), 7.21 (d, J=7.6 Hz, 2H), 7.40 (d, J=8.0 Hz, 2H); LCMS: m/z=190.3 [M+1-56].

Method 14, step 4. tert-Butyl (4-(1H-1,2,3-triazol-4-yl) phenethyl)carbamate:

A mixture of tert-butyl (4-ethynylphenethyl)carbamate (0.95 g, 3.87 mmol), sodium azide (0.503 g, 7.75 mmol), acetic acid (0.465 g, 7.75 mmol), sodium ascorbate (0.306 g, 1.54 mmol) and CuSO₄ (0.061 g, 0.387 mmol) in THF (10 ml) under nitrogen atmosphere was stirred and heated at 65° C. for 24 hours. The reaction mixture was poured into water (30 ml) and extracted with ethyl acetate (2×20 ml). The combined organic layers were washed with brine (20 ml), dried over anhydrous Na₂SO₄ and concentrated under reduced pressure. The resulting residue was purified by silica gel chromatography to afford the title compound (0.2 g, 19%) as solid. ¹H NMR (400 MHz, DMSO-d₆): 1.38 (s, 9H), 2.73 (t, J=7.2 Hz, 2H), 3.14-3.19 (m, 2H), 6.92 (t, J=5.2 Hz, 1H, —NH), 7.28 (d, J=7.6 Hz, 2H), 7.79 (d, J=7.2 Hz, 2H), 8.23 (s, 1H), 14.93 (s, 1H, —NH); LCMS: m/z=233.1 [M+1-56].

Method 14, step 5. 2-(4-(1H-1,2,3-triazol-4-yl)phenyl) ethan-1-amine:

To a stirred solution of tert-butyl (4-(1H-1,2,3-triazol-4-yl)phenethyl)carbamate (0.2 g, 0.693 mmol) in 1,4-dioxane (2 ml) was added a solution of HCl (4M in dioxane; 0.4 ml) drop wise at 0° C. The resulting mixture was allowed to warm to room temperature over a period of 2 hours. The reaction mixture was concentrated under reduced pressure to afford the title compound (0.1 g, 77%) as solid. LCMS: m/z=189.3 [M+1].

Method 15

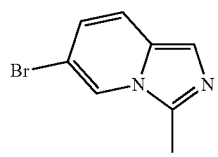

6-Bromo-3-methylimidazo[1,5-a]pyridine

Method 15. 6-Bromo-3-methylimidazo[1,5-a]pyridine-one: To a stirred solution of (5-bromopyridin-2-yl)methanamine (1 g, 5.34 mmol) in acetic anhydride (12 ml) was added p-toluene sulfonic acid (1.84 g, 10.69 mmol) portion wise at room temperature. The resulting reaction mixture was stirred at 100° C. for 2 hours. The reaction was quenched with 1N sodium hydroxide (20 ml) and extracted with ethyl acetate (2×30 ml). The combined organic layers were washed with water (20 ml) and brine (30 ml), dried over anhydrous Na₂SO₄ and concentrated under reduced pressure. The residue was purified by silica gel column chromatography to afford the title compound (0.75 g, 66%). LCMS: m/z=211.0 [M+1], 213.0 [M+2].

Method 16

N-Ethyl-3-(2-phenylacetyl)pyrazolo[1,5-a]pyridine-6-carboxamide

Method 16, step 1. Ethyl 3-(2-phenylacetyl)pyrazolo[1,5-a]pyridine-6-carboxylate:

To a stirred solution of 1-(6-bromopyrazolo[1,5-a]pyridin-3-yl)-2-phenylethan-1-one (2.8 g, 8.88 mmol) in ethanol (120 ml) in an autoclave was added PdCl₂(dppf) (1.29 g, 1.77 mmol), xanthphos (2.31 g, 3.99 mmol) and triethylamine (7.41 ml, 53.3 mmol). Then autoclave was filled with CO gas (200 PSI). The reaction mixture was stirred at 100° C. overnight. The reaction mixture was diluted with ethyl acetate (30 ml) and filtered through a pad of celite. The resulting filtrate was concentrated under reduced pressure. The residue was purified by silica gel column chromatography to afford the title compound (1.75 g, 63%). LCMS: m/z=309.2 [M+1].

Method 16, step 2. N-Ethyl-3-(2-phenylacetyl)pyrazolo [1,5-a]pyridine-6-carboxamide:

To a mixture of 3-(2-phenylacetyl)pyrazolo[1,5-a]pyridine-6-carboxylate (1 g, 3.20 mmol) and ethyl amine (3.2 ml, 2M solution in THF, 6.40 mmol) in toluene (12 ml) was added trimethylaluminium (6.4 ml, 2M in toluene, 6.4 mmol) at 0° C. The reaction mixture was heated at 100° C. for 16 hours. The reaction mixture was quenched by the addition of water (20 ml) and then extracted with ethyl acetate (2×30 ml). The combined organic layers were washed with brine (10 ml), dried over anhydrous Na₂SO₄ and concentrated under reduced pressure. The resulting residue was purified by silica gel column chromatography to afford the title compound (0.75 g, 75%). LCMS: m/z=308.3 [M+1].

Method 17

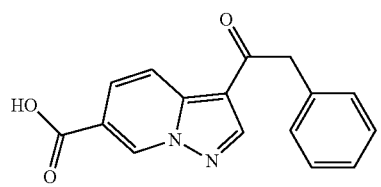 [SMILES: O=C(O)c1ccc2c(C(=O)Cc3ccccc3)cnn2c1]

3-(2-Phenylacetyl)pyrazolo[1,5-a]pyridine-6-carboxylic acid

Method 17. 3-(2-Phenylacetyl)pyrazolo[1,5-a]pyridine-6-carboxylic acid:

To a stirred solution of ethyl 3-(2-phenylacetyl)pyrazolo [1,5-a]pyridine-6-carboxylate (0.7 g, 2.2 mmol) in MeOH (10 ml) was added LiOH (2.8 ml, 2M Solution in H₂O). The resulting reaction mixture was stirred at room temperature for 1 hour. After completion of the reaction, the reaction mixture was concentrated, diluted with water (10 ml) and extracted with ethyl acetate (2×10 ml) to remove any impurities. The pH of the aqueous layer was then adjusted to 6 with 1N HCl and the resulting mixture was extracted with ethyl acetate (2×40 ml). The combined organic layers were washed with brine (20 ml), dried over anhydrous Na$_2$SO$_4$ and concentrated under reduced pressure to afford the title compound (0.60 g, 94%). LCMS: m/z=281.1 [M+1].

Method 18

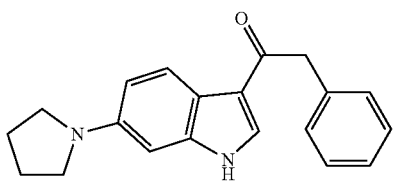 [SMILES: O=C(Cc1ccccc1)c1c[nH]c2cc(N3CCCC3)ccc12]

2-Phenyl-1-(6-(pyrrolidin-1-yl)-1H-indol-3-yl)ethan-1-one

Method 18, step 1. 1-(6-Bromo-1-(phenylsulfonyl)-1H-indol-3-yl)-2-phenylethan-1-one:

To a solution of 1-(6-bromo-1H-indol-3-yl)-2-phenylethan-1-one (1 g, 3.18 mmol) in dry DMF (10 ml) under an atmosphere of nitrogen was added sodium hydride (0.087 g, 95%, 3.66 mmol) portion wise at 0° C. After 30 minutes, benzenesulphonyl chloride (0.616 g, 3.50 mmol) was added at 0° C. and the resulting reaction mixture was stirred at room temperature for 2 hours. After completion of the reaction, a mixture of ice-cold water (25 ml) was added to the reaction mixture and extracted with ethyl acetate (2×25 ml). The combined organic layers were washed with brine (25 ml), dried over anhydrous Na$_2$SO$_4$ and concentrated under reduced pressure. The resulting residue was purified by column chromatography to afford the title compound (1.3 g, 89%). $^1$H NMR (400 MHz, DMSO-d6): δ 4.38 (s, 2H), 7.23-7.26 (m, 1H), 7.32-7.40 (m, 4H), 7.54-7.60 (m, 1H), 7.65-7.72 (m, 2H), 7.78-7.82 (m, 1H), 8.05-8.11 (m, 2H), 8.18 (d, J=7.6 Hz, 2H), 9.08 (s, 1H,). LCMS: m/z=454.2 [M+1].

Method 18, step 2. 2-phenyl-1-(6-(pyrrolidin-1-yl)-1H-indol-3-yl)ethan-1-one:

To a stirred solution of 1-(6-bromo-1-(phenylsulfonyl)-1H-indol-3-yl)-2-phenylethan-1-one (1.1 g, 2.42 mmol) in DMSO (5 ml), pyrrolidine (1.72 g, 24.2 mmol), cesium carbonate (0.789 g, 2.42 mmol), CuI (0.046 g, 0.24 mmol), and L-proline (0.306 g, 2.66 mmol) were added. The reaction mixture was heated at 95° C. overnight. The reaction was quenched with water (20 ml) and the aqueous layer was extracted with ethyl acetate (3×20 ml). The combined organic layers were washed with brine (30 ml), dried over anhydrous Na$_2$SO$_4$ and concentrated under reduced pressure. The resulting residue was purified by silica gel chromatography to afford the title compound (0.2 g, 27%). $^1$H NMR (400 MHz, DMSO-d6): δ 1.98 (bs, 4H), 3.25 (bs, 4H), 4.09 (s, 2H), 6.48 (s, 1H), 6.57 (d, J=8.4 Hz, 1H), 7.19-7.23 (m, 1H), 7.28-7.36 (m, 4H), 7.92 (d, J=8.8 Hz, 1H), 8.27 (d, J=2.4 Hz, 1H), 11.52 (s, 1H, —NH). LCMS: m/z=305 [M+1].

Method 19

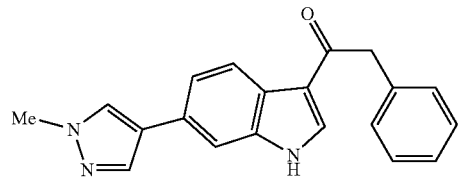 [SMILES: Cn1cc(-c2ccc3c(C(=O)Cc4ccccc4)c[nH]c3c2)cn1]

1-(6-(1-Methyl-1H-pyrazol-4-yl)-1H-indol-3-yl)-2-phenylethan-1-one

Method 19. 1-(6-(1-Methyl-1H-pyrazol-4-yl)-1H-indol-3-yl)-2-phenylethan-1-one:

To a stirred solution of 1-(6-bromo-1H-indol-3-yl)-2-phenylethan-1-one (2.0 g, 6.37 mmol) and 1-methyl-4-(4,4,5,5-tetramethyl-1,3,2-dioxaborolan-2-yl)-1H-pyrazole (2.26 g, 10.83 mmol) in 4:1 dioxane:water (50 ml) was added cesium carbonate (6.27 g, 19.11 mmol). The reaction mixture was purged for 20 minutes with argon. To the reaction mixture, Pd(dppf)Cl$_2$ (0.47 g, 10.40 mmol) was added and purging was continued for another 10 minutes. The reaction mixture was heated at 100° C. for 1.5 hours. The reaction mixture was poured into water (30 ml) and extracted with ethyl acetate (2×40 ml). The combined organic layers were washed with brine (25 ml), dried over anhydrous Na$_2$SO$_4$ and concentrated under reduced pressure. The residue was purified by column chromatography to afford the title compound (1.65 g, 82%) as solid. LCMS: m/z=316.39 [M+1].

Method 20

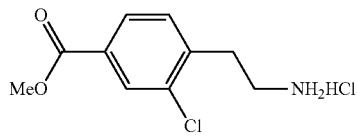

Methyl 4-(2-aminoethyl)-3-chlorobenzoate hydrochloride

Method 20, step 1. Methyl 3-chloro-4-(cyanomethyl)benzoate:

To a stirred solution of methyl 4-(bromomethyl)-3-chlorobenzoate (3 g, 11.39 mmol) in dry acetonitrile (30 ml) was added TMSCN (2.14 ml, 17.08 mmol) and TBAF (17.2 ml, 1M in THF, 17.08 mmol) at room temperature under an atmosphere of nitrogen. Then the reaction mixture was stirred for 15 minutes at room temperature. The reaction mixture was diluted with water (30 ml) and extracted with ethyl acetate (2×50 ml). The combined organic layers were washed with brine (50 ml), dried over anhydrous Na$_2$SO$_4$ and concentrated under reduced pressure. The resulting residue was purified by silica gel chromatography to afford the title compound (1.3 g, 55%). $^1$H NMR (400 MHz, DMSO-d$_6$): 3.94 (s, 3H), 4.23 (s, 2H), 7.73 (d, J=8 Hz, 1H), 7.90-8.10 (m, 2H).

Method 20, step 2. Methyl 4-(2-((tert-butoxycarbonyl)amino)ethyl)-3-chlorobenzoate:

To a stirred solution of methyl 3-chloro-4-(cyanomethyl)benzoate (1.5 g, 7.18 mmol) in methanol (15 ml) was added $NiCl_2 6H_2O$ (1.87 g, 7.90 mmol) and $NaBH_4$ (1.87 g, 50.26 mmol) carefully at 0° C. Then reaction mixture was stirred at room temperature for 15 minutes. The reaction mixture was cooled to 0° C. and triethylamine (2.0 ml, 14.36 mmol) and $Boc_2O$ (3.14 g, 14.36 mmol) were added and the reaction was stirred at room temperature overnight. The reaction mixture was diluted with ethyl acetate and filtered through a pad of celite. The combined organic layers were concentrated under reduced pressure and the residue was purified by silica gel chromatography to afford the title compound (1.5 g, 66%). LCMS: m/z=258.1 [M+1-56].

Method 20, step 3. Methyl 4-(2-aminoethyl)-3-chlorobenzoate hydrochloride:

To a stirred solution of methyl 4-(2-((tert-butoxycarbonyl)amino)ethyl)-3-chlorobenzoate (1.5 g, 4.78 mmol) in dioxane (15 ml) was added a solution of 4M HCl in dioxane (15 ml, 10 vol.) drop wise at 0° C. The resulting mixture was allowed to warm to room temperature over a period of 2 hours. The reaction mixture was concentrated under reduced pressure to afford the title compound (1.1 g, 91%) as solid. LCMS: m/z=214.32 [M+1].

Method 21

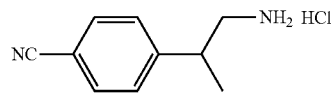

4-(1-Aminopropan-2-yl)benzonitrile hydrochloride

Method 21, step 1. Ethyl (E,Z)-3-(4-cyanophenyl)but-2-enoate:

To a stirred solution of potassium tert-butoxide (10.09 g, 89.7 mmol) in dry THF (90 ml) was added triethyl phosphonoacetate (20.08 g, 89.7 mmol) at 0 to −5° C. under an atmosphere of nitrogen. Then the reaction mixture was stirred for 15 minutes at the same temperature. The reaction was warmed to room temperature and stirred for 1 hour. 4-acetylbenzonitrile (10.0 g, 69.0 mmol) in THF was added to the reaction mixture and the reaction was heated to 70° C. for 3 hours. The reaction mixture was treated with 1N HCl and concentrated under reduced pressure. The aqueous layer was extracted with ethyl acetate (2×50 ml). The combined organic layers were washed with brine (50 ml), dried over anhydrous $Na_2SO_4$ and concentrated under reduced pressure. The resulting residue was purified by silica gel chromatography to afford the title compound (8.5 g, 58%) as a 2:1 mixture of the E- and Z-isomers. $^1$H NMR (400 MHz, DMSO-d6): 1.15 (t, J=6.8 Hz, 1.5H), 1.36 (t, J=6.8 Hz, 3H), 2.21 (s, 1.5H), 2.60 (s, 3H), 4.05 (q, J=7.1 Hz, 1H), 4.27 (q, J=7.2 Hz, 2H), 6.01 (s, 0.5H), 6.19 (s, 1H), 7.30-7.71 (m, 6H).

Method 21, step 2. Ethyl 3-(4-cyanophenyl)butanoate:

To a stirred solution of ethyl (E,Z)-3-(4-cyanophenyl)but-2-enoate (8.0 g, 37.2 mmol) in 1:4 Methanol:Ethyl Acetate (140 ml) was added Pd/C (0.8 g, 10% w/w; 50% moisture) carefully. Then reaction mixture was stirred at room temperature under $H_2$ gas atmosphere for 3 hours. After completion of reaction the reaction mixture was diluted with ethyl acetate (50 ml) and filtered through a pad of celite. The combined organic layers were concentrated under reduced pressure to afford the title compound (4.5 g, 56%). $^1$H NMR (400 MHz, $CDCl_3$): 1.23 (t, J=7.2 Hz, 3H), 1.33 (d, J=6.8, 3H), 2.62 (dd, J=7.6 Hz, 1.2 Hz, 2H), 3.70 (q, J=7.2 Hz, 1H), 4.07-4.15 (m, 2H), 7.37 (d, J=8.0 Hz, 2H), 7.37 (d, J=8.4 Hz, 2H).

Method 21, step 3. 3-(4-cyanophenyl)butanoic acid:

To a stirred solution of ethyl 3-(4-cyanophenyl)butanoate (4.5 g, 20.71 mmol) in a mixture of $MeOH:THF:H_2O$ (4:2:1, 100 ml) was added LiOH (3.48 g, 82.95 mmol) at 5 to 10° C. The resulting reaction mixture was stirred at room temperature for 1.5 hours. After completion of reaction, the reaction solvent was removed under reduced pressure. The crude material was dissolved in water (10 ml) and extracted with ethyl acetate (2×15 ml) to remove impurities. The pH of the aqueous layer was adjusted to 3-4 with concentrated HCl. The desired compound precipitated during this process. The solid compound was filtered off to afford the title compound (3.8 g, 97%) as white solid. $^1$H NMR (400 MHz, DMSO-$d_6$): 1.23 (d, J=6.8, 3H), 2.58 (d, J=7.6 Hz, 2H), 3.24 (q, J=7.2, 1H), 7.49 (d, J=8.4 Hz, 2H), 7.77 (d, J=8.4 Hz, 2H), 12.15 (s, 1H).

Method 21, step 4. tert-Butyl (2-(4-cyanophenyl)propyl)carbamate:

To a stirred solution of 3-(4-cyanophenyl)butanoic acid (5 g, 26.45 mmol) in tert-butanol (65 ml) was added triethylamine (11.04 ml, 79.36 mmol) at room temperature. Then the reaction mixture cooled to 5 to 10° C. and DPPA (12.30 g, 44.97 mmol) was added drop wise. After formation of the acylazide was confirmed by the TLC the reaction was stirred at 90° C. overnight. The reaction mixture was quenched with water (40 ml) and extracted with ethyl acetate (2×40 ml). The combined organic layers were washed with brine (25 ml), dried over anhydrous $Na_2SO_4$ and concentrated under reduced pressure. The resulting residue was purified by silica gel chromatography to afford the title compound (4.5 g, 66%) as solid. $^1$H NMR (400 MHz, DMSO-$d_6$): 1.17 (d, J=6.8 Hz, 2H), 1.33 (s, 9H), 2.90-3.00 (m, 1H), 3.04-3.15 (m, 2H), 6.91 (t, J=5.2 Hz, 1H, —NH), 7.42 (d, J=8.4 Hz, 2H), 7.77 (d, J=7.2 Hz, 2H).

Method 21, step 5. 4-(1-Aminopropan-2-yl)benzonitrile hydrochloride:

To a stirred solution of tert-butyl (2-(4-cyanophenyl)propyl)carbamate (4.5 g, 17.29 mmol) in methanol (9 ml) was added a solution of 4M HCl in dioxane (10.8 ml, 2.4 vol.) drop wise at 0° C. The resulting reaction mixture was warmed to room temperature over a period of 2 hours. The reaction mixture was concentrated under reduced pressure to afford the title compound (2.81 g, 83%) as solid. $^1$H NMR (400 MHz, DMSO-$d_6$): 1.28 (d, J=6.8 Hz, 2H), 3.03 (d, J=5.6 Hz, 2H), 3.15-3.26 (m, 1H), 7.55 (d, J=8.0 Hz, 2H), 7.83 (d, J=8.0 Hz, 2H), 8.21 (s, 3H). LCMS: m/z=161.6 [M+1].

Method 22

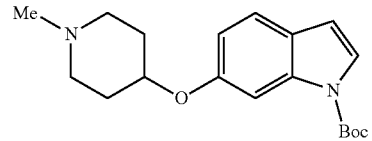 [SMILES: CN1CCC(Oc2ccc3ccn(C(=O)OC(C)(C)C)c3c2)CC1]

tert-Butyl 6-((1-methylpiperidin-4-yl)oxy)-1H-indole-1-carboxylate

Method 22, step 1. tert-Butyl 6-(benzyloxy)-1H-indole-1-carboxylate:

To a solution of 6-(benzyloxy)-1H-indole (5 g, 22.3 mmol) in DCM (75 ml) was added Boc₂O (5.3 g, 24.6 mmol) and DMAP (1.3 g, 11.2 mmol). The reaction mixture was allowed to stir at room temperature for 2 hours. After completion of the reaction, the reaction mixture was diluted with water (150 ml) and extracted with ethyl acetate (2×100 ml). The combined organic layers were washed with brine (100 ml), dried over anhydrous Na₂SO₄ and concentrated under reduced pressure. The resulting residue was purified by silica gel chromatography to afford the title compound as a solid (6.0 g, 82%). ¹H NMR (400 MHz, DMSO-d6): δ 1.62 (s, 9H), 5.16 (s, 2H), 6.64 (d, J=3.6 Hz, 1H), 6.97 (dd, J=8.4 Hz, 2.0 Hz, 1H), 7.34-7.55 (m, 7H), 7.73 (s, 1H). LCMS: m/z=324.3 [M+1].

Method 22, step 2. tert-Butyl 6-hydroxy-1H-indole-1-carboxylate:

To a stirred solution of tert-butyl 6-(benzyloxy)-1H-indole-1-carboxylate (5.5 g, 17.0 mmol) in ethyl acetate (100 ml) was added Pd/C (0.5 g, 10% of w/w; 50% moisture) and ammonium formate (5.3 g, 85.0 mmol). The resulting reaction mixture was stirred at 60° C. for 1 hour. After completion of the reaction, the mixture was filtered through a pad of celite pad eluting with ethyl acetate and the eluent was concentrated under reduced pressure. The residue was purified by silica gel chromatography to afford the title compound (3.4 g, 85%) as a solid. ¹H NMR (400 MHz, DMSO-d6): δ 1.62 (s, 9H), 6.56-6.57 (d, J=3.6 Hz, 1H), 6.72 (dd, J=8.4 Hz, 2.0 Hz, 1H), 7.37-7.39 (d, J=8.8 Hz, 1H), 7.44-7.45 (d, J=3.6 Hz, 1H), 7.52 (s, 1H), 9.45 (s, 1H, —OH). LCMS: m/z=178.1 [M+1-56].

Method 22, step 3. tert-butyl 6-((1-methylpiperidin-4-yl)oxy)-1H-indole-1-carboxylate:

To a solution of tert-butyl 6-hydroxy-1H-indole-1-carboxylate (1.1 g, 4.2 mmol) in THF (15 ml) was added 1-methylpiperidin-4-ol (0.98 g, 8.5 mmol), triphenylphosphine (2.2 g, 8.5 mmol) and DIAD (1.7 g, 8.5 mmol) at 0° C. The resulting reaction mixture was stirred at room temperature for 16 hours. After completion of the reaction, the reaction mixture was diluted with water (50 ml) and extracted with ethyl acetate (2×50 ml). The combined organic layers were washed with brine (50 ml), dried over anhydrous Na₂SO₄ and concentrated under reduced pressure. The resulting residue was purified by silica gel chromatography to afford the title compound (1.1 g, 77%) as a solid. LCMS: m/z=331.5 [M+1].

Method 23

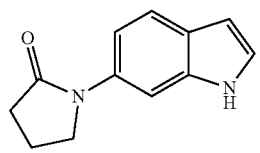 [SMILES: O=C1CCCN1c1ccc2cc[nH]c2c1]

1-(1H-indol-6-yl)pyrrolidin-2-one

Method 23, step 1. 4-Chloro-N-(1H-indol-6-yl)butanamide:

To a stirred solution of 1H-indol-6-amine (1.0 g, 7.5 mmol) and triethylamine (0.92 g, 9.1 mmol) in DCM (20 ml) at 0° C. was added 4-chlorobutanoyl chloride (1.17 g, 8.3 mmol). The reaction mixture was stirred at room temperature for 2 hours. After completion of the reaction, the reaction was quenched with saturated NaHCO₃ and extracted with DCM (2×30 ml). The combined organic layers were dried over anhydrous Na₂SO₄ and concentrated under reduced pressure to afford the title compound (0.5 g, 28%). LCMS: m/z=237.2 [M+1].

Method 23, step 2. 1-(1H-Indol-6-yl)pyrrolidin-2-one:

To a stirred solution of 4-chloro-N-(1H-indol-6-yl)butanamide (0.5, 2.12 mmol) in DMF (5 ml) at 0° C. was added NaH (0.107 g, 95%, 4.24 mmol). The reaction mixture was stirred at room temperature for 1 hour. After completion of the reaction, reaction mixture was quenched with water and extracted with ethyl acetate (2×15 ml). The combined organic layers were dried over anhydrous Na₂SO₄ and concentrated under reduced pressure to afford the title compound (0.35 g, 83%). LCMS: m/z=201.3 [M+1].

Method 24

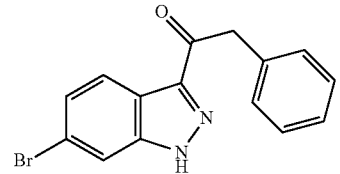 [SMILES: O=C(Cc1ccccc1)c1n[nH]c2cc(Br)ccc12]

1-(6-Bromo-1H-indazol-3-yl)-2-phenylethan-1-one
(CL-A-643)

Method 24, step 1. 6-Bromo-1H-indazole-3-carboxylic acid:

To a stirred solution of sodium hydroxide (0.48 g, 12.0 mmol) in water (8 ml) was added 6-bromoisatin (2.5 g, 11.0 mmol). The reaction mixture was gently heated until it became dark red. This dark-red solution was cooled to 0° C. and mixed with a solution of sodium nitrite (0.76 g, 11 mmol) in water (3 ml) at 0° C. The combined solution was then added to a rapidly stirred solution of sulphuric acid (1.1 ml, 22.0 mmol) in water (42 ml) via dropping funnel at 0° C. The rate of addition was maintained such that the temperature of reaction mixture should not rise above 5° C. After completion of addition, the brownish-yellow solution was stirred for 15 minutes. Then a cold solution of stannous chloride dihydrate (6 g, 26.5 mmol) in concentrated hydrochloric acid (10 ml) was added from a dropping funnel to the stirred solution of the diazo-compound. The mixture was stirred for another 1 hour after the addition was complete. The crude product, a yellow to brown paste, was collected on a Buckner funnel (1.75 g, 65%) and used for the subsequent step directly without further purification. LCMS: m/z=239.16 [M−1], 241.20 [M+1].

Method 24, step 2. 6-Bromo-N-methoxy-N-methyl-1H-indazole-3-carboxamide:

To a stirred solution of 6-bromo-1H-indazole-3-carboxylic acid (1.0 g, 4.16 mmol) in DMF (10 ml) at room temperature was added CDI (0.742 g, 4.58 mmol). The reaction mixture was stirred at 65° C. for 1 hour. The reaction was cooled to room temperature and hydroxylamine hydrochloride (0.447 g, 4.58 mmol) was added. The resulting reaction mixture was stirred at 65° C. for 12 hours. After completion of the reaction, the reaction was diluted with water (30 ml) and extracted with ethyl acetate (2×35 ml). The combined organic layers were dried over anhydrous $Na_2SO_4$ and concentrated under reduced pressure to afford the title compound (0.35 g, 30%). LCMS: m/z=284.0 [M+1], 286.0 [M+2].

Method 24, step 3. 1-(6-Bromo-1H-indazol-3-yl)-2-phenylethan-1-one:

To a stirred solution of 6-bromo-N-methoxy-N-methyl-1H-indazole-3-carboxamide (0.284, 1.0 mmol) in THF (3 ml) cooled to 0° C. was added benzylmagnesium bromide (2 ml, 2M solution in THF 4.0 mmol). The reaction mixture was stirred at 0° C. for 2 hours. After completion of the reaction, the reaction mixture was quenched with saturated aqueous ammonium chloride solution. The aqueous layer was extracted with ethyl acetate. The combined organic extracts were dried over $Na_2SO_4$, filtered, and concentrated under reduced pressure to afford the title compound (0.29 g, 92%). LCMS: m/z=315.0 [M+1].

Scheme 1

The starting materials required for the synthesis of examples prepared using Scheme 1 were generally prepared using methods 1 through 4. Starting materials for methods 1 through 4 were either commercially available or were synthesized using methods 5 through 24.

Example 1

(S)- and (R)-4-(2-((2-oxo-1-phenyl-2-(6-(trifluoromethyl)-1H-indol-3-yl) ethyl) amino) ethyl)benzenesulfonamide Scheme 1. (S)- and (R)-4-(2-((2-oxo-1-phenyl-2-(6-(trifluoromethyl)-1H-indol-3-yl) ethyl) amino) ethyl)benzenesulfonamide:

A mixture of 2-bromo-2-phenyl-1-(6-(trifluoromethyl)-1H-indol-3-yl)ethan-1-one (0.96 g, 2.51 mmol), 4-(2-aminoethyl)benzene sulfonamide (1.00 g, 5.02 mmol) and $Et_3N$ (0.71 ml, 5.02 mmol) in DMF (19 ml) was heated for 2-3 hours at 60° C. The reaction mixture was poured into ice cold water (25 ml) and extracted with ethyl acetate (2×25 ml). The combined organic layers were washed with brine, dried over anhydrous $Na_2SO_4$ and concentrated under reduced pressure. The residue was purified by reverse phase HPLC to afford the title compound (0.060 g) as an off-white solid in racemic form.

The racemic title compound was resolved by chiral SFC-HPLC (Chiralpak AD-H; 22% MeOH with 0.1% DEA in $CO_2$) to furnish the enantiopure compounds. The faster-eluting enantiomer of the title compound was obtained as a solid (Isomer 1): $^1H$ NMR (400 MHz, DMSO-d6): δ 2.63-2.74 (m, 2H), 2.77-2.84 (m, 2H), 5.33 (s, 1H), 7.19-7.21 (m, 1H), 7.26-7.30 (m, 2H), 7.38 (d, J=8.4 Hz, 2H), 7.45-7.49 (m, 3H), 7.71 (d, J=8.4 Hz, 2H), 7.78 (s, 1H), 8.34 (d, J=8.4 Hz, 1H), 8.80 (s, 1H), 11.99 (s, —NH). LCMS: m/z=502.5 [M+1]. The slower-eluting enantiomer of the title compound was obtained as a solid (Isomer 2): $^1H$ NMR (400 MHz, DMSO-d6): δ 2.61-2.74 (m, 2H), 2.77-2.84 (m, 2H), 5.33 (s, 1H), 7.17-7.21 (m, 1H), 7.26-7.30 (m, 2H), 7.37 (d, J=8.4 Hz, 2H), 7.45-7.48 (m, 3H), 7.71 (d, J=8.0 Hz, 2H), 7.78 (s, 1H), 8.34 (d, J=8.0 Hz, 1H), 8.80 (s, 1H), 11.95 (s, —NH). LCMS: m/z=502.5 [M+1].

The following compounds were prepared using similar procedures to those described for Example 1 using the appropriate starting materials. The separated isomers for each compound are listed in the order to which they elute. For example, in instances where there are two isomers, Isomer 1 is the faster eluting isomer. In instances where there are four isomers, Isomer 1 is the fastest eluting isomer followed by Isomer 2, then Isomer 3, and then Isomer 4. This convention is followed throughout the entirety of the application. The stereochemical representation (i.e., R or S) of each isomer of a compound is not drawn in the table and rather named to make clear that support for both is intended. Chiral carbon atom(s) are designated by the asterisk (*). In instances where a compound is racemic, it has been noted as such. In one aspect, the present disclosure relates to the racemic form of any compound described herein.

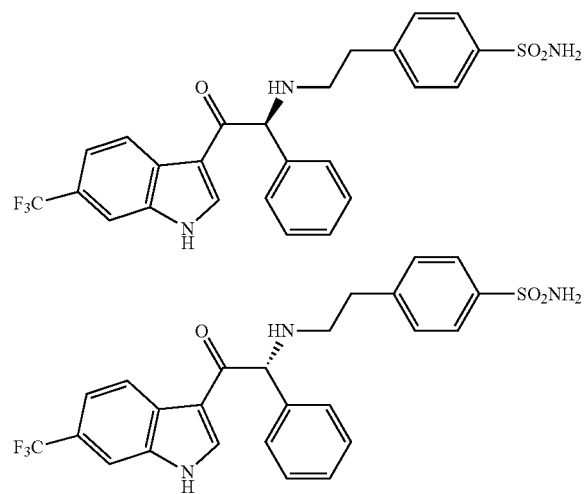

TABLE 1

| Example Nos. | Structure (Methods and Schemes for Preparation) | IUPAC Name | Exact Mass [M + 1] | Chiral Column; Mobile Phase |
|---|---|---|---|---|
| 2 Isomer 1 Isomer 2 | | (S)- and (R)-1-(1H-indol-3-yl)-2-(phenethylamino)-2-phenylethan-1-one | Calc'd 355.2, Found 355.3 and 355.3 | CHIRALPAK AD; 18% (70:30 MeOH:IPA) in hexanes + 0.1% DEA |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 3 Isomer 1 Isomer 2 | | (S)- and (R)-2-((2-chlorophenethyl)amino)-1-(1H-indol-3-yl)-2-phenylethan-1-one | Calc'd 389.1, Found 389.2 and 389.2 | CHIRALPAK ID; 20% (70:30 MeOH:IPA) in hexanes + 0.1% DEA |
| 4 Isomer 1 Isomer 2 | | (S)- and (R)-2-((3-chlorophenethyl)amino)-1-(1H-indol-3-yl)-2-phenylethan-1-one | Calc'd 389.1, Found 389.4 and 389.3 | CHIRALPAK IB; 20% (70:30 MeOH:IPA) in hexanes + 0.1% DEA |
| 5 Isomer 1 Isomer 2 | | (S)- and (R)-2-((4-chlorophenethyl)amino)-1-(1H-indol-3-yl)-2-phenylethan-1-one | Calc'd 389.1, Found 389.3 and 389.3 | CHIRALPAK IB; 20% (70:30 MeOH:IPA) in hexanes + 0.1% DEA |
| 6 Isomer 1 Isomer 2 | | (S)- and (R)-1-(1H-indol-3-yl)-2-((2-methoxyphenethyl)amino)-2-phenylethan-1-one | Calc'd 385.2, Found 385.3 and 385.3 | CHIRALPAK IB; 15% (70:30 MeOH:IPA) in hexanes + 0.1% DEA |
| 7 Isomer 1 Isomer 2 | | (S)- and (R)-1-(1H-indol-3-yl)-2-((3-methoxyphenethyl)amino)-2-phenylethan-1-one | Calc'd 385.2, Found 385.4 and 385.4 | CHIRALPAK IB; 18% (50:50 MeOH:IPA) in hexanes + 0.1% DEA |
| 8 Isomer 1 Isomer 2 | | (S)- and (R)-1-(1H-indol-3-yl)-2-((4-methoxyphenethyl)amino)-2-phenylethan-1-one | Calc'd 385.2, Found 385.3 and 385.3 | CHIRALPAK IB; 15% (50:50 MeOH:IPA) in hexanes + 0.1% DEA |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 9 Isomer 1 Isomer 2 | | (S)- and (R)-1-(1H-indol-3-yl)-2-phenyl-2-((2-(pyridin-2-yl)ethyl)-amino)ethan-1-one | Calc'd 356.2, Found 356.4 and 356.4 | CHIRALPAK IB; 08% (50:50 MeOH:IPA) in hexanes + 0.1% DEA |
| 10 Isomer 1 Isomer 2 | | (S)- and (R)-1-(1H-indol-3-yl)-2-phenyl-2-((2-(pyridin-3-yl)ethyl)-amino)ethan-1-one | Calc'd 356.2, Found 356.2 and 356.2 | CHIRALPAK IB; 15% (70:30 MeOH:IPA) in hexanes + 0.1% DEA |
| 11 Isomer 1 Isomer 2 | | (S)- and (R)-1-(1H-indol-3-yl)-2-phenyl-2-((2-(pyridin-4-yl)ethyl)-amino)ethan-1-one | Calc'd 356.2, Found 356.2 and 356.2 | CHIRALPAK IB; 20% (70:30 MeOH:IPA) in hexanes + 0.1% DEA |
| 12 Isomer 1 Isomer 2 | | (S)- and (R)-4-(2-((2-(4-chloro-1H-indol-3-yl)-2-oxo-1-phenylethyl)-amino)ethyl)benzene-sulfonamide | Calc'd 468.1, Found 468.3 and 468.3 | CHIRALPAK IB; 25% (50:50 MeOH:IPA) in hexanes + 0.1% DEA |
| 13 Isomer 1 Isomer 2 | | (S)- and (R)-4-(2-((2-(6-chloro-1H-indol-3-yl)-2-oxo-1-phenylethyl)-amino)ethyl)benzene-sulfonamide | Calc'd 468.1, Found 468.4 and 468.5 | CHIRALPAK IB; 20% (50:50 MeOH:IPA) in hexanes + 0.1% DEA |
| 14 Isomer 1 Isomer 2 | | (S)- and (R)-4-(2-((2-(5-chloro-1H-indol-3-yl)-2-oxo-1-phenylethyl)-amino)ethyl)benzene-sulfonamide | Calc'd 468.1, Found 468.4 and 468.5 | CHIRALPAK IB; 25% (50:50 MeOH:IPA) in hexanes + 0.1% DEA |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 15 Isomer 1 Isomer 2 | 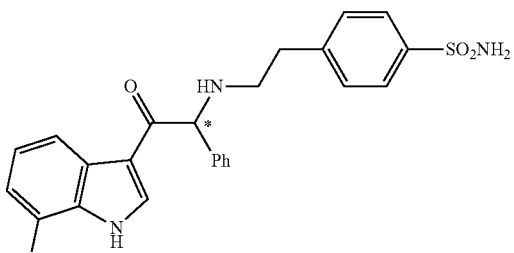 | (S)- and (R)-4-(2-((2-(6-chloro-1H-indol-3-yl)-2-oxo-1-phenylethyl)amino)ethyl)benzenesulfonamide | Calc'd 468.1, Found 468.4 and 468.4 | CHIRALPAK IB; 25% (50:50 MeOH:IPA) in hexanes + 0.1% DEA |
| 16 Isomer 1 Isomer 2 | 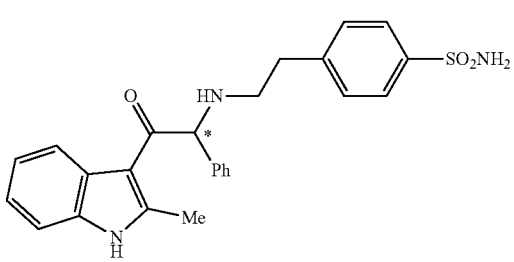 [SMILES: Cc1[nH]c2ccccc2c1C(=O)C(NCCc1ccc(S(N)(=O)=O)cc1)c1ccccc1] | (R)- and (S)-4-(2-((2-(2-methyl-1H-indol-3-yl)-2-oxo-1-phenylethyl)-amino)-ethyl)benzenesulfonamide | Calc'd 448.2, Found 448.2 and 448.2 | CHIRALPAK AD-H; 30% (50:50 MeOH:IPA) in Liquid $CO_2$ + 0.1% DEA |
| 17 Isomer 1 Isomer 2 | 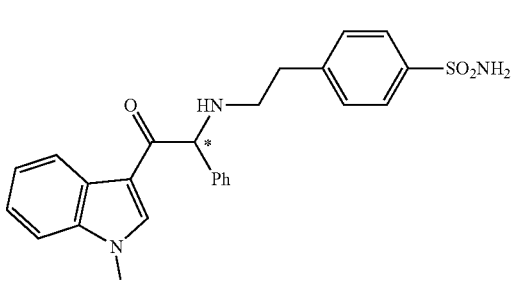 | (S)- and (R)-4-(2-((2-(1-methyl-1H-indol-3-yl)-2-oxo-1-phenylethyl)amino)ethyl)benzenesulfonamide | Calc'd 448.2, Found 448.4 and 448.5 | CHIRALPAK IB; 40% (50:50 MeOH:IPA) in hexanes + 0.1% DEA |
| 18 Isomer 1 Isomer 2 | 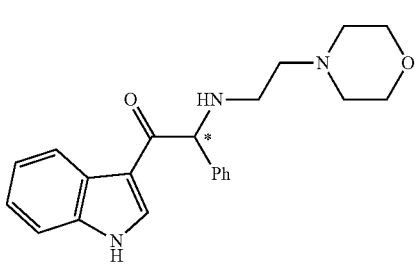 [SMILES: O=C(c1c[nH]c2ccccc12)C(NCCN1CCOCC1)c1ccccc1] | (S)- and (R)-1-(1H-indol-3-yl)-2-((2-morpholinoethyl)amino)-2-phenyl-ethan-1-one | Calc'd 364.2, Found 364.5 and 364.4 | CHIRALPAK AD-H; 33% (50:50 MeOH:IPA) in hexanes + 0.1% DEA |
| 19 Isomer 1 Isomer 2 | 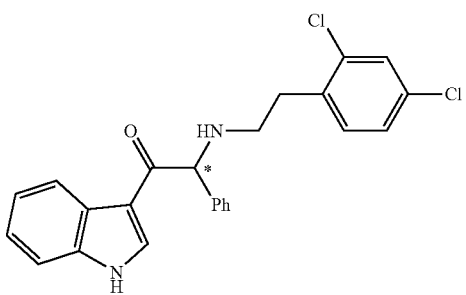 [SMILES: O=C(c1c[nH]c2ccccc12)C(NCCc1ccc(Cl)cc1Cl)c1ccccc1] | (S)- and (R)-2-((2,4-dichlorophenethyl)amino)-1-(1H-indol-3-yl)-2-phenylethan-1-one | Calc'd 423.1, Found 423.2 and 423.3 | CHIRALCEL OX-H; 15% (30:70 ACN:IPA) in hexanes + 0.1% DEA |

| Example Nos. | Structure (Methods and Schemes for Preparation) | IUPAC Name | Exact Mass [M + 1] | Chiral Column; Mobile Phase |
|---|---|---|---|---|
| 20 Isomer 1 Isomer 2 | 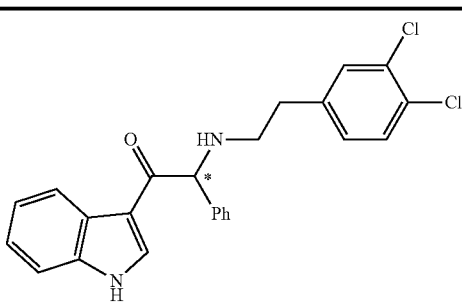 | (S)- and (R)-2-((3,4-dichlorophenethyl)amino)-1-(1H-indol-3-yl)-2-phenylethan-1-one | Calc'd 423.1, Found 423.2 and 423.2 | CHIRALCEL OX-H; 18% (50:50 ACN:IPA) in Liquid CO$_2$ + 0.1% DEA |
| 21 Isomer 1 Isomer 2 | 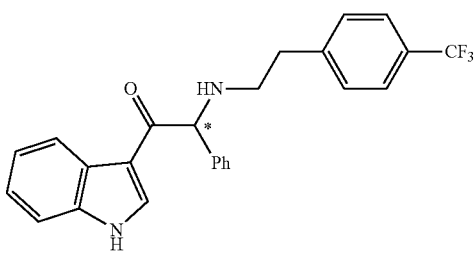 [SMILES: O=C(c1c[nH]c2ccccc12)C(NCCc1ccc(C(F)(F)F)cc1)c1ccccc1] | (S)- and (R)-1-(1H-indol-3-yl)-2-phenyl-2-((4-(trifluoromethyl)phenethyl)amino)ethan-1-one | Calc'd 423.2, Found 423.4 and 423.3 | CHIRALPAK AD-H; 25% MeOH in Liquid CO$_2$ + 0.1% DEA |
| 22 Isomer 1 Isomer 2 | 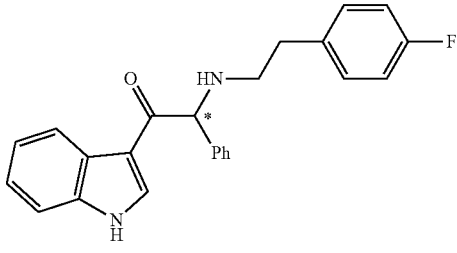 [SMILES: O=C(c1c[nH]c2ccccc12)C(NCCc1ccc(F)cc1)c1ccccc1] | (S)- and (R)-2-((4-fluorophenethyl)amino)-1-(1H-indol-3-yl)-2-phenylethan-1-one | Calc'd 373.2, Found 373.5 and 373.4 | CHIRALPAK IB; 20% (50:50 ACN:IPA) in Liquid CO$_2$ + 0.1% DEA |
| 23 Isomer 1 Isomer 2 | 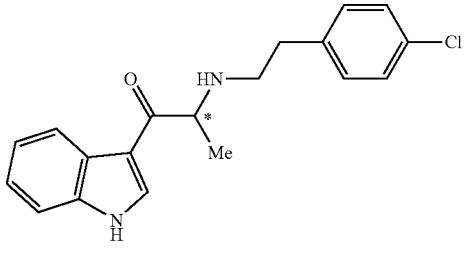 [SMILES: CC(NCCc1ccc(Cl)cc1)C(=O)c1c[nH]c2ccccc12] | (S)- and (R)-2-((4-chlorophenethyl)amino)-1-(1H-indol-3-yl)propan-1-one | Calc'd 327.1, Found 327.3 and 327.3 | CHIRALPAK AD-H; 10% (IPA) in hexanes + 0.1% DEA |
| 24 Isomer 1 Isomer 2 | 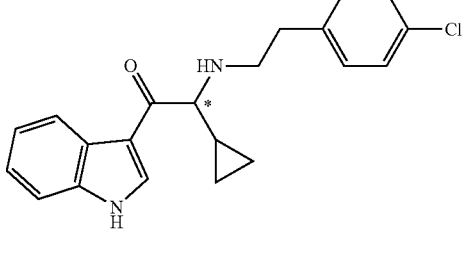 | (S)- and (R)-2-((4-chlorophenethyl)amino)-2-cyclopropyl-1-(1H-indol-3-yl)ethan-1-one | Calc'd 353.1, Found 353.3 and 353.3 | CHIRALPAK AD-H; 25% MeOH in Liquid CO$_2$ + 0.1% DEA |
| 25 Isomer 1 Isomer 2 | 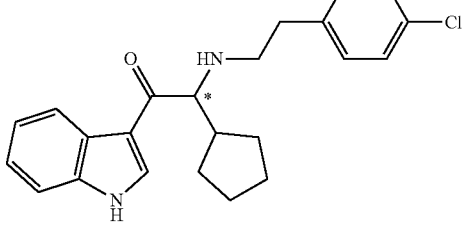 | (S)- and (R)-2-((4-chlorophenethyl)amino)-2-cyclopentyl-1-(1H-indol-3-yl)ethan-1-one | Calc'd 381.2, Found 381.5 and 381.5 | CHIRALPAK IB; 20% (50:50 MeOH:IPA) in hexanes + 0.1% DEA |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 26 Isomer 1 Isomer 2 Isomer 3 Isomer 4 | | (S,S)-, (S,R)-, (R,R)-, and (R,S)-2-((2-(4-chlorophenyl)propyl)amino)-1-(1H-indol-3-yl)-2-phenylethan-1-one | Calc'd 403.2, Found 403.5, 403.5, 403.5 and 403.5 | 1-CHIRALPAK AD-H; 18% MeOH in Liquid CO$_2$ + 0.1% DEA 2-CHIRALPAK IB; 18% (50:50 MeOH:IPA) in hexanes + 0.1% DEA |
| 27 Isomer 1 Isomer 2 Isomer 3 Isomer 4 | | (S,S)-, (S,R)-, (R,R)-, and (R,S)-2-((1-(4-chlorophenyl)propan-2-yl)amino)-1-(1H-indol-3-yl)-2-phenylethan-1-one | Calc'd 403.2, Found 403.6, 403.4, 403.4 and 403.4 | 1-CHIRALPAK AD-H; 15% (50:50 ACN:IPA) in Liquid CO$_2$ + 0.1% DEA 2-CHIRALPAK AD-H; 40% (50:50 MeOH:IPA) in Liquid CO$_2$ + 0.1% DEA |
| 28 Isomer 1 Isomer 2 | | (S)- and (R)-1-(7-chloro-1H-indol-3-yl)-2-((4-methoxyphenethyl)amino)-2-phenylethan-1-one | Calc'd 419.1, Found 419.4 and 419.4 | CHIRALCEL OX-H; 30% MeOH in Liquid CO$_2$ + 0.1% DEA |
| 29 Isomer 1 Isomer 2 | | (S)- and (R)-3-(3-(2-((4-methoxyphenethyl)amino)-2-phenylacetyl)-1H-indol-7-yl)-N,N-dimethylpropanamide | Calc'd 484.3, Found 484.4 and 484.8 | CHIRALPAK AD-H; 35% (50:50 MeOH:IPA) in Liquid CO$_2$ + 0.1% DEA |
| 30 racemic | | (rac)-4-(2-((2-oxo-1-phenyl-2-(1H-pyrrolo[3,2-b]pyridin-3-yl)ethyl)amino)ethyl)benzenesulfonamide | Calc'd 435.1, Found 435.6 | racemic |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 31 racemic | | (rac)-4-(2-((2-oxo-1-phenyl-2-(1H-pyrrolo[3,2-c]pyridin-3-yl)ethyl)amino)ethyl)benzenesulfonamide | Calc'd 435.1, Found 435.6 | racemic |
| 32 Isomer 1 Isomer 2 | | (S)- and (R)-4-(2-((2-oxo-1-phenyl-2-(1H-pyrrolo[2,3-c]pyridin-3-yl)ethyl)amino)ethyl)benzenesulfonamide | Calc'd 435.1, Found 434.4 and 434.5 | CHIRALPAK AD-H; 35% (50:50 MeOH:IPA) in hexanes + 0.1% DEA |
| 33 Isomer 1 Isomer 2 | | (S)- and (R)-4-(2-((2-oxo-1-phenyl-2-(1H-pyrrolo[2,3-b]pyridin-3-yl)ethyl)amino)ethyl)benzenesulfonamide | Calc'd 435.1, Found 435.6 and 435.6 | CHIRALPAK AD-H; 25% MeOH in Liquid CO$_2$ + 0.1% DEA |
| 34 Isomer 1 Isomer 2 | | (S)- and (R)-2-((2-(1H-pyrazol-4-yl)ethyl)amino)-1-(1H-indol-3-yl)-2-phenylethan-1-one | Calc'd 345.2, Found 345.3 and 345.4 | CHIRALCEL OX-H; (50:50 MeOH:IPA) in hexanes + 0.1% DEA |
| 35 Isomer 1 Isomer 2 | | (S)- and (R)-1-(1H-indol-3-yl)-2-((2-(1-methyl-1H-pyrazol-4-yl)ethyl)amino)-2-phenylethan-1-one | Calc'd 359.2, Found 359.3 and 359.3 | CHIRALPAK AD-H; 20% MeOH in Liquid CO$_2$ + 0.1% DEA |
| 36 Isomer 1 Isomer 2 | | (S)- and (R)-2-((2-(1H-imidazol-1-yl)ethyl)amino)-1-(1H-indol-3-yl)-2-phenylethan-1-one | Calc'd 345.2, Found 345.4 and 345.4 | CHIRALPAK IB; 25% (IPA) in hexanes + 0.1% DEA |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 37 Isomer 1 Isomer 2 | | (S)- and (R)-2-((2-(1H-benzo[d]imidazol-1-yl)ethyl)amino)-1-(1H-indol-3-yl)-2-phenylethan-1-one | Calc'd 395.2, Found 395.8 and 395.8 | CHIRALPAK IB; 35% (50:50 MeOH:IPA) in hexanes + 0.1% DEA |
| 38 Isomer 1 Isomer 2 | | (S)- and (R)-1-(1H-indol-3-yl)-2-((4-methylphenethyl)amino)-2-phenyl-ethan-1-one | Calc'd 369.2, Found 369.4 and 369.4 | CHIRALPAK IB; 25% (50:50 MeOH:IPA) in hexanes + 0.1% DEA |
| 39 Isomer 1 Isomer 2 | | (S)- and (R)-2-((4-(dimethylamino)phenethyl)amino)-1-(1H-indol-3-yl)-2-phenylethan-1-one | Calc'd 398.2, Found 398.6 and 398.6 | CHIRALPAK IB; 10% (50:50 MeOH:IPA) in hexanes + 0.1% DEA |
| 40 Isomer 1 Isomer 2 | | (S)- and (R)-1-(1H-indol-3-yl)-2-phenyl-2-((4-(trifluoromethoxy)phenethyl)amino)ethan-1-one | Calc'd 439.2, Found 439.6 and 439.7 | CHIRALPAK IB; 25% (50:50 MeOH:IPA) in hexanes + 0.1% DEA |
| 41 Isomer 1 Isomer 2 | | (S)- and (R)-1-(2-((2-(1H-indol-3-yl)-2-oxo-1-phenylethyl)amino)ethyl)piperidin-2-one | Calc'd 376.2, Found 376.6 and 376.6 | CHIRALPAK AD-H; 25% MeOH in Liquid $CO_2$ + 0.1% DEA |
| 42 racemic | | (rac)-2-((4-chlorophenethyl)amino)-1-(1H-indol-3-yl)-2-(pyridin-2-yl)ethan-1-one | Calc'd 390.2, Found 390.4 | racemic |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 43 racemic | | (rac)-2-((4-chlorophenethyl)amino)-1-(1H-indol-3-yl)-2-(pyridin-3-yl)ethan-1-one | Calc'd 390.2, Found 390.2 | racemic |
| 44 racemic | | (rac)-2-((4-chlorophenethyl)amino)-1-(1H-indol-3-yl)-2-(pyridin-4-yl)ethan-1-one | Calc'd 390.2, Found 390.4 | racemic |
| 45 Isomer 1 Isomer 2 | | (S)- and (R)-2-((4-chlorophenethyl)amino)-1-(3-methylimidazo[1,5-a]pyridin-1-yl)-2-phenylethan-1-one | Calc'd 404.2, Found 404.5 and 404.5 | CHIRALPAK AD-H; 20% MeOH in Liquid $CO_2$ + 0.1% DEA |
| 46 Isomer 1 Isomer 2 | | (S)- and (R)-2-((4-chlorophenethyl)amino)-1-(imidazo[1,2-a]pyridin-3-yl)-2-phenylethan-1-one | Calc'd 390.1, Found 390.5 and 390.5 | CHIRALPAK IB; 15% (50:50 MeOH:IPA) in hexanes + 0.1% DEA |
| 47 Isomer 1 Isomer 2 | | (S)- and (R)-2-((4-chlorophenethyl)amino)-1-(1H-indazol-3-yl)-2-phenylethan-1-one | Calc'd 390.1, Found 390.4 and 390.4 | CHIRALPAK AD-H; 35% MeOH in Liquid $CO_2$ + 0.1% DEA |
| 48 Isomer 1 Isomer 2 | | (S)- and (R)-2-((4-fluorophenethyl)amino)-1-(6-methyl-1H-indol-3-yl)-2-phenylethan-1-one | Calc'd 387.2, Found 387.6 and 387.6 | CHIRALPAK IB; 20% (50:50 MeOH:IPA) in Hexanes + 0.1% DEA |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 49 Isomer 1 Isomer 2 | | (S)- and (R)-3-(3-(2-((4-fluorophenethyl)amino)-2-phenylacetyl)-1H-indol-6-yl)-N,N-dimethylpropanamide | Calc'd 472.2, Found 472.7 and 472.7 | CHIRALPAK IB; 35% (50:50 MeOH:IPA) in hexanes + 0.1% DEA |
| 50 Isomer 1 Isomer 2 | | (S)- and (R)-4-(2-((2-oxo-1-phenyl-2-(7-(trifluoromethyl)-1H-indol-3-yl)ethyl)amino)ethyl)benzenesulfonamide | Calc'd 502.1, Found 502.5 and 502.5 | CHIRALPAK IB; 25% (50:50 MeOH:IPA) in hexanes + 0.1% DEA |
| 51 Isomer 1 Isomer 2 | | (S)- and (R)-4-(2-((2-(6-methoxy-1H-indol-3-yl)-2-oxo-1-phenylethyl)amino)ethyl)benzenesulfonamide | Calc'd 464.2, Found 464.5 and 464.6 | CHIRALPAK IB; 30% (50:50 MeOH:IPA) in hexanes + 0.1% DEA |
| 52 Isomer 1 Isomer 2 | | (S)- and (R)-2-((2-(6-chloropyridin-3-yl)ethyl)amino)-1-(1H-indol-3-yl)-2-phenylethan-1-one | Calc'd 390.1, Found 390.5 and 390.5 | CHIRALPAK IB; 20% (MeOH) in Liquid $CO_2$ + 0.1% DEA |
| 53 Isomer 1 Isomer 2 | | (S)- and (R)-2-((2-(6-(ethylamino)pyridin-3-yl)ethyl)amino)-1-(1H-indol-3-yl)-2-phenylethan-1-one | Calc'd 400.2 [M + 2], Found 400.6 and 400.6 | CHIRALPAK IB; 25% (50:50 MeOH:IPA) in hexanes + 0.1% DEA |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 54 Isomer 1 Isomer 2 | | (S)- and (R)-1-(1H-indol-3-yl)-2-((2-(6-((2-methoxyethyl)amino)pyridin-3-yl)ethyl)amino)-2-phenylethan-1-one | Calc'd 429.5, Found 429.6 and 429.6 | CHIRALPAK IB; 25% (50:50 MeOH:IPA) in hexanes + 0.1% DEA |
| 55 Isomer 1 Isomer 2 | | (S)- and (R)-4-(2-((2-(6,7-dichloro-1H-indol-3-yl)-2-oxo-1-phenylethyl)amino)ethyl)benzenesulfonamide | Calc'd 502.1, Found 502.4 and 502.4 | CHIRALPAK AD-H; 35% (50:50 MeOH:IPA) in Liquid $CO_2$ + 0.1% DEA |
| 56 Isomer 1 Isomer 2 | | (S)- and (R)-4-(2-((2-(6-methyl-1H-indol-3-yl)-2-oxo-1-phenylethyl)amino)ethyl)benzenesulfonamide | Calc'd 448.2, Found 448.7 and 448.7 | CHIRALPAK IB; 30% (50:50 MeOH:IPA) in Hexanes + 0.1% DEA |
| 57 Isomer 1 Isomer 2 | | (S)- and (R)-2-((4-(1H-1,2,3-triazol-4-yl)phenethyl)amino)-1-(1H-indol-3-yl)-2-phenylethan-1-one | Calc'd 422.2, Found 422.2 and 422.2 | CHIRALPAK AD-H; 25% (50:50 ACN:IPA) in Liquid $CO_2$ + 0.1% DEA |
| 58 Isomer 1 Isomer 2 | | (S)- and (R)-4-(2-((2-(1H-indol-3-yl)-2-oxo-1-phenylethyl)amino)ethyl)benzonitrile | Calc'd 380.2, Found 380.4 and 380.4 | CHIRALPAK IB; 22% (50:50 MeOH:IPA) in hexanes + 0.1% DEA |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 59 Isomer 1 Isomer 2 Isomer 3 Isomer 4 | | (S,S)-, (S,R)-, (R,R)-, and (R,S)-2-((2-(4-chlorophenyl)butyl)amino)-1-(1H-indol-3-yl)-2-phenylethan-1-one | Calc'd 417.2, Found 417.5, 417.2, 417.5 and 417.5 | 1-CHIRALPAK IB; 15% (MeOH) in Liquid CO$_2$ + 0.1% DEA 2-CHIRALPAK AD-H; 20% (MeOH) in Liquid CO$_2$ + 0.1% DEA |
| 60 Isomer 1 Isomer 2 | | (S)- and (R)-2-((4-chlorophenethyl)amino)-1-(6-methoxy-1H-indol-3-yl)-2-phenyl-ethan-1-one | Calc'd 419.1, Found 419.3 and 419.3 | CHIRALPAK IB; 20% (MeOH) in Liquid CO$_2$ + 0.1% DEA |
| 61 Isomer 1 Isomer 2 | | (S)- and (R)-1-(6-(benzyloxy)-1H-indol-3-yl)-2-((4-fluorophenethyl)amino)-2-phenyl-ethan-1-one | Calc'd 479.2, Found 479.6 and 479.6 | CHIRALPAK IB; 25% (50:50 MeOH:IPA) in hexanes + 0.1% DEA |
| 62 Isomer 1 Isomer 2 | | (S)- and (R)-2-(3-(2-((4-cyanophenethyl)amino)-2-phenylacetyl)-1H-indol-6-yl)-N-methylacetamide | Calc'd 451.2, Found 451.4 and 451.4 | CHIRALPAK AD-H; 30% (50:50 ACN:IPA) in Liquid CO$_2$ + 0.1% DEA |
| 63 Isomer 1 Isomer 2 | | (S)- and (R)-2-(3-(2-((4-cyanophenethyl)amino)-2-phenylacetyl)-1H-indol-6-yl)-N,N-dimethylacetamide | Calc'd 465.2, Found 465.5 and 465.5 | CHIRALPAK AD-H; 30% (50:50 ACN:IPA) in Liquid CO$_2$ + 0.1% DEA |
| 64 Isomer 1 Isomer 2 | | (S)- and (R)-4-(2-((2-(6-(1-methylpiperidin-4-yl)-1H-indol-3-yl)-2-oxo-1-phenylethyl)amino)ethyl)benzonitrile | Calc'd 477.3, Found 477.2 and 477.2 | CHIRALPAK IB; 30% (70:30 MeOH:IPA) in hexanes + 0.1% DEA |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 65 Isomer 1 Isomer 2 | | (S)- and (R)-1-(6-(1-acetylpiperidin-4-yl)-1H-indol-3-yl)-2-((4-chlorophenethyl)amino)-2-phenyl-ethan-1-one | Calc'd 514.2, Found 514.6 and 514.6 | CHIRALPAK IB; 30% (50:50 MeOH:IPA) in hexanes + 0.1% DEA |
| 66 Isomer 1 Isomer 2 | | (S)- and (R)-4-(2-((2-(6-(1-methyl-1H-pyrazol-4-yl)-1H-indol-3-yl)-2-oxo-1-phenylethyl)amino)ethyl)benzenesulfonamide | Calc'd 514.2, Found 514.6 and 514.5 | CHIRALPAK IB; 35% (50:50 MeOH:IPA) in hexanes + 0.1% DEA |
| 67 Isomer 1 Isomer 2 | | (S)- and (R)-3-(2-((4-cyanophenethyl)amino)-2-phenylacetyl)-N-methyl-1H-pyrrolo[2,3-b]pyridine-6-carboxamide | Calc'd 438.2, Found 438.3 and 438.3 | CHIRALPAK AD-H; 30% (50:50 ACN:IPA) in Liquid CO$_2$ + 0.1% DEA |
| 68 Isomer 1 Isomer 2 Isomer 3 Isomer 4 | | (S,S)-, (S,R)-, (R,R)-, and (R,S)-2-((1-(2,4-dichlorophenyl)propan-2-yl)amino)-1-(7-methyl-1H-indol-3-yl)-2-phenylethan-1-one | Calc'd 451.2, Found 450.8, 450.9, 450.8, 450.9 | 1-CHIRALPAK OD-H; 35% EtOH in Liquid CO$_2$ + 0.25% isopropylamine; 2-CHIRALPAK AD-H; 43% EtOH in Liquid CO$_2$ + 0.25% isopropylamine |
| 69 Isomer 1 Isomer 2 Isomer 3 Isomer 4 | | (S,S)-, (S,R)-, (R,R)-, and (R,S)-3-(2-((2-(4-cyanophenyl)propyl)amino)-2-phenylacetyl)-N-ethylpyrazolo[1,5-a]pyridine-6-carboxamide | Calc'd 466.2, Found 466.3, 466.4, 466.4, 466.4 | CHIRALPAK AD-H; 25% (MeOH) in Liquid CO$_2$ + 0.1% DEA |
| 70 Isomer 1 Isomer 2 Isomer 3 Isomer 4 | | (S,S)-, (S,R)-, (R,R)-, and (R,S)-3-(2-((2-(4-cyanophenyl)propyl)amino)-2-phenylacetyl)-N-((R)-2-hydroxypropyl)pyrazolo[1,5-a]pyridine-6-carboxamide | Calc'd 496.2, Found 496.9, 496.8, 496.6, 496.6 | 1-CHIRALPAK IC; 25% (70:30 IPA:ACN) in hexanes + 0.1% DEA 2-CHIRALPAK IB; 20% (50:50 MeOH:IPA) in hexanes + 0.1% DEA |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 71 Isomer 1 Isomer 2 | | (S)- and (R)-3-(2-((2-chloro-4-cyanophenethyl)amino)-2-phenylacetyl)-N-ethyl-1H-indole-6-carboxamide | Calc'd 485.2, Found 485.3 and 485.4 | CHIRALPAK IB; 25% (50:50 MeOH:IPA) in hexanes + 0.1% DEA |
| 72 Isomer 1 Isomer 2 | | (S)- and (R)-3-chloro-4-(2-((2-(6-(1-methyl-1H-pyrazol-4-yl)-1H-indol-3-yl)-2-oxo-1-phenylethyl)amino)ethyl)benzonitrile | Calc'd 494.2, Found 494.3 and 494.4 | CHIRALPAK IC; 40% (50:50 MeOH:IPA) in hexanes + 0.1% DEA |
| 73 Isomer 1 Isomer 2 | | (S)- and (R)-3-(2-((4-cyanophenethyl)amino)-2-phenylacetyl)-N-ethylpyrazolo[1,5-a]pyridine-6-carboxamide | Calc'd 452.2, Found 452.5 and 452.3 | CHIRALPAK IC; 25% MeOH in Liquid $CO_2$ + 0.1% DEA |
| 74 Isomer 1 Isomer 2 | | (S)- and (R)-1-(3-(2-((4-chlorophenethyl)amino)-2-phenylacetyl)-1H-indol-6-yl)pyrrolidin-2-one | Calc'd 472.2, Found 472.4 and 472.3 | CHIRALPAK IC; 65% (50:50 MeOH:IPA) in hexanes + 0.1% DEA |

TABLE 1-continued

| Example Nos. | Structure (Methods and Schemes for Preparation) | IUPAC Name | Exact Mass [M + 1] | Chiral Column; Mobile Phase |
|---|---|---|---|---|
| 75 Isomer 1 Isomer 2 Isomer 3 Isomer 4 | | (S,S)-, (S,R)-, (R,R)-, and (R,S)-3-(2-((2-(4-cyanophenyl)propyl)amino)-2-phenylacetyl)-N-ethyl-1H-indole-6-carboxamide | Calc'd 465.2, Found 465.4, 465.4, 465.6, and 465.6 | CHIRALPAK IB; 12% (50:50 MeOH:IPA) in hexanes + 0.1% DEA |
| 76 Isomer 1 Isomer 2 | | (S)- and (R)-3-((4-cyanophenethyl)alanyl)-N-ethyl-1H-indole-6-carboxamide | Calc'd 389.2, Found 389.2 and 389.2 | CHIRALPAK IG; 25% (50:50 MeOH:IPA) in hexanes + 0.1% DEA |
| 77 Racemic | | (S)- and (R)-4-(2-((2-(6-(1-methyl-1H-pyrazol-4-yl)-1H-indazol-3-yl)-2-oxo-1-phenylethyl)amino)ethyl)benzonitrile | Calc'd 461.2, Found 461.5 | Racemic |

Scheme 2

The starting materials required for the synthesis of examples prepared using Scheme 2 were generally prepared using methods 1 through 4 and scheme 1. Starting materials for methods 1 through 4 and scheme 1 were either commercially available or were synthesized using methods 5 through 24.

Example 78

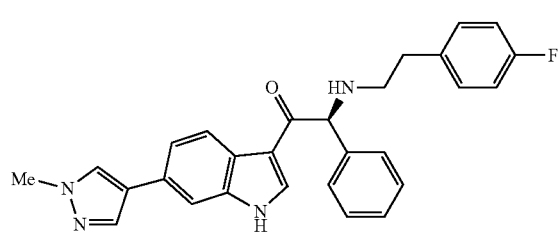

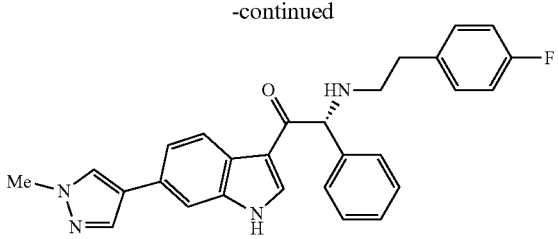

(S)- and (R)-2-((4-Fluorophenethyl)amino)-1-(6-(1-methyl-1H-pyrazol-4-yl)-1H-indol-3-yl)-2-phenylethan-1-one Scheme 2. (S)- and (R)-2-((4-Fluorophenethyl)amino)-1-(6-(1-methyl-1H-pyrazol-4-yl)-1H-indol-3-yl)-2-phenylethan-1-one:

A mixture of 1-(6-chloro-1H-indol-3-yl)-2-((4-fluorophenethyl)amino)-2-phenylethan-1-one (0.10 g, 0.24 mmol), 1-methyl-4-(4,4,5,5-tetramethyl-1,3,2-dioxaborolan-2-yl)-1H-pyrazole (0.076 g, 0.36 mmol), and cesium carbonate (0.20 g, 0.61 mmol) in a mixture of 4:1 dioxane: water (5 ml) was degassed for 20 minutes with argon. S-Phos Pd precatalyst G3 (0.018 g, 0.02 mmol) was added and degassing was continued for another 10 minutes. The reaction mixture was heated in a sealed tube with microwave irradiation at 135° C. for 45 minutes. After completion of reaction (monitored by TLC), the reaction mixture was treated with water (20 ml) and extracted with ethyl acetate (2×20 ml). The combined organic layers were washed with brine, dried over anhydrous $Na_2SO_4$ and concentrated under reduced pressure. The residue was purified by silica gel chromatography to afford the title compound as an off-white solid (0.065 g, 58%) in racemic form.

The racemic title compound was resolved by chiral HPLC (Chiralpak AD-H; 20% MeOH with 0.1% DEA in $CO_2$) to furnish the enantiopure compounds. The faster-eluting enantiomer of the title compound was obtained as a solid (Isomer 1): $^1$H NMR (400 MHz, DMSO-d6): δ 2.68-2.76 (m, 4H), 3.86 (s, 3H), 5.29 (s, 1H), 7.08 (t, J=8.8 Hz, 2H), 7.18-7.24 (m, 3H), 7.28 (t, J=7.6 Hz, 2H), 7.40 (d, J=9.2 Hz, 1H), 7.47 (d, J=7.2 Hz, 2H), 7.55 (s, 1H), 7.85 (s, 1H), 8.10-8.12 (m, 2H), 8.56 (s, 1H), 12.02 (s, —NH). LCMS: m/z=453.5 [M+1]. The slower-eluting enantiomer of the title compound was obtained as a solid (Isomer 2): $^1$H NMR (400 MHz, DMSO-d6): δ 2.69-2.76 (m, 4H), 3.86 (s, 3H), 5.28 (s, 1H), 7.08 (t, J=8.8 Hz, 2H), 7.18-7.24 (m, 3H), 7.28 (t, J=7.6 Hz, 2H), 7.39 (d, J=9.2 Hz, 1H), 7.47 (d, J=7.2 Hz, 2H), 7.55 (s, 1H), 7.85 (s, 1H), 8.10-8.12 (m, 2H), 8.56 (s, 1H), 12.00 (s, —NH). LCMS: m/z=453.5 [M+1].

Example 79

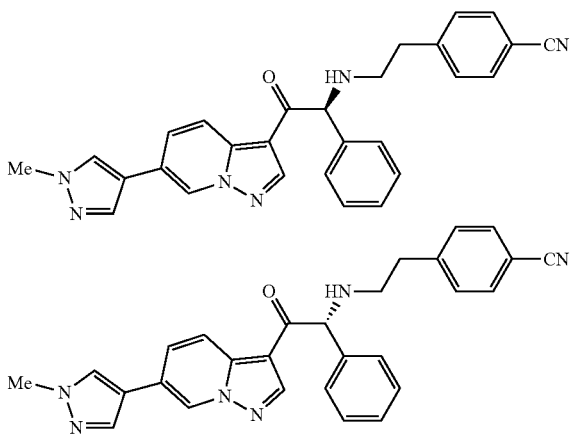

(S)- and (R)-4-(2-((2-(6-(1-methyl-1H-pyrazol-4-yl)pyrazolo[1,5-a]pyridin-3-yl)-2-oxo-1-phenylethyl)amino)ethyl)benzonitrile Scheme 2. (S)- and (R)-4-(2-((2-(6-(1-methyl-1H-pyrazol-4-yl)pyrazolo[1,5-a]pyridin-3-yl)-2-oxo-1-phenylethyl)amino)ethyl)benzonitrile: A mixture of 4-(2-((2-(6-bromopyrazolo[1,5-a]pyridin-3-yl)-2-oxo-1-phenylethyl)amino)ethyl)benzonitrile (0.6 g, 1.31 mmol), 1-methylpyrazole-4-boronic acid pinacol ester (0.41 g, 1.97 mmol) and cesium carbonate (1.29 g, 3.92 mmol) in a mixture of 2:1 dioxane-water (18 ml) was purged for 20 minutes with argon. Then, S-Phos palladium G3 precatalyst (0.102 g, 0.131 mmol) was added and purging was continued for another 10 minutes. The reaction mixture was heated at 100° C. for 1.5 hours. After completion of reaction (monitored by TLC), the reaction mixture was quenched with water (20 ml) and extracted with ethyl acetate (2×20 ml). The combined organic layers were washed with brine (20 ml), dried over anhydrous $Na_2SO_4$ and concentrated under reduced pressure. The resulting residue was purified by silica gel chromatography to afford the title compound (0.3 g, 50%) in racemic form.

The racemic title compound was resolved by chiral HPLC (CHIRALPAK IB; 30% (50:50 MEOH:IPA) in hexanes+ 0.1% DEA) to furnish the enantiopure compounds. The faster-eluting enantiomer of the title compound was obtained as a solid (Isomer 1): $^1$H NMR (400 MHz, DMSO-d6): δ 2.68-2.73 (m, 2H), 2.80-2.90 (m, 2H), 3.88 (s, 3H), 5.29 (s, 1H), 7.22-7.25 (m, 1H), 7.31 (t, J=7.6 Hz, 2H), 7.43 (d, J=8.0 Hz, 2H), 7.48 (d, J=7.2 Hz, 2H), 7.73 (d, J=8.0 Hz, 2H), 7.91 (d, J=9.2 Hz, 1H), 8.05 (s, 1H), 8.21 (d, J=9.2 Hz, 1H), 8.31 (s, 1H), 8.87 (s, 1H), 9.19 (s, 1H). LCMS: m/z=461.6 [M+1]. The slower-eluting enantiomer of the title compound was obtained as a solid (Isomer 2): $^1$H NMR (400 MHz, DMSO-d6): δ 2.68-2.75 (m, 2H), 2.80-2.90 (m, 2H), 3.88 (s, 3H), 5.30 (s, 1H), 7.21-7.25 (m, 1H), 7.31 (t, J=7.6 Hz, 2H), 7.43 (d, J=8.0 Hz, 2H), 7.49 (d, J=7.2 Hz, 2H), 7.74 (d, J=8.0 Hz, 2H), 7.91 (d, J=8.8 Hz, 1H), 8.06 (s, 1H), 8.22 (d, J=9.2 Hz, 1H), 8.32 (s, 1H), 8.88 (s, 1H), 9.20 (s, 1H). LCMS: m/z=461.6 [M+1].

The following compounds were prepared using similar procedures to those described for Examples 78 and 79 using the appropriate starting materials.

TABLE 2

| Example Nos. | Structure (Methods and Schemes for Preparation) | IUPAC Name | Exact Mass [M + 1] | Chiral Column and Mobile Phase |
|---|---|---|---|---|
| 80 Isomer 1 Isomer 2 | | (S)- and (R)-2-((4-methoxyphenethyl)amino)-1-(7-methyl-1H-indol-3-yl)-2-phenylethan-1-one | Calc'd 399.2, Found 399.6 and 399.6 | CHIRALPAK IB 15% (50:50 MeOH:IPA) in hexanes + 0.1% DEA |

TABLE 2-continued

| Example Nos. | Structure (Methods and Schemes for Preparation) | IUPAC Name | Exact Mass [M + 1] | Chiral Column and Mobile Phase |
|---|---|---|---|---|
| 81 Isomer 1 Isomer 2 | | (S)- and (R)-2-((4-fluorophenethyl)amino)-2-phenyl-1-(6-(pyridin-3-yl)-1H-indol-3-yl)ethan-1-one | Calc'd 450.2, Found 450.6 and 450.7 | CHIRALPAK IB 18% 50:50 MeOH:IPA in hexanes + 0.1% DEA |
| 82 Isomer 1 Isomer 2 | | (S)- and (R)-2-((4-fluorophenethyl)amino)-2-phenyl-1-(6-(pyridin-4-yl)-1H-indol-3-yl)ethan-1-one | Calc'd 450.2, Found 450.6 and 450.7 | CHIRALPAK IB 25% 50:50 MeOH:IPA in hexanes + 0.1% DEA |
| 83 Isomer 1 Isomer 2 | | (S)- and (R)-2-((4-chlorophenethyl)amino)-1-(6-(1-methyl-1H-pyrazol-4-yl)-1H-indol-3-yl)-2-phenylethan-1-one | Calc'd 469.2, Found 469.4 and 469.4 | CHIRALPAK IB; 35% MeOH in Liquid CO2 + 0.1% DEA |
| 84 Isomer 1 Isomer 2 | | (S)- and (R)-4-(2-((2-(6-(1-methyl-1H-pyrazol-4-yl)-1H-indol-3-yl)-2-oxo-1-phenylethyl)amino)ethyl)benzonitrile | Calc'd 460.2, Found 460.6 and 460.6 | CHIRALPAK IB; 35% (50:50 MeOH:IPA) in hexanes + 0.1% DEA |
| 85 Isomer 1 Isomer 2 | | (S)- and (R)-2-((2,4-difluorophenethyl)amino)-1-(6-(1-methyl-1H-pyrazol-4-yl)-1H-indol-3-yl)-2-phenylethan-1-one | Calc'd 471.2, Found 471.7 and 471.6 | CHIRALPAK IB 25% 50:50 MeOH:IPA in hexanes + 0.1% DEA |
| 86 Isomer 1 Isomer 2 | | (S)- and (R)-2-((4-chlorophenethyl)amino)-1-(6-(1-ethyl-1H-pyrazol-4-yl)-1H-indol-3-yl)-2-phenylethan-1-one | Calc'd 483.2, Found 483.5 and 483.5 | CHIRALPAK IB 30% (50:50 MeOH:IPA) in hexanes + 0.1% DEA |

TABLE 2-continued

| Example Nos. | Structure (Methods and Schemes for Preparation) | IUPAC Name | Exact Mass [M + 1] | Chiral Column and Mobile Phase |
|---|---|---|---|---|
| 87 Isomer 1 Isomer 2 | | (S)- and (R)-2-(4-(3-(2-((4-chlorophenethyl)amino)-2-phenylacetyl)-1H-indol-6-yl)-1H-pyrazol-1-yl)-N-methylacetamide | Calc'd 526.2, Found 526.6 and 526.6 | CHIRALPAK IB 30% (50:50 MeOH:IPA) in hexanes + 0.1% DEA |
| 88 Isomer 1 Isomer 2 | | (S)- and (R)-2-((4-chlorophenethyl)amino)-1-(6-(6-methylpyridin-3-yl)-1H-indol-3-yl)-2-phenylethan-1-one | Calc'd 480.2, Found 480.5 and 480.5 | CHIRALPAK IB 27% (50:50 MeOH:IPA) in hexanes + 0.1% DEA |
| 89 Isomer 1 Isomer 2 | | (S)- and (R)-2-((4-chlorophenethyl)amino)-2-phenyl-1-(6-(pyridin-4-yl)-1H-indol-3-yl)ethan-1-one | Calc'd 466.2, Found 466.5 and 466.5 | CHIRALPAK IB 25% (50:50 MeOH:IPA) in hexanes + 0.1% DEA |
| 90 Isomer 1 Isomer 2 | | (S)- and (R)-2-((4-chlorophenethyl)amino)-2-phenyl-1-(6-(pyridin-3-yl)-1H-indol-3-yl)ethan-1-one | Calc'd 466.2, Found 466.5 and 466.6 | CHIRALPAK IB 20% (50:50 MeOH:IPA) in hexanes + 0.1% DEA |
| 91 Isomer 1 Isomer 2 Isomer 3 Isomer 4 | | (S,S)-, (S,R)-, (R,R)-, and (R,S)-2-((2-(4-chlorophenyl)propyl)amino)-1-(6-(1-methyl-1H-pyrazol-4-yl)-1H-indol-3-yl)-2-phenylethan-1-one | Calc'd 483.2, Found 483.6, 483.7, 483.7 and 483.7 | 1-CHIRALPAK IB; 20% (50:50 MeOH:IPA) in hexanes + 0.1% DEA 2- CHIRALPAK AD-H; 30% (50:50 ACN:IPA) in Liquid CO$_2$ + 0.1% DEA |

TABLE 2-continued

| Example Nos. | Structure (Methods and Schemes for Preparation) | IUPAC Name | Exact Mass [M + 1] | Chiral Column and Mobile Phase |
|---|---|---|---|---|
| 92 Isomer 1 Isomer 2 Isomer 3 Isomer 4 | | (S,S)-, (S,R)-, (R,R)-, and (R,S)-2-((1-(4-chlorophenyl)propan-2-yl)amino)-1-(6-(1-methyl-1H-pyrazol-4-yl)-1H-indol-3-yl)-2-phenylethan-1-one | Calc'd 483.2, Found 483.6, 483.6, 483.5 and 483.6 | 1-CHIRALPAK IB; 25% (50:50 MeOH:IPA) in hexanes + 0.1% DEA 2-CHIRALCEL OX-H; 20% (50:50 MeOH:IPA) in Liquid CO$_2$ + 0.1% DEA 3-CHIRALPAK AD-H; 25% (MEOH) in Liquid CO2 + 0.1% DEA |
| 93 Isomer 1 Isomer 2 | | (S)- and (R)-4-(2-((2-(3-methyl-6-(1-methyl-1H-pyrazol-4-yl)imidazo[1,5-a]pyridin-1-yl)-2-oxo-1-phenylethyl)amino)ethyl)benzonitrile | Calc'd 475.2, Found 475.4 and 475.4 | CHIRALPAK IB; 45% (50:50 MeOH:IPA) in hexanes + 0.1% DEA |
| 94 Isomer 1 Isomer 2 | | (S)- and (R)-4-(2-((2-(6-(1-methyl-1H-pyrazol-4-yl)-1H-pyrrolo[2,3-b]pyridin-3-yl)-2-oxo-1-phenylethyl)amino)ethyl)benzonitrile | Calc'd 461.2, Found 461.2 and 461.2 | CHIRALPAK IB; 25% (50:50 MeOH:IPA) in hexanes + 0.1% DEA |
| 95 Isomer 1 Isomer 2 | | (S)- and (R)-4-(2-((2-(6-(1-(2-hydroxyethyl)-1H-pyrazol-4-yl)-1H-indol-3-yl)-2-oxo-1-phenylethyl)amino)ethyl)benzonitrile | Calc'd 490.2, Found 490.5 and 490.5 | CHIRALPAK IB; 35% (50:50 MeOH:IPA) in hexanes + 0.1% DEA |
| 96 Isomer 1 Isomer 2 | | (S)- and (R)-4-(2-((2-(6-(1-(2-methoxyethyl)-1H-pyrazol-4-yl)-1H-indol-3-yl)-2-oxo-1-phenylethyl)amino)ethyl)benzonitrile | Calc'd 504.2, Found 504.2 and 504.5 | CHIRALPAK IB; 35% (50:50 MeOH:IPA) in hexanes + 0.1% DEA |

TABLE 2-continued

| Example Nos. | Structure (Methods and Schemes for Preparation) | IUPAC Name | Exact Mass [M + 1] | Chiral Column and Mobile Phase |
|---|---|---|---|---|
| 97 Isomer 1 Isomer 2 Isomer 3 Isomer 4 | | (S,S)-, (S,R)-, (R,R)-, and (R, S)-2-((1-(2,4-dichlorophenyl)propan-2-yl)amino)-1-(6-(1-methyl-1H-pyrazol-4-yl)-1H-indol-3-yl)-2-phenylethan-1-one | Calc'd, 517.2, Found 517.4 | 1-CHIRALPAK OD-H; 40% (50:50 MeOH:IPA) in $CO_2$ + 0.1% DIPA 2-CHIRALPAK IC; 35% (3:1 ACN:MeOH) in $CO_2$ + 0.1% DIPA |
| 98 Isomer 1 Isomer 2 | | (S)- and (R)-4-(2-((2-(6-(1H-pyrazol-4-yl)-1H-indol-3-yl)-2-oxo-1-phenylethyl)amino)ethyl)benzonitrile | Calc'd 446.2, Found 446.6 and 446.5 | CHIRALPAK IB; 35% (50:50 MeOH:IPA) in hexanes + 0.1% DEA |
| 99 Isomer 1 Isomer 2 | | (S)- and (R)-4-(2-((2-(6-(1H-pyrazol-4-yl)pyrazolo[1,5-a]pyridin-3-yl)-2-oxo-1-phenylethyl)amino)ethyl)benzonitrile | Calc'd 447.2, Found 447.3 and 447.3 | CHIRALPAK IB; 30% (50:50 MeOH:IPA) in hexanes + 0.1% DEA |
| 100 Isomer 1 Isomer 2 | | (S)- and (R)-4-(2-((2-(7-(1-methyl-1H-pyrazol-4-yl)imidazo[1,2-a]pyridin-3-yl)-2-oxo-1-phenylethyl)amino)ethyl)benzonitrile | Calc'd 461.2, Found 461.5 and 461.5 | CHIRALCEL OX-H; 25% MeOH in Liquid $CO_2$ + 0.1% DEA |
| 101 Isomer 1 Isomer 2 | | (S)- and (R)-4-(2-((2-(6-(1-methyl-1H-pyrazol-4-yl)pyrazolo[1,5-a]pyridin-3-yl)-2-oxo-1-phenylethyl)amino)ethyl)benzenesulfonamide | Calc'd 515.2, Found 515.3 and 515.3 | CHIRALCEL OJ-H; 25% MeOH in Liquid $CO_2$ + 0.1% DEA |

TABLE 2-continued

| Example Nos. | Structure (Methods and Schemes for Preparation) | IUPAC Name | Exact Mass [M + 1] | Chiral Column and Mobile Phase |
|---|---|---|---|---|
| 102 Isomer 1 Isomer 2 Isomer 3 Isomer 4 | | (S,S)-, (S,R)-, (R,R)-, and (R, S)-4-(1-((2-(6-(1-methyl-1H-pyrazol-4-yl)pyrazolo[1,5-a]pyridin-3-yl)-2-oxo-1-phenylethyl)amino)propan-2-yl)benzonitrile | Calc'd 475.2, Found 475.4, 475.4, 475.5, and 475.5 | 1-CHIRALPAK IB; 30% (50:50 MeOH:IPA) in hexanes + 0.1% DEA 2-CHIRALCEL OJ-H; 15% MeOH in Liquid $CO_2$ + 0.1% DEA |
| 103 Isomer 1 Isomer 2 | | (S)- and (R)-4-(2-((2-(7-fluoro-6-(1-methyl-1H-pyrazol-4-yl)-1H-indol-3-yl)-2-oxo-1-phenylethyl)amino)ethyl)benzonitrile | Calc'd 478.2, Found 478.3 and 478.5 | CHIRALPAK IB; 25% (50:50 MeOH:IPA) in hexanes + 0.1% DEA |

Scheme 3

The starting materials required for the synthesis of examples prepared using Scheme 3 were generally prepared using methods 1 through 4 and scheme 1. Starting materials for methods 1 through 4 and scheme 1 were either commercially available or were synthesized using methods 5 through 24.

Example 104

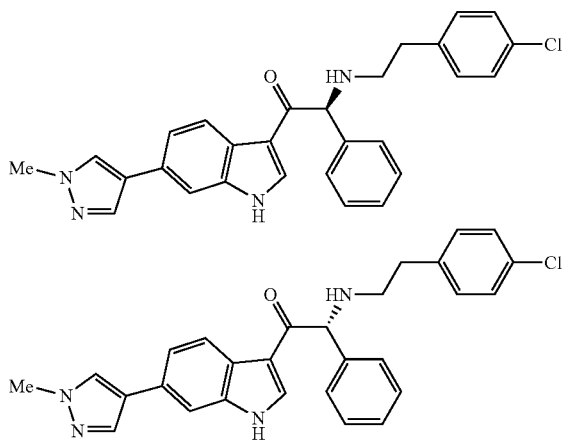

(S)- and (R)-2-((4-Chlorophenethyl)amino)-1-(6-(1-methyl-1H-1,2,3-triazol-4-yl)-1H-indol-3-yl)-2-phenylethan-1-one Scheme 3, step 1: 2-((4-Chlorophenethyl)amino)-2-phenyl-1-(6-(4,4,5,5-tetramethyl-1,3,2-dioxaborolan-2-yl)-1H-indol-3-yl)ethan-1-one:

A mixture of 1-(6-bromo-1H-indol-3-yl)-2-((4-chlorophenethyl)amino)-2-phenylethan-1-one (1 g, 2.14 mmol), bis(pinacolato)diborane (0.65 g, 2.56 mmol), and KOAc (0.63 g, 6.42 mmol) in 1,4-dioxane (20 ml) was degassed for 20 minutes with argon. To this mixture 1,1'-Bis(diphenylphosphino)ferrocene-palladium(II)dichloride (0.13 g, 0.21 mmol) was added and degassing was continued for another 10 minutes. The reaction mixture was heated in a sealed tube at 90° C. for 6 hours. After the completion of reaction (monitored by TLC), the reaction mixture was treated with water (20 ml) and extracted with ethyl acetate (3×20 ml). The combined organic layers were washed with brine, dried over anhydrous $Na_2SO_4$ and concentrated under reduced pressure. The residue was purified by silica gel chromatography to give the title compound as a brown solid (0.59 g, 53%). $^1$H NMR (400 MHz, DMSO-d6): δ 1.30 (s, 12H), 2.62-2.78 (m, 4H), 5.31 (s, 1H), 7.17-7.23 (m, 3H), 7.26-7.33 (m, 4H), 7.44-7.51 (m, 3H), 7.77 (s, 1H), 8.17 (d, J=8.0 Hz, 1H), 8.69 (d, J=2.0 Hz, 1H), 12.13 (s, —NH). LCMS: m/z=515.7 [M+1].

Scheme 3, step 2: (S)- and (R)-2-((4-Chlorophenethyl)amino)-1-(6-(1-methyl-1H-1,2,3-triazol-4-yl)-1H-indol-3-yl)-2-phenylethan-1-one:

A mixture of 2-((4-chlorophenethyl)amino)-2-phenyl-1-(6-(4,4,5,5-tetramethyl-1,3,2-dioxaborolan-2-yl)-1H-indol-3-yl)ethan-1-one (0.06 g, 0.11 mmol), 4-bromo-1-methyl-1H-1,2,3-triazole (0.019 g, 0.11 mmol), and cesium carbonate (0.095 g, 0.29 mmol) in a mixture of 4:1 dioxane: water (5 ml) was degassed for 20 minutes with argon. S-Phos Pd precatalyst G3 (0.009 g, 0.01 mmol) was added and degassing was continued for another 10 minutes. The reaction mixture was heated in a sealed tube with microwave heating at 135° C. for 1 hour. After completion of the reaction (monitored by TLC), the reaction mixture was treated with water (15 ml) and extracted with ethyl acetate (2×15 ml). The combined organic layers were washed with brine, dried over anhydrous $Na_2SO_4$ and concentrated under reduced pressure. The residue was purified by silica gel chromatography to afford the title compound as solid (0.040 g, 74%) in racemic form.

The racemic title compound was resolved by chiral HPLC (Chiralpak IB; 20% (50:50 MeOH:IPA) in hexanes+0.1%

DEA) to furnish the enantiopure compounds. The faster-eluting enantiomer of the title compound was obtained as a solid (Isomer 1): $^1$H NMR (400 MHz, DMSO-d6): δ 2.67-2.76 (m, 4H), 4.08 (s, 3H), 5.30 (s, 1H), 7.19-7.23 (m, 3H), 7.26-7.32 (m, 4H), 7.47 (d, J=7.2 Hz, 2H), 7.63 (d, J=8.0 Hz, 1H), 7.91 (s, 1H), 8.18 (d, J=8.0 Hz, 1H), 8.50 (s, 1H), 8.64 (s, 1H), 12.15 (s, —NH). LCMS: m/z=470.6 [M+1]. The slower-eluting enantiomer of the title compound was obtained as a solid (Isomer 2): $^1$H NMR (400 MHz, DMSO-d6): δ 2.61-2.78 (m, 4H), 4.08 (s, 3H), 5.30 (s, 1H), 7.17-7.23 (m, 3H), 7.26-7.32 (m, 4H), 7.47 (d, J=7.2 Hz, 2H), 7.63 (d, J=8.4 Hz, 1H), 7.91 (s, 1H), 8.18 (d, J=8.0 Hz, 1H), 8.50 (s, 1H), 8.64 (s, 1H), 12.18 (s, —NH). LCMS: m/z=470.6 [M+1].

The following compounds were prepared using similar procedures to those described for Example 104 using the appropriate starting materials.

TABLE 3

| Example No. | Structure (Methods and Schemes for Preparation) | IUPAC Name | Exact Mass [M + 1] | Chiral Column and Mobile Phase |
|---|---|---|---|---|
| 105 Isomer 1 Isomer 2 | | (S)- and (R)-2-((4-fluorophenethyl)amino)-2-phenyl-1-(6-(pyridin-2-yl)-1H-indol-3-yl)ethan-1-one | Calc'd 450.2, Found 450.6 and 450.6 | CHIRALPAK IB; 20% (50:50 MeOH:IPA) in hexanes + 0.1% DEA |
| 106 Isomer 1 Isomer 2 | | (S)- and (R)-2-((4-chlorophenethyl)amino)-1-(6-(1-methyl-1H-imidazol-4-yl)-1H-indol-3-yl)-2-phenylethan-1-one | Calc'd 469.2, Found 469.4 and 469.4 | CHIRALPAK IB; 25% (50:50 MeOH:IPA) in hexanes + 0.1% DEA |
| 107 Isomer 1 Isomer 2 | | (S)- and (R)-2-((4-chlorophenethyl)amino)-1-(6-(5-methyl-1,3,4-oxadiazol-2-yl)-1H-indol-3-yl)-2-phenylethan-1-one | Calc'd 471.2, Found 471.5 and 471.3 | CHIRALPAK AD-H; 50% (50:50 MeOH:IPA) in hexanes + 0.1% DEA |
| 108 Isomer 1 Isomer 2 | | (S)- and (R)-2-((4-chlorophenethyl)amino)-2-phenyl-1-(6-(pyridin-2-yl)-1H-indol-3-yl)ethan-1-one | Calc'd 466.2, Found 466.3 and 466.3 | CHIRALPAK AD-H; 30% (MeOH) in Liquid CO$_2$ + 0.1% DEA |
| 109 Isomer 1 Isomer 2 | | (S)- and (R)-2-((4-chlorophenethyl)amino)-1-(6-(5-methyl-1H-imidazol-2-yl)-1H-indol-3-yl)-2-phenylethan-1-one | Calc'd 469.2, Found 469.1 and 469.2 | CHIRALPAK AD-H; (30:70 ACN:IPA) in hexanes + 0.1% DEA |

TABLE 3-continued

| Example No. | Structure (Methods and Schemes for Preparation) | IUPAC Name | Exact Mass [M + 1] | Chiral Column and Mobile Phase |
|---|---|---|---|---|
| 110 Isomer 1 Isomer 2 | | (S)- and (R)- 2-((4-chlorophenethyl)amino)-1-(6-(2-methyl-1H-imidazol-5-yl)-1H-indol-3-yl)-2-phenylethan-1-one | Calc'd 469.2, Found 469.6 and 469.5 | CHIRALCEL OJ-H; MeOH in Liquid $CO_2$ + 0.1% DEA |
| 111 Isomer 1 Isomer 2 | | (S)- and (R)-2-((4-chlorophenethyl)amino)-2-phenyl-1-(6-(pyrimidin-4-yl)-1H-indol-3-yl)ethan-1-one | Calc'd 467.2, Found 467.2 and 467.3 | CHIRALPAK IB; 30% (50:50 MeOH:IPA) in hexanes + 0.1% DEA |
| 112 Isomer 1 Isomer 2 | | (S)- and (R)-2-((4-chlorophenethyl)amino)-2-phenyl-1-(6-(pyridazin-3-yl)-1H-indol-3-yl)ethan-1-one | Calc'd 467.2, Found 467.6 and 467.5 | CHIRALCEL OJ-H; MeOH in Liquid $CO_2$ + 0.1 DEA |
| 113 Isomer 1 Isomer 2 | | (S)- and (R)-4-(2-((2-(6-(1-methyl-1H-imidazol-4-yl)-1H-indol-3-yl)-2-oxo-1-phenylethyl)amino)ethyl)benzonitrile | Calc'd 460.2, Found 460.1 and 460.1 | CHIRALPAK IB; 30% MeOH in Liquid $CO_2$ + 0.1% DEA |
| 114 Isomer 1 Isomer 2 | | (S)- and (R)-4-(2-((2-(6-(1-methyl-1H-1,2,3-triazol-4-yl)-1H-indol-3-yl)-2-oxo-1-phenylethyl)amino)ethyl)benzonitrile | Calc'd 461.2, Found 4615 and 461.1 | CHIRALPAK IB; 30% MeOH in Liquid $CO_2$ + 0.1% DEA |

TABLE 3-continued

| Example No. | Structure (Methods and Schemes for Preparation) | IUPAC Name | Exact Mass [M + 1] | Chiral Column and Mobile Phase |
|---|---|---|---|---|
| 115 Isomer 1 Isomer 2 | ![structure] | (S)- and (R)-4-(2-((2-(6-(1-methyl-1H-imidazol-4-yl)-1H-indol-3-yl)-2-oxo-1-phenylethyl)amino)ethyl)benzenesulfonamide | Calc'd 514.2, Found 514.6 and 514.4 | CHIRALCEL OJ-H; MeOH in Liquid $CO_2$ + 0.1% DEA |
| 116 Isomer 1 Isomer 2 | ![structure] | (S)- and (R)-4-(2-((2-(6-(1-methyl-1H-1,2,3-triazol-4-yl)-1H-indol-3-yl)-2-oxo-1-phenylethyl)amino)ethyl)benzenesulfonamide | Calc'd 515.2, Found 515.4 and 515.4 | CHIRALPAK IB; 30% MeOH in Liquid $CO_2$ + 0.1% DEA |

Scheme 4

The starting materials required for the synthesis of examples prepared using Scheme 4 were generally prepared using methods 1 through 4 and scheme 1. Starting materials for methods 1 through 4 and scheme 1 were either commercially available or were synthesized using methods 5 through 24.

Example 117

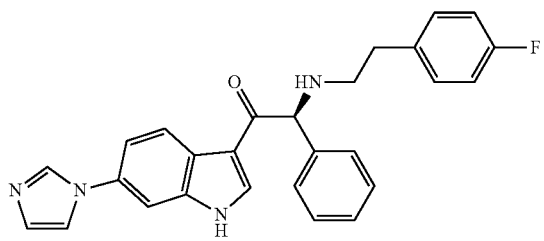

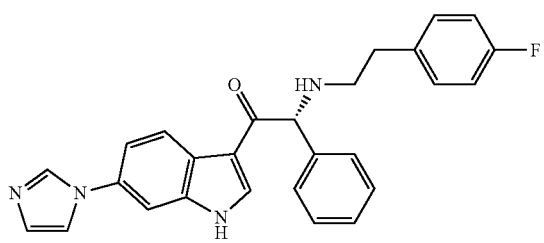

(S)- and (R)-1-(6-(1H-Imidazol-1-yl)-1H-indol-3-yl)-2-((4-fluorophenethyl)amino)-2-phenylethan-1-one Scheme 4. (S)- and (R)-1-(6-(1H-imidazol-1-yl)-1H-indol-3-yl)-2-((4-fluorophenethyl)amino)-2-phenylethan-1-one:

A mixture of 1-(6-bromo-1H-indol-3-yl)-2-((4-fluorophenethyl)amino)-2-phenylethan-1-one (200 mg, 0.44 mmol), imidazole (300 mg, 4.4 mmol), potassium phosphate (200 mg, 0.9 mmol) and L-proline (15.3 mg, 0.13 mmol) in dioxane (5 ml) was purged with argon for 20 minutes. CuI (40 mg, 0.2 mmol) was added and purging was continued for another 10 minutes. The reaction mixture was heated in a sealed tube at 190° C. for 12 hours. After completion of reaction (monitored by TLC), the reaction mixture was quenched with water (15 ml) and extracted with ethyl acetate (3×20 ml). The combined organic layers were washed with brine (20 ml), dried over anhydrous $Na_2SO_4$ and concentrated under reduced pressure. The crude product was purified by silica gel chromatography to afford the title compound product as solid (62 mg, 38%) in racemic form.

The racemic title compound was resolved by chiral HPLC (CHIRALPAK AD-H; 30% (MEOH) in Liquid $CO_2$+0.1% DEA) to furnish the enantiopure compounds. The faster-eluting enantiomer of the title compound was obtained as a solid (Isomer 1): $^1$H NMR (400 MHz, DMSO-d6): δ 2.69-2.76 (m, 4H), 5.32 (s, 1H), 7.07-7.11 (m, 3H), 7.18-7.25 (m, 3H), 7.27-7.30 (m, 2H), 7.44-7.49 (m, 3H), 7.64 (d, J=2.0 Hz, 1H), 7.73 (s, 1H), 8.22-8.25 (m, 2H), 8.68 (s, 1H), 12.24 (s, 1H, —NH). LCMS: m/z=439.4 [M+1]. The slower-eluting enantiomer of the title compound was obtained as a solid (Isomer 2): $^1$HNMR (400 MHz, DMSO-d6): δ 2.69-2.76 (m, 4H), 5.32 (s, 1H), 7.06-7.11 (m, 3H), 7.18-7.25 (m, 3H), 7.27-7.30 (m, 2H), 7.44-7.49 (m, 3H), 7.64 (d, J=2.0 Hz, 1H), 7.73 (s, 1H), 8.22-8.26 (m, 2H), 8.68 (s, 1H), 12.24 (s, 1H, —NH). LCMS: m/z=439.6 [M+1].

The following compounds were prepared using similar procedures to those described for Example 117 using the appropriate starting materials.

TABLE 4

| Example No. | Structure (Methods and Schemes for Preparation) | IUPAC Name | Exact Mass [M + 1] | Chiral Column and Mobile Phase |
|---|---|---|---|---|
| 118 Isomer 1 Isomer 2 | | (S)- and (R)-1-(6-(1H-pyrazol-1-yl)-1H-indol-3-yl)-2-((4-fluorophenethyl)amino)-2-phenylethan-1-one | Calc'd 439.2, Found 439.6 and 439.6 | CHIRALCEL OJ-H; 25% (50:50 ACN:IPA) in Liquid CO₂ + 0.1% DEA |
| 119 Isomer 1 Isomer 2 | | (S)- and (R)-4-(2-((2-(6-(1H-imidazol-1-yl)-1H-indol-3-yl)-2-oxo-1-phenylethyl)amino)ethyl)benzenesulfonamide | Calc'd 500.2, Found 500.5 and 500.4 | CHIRALPAK IB; (25:75 MeOH:IPA) in hexanes + 0.1% DEA |
| 120 Isomer 1 Isomer 2 | | (S)- and (R)-4-(2-((2-(6-(1H-imidazol-1-yl)-1H-indol-3-yl)-2-oxo-1-phenylethyl)amino)ethyl)benzonitrile | Calc'd 446.2, Found 446.5 and 446.6 | CHIRALPAK IB; 20% (50:50 MeOH:IPA) in hexanes + 0.1% DEA |

Scheme 5

The starting materials required for the synthesis of examples prepared using Scheme 5 were generally prepared using methods 1 through 4 and scheme 1. Starting materials for methods 1 through 4 and scheme 1 were either commercially available or were synthesized using methods 5 through 17.

Example 121

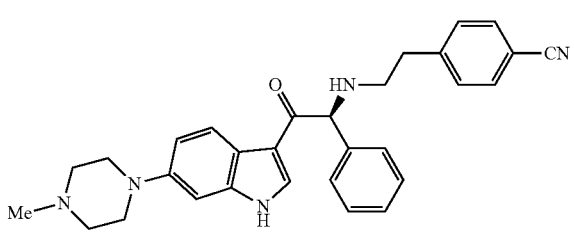

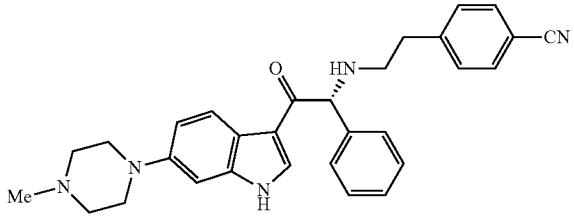

(S)- and (R)-4-(2-((2-(6-(4-Methylpiperazin-1-yl)-1H-pyrrolo[2,3-b]pyridin-3-yl)-2-oxo-1-phenylethyl)amino)ethyl)benzonitrile Scheme 5. (S)- and (R)-4-(2-((2-(6-(4-Methylpiperazin-1-yl)-1H-pyrrolo[2,3-b]pyridin-3-yl)-2-oxo-1-phenylethyl)amino)ethyl)benzonitrile:

4-(2-((2-(6-bromo-1H-pyrrolo[2,3-b]pyridin-3-yl)-2-oxo-1-phenylethyl) amino) ethyl) benzonitrile (0.2 g, 0.43 mmol) was dissolved in NMP (1 ml) and 1-methylpiprazine (4 ml) was added to it. The reaction mixture was purged with argon for 20 minutes. The reaction mixture was heated in a sealed tube at 135° C. for 1 hour. After completion of the reaction (monitored by TLC), the mixture was quenched with water (10 ml) and extracted with ethyl acetate (2×10 ml). The combined organic layers were washed with brine (10 ml), dried over anhydrous Na₂SO₄ and concentrated under reduced pressure. The crude product was purified by silica gel chromatography to afford the title compound (0.15 g, 72%) as solid in racemic form.

The racemic title compound was resolved by chiral HPLC (CHIRALPAK IB; 35% (50:50; MeOH:IPA) in hexanes+ 0.1% DEA) to furnish the enantiopure compounds. The faster-eluting enantiomer of the title compound was obtained as a solid (Isomer 1): $^1$HNMR (400 MHz, DMSO-d6): δ 2.21 (s, 3H), 2.39-2.41 (m, 4H), 2.65-2.77 (m, 2H), 2.79-2.87 (m, 2H), 3.45-3.48 (m, 4H), 5.30 (s, 1H), 6.79 (d, J=8.8 Hz, 1H), 7.18-7.21 (m, 1H), 7.28 (t, J=7.6 Hz, 2H), 7.40-7.46 (m, 4H), 7.73 (d, J=8.4 Hz, 2H), 8.17 (d, J=8.8 Hz, 1H), 8.35 (s, 1H), 12.01 (s, 1H, —NH). LCMS: m/z=479.3 [M+1]. The slower-eluting enantiomer of the title compound was obtained as a solid (Isomer 2): $^1$HNMR (400 MHz, DMSO-d6): 2.20 (s, 3H), 2.39-2.41 (m, 4H), 2.67-2.70 (m, 2H), 2.81-2.85 (m, 2H), 3.45-3.47 (m, 4H), 5.24 (s, 1H), 6.78 (d, J=8.8 Hz, 1H), 7.18-7.21 (m, 1H), 7.27 (t, J=7.6 Hz, 2H), 7.39-7.45 (m, 4H), 7.72 (d, J=8.4 Hz, 2H), 8.16 (d, J=9.2 Hz, 1H), 8.35 (s, 1H), 12.01 (s, 1H, —NH). LCMS: m/z=479.5 [M+1].

Scheme 6

The starting materials required for the synthesis of examples prepared using Scheme 6 were generally prepared using method 8, method 4, and scheme 1. The starting materials for method 8, method 4, and scheme 1 were either commercially available or were synthesized using methods 5 through 24.

Example 122

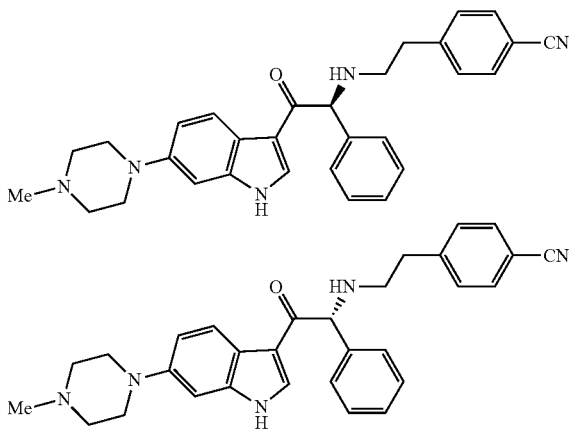

(S)- and (R)-4-(2-((2-(6-(4-Methylpiperazin-1-yl)-1H-indol-3-yl)-2-oxo-1-phenylethyl)amino)ethyl) benzonitrile Scheme 6. (S)- and (R)-4-(2-((2-(6-(4-Methylpiperazin-1-yl)-1H-indol-3-yl)-2-oxo-1-phenylethyl)amino)-ethyl) benzonitrile:

To a stirred solution of tert-butyl 3-(2-((4-cyanophenethyl)-amino)-2-phenylacetyl)-6-(4-methylpiperazin-1-yl)-1H-indole-1-carboxylate (0.56 g, 9.7 mmol) in dry DCM (10 ml) was added TFA (5.6 ml, 10 vol) at 0° C. The resulting reaction mixture was then heated to 50° C. for 2 hours. The reaction mixture was concentrated and to the residue was portioned between saturated sodium bicarbonate (50 ml) and ethyl acetate (3×50 ml). The combined organic layers were washed with brine (50 ml), dried over anhydrous Na$_2$SO$_4$ and concentrated under reduced pressure. The resulting residue was purified by silica gel chromatography to afford the title compound as a solid (0.075 g, 29%) in racemic form.

The racemic title compound was resolved by chiral HPLC (CHIRALPAK IB; (25:75 MeOH:IPA) in hexanes+0.1% DEA) to furnish the enantiopure compounds. The faster-eluting enantiomer of the title compound was obtained as a solid (Isomer 1): $^1$H NMR (400 MHz, DMSO-d6): δ 2.22 (s, 3H), 2.47-2.49 (m, 4H), 2.68-2.74 (m, 2H), 2.84-2.87 (m, 2H), 3.07-3.09 (m, 4H), 5.23 (d, J=8.8 Hz, 1H), 6.92 (dd, J=2.0 Hz, 8.8 Hz, 2H), 7.17-7.29 (m, 3H), 7.41-7.45 (m, 4H), 7.72 (d, J=8 Hz, 2H), 7.94 (d, J=8.8 Hz, 1H), 8.40 (s, 1H), 11.72 (s, —NH). LCMS: m/z=478.5 [M+1].The slower-eluting enantiomer of the title compound was obtained as a solid (Isomer 2): $^1$H NMR (400 MHz, DMSO-d6): δ 2.22 (s, 3H), 2.47-2.49 (m, 4H), 2.68-2.71 (m, 2H), 2.84-2.85 (m, 2H), 3.07-3.10 (m, 4H), 5.23 (s, 1H), 6.86-6.93 (m, 2H), 7.16-7.29 (m, 3H), 7.41-7.45 (m, 4H), 7.72 (d, J=8 Hz, 2H), 7.94 (d, J=8.4 Hz, 1H), 8.40 (s, 1H), 11.96 (s, 1H, —NH). LCMS: m/z=478.5 [M+1].

The following compounds were prepared using similar procedures to those described for Example 122 using the appropriate starting materials.

TABLE 5

| Example No. | Structure (Methods and Schemes for Preparation) | IUPAC Name | Exact Mass [M + 1] | Chiral Column and Mobile Phase |
|---|---|---|---|---|
| 123 Isomer 1 Isomer 2 | | (S)- and (R)-2-((4-fluorophenethyl)amino)-1-(6-(4-methylpiperazin-1-yl)-1H-indol-3-yl)-2-phenylethan-1-one | Calc'd 471.3, Found 469.9 and 469.6 | CHIRALPAK IB; 30% (50:50 MeOH:IPA) in hexanes + 0.1% DEA |

TABLE 5-continued

| Example No. | Structure (Methods and Schemes for Preparation) | IUPAC Name | Exact Mass [M + 1] | Chiral Column and Mobile Phase |
|---|---|---|---|---|
| 124 Isomer 1 Isomer 2 | | (S)- and (R)- 4-(2-((2-(6-(4-methylpiperazin-1-yl)-1H-indol-3-yl)-2-oxo-1-phenyl-ethyl)amino)ethyl)benzenesulfonamide | Calc'd 532.2, Found 532.5 and 532.6 | CHIRALPAK IB; 35% (50:50 MeOH:IPA) in hexanes + 0.1% DEA |
| 125 Isomer 1 Isomer 2 | | (S)- and (R)- 4-(2-((2-oxo-1-phenyl-2-(6-(pyrrolidin-1-yl)-1H-indol-3-yl)eth-yl)amino)ethyl)benzo-nitrile | Calc'd 449.2, Found 449.9 and 449.6 | CHIRALPAK IB; 30% (MeOH) in Liquid CO$_2$ + 0.1% DEA |
| 126 Isomer 1 Isomer 2 | | (S)- and (R)-4-(2-((2-(6-((1-methylpiperidin-4-yl)oxy)-1H-indol-3-yl)-2-oxo-1-phenyl-ethyl)amino)ethyl)benzonitrile | Calc'd 493.3, Found 493.4 and 493.4 | CHIRALPAK IB; 25% (50:50 MeOH:IPA) in hexanes + 0.1% DEA |

Scheme 7

The starting materials required for the synthesis of examples prepared using Scheme 7 were generally prepared using methods 1 through 4 and scheme 1. The starting materials for methods 1 through 4 and scheme 1 were either commercially available or were synthesized using methods 5 through 24.

Example 127

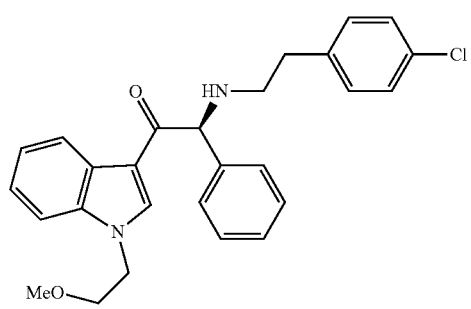

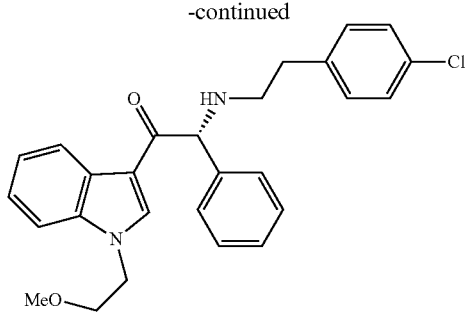

(S)- and (R)-2-((4-Chlorophenethyl)amino)-1-(1-(2-methoxyethyl)-1H-indol-3-yl)-2-phenylethan-1-one Scheme 7, step 1. tert-Butyl (2-(1H-indol-3-yl)-2-oxo-1-phenylethyl)(4-chlorophenethyl)carbamate:

To a stirred solution of 2-((4-chlorophenethyl)amino)-1-(1H-indol-3-yl)-2-phenylethan-1-one (0.240 g, 0.61 mmol) in DCM (3 ml) was added di-tert-butyl dicarbonate (0.134 g, 0.61 mmol) drop wise at 0° C. The reaction mixture was allowed to stir at room temperature for 16 hours. The reaction mixture was concentrated under reduced pressure and the resulting residue was purified by silica gel chromatography to afford the title compound as a solid (0.25 g, 83%). LCMS: m/z=489.4 [M+1].

Scheme 7, step 2: tert-Butyl (4-chlorophenethyl)(2-(1-(2-methoxyethyl)-1H-indol-3-yl)-2-oxo-1-phenylethyl)carbamate:

To a stirred solution of tert-butyl (2-(1H-indol-3-yl)-2-oxo-1-phenylethyl)(4-chlorophenethyl)carbamate (0.1 g, 0.20 mmol) in dry DMF (2 ml) under an atmosphere of nitrogen was added NaH (0.005 g, 0.20 mmol, 95%) at 0° C. The reaction mixture was allowed to stir for 30 minutes at 0° C. and then 1-bromo-2-methoxyethane (0.028 g, 0.20 mmol) was added slowly. The reaction mixture was stirred at room temperature for 4 hours. Water (10 ml) was added and the reaction mixture was extracted with ethyl acetate (2×10 ml). The combined organic layer was washed with brine (10 ml), dried over anhydrous $Na_2SO_4$ and concentrated under reduced pressure to obtain product tert-butyl (4-chlorophenethyl)(2-(1-(2-methoxyethyl)-1H-indol-3-yl)-2-oxo-1-phenylethyl)carbamate as solid (0.06 g, 54%) which was used for next step without further purification. LCMS: m/z=547.5 [M+1].

Scheme 7, step 3: (S)- and (R)-2-((4-Chlorophenethyl)amino)-1-(1-(2-methoxyethyl)-1H-indol-3-yl)-2-phenylethan-1-one:

To a stirred solution of tert-butyl (4-chlorophenethyl)(2-(1-(2-methoxyethyl)-1H-indol-3-yl)-2-oxo-1-phenylethyl)carbamate (0.08 g, 0.14 mmol) in dry DCM (2 ml) was added HCl (0.1 ml, 4.0 M solution in dioxane) at 0° C. The resulting reaction mixture was allowed to stir for 1 hour at room temperature. The reaction mixture was concentrated and saturated sodium bicarbonate (10 ml) was added and the product was extracted with ethyl acetate (2×10 ml). The combined organic layers were washed with brine (10 ml), dried over anhydrous $Na_2SO_4$ and concentrated under reduced pressure. The resulting residue was purified by silica gel chromatography to afford the title compound (0.038 g, 58%) in racemic form.

The racemic title compound was resolved by chiral HPLC (CHIRALPAK IB; (50:50; MeOH:IPA) in hexanes+0.1% DEA) to furnish the enantiopure compounds. The faster-eluting enantiomer of the title compound was obtained as a solid (Isomer 1): $^1$H NMR (400 MHz, DMSO-d6): δ 2.68-2.77 (m, 4H), 3.21 (s, 3H), 3.67-3.72 (m, 2H), 4.42 (t, J=4.8 Hz, 2H), 5.24 (s, 1H), 7.18-7.33 (m, 9H), 7.46 (d, J=7.6 Hz, 2H), 7.59 (d, J=8.0 Hz, 1H), 8.17 (d, J=7.2 Hz, 1H), 8.64 (s, 1H). LCMS: m/z=447.5 [M+1]. The slower-eluting enantiomer of the title compound was obtained as a solid (Isomer 2): $^1$HNMR (400 MHz, DMSO-d6): δ 2.69-2.77 (m, 4H), 3.22 (s, 3H), 3.68-3.72 (m, 2H), 4.42 (t, J=4.0 Hz, 2H), 5.24 (s, 1H), 7.18-7.34 (m, 9H), 7.46 (d, J=7.6 Hz, 2H), 7.59 (d, J=8.0 Hz, 1H), 8.18 (d, J=7.2 Hz, 1H), 8.65 (s, 1H). LCMS: m/z=447.6 [M+1]

The following compounds were prepared using similar procedures to those described for Example 127 using the appropriate starting materials.

TABLE 6

| Example No. | Structure (Methods and Schemes for Preparation) | IUPAC Name | Exact Mass [M + 1] | Chiral Column and Mobile Phase |
|---|---|---|---|---|
| 128 Isomer 1 Isomer 2 | | (S)- and (R)-2-((4-chlorophenethyl)amino)-1-(1-(2-hydroxyethyl)-1H-indol-3-yl)-2-phenylethan-1-one | Calc'd 433.2, Found 433.3 and 433.3 | CHIRALPAK IB; 24% MeOH in Liquid $CO_2$ + 0.1% DEA |
| 129 Isomer 1 Isomer 2 | | (S)- and (R)-2-((4-chlorophenethyl)amino)-1-(1-ethyl-1H-indol-3-yl)-2-phenylethan-1-one | Calc'd 417.2, Found 417.6 and 417.4 | CHIRALPAK IB; 20% (50:50 MeOH:IPA) in hexanes + 0.1% DEA |

TABLE 6-continued

| Example No. | Structure (Methods and Schemes for Preparation) | IUPAC Name | Exact Mass [M + 1] | Chiral Column and Mobile Phase |
|---|---|---|---|---|
| 130 Isomer 1 Isomer 2 | | (S)- and (R)-2-((4-chlorophenethyl)amino)-2-phenyl-1-(1-(2,2,2-trifluoroethyl)-1H-indol-3-yl)ethan-1-one | Calc'd 471.1, Found 471.5 and 471.5 | CHIRALPAK AD-H; 30% MeOH in Liquid $CO_2$ + 0.1% DEA |

Scheme 8

The starting materials required for the synthesis of examples prepared using Scheme 8 were generally prepared using methods 1 through 4 and schemes 1, 2, and 3. The starting materials for methods 1 through 4 and schemes 1, 2, and 3 were either commercially available or were synthesized using methods 5 through 24.

Example 131

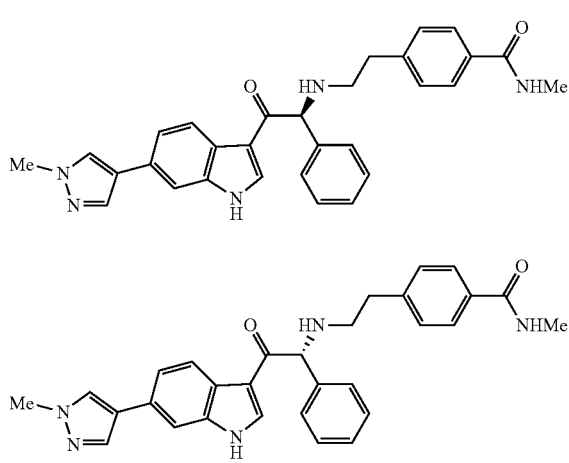

(S)- and (R)—N-methyl-4-(2-((2-(6-(1-methyl-1H-pyrazol-4-yl)-1H-indol-3-yl)-2-oxo-1-phenylethyl) amino)ethyl)benzamide Scheme 8, Step 1: 4-(2-((2-(6-(1-methyl-1H-pyrazol-4-yl)-1H-indol-3-yl)-2-oxo-1-phenylethyl)amino) ethyl)benzoic acid:

To a stirred solution of methyl 4-(2-((2-(6-(1-methyl-1H-pyrazol-4-yl)-1H-indol-3-yl)-2-oxo-1-phenylethyl)amino) ethyl)benzoate (0.15 g, 0.30 mmol) in a mixture of 4:2:1 MeOH:THF:Water (16 ml) was added LiOH (0.025 g, 0.60 mmol) and the resulting reaction mixture was allow to stir at room temperature for 16 hours. After the completion of reaction, the reaction mixture was concentrated, diluted with water (15 ml) and extracted with ethyl acetate (2×7 ml) to remove the nonpolar impurities. The aqueous layer was then acidified with 1N HCl and the resulting precipitate was extracted with ethyl acetate (2×10 ml). The combined organic layers were washed with brine, dried over anhydrous $Na_2SO_4$ and concentrated under reduced pressure. The crude product was purified by silica gel chromatography to afford the title compound as an off-white solid (0.095 g, 65%). $^1$H NMR (400 MHz, DMSO-d6): δ 2.69-2.79 (m, 4H), 3.87 (s, 3H), 5.30 (s, 1H), 7.11-721 (m, 3H), 7.29 (t, J=7.6 Hz, 2H), 7.39 (d, J=8.4 Hz, 1H), 7.47 (d, J=7.6 Hz, 2H), 7.56 (s, 1H), 7.79 (d, J=8.0 Hz, 2H), 7.84 (s, 1H), 8.10-8.12 (m, 2H), 8.55 (s, 1H), 12.09 (s, —NH). LCMS: m/z=479.7 [M+1].

Scheme 8, Step 2. (R)- and (S)—N-methyl-4-(2-((2-(6-(1-methyl-1H-pyrazol-4-yl)-1H-indol-3-yl)-2-oxo-1-phenylethyl) amino)ethyl)benzamide:

To a stirring solution of 4-(2-((2-(6-(1-methyl-1H-pyrazol-4-yl)-1H-indol-3-yl)-2-oxo-1-phenylethyl)amino)ethyl) benzoic acid (0.045 g, 0.09 mmol) in DMF (3 ml) was added methyl amine (0.094 ml, 0.18 mmol; 2.0 M in THF) and DIPEA (0.032 ml, 0.18 mmol) followed by HATU (0.043 g, 0.11 mmol) at 0° C. The resulting reaction mixture was stirred at room temperature for 16 hours. After completion of the reaction, the reaction mixture was diluted with water (10 ml) and extracted with ethyl acetate (2×10 ml). The combined organic layers were washed with brine, dried over anhydrous $Na_2SO_4$ and concentrated under reduced pressure. The residue was purified by silica gel chromatography to afford the racemic title compound (0.025 g, 54%).

The racemic title compound was resolved by chiral SFC (Chiralpak IB; 30% MeOH in $CO_2$+0.1% DEA) to furnish the enantiopure compounds. The faster-eluting enantiomer of the title compound was obtained as a solid (Isomer 1): $^1$H NMR (400 MHz, DMSO-d6): δ 2.62-2.72 (m, 7H), 3.87 (s, 3H), 5.31 (s, 1H), 7.19-7.22 (m, 1H), 7.26-7.31 (m, 3H), 7.40 (d, J=8.4 Hz, 1H), 7.47 (d, J=7.6 Hz, 2H), 7.55 (s, 1H), 7.74 (d, J=8.4 Hz, 2H), 7.85 (s, 1H), 8.10-8.13 (m, 2H), 8.34-8.35 (m, 1H), 8.57 (s, 1H), 11.99 (s, —NH). LCMS: m/z=492.6 [M+1]. The slower-eluting enantiomer of the title compound was obtained as a solid (Isomer 2): $^1$H NMR (400 MHz, DMSO-d6): δ 2.68-2.82 (m, 7H), 3.87 (s, 3H), 5.30 (s, 1H), 7.19-7.22 (m, 1H), 7.26-7.31 (m, 3H), 7.40 (d, J=8.4 Hz, 1H), 7.47 (d, J=7.6 Hz, 2H), 7.55 (s, 1H), 7.74 (d, J=8.0 Hz, 2H), 7.85 (s, 1H), 8.10-8.13 (m, 2H), 8.34-8.35 (m, 1H), 8.57 (s, 1H), 11.99 (s, —NH). LCMS: m/z=492.6 [M+1].

The following compounds were prepared using similar procedures to those described for Example 131 using the appropriate starting materials.

TABLE 7

| Example No. | Structure (Methods and Schemes for Preparation) | IUPAC Name | Exact Mass [M + 1] | Chiral Column and Mobile Phase |
|---|---|---|---|---|
| 132 Isomer 1 Isomer 2 | | (S)- and (R)-4-(2-((2-(1H-indol-3-yl)-2-oxo-1-phenyl-ethyl)amino)eth-yl)benzoic acid | Calc'd 399.2, Found 399.7 and 399.7 | CHIRALPAK AD-H; 35% (50:50 MeOH:IPA) in Liquid $CO_2$ + 0.1% DEA |
| 133 Isomer 1 Isomer 2 | | (S)- and (R)-4-(2-((2-(1H-indol-3-yl)-2-oxo-1-phenyl-ethyl)amino)eth-yl)benzamide | Calc'd 398.2, Found 398.6 and 398.6 | CHIRALPAK IB; 20% (50:50 MeOH:IPA) in hexanes + 0.1% DEA |
| 134 Isomer 1 Isomer 2 | | (S)- and (R)-4-(2-((2-(1H-indol-3-yl)-2-oxo-1-phenyl-ethyl)amino)eth-yl)-N-methylbenzamide | Calc'd 412.2, Found 412.5 and 412.5 | CHIRALPAK IB; 15% (50:50 MeOH:IPA) in hexanes + 0.1% DEA |
| 135 Isomer 1 Isomer 2 | | (S)- and (R)- 4-(2-((2-(1H-indol-3-yl)-2-oxo-1-phenyl-ethyl)amino)eth-yl)-N,N-dimethylbenzamide | Calc'd 426.2, Found 426.6 and 426.6 | CHIRALPAK IB; 20% (50:50 MeOH:IPA) in hexanes + 0.1% DEA |
| 136 Isomer 1 Isomer 2 | | (S)- and (R)-2-(4-(2-((2-(1H-indol-3-yl)-2-oxo-1-phenyl-ethyl)amino)eth-yl)phenyl)-N-methylacetamide | Calc'd 426.2 Found 426.4 and 426.4 | CHRALPAK AD-H; 30% (50:50 MeOH:IPA) in hexanes + 0.1% DEA |
| 137 Isomer 1 Isomer 2 | | (S)- and (R)-2-(4-(2-((2-(1H-indol-3-yl)-2-oxo-1-phenyl-ethyl)amino)eth-yl)phenyl)-N,N-dimethylacetamide | Calc'd 440.2, Found 440.5 and 440.5 | CHIRALPAK AD-H; 35% MeOH in Liquid $CO_2$ + 0.1% DEA |

TABLE 7-continued

| Example No. | Structure (Methods and Schemes for Preparation) | IUPAC Name | Exact Mass [M + 1] | Chiral Column and Mobile Phase |
|---|---|---|---|---|
| 138 Isomer 1 Isomer 2 | 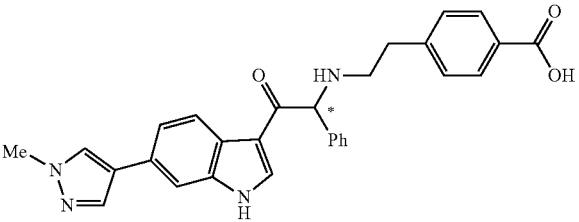 [SMILES: Cn1cc(-c2ccc3c(C(=O)C(NCCc4ccc(C(=O)O)cc4)c4ccccc4)c[nH]c3c2)cn1] | (S)- and (R)-4-(2-((2-(6-(1-methyl-1H-pyrazol-4-yl)-1H-indol-3-yl)-2-oxo-1-phenylethyl)amino)ethyl)benzoic acid | Calc'd 479.2, Found 479.7 and 479.6 | CHIRALPAK AD-H; (50:50 MeOH:IPA) in hexanes + 0.1% DEA |
| 139 Isomer 1 Isomer 2 | 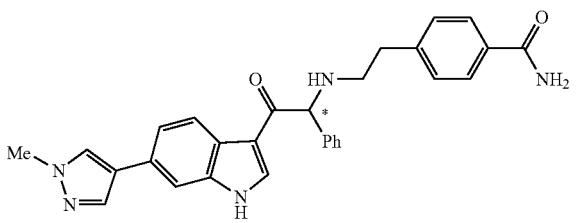 [SMILES: Cn1cc(-c2ccc3c(C(=O)C(NCCc4ccc(C(N)=O)cc4)c4ccccc4)c[nH]c3c2)cn1] | (S)- and (R)-4-(2-((2-(6-(1-methyl-1H-pyrazol-4-yl)-1H-indol-3-yl)-2-oxo-1-phenylethyl)amino)ethyl)benzamide | Calc'd 478.2, Found 478.7 and 478.6 | CHIRALPAK IB; 30% (50:50 MeOH:IPA) in hexanes + 0.1% DEA |
| 140 Isomer 1 Isomer 2 Isomer 3 Isomer 4 | 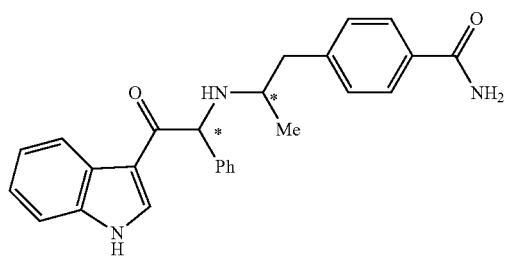 [SMILES: CC(Cc1ccc(C(N)=O)cc1)NC(C(=O)c1c[nH]c2ccccc12)c1ccccc1] | (S,S)-, (S,R)-, (R, R)-, and (R,S)-4-(2-((2-(1H-indol-3-yl)-2-oxo-1-phenyl-ethyl)amino)pro-pyl)benzamide | Calc'd 412.2, Found 412.4, 412.4, 412.5 and 412.4 | 1-CHIRALPAK IC; 20% (50:50 MeOH:IPA) in Liquid CO$_2$ + 0.1% DEA 2-CHIRALPAK IC; 25% (50:50 MeOH:IPA) in hexanes + 0.1% DEA 3-CHIRALPAK IC; 22% (50:50 MeOH:IPA) in hexanes + 0.1% DEA |
| 141 Isomers 1 and 2 Isomers 3 and 4 | 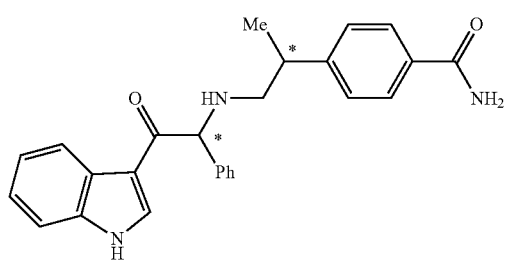 [SMILES: CC(CNC(C(=O)c1c[nH]c2ccccc12)c1ccccc1)c1ccc(C(N)=O)cc1] | (S,S)-, (S,R)-, (R,R)-, and (R,S)-4-(1-((2-(1H-indol-3-yl)-2-oxo-1-phenyl-ethyl)amino)pro-pan-2-yl)benzamide | Calc'd 412.2, Found 412.3 and 412.5 | CHIRALPAK IB; 15% (50:50 MeOH:IPA) in hexanes + 0.1% DEA |
| 142 Isomer 1 Isomer 2 | 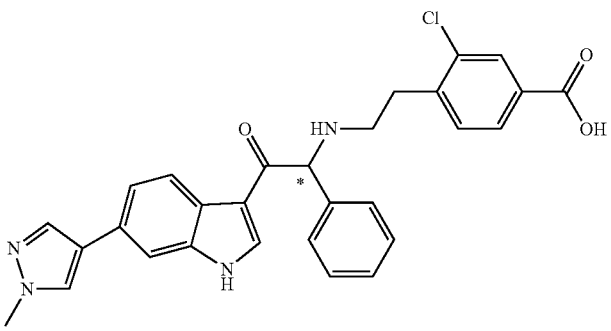 [SMILES: Cn1cc(-c2ccc3c(C(=O)C(NCCc4ccc(C(=O)O)cc4Cl)c4ccccc4)c[nH]c3c2)cn1] | (S)- and (R)-3-chloro-4-(2-((2-(6-(1-methyl-1H-pyrazol-4-yl)-1H-indol-3-yl)-2-oxo-1-phenyl-ethyl)amino)ethyl)benzoic acid | Calc'd 513.2, Found 513.2 and 513.2 | CHIRALPAK IB; 45% (50:50 MeOH: IPA) in hexanes + 0.1% DEA |

TABLE 7-continued

| Example No. | Structure (Methods and Schemes for Preparation) | IUPAC Name | Exact Mass [M + 1] | Chiral Column and Mobile Phase |
|---|---|---|---|---|
| 143 Racemic | | 3-chloro-4-(2-((2-(6-(1-methyl-1H-pyrazol-4-yl)-1H-indol-3-yl)-2-oxo-1-phenyleth-yl)amino)eth-yl)benzamide | Calc'd 512.2, Found 512.6 | Racemic mixture |

Scheme 9

The starting materials required for the synthesis of examples prepared using Scheme 9 were generally prepared using methods 1 through 4 and scheme 1. The starting materials for methods 1 through 4 and scheme 1 were either commercially available or were synthesized using methods 5 through 24.

Example 144

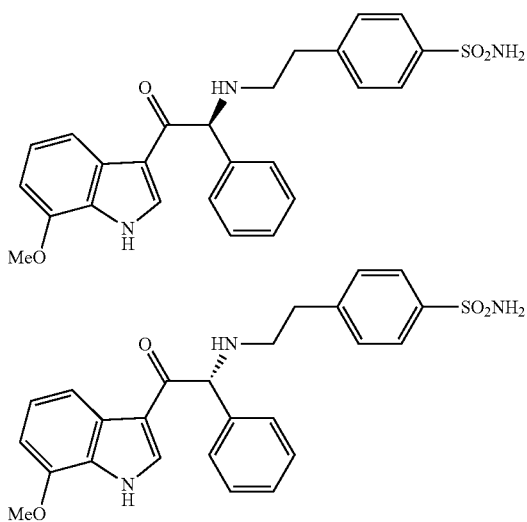

(S)- and (R)-4-(2-((2-(7-Methoxy-1H-indol-3-yl)-2-oxo-1-phenylethyl)amino)ethyl)benzenesulfonamide Scheme 9: (S)- and (R)-4-(2-((2-(7-Methoxy-1H-indol-3-yl)-2-oxo-1-phenylethyl)amino)ethyl)-benzenesulfonamide:
A solution of 4-(2-(2-(7-methoxy-1-(phenylsulfonyl)-1H-indol-3-yl)-2-oxo-1-phenylethylamino)ethyl)benzene sulfonamide (400 mg, 0.66 mmol) and $K_2CO_3$ (450 mg, 3.31 mmol) in methanol (4 ml) was stirred at 50° C. for 3 hours. The reaction mixture was diluted with water (15 ml) and extracted with ethyl acetate (2×20 ml). The combined organic layers were washed with brine (20 ml), dried over anhydrous $Na_2SO_4$ and concentrated under reduced pressure. The resulting residue was purified by silica gel chromatography to afford the title compound (100 mg, 32%) as solid in racemic form.

The racemic title compound was resolved by chiral HPLC (CHIRALPAK IB; 25% (MEOH) in Liquid $CO_2$+0.1% DEA) to furnish the enantiopure compounds. The faster-eluting enantiomer of the title compound was obtained as a solid (Isomer 1): $^1$HNMR (400 MHz, DMSO-d6): 2.82-2.72 (m, 4H), 4.00 (s, 3H), 5.62 (s, 1H), 6.73 (d, J=8.4 Hz, 1H), 7.15-7.02 (m, 1H), 7.10-7.19 (m, 2H), 7.22-7.28 (m, 4H), 7.43-7.35 (m, 4H), 7.72 (d, J=8.4 Hz, 2H), 8.02 (d, J=8.4 Hz, 1H), 11.58 (s, 1H, —NH). LCMS: m/z=464.5 [M+1]. The slower-eluting enantiomer of the title compound was obtained as a solid (Isomer 2): $^1$HNMR (400 MHz, DMSO-d6): 2.84-2.69 (m, 4H), 4.00 (s, 3H), 5.62 (s, 1H), 6.73 (d, J=8.4 Hz, 1H), 7.08-7.22 (m, 2H), 7.22-7.36 (m, 4H), 7.36-7.43 (m, 5H), 7.73 (d, J=8.4 Hz, 2H), 8.02 (d, J=8.4 Hz, 1H), 11.58 (s, 1H, —NH). LCMS: m/z=464.5 [M+1].

Scheme 10

The starting materials required for the synthesis of examples prepared using Scheme 10 were generally prepared using methods 1 through 4 and scheme 1. The starting materials for methods 1 through 4 and scheme 1 were either commercially available or were synthesized using methods 5 through 24.

Example 145

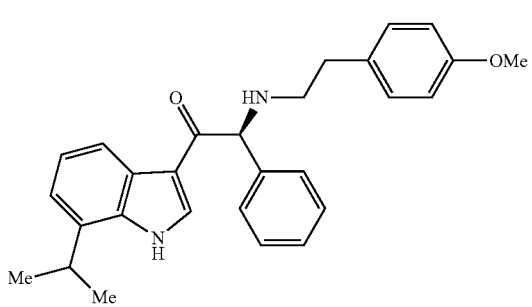

185
-continued

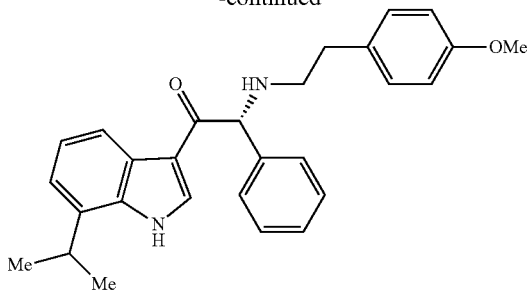

(S)- and (R)-1-(7-Isopropyl-1H-indol-3-yl)-2-((4-methoxyphenethyl)amino)-2-phenylethan-1-one Scheme 10, step 1. 2-((4-Methoxyphenethyl)amino)-2-phenyl-1-(7-(prop-1-en-2-yl)-1H-indol-3-yl)ethan-1-one:

A mixture of 1-(7-chloro-1H-indol-3-yl)-2-((4-methoxyphenethyl)amino)-2-phenylethan-1-one (160 mg, 0.38 mmol), potassium isopropenyltrifluoroborate (60 mg, 0.4 mmol), X-Phos (11 mg, 0.023 mmol) and cesium carbonate (374 mg, 1.15 mmol) in a mixture of 10:1 THF:water (1.6 ml) was purged for 20 minutes with argon. Pd(OAc)$_2$ (4.3 mg, 0.019 mmol) was added and purging was continued for another 10 minutes. The reaction mixture was heated in a sealed tube at 100° C. for 12 hours. After completion of the reaction (monitored by TLC), the reaction mixture was quenched with water (15 ml) and extracted with ethyl acetate (2×15 ml). The combined organic layers were washed with brine (10 ml), dried over anhydrous Na$_2$SO$_4$ and concentrated under reduced pressure. The resulting residue was purified by silica gel chromatography to afford the title compound as a solid (95 mg, 59%). LCMS: m/z=424.22 [M+1] and 425.44 [M+2].

Scheme 10, step 2. (S)- and (R)-1-(7-isopropyl-1H-indol-3-yl)-2-((4-methoxyphenethyl)amino)-2-phenylethan-1-one:

A mixture of 2-((4-methoxyphenethyl)amino)-2-phenyl-1-(7-(prop-1-en-2-yl)-1H-indol-3-yl)ethan-1-one (30 mg, 0.07 mmol), 10% Pd/C (5 mg, 50% moisture) and ethanol (5 ml) was stirred under an atmosphere of hydrogen room temperature for 12 hours. After completion of the reaction (monitored by TLC), the reaction mixture was filtered through a pad of celite, washed with ethanol (2×15 ml) and the filtrate was concentrated under reduced pressure. The resulting residue was purified by silica gel chromatography to afford the title compound as white solid (25 mg, 83%) in racemic form.

The racemic title compound was resolved by chiral HPLC (CHIRALPAK AD-H; 40% (50:50 MeOH:IPA) in hexanes+ 0.1% DEA) to furnish the enantiopure compounds. The faster-eluting enantiomer of the title compound was obtained as a solid (Isomer 1): $^1$HNMR (400 MHz, CDCl$_3$): δ 1.29-1.41 (m, 6H), 2.83-2.93 (m, 4H), 3.19-3.22 (m, 1H), 3.82 (s, 3H), 5.05 (s, 1H), 6.85 (d, J=8.4 Hz, 2H), 7.13-7.19 (m, 3H), 7.23-7.33 (m, 5H), 7.39 (s, 2H), 7.88 (s, 1H), 8.32 (d, J=8.0 Hz, 1H), 8.56 (s, 1H, —NH). LCMS: m/z=427.5 [M+1]. The slower-eluting enantiomer of the title compound was obtained as a solid (Isomer 2): $^1$HNMR (400 MHz, CDCl$_3$): δ 1.29-1.41 (m, 6H), 2.79-2.93 (m, 4H), 3.19-3.22 (m, 1H), 3.82 (s, 3H), 5.06 (s, 1H), 6.85 (d, J=8.8 Hz, 2H), 7.13-7.19 (m, 3H), 7.23-7.33 (m, 4H), 7.39 (s, 2H), 7.88 (s, 1H), 8.32 (d, J=8.0 Hz, 1H), 8.54 (s, 1H, —NH). LCMS: m/z=427.7 [M+1].

Scheme 11

The starting materials required for the synthesis of examples prepared using Scheme 11 were generally prepared using methods 1 through 4, method 7, and scheme 1. The starting materials for methods 1 through 4, method 7, and scheme 1 were either commercially available or were synthesized using methods 5 through 24.

Example 146

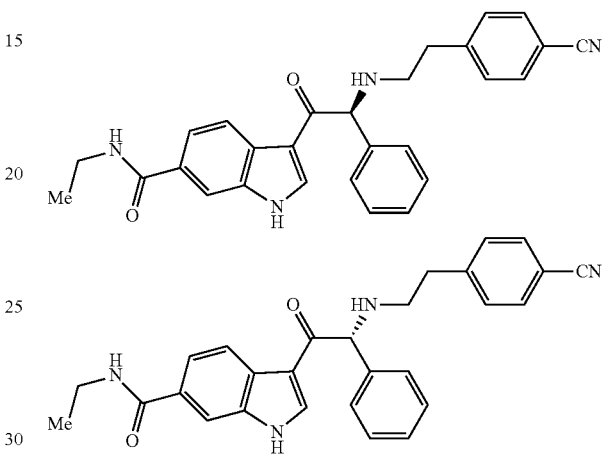

(S)- and (R)-3-(2-((4-Cyanophenethyl)amino)-2-phenylacetyl)-N-ethyl-1H-indole-6-carboxamide Scheme 11, Step 1: 3-(2-((4-Cyanophenethyl)amino)-2-phenylacetyl)-1H-indole-6-carboxylic acid:

To a solution of methyl 3-(2-((4-cyanophenethyl)amino)-2-phenylacetyl)-1H-indole-6-carboxylate (0.12 g, 0.27 mmol) in of 4:2:1 MeOH:THF:Water (7 ml) was added LiOH (0.057 g, 1.37 mmol) and the reaction mixture was allowed to stir at room temperature for 16 hours. After completion of the reaction, the mixture was concentrated, diluted with water (10 ml) and extracted with ethyl acetate (2×15 ml). The aqueous layer was then acidified by using 1N aqueous HCl and the aqueous layer was extracted with ethyl acetate (2×10 ml). The combined organic layer was washed with brine (10 ml), dried over anhydrous Na$_2$SO$_4$ and concentrated under reduced pressure. The crude product was purified by silica gel chromatography to afford the title compound as a solid (0.025 g, 21%) in racemic form. $^1$H NMR (400 MHz, DMSO-d6): δ 2.66-2.76 (m, 2H), 2.87-2.89 (m, 2H), 5.36 (s, 1H), 7.20-7.24 (m, 1H), 7.30 (t, J=7.2 Hz, 2H), 7.43 (d, J=8.4 Hz, 2H), 7.49 (d, J=7.6 Hz, 2H), 7.73-7.79 (m, 3H), 8.06 (s, 1H), 8.23 (d, J=8.4 Hz, 1H), 8.76 (s, 1H), 12.34 (s, 1H, —NH). LCMS: m/z=424.3 [M+1].

Scheme 11, step 2: (S)- and (R)-3-(2-((4-cyanophenethyl)amino)-2-phenylacetyl)-N-ethyl-1H-indole-6-carboxamide:

To a solution of 3-(2-((4-cyanophenethyl)amino)-2-phenylacetyl)-1H-indole-6-carboxylic acid (0.05 g, 0.11 mmol) in THF (4 ml) was added ethyl amine (0.06 ml, 2.0 M in THF, 0.13 mmol), DIPEA (0.040 ml, 0.23 mmol) and HATU (0.089 g, 0.23 mmol) at 0° C. The resulting reaction mixture was allowed to stir at room temperature for 16 hours. After completion of the reaction, the mixture was diluted with water (10 ml) and extracted with ethyl acetate (2×10 ml).

The combined organic layers were washed with brine (10 ml), dried over anhydrous Na$_2$SO$_4$ and concentrated under reduced pressure. The resulting residue was purified by silica gel chromatography to afford the title compound as a solid (0.048 g, 90%) in racemic form.

The racemic title compound was resolved by chiral SFC (CHIRALPAK IB; 15% (50:50 MeOH:IPA) in hexanes+ 0.1% DEA) to furnish the enantiopure compounds. The faster-eluting enantiomer of the title compound was obtained as a solid (Isomer 1): $^1$HNMR (400 MHz, DMSO-d6): δ 1.12 (t, J=6.8 Hz, 3H), 2.68-2.72 (m, 2H), 2.85-2.88 (m, 2H), 3.28-3.32 (m, 2H), 5.30 (s, 1H), 7.18-7.21 (m, 1H), 7.28 (t, J=7.2 Hz, 2H), 7.41 (d, J=7.6 Hz, 2H), 7.46 (d, J=7.2 Hz, 2H), 7.68 (d, J=8.4 Hz, 1H), 7.72 (d, J=8.0 Hz, 2H), 7.95 (s, 1H), 8.16 (d, J=8.4 Hz, 1H), 8.45-8.47 (m, 1H, —NH), 8.71 (s, 1H), 12.26 (s, 1H, —NH). LCMS: m/z=451.6 [M+1]. The slower-eluting enantiomer of the title compound was obtained as a solid (Isomer 2): $^1$HNMR (400 MHz, DMSO-d6): δ 1.12 (t, J=7.2 Hz, 3H), 2.68-2.72 (m, 2H), 2.84-2.86 (m, 2H), 3.27-3.31 (m, 2H), 5.31 (s, 1H), 7.17-7.21 (m, 1H), 7.28 (t, J=7.6 Hz, 2H), 7.41 (d, J=8.0 Hz, 2H), 7.47 (d, J=7.2 Hz, 2H), 7.68 (d, J=8.4 Hz, 1H), 7.72 (d, J=8.0 Hz, 2H), 7.95 (s, 1H), 8.16 (d, J=8.4 Hz, 1H), 8.45-8.47 (m, 1H, —NH), 8.71 (d, J=2.8 Hz, 1H), 12.26 (s, 1H, —NH). LCMS: m/z=451.6 [M+1].

The following compounds were prepared using similar procedures to those described for Example 146 using the appropriate starting materials.

TABLE 8

| Example No. | Structure (Methods and Schemes for Preparation) | IUPAC Name | Exact Mass [M + 1] | Chiral Column and Mobile Phase |
|---|---|---|---|---|
| 147 Isomer 1 Isomer 2 | | (S)- and (R)-3-(2-((2,4-dichlorophenethyl)amino)-2-phenylacetyl)-N-methyl-1H-indole-7-carboxamide | Calc'd 480.1, Found 480.6 and 480.7 | CHIRALPAK AD-H; 25% MeOH in Liquid CO$_2$ + 0.1% DEA |
| 148 Isomer 1 Isomer 2 | | (S)- and (R)-3-(2-((2,4-dichlorophenethyl)amino)-2-phenylacetyl)-N,N-dimethyl-1H-indole-7-carboxamide | Calc'd 494.1, Found 494.6 and 494.6 | CHIRALPAK IB; 25% (50:50 MeOH:IPA) in hexanes + 0.1% DEA |
| 149 Isomer 1 Isomer 2 | | (S)- and (R)-3-(2-((2,4-dichlorophenethyl)amino)-2-phenylacetyl)-N-(2-(dimethylamino)ethyl)-1H-indole-7-carboxamide | Calc'd 537.2, Found 535.3 and 535.3 | CHIRALCEL OX-H; 30% (50:50 MeOH:IPA) in Liquid CO$_2$ + 0.1% DEA |

TABLE 8-continued

| Example No. | Structure (Methods and Schemes for Preparation) | IUPAC Name | Exact Mass [M + 1] | Chiral Column and Mobile Phase |
|---|---|---|---|---|
| 150 Isomer 1 Isomer 2 | | (S)- and (R)-3-(2-((2,4-dichlorophenethyl)amino)-2-phenylacetyl)-N-(2-methoxyethyl)-1H-indole-7-carboxamide | Calc'd 524.1, Found 524.6 and 524.6 | CHIRALCEL OX-H; 35% (MeOH) in Liquid CO$_2$ + 0.1% DEA |
| 151 Isomer 1 Isomer 2 | | (S)- and (R)-3-(2-((2,4-dichlorophenethyl)amino)-2-phenylacetyl)-N-methyl-1H-indole-6-carboxamide | Calc'd 480.1, Found 480.5 and 480.6 | CHIRALPAK IB; 15% (50:50 MeOH:IPA) in hexanes + 0.1% DEA |
| 152 Isomer 1 Isomer 2 | | (S)- and (R)-3-(2-((2,4-dichlorophenethyl)amino)-2-phenylacetyl)-N,N-dimethyl-1H-indole-6-carboxamide | Calc'd 494.1, Found 494.5 and 494.5 | CHIRALPAK IB; 25% (50:50 MeOH:IPA) in hexanes + 0.1% DEA |
| 153 Isomer 1 Isomer 2 | | (S)- and (R)-3-(2-((2,4-dichlorophenethyl)amino)-2-phenylacetyl)-N-(2-(dimethylamino)ethyl)-1H-indole-6-carboxamide | Calc'd 537.2, Found 535 and 535 | CHIRALPAK IC; 35% (50:50 ACN:IPA) in hexanes + 0.1% DEA |
| 154 Isomer 1 Isomer 2 | | (S)- and (R)-3-(2-((2,4-dichlorophenethyl)amino)-2-phenylacetyl)-N-(2-methoxyethyl)-1H-indole-6-carboxamide | Calc'd 524.1, Found 524.5 and 524.5 | CHIRALPAK IB; 25% (50:50 MeOH:IPA) in Liquid CO2 + 0.1% DEA |
| 155 Isomer 1 Isomer 2 | | (S)- and (R)-3-(2-((4-cyanophenethyl)amino)-2-phenylacetyl)-1H-indole-6-carboxylic acid | Calc'd 424.2, Found 424.3 and 424.3 | CHIRALPAK AD-H; 25% MeOH in Liquid CO$_2$ + 0.1% DEA |

TABLE 8-continued

| Example No. | Structure (Methods and Schemes for Preparation) | IUPAC Name | Exact Mass [M + 1] | Chiral Column and Mobile Phase |
|---|---|---|---|---|
| 156 Isomer 1 Isomer 2 | | (S)- and (R)-3-(2-((4-cyanophenethyl)amino)-2-phenylacetyl)-N-methyl-1H-indole-6-carboxamide | Calc'd 437.2, Found 437.3 and 437.7 | CHIRALPAK IB; 25% (50:50 MeOH:IPA) in hexanes + 0.1% DEA |
| 157 Isomer 1 Isomer 2 | | (S)- and (R)-3-(2-((4-cyanophenethyl)amino)-2-phenylacetyl)-N-(2,2,2-trifluoroethyl)-1H-indole-6-carboxamide | Calc'd 505.2, Found 505.4 and 505.4 | CHIRALPAK IC; 35% (50:50 MeOH:IPA) in hexanes + 0.1% DEA |
| 158 Isomer 1 Isomer 2 | | (S)- and (R)-3-(3-(2-((4-fluorophenethyl)amino)-2-phenylacetyl)-1H-indol-6-yl)-N-methylpropanamide | Calc'd 458.2, Found 458.5 and 458.4 | CHIRALPAK IB; 40% (50:50 MeOH:IPA) in hexanes + 0.1% DEA |
| 159 Isomer 1 Isomer 2 | | (S)- and (R)- (3-(3-(2-((4-fluorophenethyl)amino)-2-phenylacetyl)-1H-indol-6-yl)propanoic acid | Calc'd 445.2, Found 445.6 and 445.6 | CHIRALPAK IC; 35% IPA in Liquid $CO_2$ + 0.1% DEA |
| 160 Isomer 1 Isomer 2 | | (S)- and (R)- 2-(3-(2-((4-cyanophenethyl)amino)-2-phenylacetyl)-1H-indol-6-yl)acetic acid | Calc'd 438.2, Found 438.2 and 438.2 | CHIRALPAK IC; (50:50 ACN:IPA) in Liquid $CO_2$ + 0.1% DEA |
| 161 Isomer 1 Isomer 2 | | (S)- and (R)-3-(2-((4-cyanophenethyl)amino)-2-phenylacetyl)-N-(2-hydroxy-2-methylpropyl)-1H-indole-6-carboxamide | Calc'd 495.2, Found 495.6 and 495.6 | CHIRALPAK IB; 18% (50:50 MeOH:IPA) in hexanes + 0.1% DEA |

TABLE 8-continued

| Example No. | Structure (Methods and Schemes for Preparation) | IUPAC Name | Exact Mass [M + 1] | Chiral Column and Mobile Phase |
|---|---|---|---|---|
| 162 Isomer 1 Isomer 2 | | (S)- and (R)-3-(2-((4-cyanophenethyl)amino)-2-phenylacetyl)-N-(1-(2,2,2-trifluoroethyl)azetidin-3-yl)-1H-indole-6-carboxamide | Calc'd 560.2 Found 560.3 and 560.3 | CHIRALPAK IB; 20% (50:50 MeOH:IPA) in hexanes + 0.1% DEA |
| 163 Isomer 1 Isomer 2 | | (S)- and (R)-3-(2-((4-cyanophenethyl)amino)-2-phenylacetyl)-N-(1-ethylazetidin-3-yl)-1H-indole-6-carboxamide | Calc'd 506.3, Found 506.3 and 506.3 | CHIRALPAK IB; 25% (25:75 MeOH:IPA) in hexanes + 0.1% DEA |
| 164 Isomer 1 Isomer 2 | | (S)- and (R)-3-(2-((4-cyanophenethyl)amino)-2-phenylacetyl)-N-(2-(2-oxopyrrolidin-1-yl)ethyl)-1H-indole-6-carboxamide | Calc'd 534.2 Found 534.6 and 534.6 | CHIRALPAK IB; 35% (50:50 MeOH:IPA) in hexanes + 0.1% DEA |
| 165 Isomer 1 Isomer 2 | | (S)- and (R)-3-(2-((4-cyanophenethyl)amino)-2-phenylacetyl)-N,N-diethyl-1H-indole-6-carboxamide | Calc'd 479.2, Found 479.3 and 479.6 | CHIRALPAK IB; 25% (50:50 MeOH:IPA) in hexanes + 0.1% DEA |
| 166 Isomer 1 Isomer 2 | | (S)- and (R)-3-(2-((4-cyanophenethyl)amino)-2-phenylacetyl)-N-(1,1-dioxidothietan-3-yl)-1H-indole-6-carboxamide | Calc'd 527.2, Found 527.2 and 527.4 | CHIRALPAK IB; 20% (50:50 MeOH:IPA) in hexanes + 0.1% DEA |
| 167 Isomer 1 Isomer 2 | | (S)- and (R)-3-(2-((4-cyanophenethyl)amino)-2-phenylacetyl)-N-isopropyl-1H-indole-6-carboxamide | Calc'd 465.2, Found 465.3 and 465.3 | CHIRALPAK AD-H; 25% MeOH in Liquid CO$_2$ + 0.1% DEA |

TABLE 8-continued

| Example No. | Structure (Methods and Schemes for Preparation) | IUPAC Name | Exact Mass [M + 1] | Chiral Column and Mobile Phase |
|---|---|---|---|---|
| 168 Isomer 1 Isomer 2 | | (S)- and (R)-3-(2-((4-cyanophenethyl)amino)-2-phenylacetyl)-N-((S)-2-hydroxypropyl)-1H-indole-6-carboxamide | Calc'd 481.2, Found 481.3 and 481.3 | CHIRALPAK IB; 35% (50:50 MeOH:IPA) in hexanes + 0.1% DEA |
| 169 Isomer 1 Isomer 2 | | (S)- and (R)-3-(2-((4-cyanophenethyl)amino)-2-phenylacetyl)-N-((S)-1,1,1-trifluoropropan-2-yl)-1H-indole-6-carboxamide | Calc'd 519.2, Found 519.4 and 519.3 | CHIRALPAK IB; 20% (50:50 MeOH:IPA) in hexanes + 0.1% DEA |
| 170 Isomer 1 Isomer 2 | | (S)- and (R)-3-(2-((4-cyanophenethyl)amino)-2-phenylacetyl)-N-((R)-1,1,1-trifluoropropan-2-yl)-1H-indole-6-carboxamide | Calc'd 519.2, Found 519.6 and 519.6 | CHIRALPAK AD-H; 25% MeOH in Liquid $CO_2$ + 0.1% DEA |
| 171 Isomer 1 Isomer 2 | | (S)- and (R)-4-(2-((2-oxo-1-phenyl-2-(6-(pyrrolidine-1-carbonyl)-1H-indol-3-yl)ethyl)amino)ethyl)benzonitrile | Calc'd 477.2, Found 477.3 and 477.3 | CHIRALPAK IB; 30% (50:50 MeOH:IPA) in Liquid $CO_2$ + 0.1% DEA |
| 172 Isomer 1 Isomer 2 | | (S)- and (R)-3-(2-((4-cyanophenethyl)amino)-2-phenylacetyl)-N,N-dimethyl-1H-indole-6-carboxamide | Calc'd 451.2, Found 449.4 and 449.3 | CHIRALPAK IB; 25% (50:50 MeOH:IPA) in hexanes + 0.1% DEA |
| 173 Isomer 1 Isomer 2 | | (S)- and (R)-3-(2-((4-cyanophenethyl)amino)-2-phenylacetyl)-N-((R)-2-hydroxypropy)-1H-indole-6-carboxamide | Calc'd 481.2, Found 481.6 and 481.4 | CHIRALPAK IB; 25% (50:50 MeOH:IPA) in hexanes + 0.1% DEA |

TABLE 8-continued

| Example No. | Structure (Methods and Schemes for Preparation) | IUPAC Name | Exact Mass [M + 1] | Chiral Column and Mobile Phase |
|---|---|---|---|---|
| 174 Isomer 1 Isomer 2 | | (S)- and (R)-3-(2-((4-cyanophenethyl)amino)-2-phenylacetyl)-N-(oxetan-3-yl)-1H-indole-6-carboxamide | Calc'd 479.2, Found 479.5 and 479.5 | CHIRALPAK IB; 30% (50:50 MeOH:IPA) in hexanes + 0.1% DEA |
| 175 Isomer 1 Isomer 2 | | (S)- and (R)-3-(2-((4-cyanophenethyl)amino)-2-phenylacetyl)-N-(3-(methylsulfonyl)propyl)-1H-indole-6-carboxamide | Calc'd 543.2, Found 543.4 and 543.3 | CHIRALPAK IB; 30% MeOH in Liquid $CO_2$ + 0.1% DEA |
| 176 Isomer 1 Isomer 2 | | (S)- and (R)-3-(2-((4-cyanophenethyl)amino)-2-phenylacetyl)-N-(2-(pyrrolidin-1-yl)ethyl)-1H-indole-6-carboxamide | Calc'd 520.3, Found 520.4 and 520.5 | CHIRALPAK AD-H; 25% MeOH in Liquid $CO_2$ + 0.1% DEA |

Scheme 12

The starting materials required for the synthesis of examples prepared using Scheme 12 were generally prepared using methods 1 through 4 and schemes 1 through 4. The starting materials for methods 1 through 4 and schemes 1 through 4 were either commercially available or were synthesized using methods 5 through 24.

Example 177

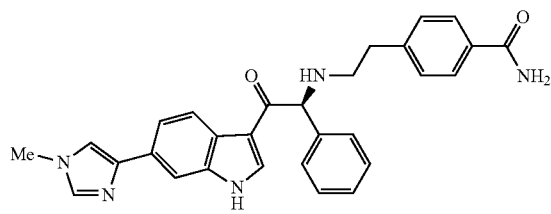

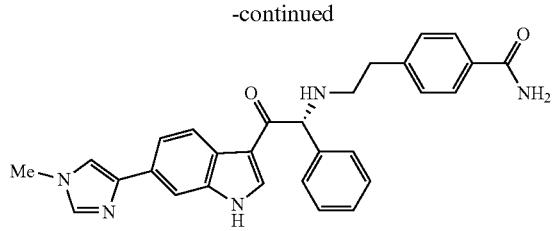

(S)- and (R)-4-(2-((2-(6-(1-Methyl-1H-imidazol-4-yl)-1H-indol-3-yl)-2-oxo-1-phenylethyl)amino)ethyl)benzamide Scheme 12. (S)- and (R)-4-(2-((2-(6-(1-Methyl-1H-imidazol-4-yl)-1H-indol-3-yl)-2-oxo-1-phenylethyl)amino)ethyl)benzamide:

To a solution of 4-(2-((2-(6-(1-methyl-1H-imidazol-4-yl)-1H-indol-3-yl)-2-oxo-1-phenylethyl) amino)ethyl)benzonitrile (0.17 g, 0.37 mmol) in DMSO (2.5 ml) under an atmosphere of nitrogen, 30% $H_2O_2$ solution (0.6 ml) and 6 N NaOH (aq.; 0.06 ml) were added dropwise at 0° C. The reaction mixture was stirred at room temperature for 1 hour. After completion of the reaction (monitored by TLC), crushed ice was added and the reaction mixture was neutralized with 1 N HCl (aq.). The resulting solid was filtered through Buchner funnel and dried for 30 minutes to afford the title compound as solid (0.080 g, 45%) in racemic form.

The racemic title compound was resolved by chiral HPLC (CHIRALPAK IB; 35% (50:50 MeOH:IPA) in hexanes+ 0.1% DEA) to furnish the enantiopure compounds. The faster-eluting enantiomer of the title compound was obtained as a solid (Isomer 1): $^1$H NMR (400 MHz, DMSO-d6): δ 2.91-3.15 (m, 4H), 3.94 (s, 3H), 6.10 (s, 1H), 7.29 (d, J=8.0 Hz, 2H), 7.34 (bs, 1H, —NH), 7.41-7.48 (m, 3H), 7.62-7.65 (m, 2H), 7.68-7.74 (m, 3H), 7.82-7.85 (m, 3H), 7.95 (bs, 1H, —NH), 8.13 (d, J=8.4 Hz, 1H), 8.53 (d, J=3.2 Hz, 1H), 12.35 (s, —NH). LCMS: m/z=478.3 [M+1]. The slower-eluting enantiomer of the title compound was obtained as a solid (Isomer 2): $^1$H NMR (400 MHz, DMSO-d6): 2.68-2.82 (m, 4H), 3.82 (s, 3H), 5.30 (s, 1H), 7.19-7.21 (m, 1H), 7.26-7.30 (m, 4H), 7.47 (d, J=7.2 Hz, 2H), 7.54-7.62 (m, 3H), 7.77-7.83 (m, 3H), 7.90 (bs, 1H, —NH), 8.09 (d, J=8.0 Hz, 1H), 8.57 (s, 1H), 12.05 (s, 1H—NH). LCMS: m/z=478.4 [M+1].

The following compounds were prepared using similar procedures to those described for Example 177 using the appropriate starting materials.

TABLE 9

| Example No. | Structure (Methods and Schemes for Preparation) | IUPAC Name | Exact Mass [M + 1] | Chiral Column and Mobile Phase |
|---|---|---|---|---|
| 178 Isomer 1 Isomer 2 | | (S)- and (R)-4-(2-((2-(6-(1-methylpiperidin-4-yl)-1H-indol-3-yl)-2-oxo-1-phenylethyl)-amino)ethyl)benzamide | Calc'd 495.3, Found 495.6 and 495.6 | CHIRALPAK IB; 30% (50:50 MeOH:IPA) in hexanes + 0.1% DEA |
| 179 Isomer 1 Isomer 2 | | (S)- and (R)-4-(2-((2-(6-(1-methyl-1H-pyrazol-4-yl)pyrazolo[1,5-a]pyridin-3-yl)-2-oxo-1-phenylethyl)-amino)ethyl)benzamide | Calc'd 479.2, Found 479.5 and 479.4 | CHIRALPAK IB; 35% (50:50 MeOH:IPA) in hexanes + 0.1% DEA |
| 180 Isomer 1 Isomer 2 | | (S)- and (R)-4-(2-((2-(6-(1-methyl-1H-1,2,3-triazol-4-yl)-1H-indol-3-yl)-2-oxo-1-phenylethyl)amino)ethyl)benzamide | Calc'd 479.2, Found 479.3 and 479.5 | CHIRALPAK IC; 37% (50:50 MeOH:IPA) in hexanes + 0.1% DEA |
| 181 Isomer 1 Isomer 2 | | (S)- and (R)-4-(2-((2-(6-(1H-imidazol-1-yl)-1H-indol-3-yl)-2-oxo-1-phenylethyl)amino)ethyl)benzamide | Calc'd 464.2, Found 464.5 and 464.2 | CHIRALPAK AD-H; (MeOH) in Liquid CO$_2$ + 0.1% DEA |
| 182 Isomer 1 Isomer 2 | | (S)- and (R)-4-(2-((2-(6-(1-(2-hydroxyethyl)-1H-pyrazol-4-yl)-1H-indol-3-yl)-2-oxo-1-phenylethyl)amino)ethyl)benzamide | Calc'd 508.2, Found 508.4 and 508.4 | CHIRALPAK IB; 35% (50:50 MeOH:IPA) in hexanes + 0.1% DEA |

TABLE 9-continued

| Example No. | Structure (Methods and Schemes for Preparation) | IUPAC Name | Exact Mass [M + 1] | Chiral Column and Mobile Phase |
|---|---|---|---|---|
| 183 Isomer 1 Isomer 2 | | (S)- and (R)-4-(2-((2-(6-(1-(2-methoxyethyl)-1H-pyrazol-4-yl)-1H-indol-3-yl)-2-oxo-1-phenylethyl)amino)ethyl)benzamide | Calc'd 522.2, Found 522.6 and 522.3 | CHIRALPAK IB; 35% (50:50 MeOH:IPA) in hexanes + 0.1% DEA |
| 184 Isomer 1 Isomer 2 | | (S)- and (R)-4-(2-((2-(3-methyl-6-(1-methyl-1H-pyrazol-4-yl)imidazo[1,5-a]pyridin-1-yl)-2-oxo-1-phenylethyl)amino)ethyl)benzamide | Calc'd 493.2, Found 493.4 and 493.4 | CHIRALPAK AD-H; 40% (MeOH) in Liquid $CO_2$ + 0.1% DEA |

Scheme 13

The starting materials required for the synthesis of examples prepared using Scheme 13 were generally prepared using methods 1 through 4 and scheme 1. The starting materials for methods 1 through 4 and scheme 1 were either commercially available or were synthesized using methods 5 through 14.

Example 185

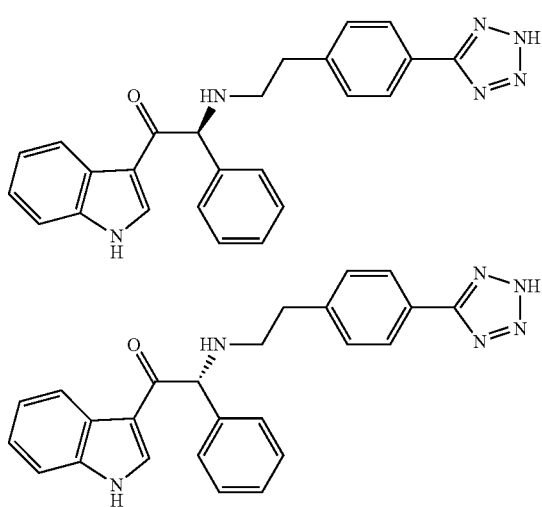

(S)- and (R)-2-((4-(2H-tetrazol-5-yl)phenethyl)amino)-1-(1H-indol-3-yl)-2-phenylethan-1-one Scheme 13. (S)- and (R)-2-((4-(2H-tetrazol-5-yl)phenethyl)amino)-1-(1H-indol-3-yl)-2-phenylethan-1-one:

A solution of 4-(2-((2-(1H-indol-3-yl)-2-oxo-1-phenylethyl)amino)ethyl)benzonitrile (0.1 g, 0.26 mmol) in toluene (3 ml) was purged with argon for 30 minutes. Then dibutyltin oxide (0.006 g, 0.026 mmol) and trimethylsilylazide (0.060 g, 0.52 mmol) were added and the solution was purged with argon for another 10 minutes. The reaction mixture was heated to reflux for 16 hours. Another portion of trimethylsilylazide (0.060 g, 0.52 mmol) was added and the reaction mixture was refluxed for an additional 6 hours. After the completion of reaction, the reaction mixture was concentrated under reduced pressure. The residue was purified by silica gel chromatography to afford the title compound as a solid (0.06 g, 54%) in racemic form.

The racemic title compound was resolved by chiral HPLC (CHIRALPAK IB; (50:50 MeOH:IPA) in hexanes+0.1% DEA) to furnish the enantiopure compounds. The faster-eluting enantiomer of the title compound was obtained as a solid (Isomer 1): $^1$HNMR (400 MHz, DMSO-d6): δ 2.80-2.96 (m, 4H), 5.60 (s, 1H), 7.23-7.29 (m, 5H), 7.35 (t, J=7.6 Hz, 2H), 7.47 (d, J=8.0 Hz, 1H), 7.56 (d, J=7.2 Hz, 2H), 7.90 (d, J=8.0 Hz, 2H), 8.19 (d, J=8.4 Hz, 1H), 8.58 (s, 1H), 12.13 (s, —NH). LCMS: m/z=423.4 [M+1]. The slower-eluting enantiomer of the title compound was obtained as a solid (Isomer 2): $^1$HNMR (400 MHz, DMSO-d6): δ 2.79-2.97 (m, 4H), 5.58 (s, 1H), 7.19-7.28 (m, 5H), 7.35 (t, J=7.6 Hz, 2H), 7.47 (d, J=8.4 Hz, 1H), 7.56 (d, J=7.2 Hz, 2H), 7.90 (d, J=8.0 Hz, 2H), 8.19 (d, J=8.4 Hz, 1H), 8.58 (s, 1H), 12.12 (s, —NH). LCMS: m/z=423.3 [M+1].

Scheme 14

The starting materials required for the synthesis of examples prepared using Scheme 14 were generally prepared using methods 1 through 4 and schemes 1, 2, 3, 4, and 13. The starting materials for methods 1 through 4 and schemes 1, 2, 3, 4, and 13 were either commercially available or were synthesized using methods 5 through 14.

Example 150

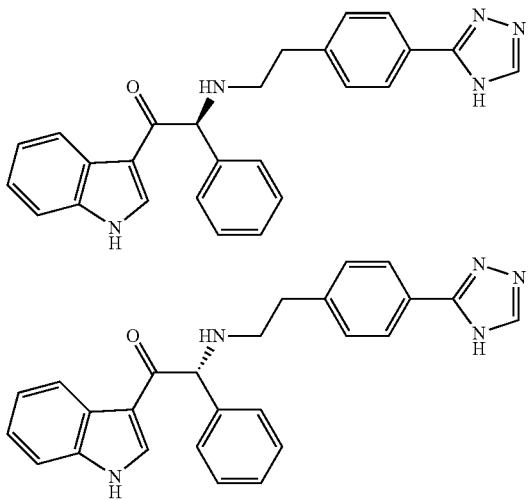

(S)- and (R)-2-((4-(4H-1,2,4-triazol-3-yl)phenethyl)amino)-1-(1H-indol-3-yl)-2-phenylethan-1-one Scheme 14. (S)- and (R)-2-((4-(4H-1,2,4-triazol-3-yl)phenethyl)amino)-1-(1H-indol-3-yl)-2-phenylethan-1-one:

A mixture of 4-(2-((2-(1H-indol-3-yl)-2-oxo-1-phenylethyl)amino)ethyl)benzamide (0.200 g, 0.126 mmol) and DMF-DMA (4 ml) was stirred at 80° C. for one hour. The volatiles were evaporated under reduced pressure. To this reaction mixture, acetic acid (4 ml) was added followed by the addition of hydrazine monohydrate (0.4 ml). The tube was sealed and the reaction mixture was stirred at 80° C. for 30 minutes. After completion of the reaction, saturated sodium bicarbonate solution was added slowly and the mixture was extracted with ethyl acetate (2×15 ml). The combined organic layers were washed with brine (15 ml), dried over anhydrous $Na_2SO_4$ and concentrated under reduced pressure. The crude residue was purified by column chromatography to afford the title compound (0.80 g, 40%) as white solid in racemic form.

The racemic title compound was resolved by chiral HPLC (CHIRALPAK AD-H; 25% (MEOH) in Liquid $CO_2$+0.1% DEA) to furnish the enantiopure compounds. The faster-eluting enantiomer of the title compound was obtained as a solid (Isomer 1): $^1$H NMR (400 MHz, DMSO-d6): δ 2.67-2.89 (m, 4H), 5.32 (d, J=7.6 Hz, 1H), 7.11-7.23 (m, 3H), 7.27-7.29 (m, 4H), 7.43-7.48 (m, 3H), 7.90 (d, J=8.0 Hz, 2H), 8.16 (d, J=7.2 Hz, 1H), 8.27 (s, 1H), 8.62 (s, 1H), 12.75 (s, 1H, —NH). LCMS: m/z=422.34 [M+1]. The slower-eluting enantiomer of the title compound was obtained as a solid (Isomer 2): $^1$HNMR (400 MHz, DMSO-d6): δ 2.67-2.80 (m, 4H), 5.32 (s, 1H), 7.14-7.20 (m, 3H), 7.26-7.30 (m, 4H), 7.40-7.54 (m, 3H), 7.90 (d, J=8.4 Hz, 2H), 8.16 (d, J=6.8 Hz, 1H), 8.24 (s, 1H), 8.61 (s, 1H), 12.12 (s, 1H, —NH). LCMS: m/z=422.34 [M+1].

Scheme 15

The starting materials required for the synthesis of examples prepared using Scheme 15 were generally prepared using methods 1 through 4 and schemes 1, 2 and 15. The starting materials for methods 1 through 4 and schemes 1, 2 and 15 were either commercially available or were synthesized using methods 5 through 24.

Example 151

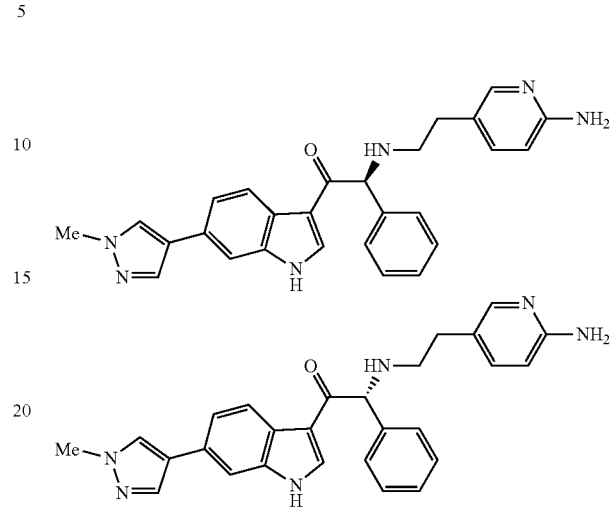

(S)- and (R)-2-((2-(6-aminopyridin-3-yl)ethyl)amino)-1-(6-(1-methyl-1H-pyrazol-4-yl)-1H-indol-3-yl)-2-phenylethan-1-one Scheme 15. (S) and (R)-2-((4-cyanophenethyl)amino)-N-(6-(1-methyl-1H-pyrazol-4-yl)pyridin-3-yl)-2-phenylacetamide: To a stirred solution of 2-((2-(6-((4-methoxybenzyl)amino)pyridin-3-yl)ethyl)amino)-1-(6-(1-methyl-1H-pyrazol-4-yl)-1H-indol-3-yl)-2-phenylethan-1-one (0.1 g, 0.17 mmol) and triethylamine (0.061 g, 0.53 mmol) in DCM (1 ml) at 0° C. was added trifluoroacetic acid (1 ml). The reaction mixture was stirred at 45° C. for 3 hours. After completion of the reaction, the reaction was quenched with saturated aqueous $NaHCO_3$ solution and extracted with DCM (2×10 ml). The combined organic layers were dried over anhydrous $Na_2SO_4$, filtered, and concentrated under reduced pressure to afford the title compound (55 mg, 70%) as a racemic mixture.

The racemic title compound was resolved by chiral HPLC (CHIRALPAK IB; 30% (50:50 MEOH: IPA) in hexanes+ 0.1% DEA) to furnish the enantiopure compound. The faster-eluting enantiomer of the title compound was obtained as a solid (Isomer 1): $^1$H NMR (400 MHz, DMSO-d6): δ 2.56-2.65 (m, 4H), 3.87 (s, 3H), 5.29 (s, 1H), 5.67 (s, 2H), 6.36 (d, J=8.4 Hz, 1H), 7.19-7.21 (m, 2H), 7.29 (t, J=7.6 Hz, 2H), 7.40 (d, J=8.4 Hz, 1H), 7.47 (d, J=7.6 Hz, 2H), 7.56 (s, 1H), 7.73 (s, 1H), 7.86 (s, 1H), 8.10-8.14 (m, 2H), 8.58 (s, 1H), 12.02 (s, 1H, —NH). LCMS: m/z=451.40 [M+1]. The slower-eluting enantiomer of the title compound was obtained as a solid (Isomer 2): $^1$H NMR (400 MHz, DMSO-d6): δ 2.56-2.65 (m, 4H), 3.87 (s, 3H), 5.29 (s, 1H), 5.67 (s, 2H), 6.36 (d, J=8.4 Hz, 1H), 7.19-7.21 (m, 2H), 7.29 (t, J=7.6 Hz, 2H), 7.40 (d, J=8.4 Hz, 1H), 7.47 (d, J=7.6 Hz, 2H), 7.56 (s, 1H), 7.73 (s, 1H), 7.86 (s, 1H), 8.10-8.14 (m, 2H), 8.58 (s, 1H), 12.02 (s, 1H, —NH). LCMS: m/z=451.40 [M+1].

Biochemical Assays

The activity of the compounds described herein as p300/CBP HAT inhibitors may be readily determined using a scintillation proximity assay (SPA) methodology (Udenfriend, S.; Gerber, L.; Nelson, N. Scintillation Proximity Assay: A Sensitive and Continuous Isotopic Method for Monitoring Ligand/Receptor and Antigen/Antibody Interactions. *Anal. Biochem.* 1987, 161, 494-500). In particular, the compounds of the following examples had activity in reference assays by exhibiting the ability to inhibit the acetylation of histone peptide by a truncated form of the p300 enzyme (p300 HAT). Any compound exhibiting an $IC_{50}$ of about 100 μM or below would be considered a p300/CBP-HAT inhibitor as defined herein.

In a typical experiment the p300 HAT inhibitory activity of the compounds described herein was determined in accordance with the following experimental method.

The p300 HAT domain (residues 1287-1666) was expressed and purified with an N-terminal His tag from Escherichia coli cells. The expressed protein was purified by Ni2+ affinity, followed by anion exchange chromatography. Appropriate fractions were pooled and buffer exchanged into 20 mM Hepes pH 7.5, 150 mM NaCl, and 1 mM TCEP.

Compounds of interest solubilized in DMSO were stamped in a Greiner black 384-well plate in a 10-point duplicate dose response using an Echo 550 (Labcyte). p300-HAT domain purified in-house (aa 1287-1666) was diluted to 6 nM in reaction buffer (50 mM Tris pH 8.0, 100 mM NaCl, 1 mM DTT, 0.069 mM Brij-35, 0.1 mM EDTA, 0.1 mg/mL BSA), combined with 4.14 μM AcCoA (Sigma-Aldrich) and 0.46 μM $^3$H-AcCoA (PerkinElmer), and 12.5 μM added to each well and incubated for 30 min at RT. Reactions were initiated with 12.5 μL 2 μM biotinylated H3(1-21) peptide (New England Peptide) and run for 1 hr at RT, then quenched with 20 μL stop solution (200 mM Tris pH 8.0, 200 mM EDTA, 2M NaCl, 160 μM anacardic acid). 35 μL of the reaction volume was transferred to a 384-well streptavidin FlashPlate (PerkinElmer) using a Bravo liquid handler (Velocity 11) and incubated for 1.5 hr at RT. Plates were aspirated, washed with 95 μL wash buffer (15 mM Tris pH 8.5, 0.069 μM Brij-35), aspirated, sealed, and scintillation counts read on a Topcount (PerkinElmer). Data were analyzed in Genedata to determine inhibitor $IC_{50}$ values.

The full length p300 SPA assay was run following the same protocol as p300 HAT SPA assay, but used 6 nM purified full length p300 (purchased from Active Motif) in place of the purified p300-HAT domain.

Select compounds were also evaluated in a H3K18Ac MSD cellular assay that measures the ability of compounds to inhibit the acetylation of chromatin at H3K18, a process catalyzed by p300 and CBP. In a typical experiment the p300 HAT inhibitory activity inside cells of the compounds described herein was determined in accordance with the following experimental method. 20 k HCT-116 cells per well are plated in 75 μL RPMI+10% FBS media the night before treatment. Compounds plated in DMSO at 4× final concentration are resuspended in 30 μL RPMI+10% FBS, then 25 μL is combined with corresponding wells containing cells. Treated cells are incubated for 2 hr at 37° C., then lysed in 500 μL final volume and frozen at −80° C. MSD plates (Meso Scale Discovery) are coated overnight at 4° C. with 60 μL 1:500α-total histone antibody (Millipore MAB3422) in PBS. Plates are then blocked with 5% BSA in TBST shaking at RT for 1 hr, washed, and 30 μL lysate added to each well for 2 hr shaking at RT. Plates are washed and 25 μL 1:216α-H3K18ac antibody (CST 9675) in PBS added, then incubated for 1 hr shaking at RT. Plates are washed again, then 25 μL 1:1000 Sulfo-Tag goat a-rabbit antibody (Meso Scale Discovery R32Ab-1) in PBS is added for 1 hr shaking at RT. Plates are washed once more, then 150 μL 1× Read Buffer (MSD #R92TD-3) is added to all wells and read on MSD SECTOR Imager 2400 using the conventional read setup.

The compounds of the following examples had activity in inhibiting the HAT domain of the p300 enzyme in the aforementioned assays with a $IC_{50}$ of less than about 100 μM. Many of compounds described herein had activity in inhibiting the HAT domain of the p300 enzyme in the aforementioned assays, with a $IC_{50}$ of less than about 10 μM, preferably less than or about 0.1 μM. Additional data is provided in the following Examples. Such a result is indicative of the intrinsic activity of the compounds in use as inhibitors of the histone acetyl transferase domain of the p300 enzyme. In general, one of ordinary skill in the art would appreciate that a substance is considered to effectively inhibit p300 HAT activity if it has a $IC_{50}$ of less than or about 1 μM, preferably less than or about 0.1 μM. The present disclosure also includes compounds which possess activity as inhibitors of other histone acetyl transferase enzymes, such as CBP-HAT. The p300 HAT $IC_{50}$ is a measure of the ability of the test compound to inhibit the action of the p300 enzyme.

P300 inhibitory activity of compounds described herein estimated from a P300 HAT SPA assay are shown by Table 10. All activities are the average of at least 2 replicate titrations.

TABLE 10

| Example number | Isomer | P300 HAT SPA $IC_{50}$ (μM) | FL P300 $IC_{50}$ (μM) | H3K18Ac MSD $EC_{50}$ (μM) |
|---|---|---|---|---|
| 1 | Isomer 1 | 14.1 | | |
|   | Isomer 2 | >30 | | |
| 2 | Isomer 1 | 4.08 | | |
|   | Isomer 2 | >60 | | |
| 3 | Isomer 1 | >60 | | |
|   | Isomer 2 | 6.39 | | |
| 4 | Isomer 1 | >60 | | |
|   | Isomer 2 | 4.40 | | |
| 5 | Isomer 1 | 8.76 | | |
|   | Isomer 2 | 0.867 | | |
| 6 | Isomer 1 | >60 | | |
|   | Isomer 2 | 1.83 | 0.082 | |
| 7 | Isomer 1 | 7.35 | | |
|   | Isomer 2 | 5.14 | 0.269 | |
| 8 | Isomer 1 | 43.2 | | |
|   | Isomer 2 | 0.873 | 0.0277 | |
| 9 | Isomer 1 | >60 | 25.9 | |
|   | Isomer 2 | 33.2 | 0.728 | |
| 10 | Isomer 1 | 21.2 | 0.63 | |
|   | Isomer 2 | 19.2 | 0.711 | |
| 11 | Isomer 1 | 9.94 | 0.204 | |
|   | Isomer 2 | 7.15 | 0.197 | |
| 12 | Isomer 1 | >60 | 8.5 | |
|   | Isomer 2 | >60 | 3.94 | |
| 13 | Isomer 1 | 18.1 | 0.472 | |
|   | Isomer 2 | 1.62 | 0.144 | |
| 14 | Isomer 1 | >60 | 9.54 | |
|   | Isomer 2 | 47.4 | 1.86 | |
| 15 | Isomer 1 | >60 | | |
|   | Isomer 2 | 1.49 | 0.0812 | 0.405 |
| 16 | Isomer 1 | 49.2 | | |
|   | Isomer 2 | 6.98 | 0.378 | |
| 17 | Isomer 1 | 7.99 | | |
|   | Isomer 2 | 1.85 | | |
| 18 | Isomer 1 | >60 | | |
|   | Isomer 2 | >60 | | |
| 19 | Isomer 1 | >60 | | |
|   | Isomer 2 | 0.706 | | 0.282 |
| 20 | Isomer 1 | >60 | | |
|   | Isomer 2 | 3.07 | | |
| 21 | Isomer 1 | 0.715 | 0.1 | 0.0913 |
|   | Isomer 2 | 32.8 | | |

TABLE 10-continued

| Example number | Isomer | P300 HAT SPA IC$_{50}$ (μM) | FL P300 IC$_{50}$ (μM) | H3K18Ac MSD EC$_{50}$ (μM) |
|---|---|---|---|---|
| 22 | Isomer 1 | >60 | | |
|    | Isomer 2 | 2.32 | 0.0208 | 1.69 |
| 23 | Isomer 1 | >60 | | |
|    | Isomer 2 | >60 | | |
| 24 | Isomer 1 | 52.2 | | |
|    | Isomer 2 | >60 | | |
| 25 | Isomer 1 | >60 | | |
|    | Isomer 2 | >60 | | |
| 26 | Isomer 1 | >30 | | >10 |
|    | Isomer 2 | 4.56 | | 2.53 |
|    | Isomer 3 | 3.79 | | 6.11 |
|    | Isomer 4 | 0.204 | | 0.139 |
| 27 | Isomer 1 | 0.636 | | 0.681 |
|    | Isomer 2 | >60 | | |
|    | Isomer 3 | >60 | | |
|    | Isomer 4 | >60 | | |
| 28 | Isomer 1 | 7.58 | | |
|    | Isomer 2 | 1.37 | | |
| 29 | Isomer 1 | 2.19 | 0.0911 | |
|    | Isomer 2 | 6.60 | 0.22 | |
| 30 |  | 32.3 | 0.732 | |
| 31 |  | 33.9 | 10.6 | |
| 32 | Isomer 1 | 1.45 | 0.102 | 3.67 |
|    | Isomer 2 | 12.9 | 0.744 | |
| 33 | Isomer 1 | >60 | 1.75 | |
|    | Isomer 2 | 10.0 | 0.554 | |
| 34 | Isomer 1 | >60 | | |
|    | Isomer 2 | 24.7 | | |
| 35 | Isomer 1 | 39.8 | | |
|    | Isomer 2 | 43.5 | | |
| 36 | Isomer 1 | >60 | | |
|    | Isomer 2 | >60 | | |
| 37 | Isomer 1 | >60 | | |
|    | Isomer 2 | >60 | | |
| 38 | Isomer 1 | 19.0 | | |
|    | Isomer 2 | 0.698 | | 1.69 |
| 39 | Isomer 1 | >60 | | |
|    | Isomer 2 | 0.77 | 0.0275 | 0.529 |
| 40 | Isomer 1 | >60 | | |
|    | Isomer 2 | 1.31 | | 4.01 |
| 41 | Isomer 1 | >60 | | |
|    | Isomer 2 | >60 | | |
| 42 | Racemic | 9.14 | 0.196 | |
| 43 | Racemic | 4.21 | 0.145 | 3.9 |
| 44 | Racemic | 3.33 | 0.12 | |
| 45 | Isomer 1 | 5.55 | 0.219 | 13.4 |
|    | Isomer 2 | 39.8 | 1.35 | |
| 46 | Isomer 1 | 9.0 | 13.1 | |
|    | Isomer 2 | 6.55 | 0.283 | 29.4 |
| 47 | Isomer 1 | 4.80 | 1.31 | |
|    | Isomer 2 | 20.3 | 1.30 | |
| 48 | Isomer 1 | >60 | | |
|    | Isomer 2 | 3.34 | | 3.2 |
| 49 | Isomer 1 | >30 | | |
|    | Isomer 2 | 2.21 | 0.0553 | 0.754 |
| 50 | Isomer 1 | 6.93 | | |
|    | Isomer 2 | >30 | | |
| 51 | Isomer 1 | >30 | | |
|    | Isomer 2 | 1.29 | 0.0255 | 0.324 |
| 52 | Isomer 1 | 15.2 | | |
|    | Isomer 2 | 2.83 | | |
| 53 | Isomer 1 | >30 | | |
|    | Isomer 2 | 4.29 | | 3.47 |
| 54 | Isomer 1 | >30 | | |
|    | Isomer 2 | 15.7 | | |
| 55 | Isomer 1 | 7.83 | | |
|    | Isomer 2 | >30 | | |
| 56 | Isomer 1 | >60 | | |
|    | Isomer 2 | 3.1 | | 1.44 |
| 57 | Isomer 1 | >5 | | |
|    | Isomer 2 | 0.287 | | |
| 58 | Isomer 1 | 25.3 | | |
|    | Isomer 2 | 0.201 | | 0.477 |
| 59 | Isomer 1 | >30 | | |
|    | Isomer 2 | 13.8 | | |
|    | Isomer 3 | >30 | | |
|    | Isomer 4 | 0.827 | | 0.829 |
| 60 | Isomer 1 | 27.8 | | |
|    | Isomer 2 | 1.09 | 0.178 | 0.546 |
| 61 | Isomer 1 | >30 | | |
|    | Isomer 2 | 1.07 | 0.0497 | 0.825 |
| 62 | Isomer 1 | 0.501 | 0.0372 | |
|    | Isomer 2 | 3.34 | 0.0513 | |
| 63 | Isomer 1 | 0.382 | 0.00878 | 0.337 |
|    | Isomer 2 | 2.50 | 0.0462 | |
| 64 | Isomer 1 | 0.097 | | |
|    | Isomer 2 | 0.080 | | |
| 65 | Isomer 1 | >30 | | |
|    | Isomer 2 | 0.422 | | 0.0717 |
| 66 | Isomer 1 | 0.960 | | |
|    | Isomer 2 | 0.281 | | 0.0433 |
| 67 | Isomer 1 | 2.36 | | |
|    | Isomer 2 | >5 | | |
| 68 | Isomer 1 | 0.728 | | 0.666 |
|    | Isomer 2 | >30 | | |
|    | Isomer 3 | >30 | | |
|    | Isomer 4 | >30 | | |
| 69 | Isomer 1 | 0.188 | | |
|    | Isomer 2 | 2.87 | | |
|    | Isomer 3 | >5 | | |
|    | Isomer 4 | 0.0207 | 0.0179 | 0.0439 |
| 70 | Isomer 1 | >2 | | |
|    | Isomer 2 | 0.0643 | | |
|    | Isomer 3 | 0.747 | | |
|    | Isomer 4 | 0.0218 | | |
| 71 | Isomer 1 | >2 | | |
|    | Isomer 2 | 0.0177 | | |
| 72 | Isomer 1 | 0.733 | | |
|    | Isomer 2 | 0.0424 | | |
| 73 | Isomer 1 | 0.286 | | |
|    | Isomer 2 | 0.954 | | |
| 74 | Isomer 1 | 0.154 | | |
|    | Isomer 2 | 0.160 | | |
| 75 | Isomer 1 | 0.718 | | |
|    | Isomer 2 | 0.343 | | |
|    | Isomer 3 | 0.447 | | |
|    | Isomer 4 | 0.00876 | 0.000711 | 0.0193 |
| 76 | Isomer 1 | >5 | | |
|    | Isomer 2 | >5 | | |
| 77 | racemic | 0.356 | | |
| 78 | Isomer 1 | 12.9 | | |
|    | Isomer 2 | 0.716 | 0.0109 | 0.104 |
| 79 | Isomer 1 | 0.692 | 0.0315 | 0.366 |
|    | Isomer 2 | 0.0171 | 0.00209 | 0.06 |
| 80 | Isomer 1 | 2.48 | | |
|    | Isomer 2 | 1.02 | 0.0335 | 0.817 |
| 81 | Isomer 1 | 12.3 | | |
|    | Isomer 2 | 1.15 | 0.0146 | 0.193 |
| 82 | Isomer 1 | >30 | | 1.61 |
|    | Isomer 2 | 0.875 | 0.0182 | 0.128 |
| 83 | Isomer 1 | 1.31 | | |
|    | Isomer 2 | 0.247 | | 0.0747 |
| 84 | Isomer 1 | 2.94 | | |
|    | Isomer 2 | 0.041 | 0.00276 | 0.0375 |
| 85 | Isomer 1 | >30 | | |
|    | Isomer 2 | 0.826 | | 0.0926 |
| 86 | Isomer 1 | 28.1 | | |
|    | Isomer 2 | 0.332 | | 0.116 |
| 87 | Isomer 1 | 1.39 | | |
|    | Isomer 2 | 0.200 | 0.0116 | 0.113 |
| 88 | Isomer 1 | >30 | | |
|    | Isomer 2 | 0.603 | | 0.379 |
| 89 | Isomer 1 | 27.2 | | |
|    | Isomer 2 | 0.966 | | |
| 90 | Isomer 1 | 0.967 | | |
|    | Isomer 2 | 0.591 | | 0.08 |
| 91 | Isomer 1 | 3.73 | | |
|    | Isomer 2 | >30 | | |
|    | Isomer 3 | 6.44 | | |
|    | Isomer 4 | 0.134 | | |
| 92 | Isomer 1 | 2.10 | | |
|    | Isomer 2 | >30 | | |
|    | Isomer 3 | 0.164 | | 0.109 |
|    | Isomer 4 | 2.22 | | |

TABLE 10-continued

| Example number | Isomer | P300 HAT SPA IC$_{50}$ (μM) | FL P300 IC$_{50}$ (μM) | H3K18Ac MSD EC$_{50}$ (μM) |
|---|---|---|---|---|
| 93 | Isomer 1 | 0.672 | | |
|  | Isomer 2 | 0.522 | | |
| 94 | Isomer 1 | 0.458 | 0.012 | |
|  | Isomer 2 | 0.669 | 0.013 | |
| 95 | Isomer 1 | 0.816 | | |
|  | Isomer 2 | 0.046 | | 0.0612 |
| 96 | Isomer 1 | 0.182 | | |
|  | Isomer 2 | 0.062 | | 0.0264 |
| 97 | Isomer 1 | 0.437 | | 0.135 |
|  | Isomer 2 | 6.26 | | 0.78 |
|  | Isomer 3 | >30 | | >10 |
|  | Isomer 4 | 6.71 | | >10 |
| 98 | Isomer 1 | 0.493 | | |
|  | Isomer 2 | 0.0583 | | 0.0186 |
| 99 | Isomer 1 | 0.212 | | |
|  | Isomer 2 | 0.0156 | | 0.0216 |
| 100 | Isomer 1 | 0.368 | | |
|  | Isomer 2 | 0.116 | | |
| 101 | Isomer 1 | 0.166 | | |
|  | Isomer 2 | 0.0592 | | 0.0471 |
| 102 | Isomer 1 | 1.88 | | |
|  | Isomer 2 | 0.239 | | |
|  | Isomer 3 | 0.212 | | |
|  | Isomer 4 | 0.00936 | 0.000818 | 0.043 |
| 103 | Isomer 1 | 3.41 | | |
|  | Isomer 2 | 0.118 | | 0.0685 |
| 104 | Isomer 1 | >5 | | |
|  | Isomer 2 | 0.388 | | |
| 105 | Isomer 1 | >30 | | |
|  | Isomer 2 | 1.38 | 0.0251 | |
| 106 | Isomer 1 | 0.755 | | |
|  | Isomer 2 | 0.283 | | |
| 107 | Isomer 1 | 1.90 | | |
|  | Isomer 2 | 3.28 | | |
| 108 | Isomer 1 | 1.60 | | 0.928 |
|  | Isomer 2 | 2.64 | | |
| 109 | Isomer 1 | 2.66 | | |
|  | Isomer 2 | 0.195 | | 0.267 |
| 110 | Isomer 1 | 2.01 | | |
|  | Isomer 2 | 0.258 | | 0.308 |
| 111 | Isomer 1 | 1.15 | | |
|  | Isomer 2 | 0.556 | | |
| 112 | Isomer 1 | 2.03 | | |
|  | Isomer 2 | 0.136 | | 0.0426 |
| 113 | Isomer 1 | 1.11 | | |
|  | Isomer 2 | 0.028 | | 0.0342 |
| 114 | Isomer 1 | 0.558 | | |
|  | Isomer 2 | 0.019 | | 0.0926 |
| 115 | Isomer 1 | 1.49 | | |
|  | Isomer 2 | 0.389 | | 0.53 |
| 116 | Isomer 1 | >5 | | |
|  | Isomer 2 | 0.413 | | 0.148 |
| 117 | Isomer 1 | 0.839 | 0.0142 | 0.162 |
|  | Isomer 2 | >30 | | |
| 118 | Isomer 1 | >30 | | |
|  | Isomer 2 | 2.65 | 0.0813 | 0.893 |
| 119 | Isomer 1 | >5 | | |
|  | Isomer 2 | 0.580 | | 0.232 |
| 120 | Isomer 1 | 0.987 | | 0.193 |
|  | Isomer 2 | 0.172 | | 0.0731 |
| 121 | Isomer 1 | 2.2 | | |
|  | Isomer 2 | 0.082 | | 0.122 |
| 122 | Isomer 1 | 0.325 | | |
|  | Isomer 2 | 0.044 | | 0.0975 |
| 123 | Isomer 1 | 7.61 | | |
|  | Isomer 2 | 0.808 | 0.0123 | 0.216 |
| 124 | Isomer 1 | >5 | | |
|  | Isomer 2 | 0.566 | | 0.429 |
| 125 | Isomer 1 | >2 | | |
|  | Isomer 2 | 0.224 | | |
| 126 | Isomer 1 | 2.84 | | |
|  | Isomer 2 | 0.0362 | 0.00219 | 0.154 |
| 127 | Isomer 1 | >60 | | |
|  | Isomer 2 | >60 | | |
| 128 | Isomer 1 | 42.1 | | |
|  | Isomer 2 | 13.4 | | |
| 129 | Isomer 1 | 11.8 | | |
|  | Isomer 2 | 1.81 | | |
| 130 | Isomer 1 | >60 | | |
|  | Isomer 2 | >60 | | |
| 131 | Isomer 1 | >30 | | |
|  | Isomer 2 | 1.29 | | 0.101 |
| 132 | Isomer 1 | 1.83 | 0.0633 | 4.45 |
|  | Isomer 2 | 17.9 | | |
| 133 | Isomer 1 | 22.9 | | |
|  | Isomer 2 | 2.12 | 0.101 | 1.44 |
| 134 | Isomer 1 | >60 | | |
|  | Isomer 2 | 5.16 | 0.151 | 1.57 |
| 135 | Isomer 1 | >60 | | |
|  | Isomer 2 | 28.8 | 0.819 | |
| 136 | Isomer 1 | 8.69 | | |
|  | Isomer 2 | >60 | | |
| 137 | Isomer 1 | 21.8 | | |
|  | Isomer 2 | >60 | | |
| 138 | Isomer 1 | 0.442 | 0.030 | |
|  | Isomer 2 | 4.30 | | |
| 139 | Isomer 1 | 8.29 | | |
|  | Isomer 2 | 0.511 | | 0.0534 |
| 140 | Isomer 1 | >5 | | |
|  | Isomer 2 | 1.54 | | |
|  | Isomer 3 | >5 | | |
|  | Isomer 4 | >5 | | |
| 141 | Isomer 1 | 0.872 | | |
|  | Isomer 2 | >5 | | |
| 142 | Isomer 1 | 3.27 | | |
|  | Isomer 2 | 0.0816 | | 1.2 |
| 143 | racemic | 0.266 | | |
| 144 | Isomer 1 | 9.95 | | |
|  | Isomer 2 | 1.41 | | 1.38 |
| 145 | Isomer 1 | 18.5 | 0.593 | |
|  | Isomer 2 | >60 | | |
| 146 | Isomer 1 | 0.786 | | 0.401 |
|  | Isomer 2 | 0.026 | 0.014 | 0.0366 |
| 147 | Isomer 1 | >30 | | |
|  | Isomer 2 | 4.91 | 0.336 | |
| 148 | Isomer 1 | >30 | | |
|  | Isomer 2 | 8.05 | 0.355 | |
| 149 | Isomer 1 | 5.92 | 0.223 | |
|  | Isomer 2 | 11.6 | | |
| 150 | Isomer 1 | 7.97 | 0.393 | |
|  | Isomer 2 | >30 | | |
| 151 | Isomer 1 | 11.5 | | |
|  | Isomer 2 | 0.101 | | 0.0535 |
| 152 | Isomer 1 | >30 | | |
|  | Isomer 2 | 1.26 | 0.0287 | 0.327 |
| 153 | Isomer 1 | 0.345 | 0.00784 | |
|  | Isomer 2 | 0.0798 | 0.00572 | |
| 154 | Isomer 1 | 0.325 | 0.0377 | |
|  | Isomer 2 | 1.62 | 0.00895 | |
| 155 | Isomer 1 | 2.24 | 0.0773 | 16.7 |
|  | Isomer 2 | 4.09 | 0.285 | |
| 156 | Isomer 1 | 0.584 | 0.0291 | |
|  | Isomer 2 | 0.017 | <0.002 | 0.0466 |
| 157 | Isomer 1 | 1.20 | | |
|  | Isomer 2 | 0.066 | | 0.0364 |
| 158 | Isomer 1 | 1.50 | | 0.641 |
|  | Isomer 2 | >5 | | |
| 159 | Isomer 1 | 25.2 | | |
|  | Isomer 2 | 5.9 | 0.274 | |
| 160 | Isomer 1 | >5 | | |
|  | Isomer 2 | 4.01 | | |
| 161 | Isomer 1 | 3.35 | | |
|  | Isomer 2 | 0.0951 | | 0.0781 |
| 162 | Isomer 1 | 4.86 | | |
|  | Isomer 2 | 0.135 | | |
| 163 | Isomer 1 | 2.84 | | |
|  | Isomer 2 | 0.0419 | | >1 |
| 164 | Isomer 1 | 3.66 | 0.190 | |
|  | Isomer 2 | 0.140 | 0.00603 | |
| 165 | Isomer 1 | 4.33 | | |
|  | Isomer 2 | 2.36 | | |
| 166 | Isomer 1 | 0.123 | | |
|  | Isomer 2 | 0.0288 | | 0.112 |

TABLE 10-continued

| Example number | Isomer | P300 HAT SPA IC$_{50}$ (μM) | FL P300 IC$_{50}$ (μM) | H3K18Ac MSD EC$_{50}$ (μM) |
|---|---|---|---|---|
| 167 | Isomer 1 | 0.0232 | | |
| | Isomer 2 | 0.746 | | |
| 168 | Isomer 1 | 4.12 | | |
| | Isomer 2 | 0.0531 | | |
| 169 | Isomer 1 | 1.79 | | |
| | Isomer 2 | 0.0871 | | |
| 170 | Isomer 1 | 0.296 | | |
| | Isomer 2 | 4.11 | | |
| 171 | Isomer 1 | >5 | | |
| | Isomer 2 | 0.932 | | |
| 172 | Isomer 1 | 4.24 | | |
| | Isomer 2 | 0.657 | | |
| 173 | Isomer 1 | 1.7 | | |
| | Isomer 2 | 0.0211 | | |
| 174 | Isomer 1 | 0.965 | | >1 |
| | Isomer 2 | 0.039 | | 0.0983 |
| 175 | Isomer 1 | 0.917 | | |
| | Isomer 2 | 0.044 | | 0.184 |
| 176 | Isomer 1 | 0.0538 | | |
| | Isomer 2 | 1.11 | | |
| 177 | Isomer 1 | >5 | | |
| | Isomer 2 | 0.838 | | 1.27 |
| 178 | Isomer 1 | >5 | | |
| | Isomer 2 | 2.07 | | |
| 179 | Isomer 1 | 0.302 | | 0.192 |
| | Isomer 2 | 0.248 | | |
| 180 | Isomer 1 | 4.33 | | |
| | Isomer 2 | 0.370 | | 0.219 |
| 181 | Isomer 1 | 0.642 | | 0.243 |
| | Isomer 2 | >5 | | |
| 182 | Isomer 1 | >5 | | |
| | Isomer 2 | 0.514 | | |
| 183 | Isomer 1 | >5 | | |
| | Isomer 2 | 0.717 | | |
| 184 | Isomer 1 | 0.672 | | |
| | Isomer 2 | 0.522 | | |
| 185 | Isomer 1 | 1.10 | | |
| | Isomer 2 | >30 | | |
| 186 | Isomer 1 | 1.97 | | |
| | Isomer 2 | 3.54 | | |
| 187 | Isomer 1 | >5 | | |
| | Isomer 2 | 0.793 | | |

While we have described a number of embodiments, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

The invention claimed is:
1. A compound of Formula I:

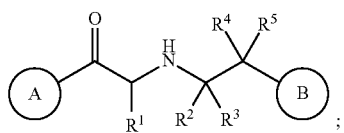

(I)

or a pharmaceutically acceptable salt thereof, wherein
Ring A is bicyclic heteroaryl optionally substituted with 1 to 4 groups selected from $R^a$;
Ring B is aryl, heterocyclyl, or heteroaryl each of which may be optionally substituted with 1 to 4 groups selected from $R^b$;
$R^1$ is $C_{1-6}$alkyl, $C_{1-6}$haloalkyl, $C_{2-6}$alkenyl, —$C_{1-6}$alkylOR$^c$, —$C_{1-6}$alkylN(R$^d$)$_2$, —$C_{1-6}$alkylC(O)OR$^d$, —$C_{1-6}$ alkylOC$_{1-6}$alkylN(R$^d$)$_2$, —$C_{1-6}$alkylSOR$^d$, —$C_{1-6}$alkylS(O)$_2$R$^d$, —$C_{1-6}$alkylSON(R$^d$)$_2$, —$C_{1-6}$alkylSO$_2$N(R$^d$)$_2$, —$C_{1-6}$alkylcycloalkyl, —$C_{1-6}$alkylheterocyclyl, —$C_{1-6}$ alkylheteroaryl, —$C_{1-6}$alkylaryl, cycloalkyl, aryl, heteroaryl, or heterocyclyl, wherein each of said cycloalkyl, heterocyclyl, aryl, and heteroaryl alone and in connection with —$C_{1-6}$alkylcycloalkyl, —$C_{1-6}$alkylaryl, —$C_{1-6}$alkylheteroaryl, and —$C_{1-6}$alkylheterocyclyl are optionally substituted with 1 to 3 groups selected from $R^c$;
each of $R^2$, $R^3$, $R^4$, and $R^5$ are independently hydrogen or $C_{1-6}$alkyl, wherein said $C_{1-6}$ alkyl is optionally substituted with 1 or 2 groups selected from halo, —C(O)OR$^d$, —OC$_{1-6}$alkylN(R$^d$)$_2$, —$C_{1-6}$alkylN(R$^d$)$_2$, —N(R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, cycloalkyl, heterocyclyl, heteroaryl, and aryl;
each of $R^a$, $R^b$, and $R^c$ are each independently halo, CN, oxo, NO$_2$, $C_{1-6}$alkyl, $C_{2-6}$alkenyl, $C_{1-6}$alkoxy, $C_{1-6}$haloalkoxy, $C_{1-6}$haloalkyl, —$C_{1-6}$alkylOR$^d$, —C(O)R$^d$, —C(O)OR$^d$, —$C_{1-6}$ alkylC(O)OR$^d$, —C(O)N(R$^d$)$_2$, —C(O)NR$^d$C$_{1-6}$alkylOR$^d$, —OC$_{1-6}$alkylN(R$^d$)$_2$, —$C_{1-6}$ alkylC(O)N(R$^d$)$_2$, —$C_{1-6}$alkylN(R$^d$)$_2$, —N (R$^d$)$_2$, —C(O)NR$^d$C$_{1-6}$alkylN(R$^d$)$_2$, —NR$^d$C$_{1-6}$alkylN (R$^d$)$_2$, —NR$^d$C$_{1-6}$alkylOR$^d$, —SOR$^d$, —S(O)$_2$R$^d$, —SON(R$^d$)$_2$, —SO$_2$N(R$^d$)$_2$, SF$_5$, —Ocycloalkyl, —Oheterocyclyl, —O—$C_{1-4}$alkylaryl, —$C_{1-6}$alkylcycloalkyl, —$C_{1-6}$alkylaryl, —$C_{1-6}$alkylheteroaryl, —$C_{1-6}$ alkylheterocyclyl, cycloalkyl, heterocyclyl, heteroaryl, or aryl, wherein each of said cycloalkyl, heterocyclyl, aryl, and heteroaryl alone and in connection with —Ocycloalkyl, —$C_{1-6}$alkylcycloalkyl, —$C_{1-6}$alkylaryl, —$C_{1-6}$ alkylheteroaryl, and —$C_{1-6}$alkylheterocyclyl are optionally substituted with 1 to 3 groups selected from halo, oxo, $C_{1-6}$alkyl, $C_{1-6}$haloalkyl, $C_{1-6}$alkoxy, $C_{1-6}$haloalkoxy, —N(R$^d$)$_2$, —C(O)R$^d$, and —$C_{1-6}$alkylOR$^d$; and
each R$^d$ is independently hydrogen, heterocyclyl, $C_{1-6}$haloalkyl, or $C_{1-6}$alkyl, wherein said heterocyclyl is optionally substituted with 1 or 2 groups selected from $C_{1-4}$haloalkyl and $C_{1-4}$alkyl and said $C_{1-6}$alkyl is optionally substituted with —SO$_2$C$_{1-4}$alkyl or heterocyclyl optionally substituted with oxo;
provided the compound is not 4-(2-((2-(1H-indol-3-yl)-2-oxo-1-phenylethyl)amino)ethyl)benzenesulfonamide; 4-[2-[[2-(7-ethyl-1H-indol-3-yl)-2-oxo-1-phenylethyl]amino]ethyl]benzenesulfonamide; 2-[[2-(3,4-dimethoxyphenyl)ethyl]amino]-1-(1H-indol-3-yl)-2-phenylethanone, or a salt thereof.

2. The compound of claim 1, wherein Ring A is selected from

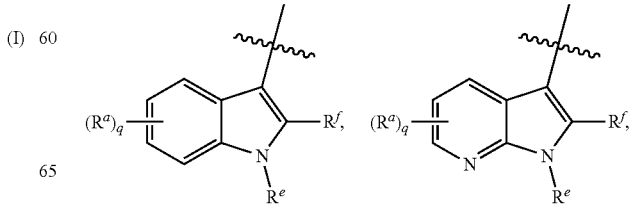

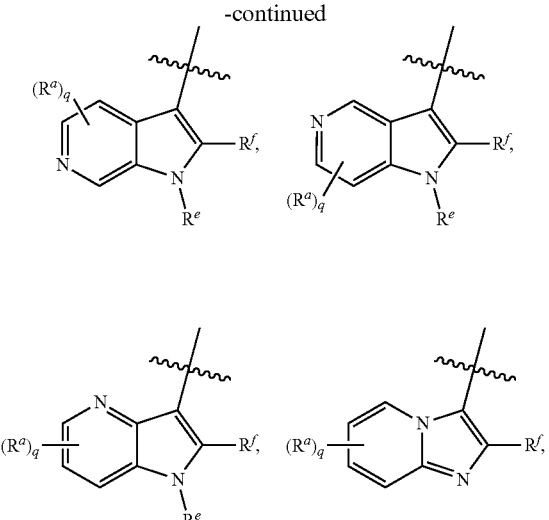

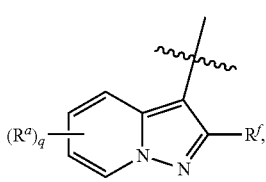

and

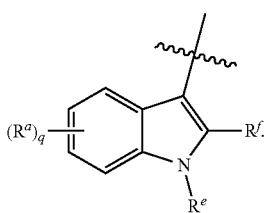

wherein each q is 0, 1, or 2; and $R^e$ and $R^f$ are each independently is hydrogen, $C_{1-6}$alkyl, and —$C_{1-6}$alkylOR$^d$.

3. The compound of claim 2, wherein Ring A is

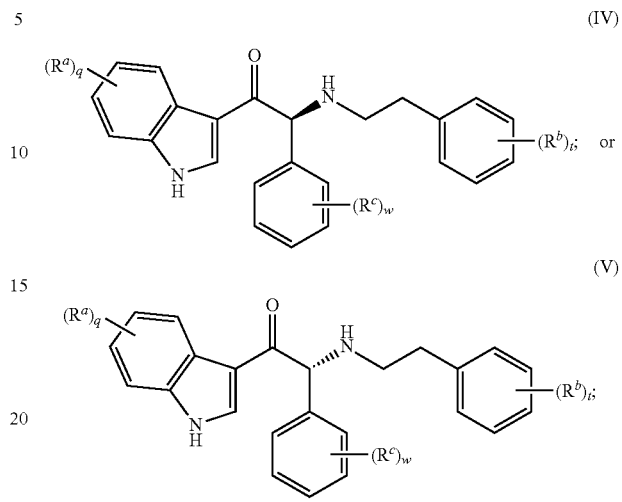

4. The compound of claim 1, wherein Ring B is phenyl, 5-6 membered heteroaryl, 9-10 membered heteroaryl, or 5-6 membered heterocyclyl, each optionally substituted with 1 to 3 groups selected from $R^b$.

5. The compound of claim 1, wherein $R^1$ is $C_{1-6}$alkyl, aryl, cycloalkyl, or heteroaryl, wherein each of said aryl, cycloalkyl, and heteroaryl are optionally substituted with 1 to 3 groups selected from $R^c$.

6. The compound of claim 1, wherein $R^3$ is hydrogen.

7. The compound of claim 1, wherein $R^5$ is hydrogen.

8. The compound of claim 1, wherein $R^2$ is hydrogen or $C_{1-4}$alkyl.

9. The compound of claim 1, wherein $R^4$ is hydrogen or $C_{1-4}$alkyl.

10. The compound of claim 1, wherein the compound is of the Formula IV or V:

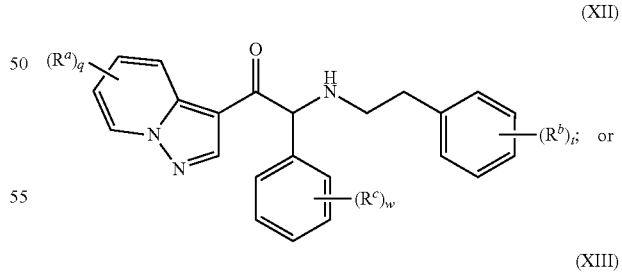

or a pharmaceutically acceptable salt thereof, wherein w and t are each independently 0, 1, or 2; and q is 0, 1, or 2.

11. The compound of claim 1, wherein $R^c$, if present, is $C_{1-6}$alkyl, $C_{1-6}$alkoxy, $C_{1-6}$haloalkoxy, or $C_{1-6}$haloalkyl.

12. The compound of claim 1, wherein $R^a$ is selected from $C_{1-4}$alkyl, $C_{1-4}$haloalkyl, $C_{1-4}$alkoxy, halo, —$C_{1-4}$alkylC(O)N($R^d$)$_2$, —$C_{1-4}$alkylC(O)OR$^d$, —C(O)OR$^d$, —C(O)NR$^d$C$_{1-4}$ alkylN($R^d$)$_2$, —C(O)NR$^d$C$_{1-4}$alkylOR$^d$, —C(O)N($R^d$)$_2$, —OC$_{1-4}$alkylaryl, heterocyclyl, and heteroaryl, wherein said heterocyclyl is optionally substituted with $C_{1-4}$alkyl or —C(O)R$^d$ and wherein said heteroaryl is optionally substituted with $C_{1-4}$alkyl, —C$_{1-4}$alkylC(O)N($R^d$)$_2$, —C$_{1-4}$alkylOR$^d$.

13. The compound of claim 1, wherein $R^b$ is selected from —SON($R^d$)$_2$, halo, $C_{1-4}$haloalkoxy, $C_{1-4}$alkoxy, $C_{1-4}$haloalkyl, $C_{1-4}$alkyl, —N($R^d$)$_2$, oxo, —NR$^d$C$_{1-6}$alkylOR$^d$, CN, heteroaryl, —C(O)N($R^d$)$_2$, C(O)OR$^d$, and —C$_{1-4}$alkylC(O)N($R^d$)$_2$.

14. The compound of claim 13, wherein $R^d$ is hydrogen or $C_{1-4}$alkyl.

15. The compound of claim 1, wherein the compound is of the Formula XII or XIII:

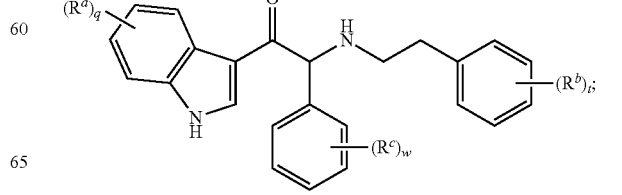

or a pharmaceutically acceptable salt thereof, wherein q, w, and t are each independently 0, 1, or 2.

16. The compound of claim 1, wherein $R^b$ is CN.

17. The compound of claim 1, wherein $R^a$ is selected from $C_{1-4}$alkyl, —C(O)NR$^d$C$_{1-4}$alkylOR$^d$, —C(O)N(R$^d$)$_2$, heterocyclyl, —Oheterocyclyl, and heteroaryl, wherein said heterocyclyl and —Oheterocyclyl are each optionally substituted with oxo and wherein said heteroaryl is optionally substituted with $C_{1-4}$alkyl.

18. The compound of claim 1, wherein each $R^d$ is independently hydrogen, heterocyclyl, $C_{1-6}$haloalkyl, or $C_{1-6}$alkyl, wherein said heterocyclyl is optionally substituted with 1 or 2 groups selected from $C_{1-4}$haloalkyl, oxo, and $C_{1-4}$alkyl and said $C_{1-6}$alkyl is optionally substituted with —SO$_2$C$_{1-4}$alkyl or heterocyclyl optionally substituted with oxo.

19. A pharmaceutical composition comprising
1) the compound of claim 1, or a pharmaceutically acceptable salt thereof, and
2) a pharmaceutically acceptable carrier.

20. The compound of claim 1, wherein the compound is selected from

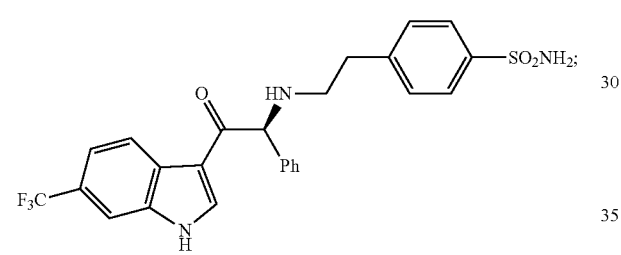

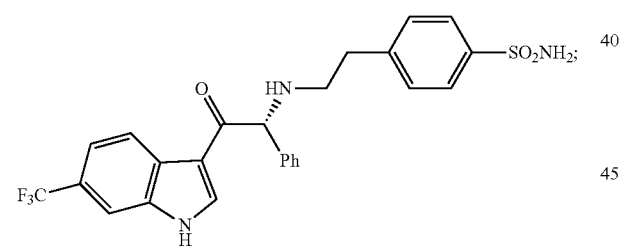

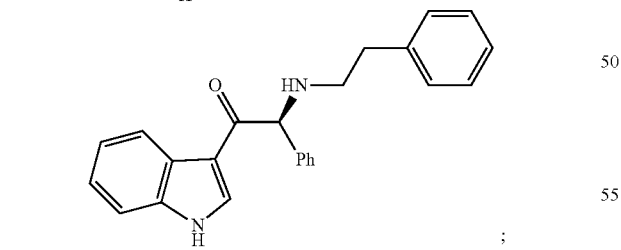

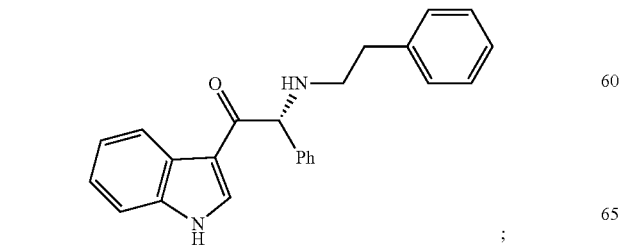

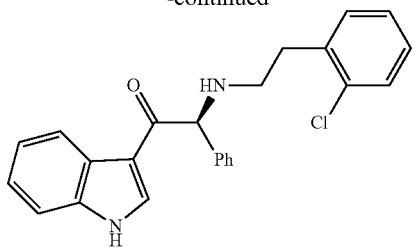

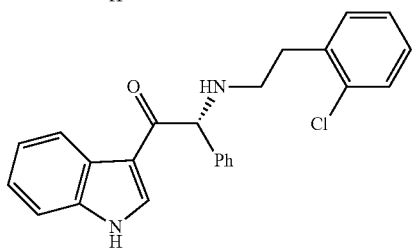

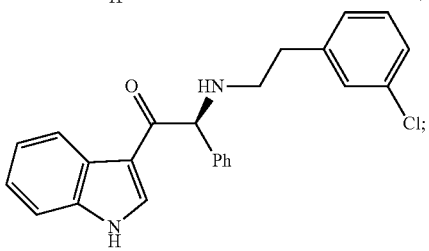

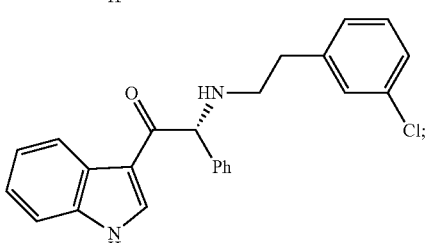

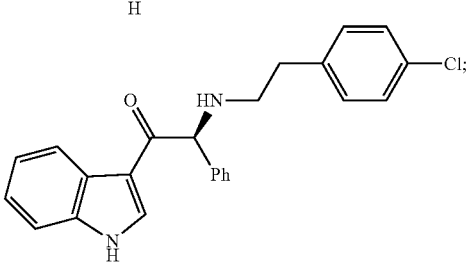

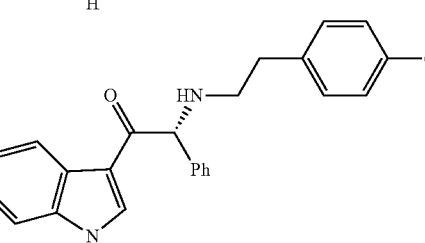

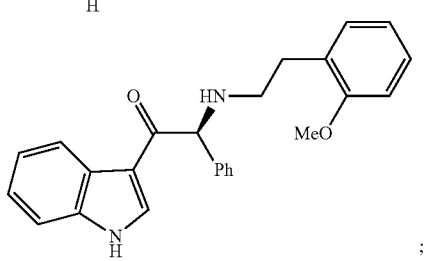

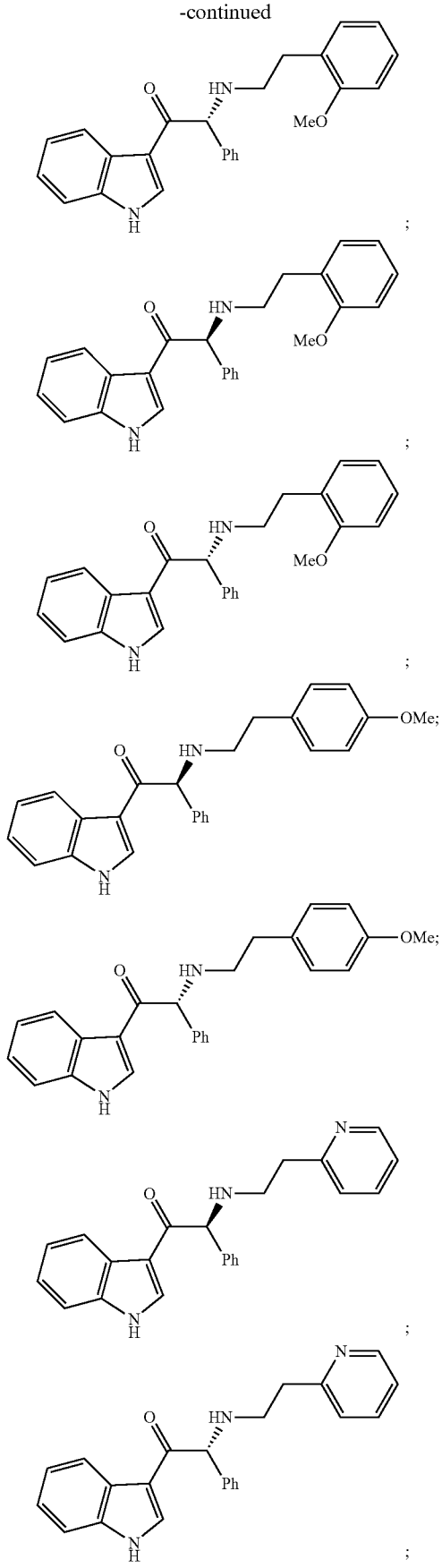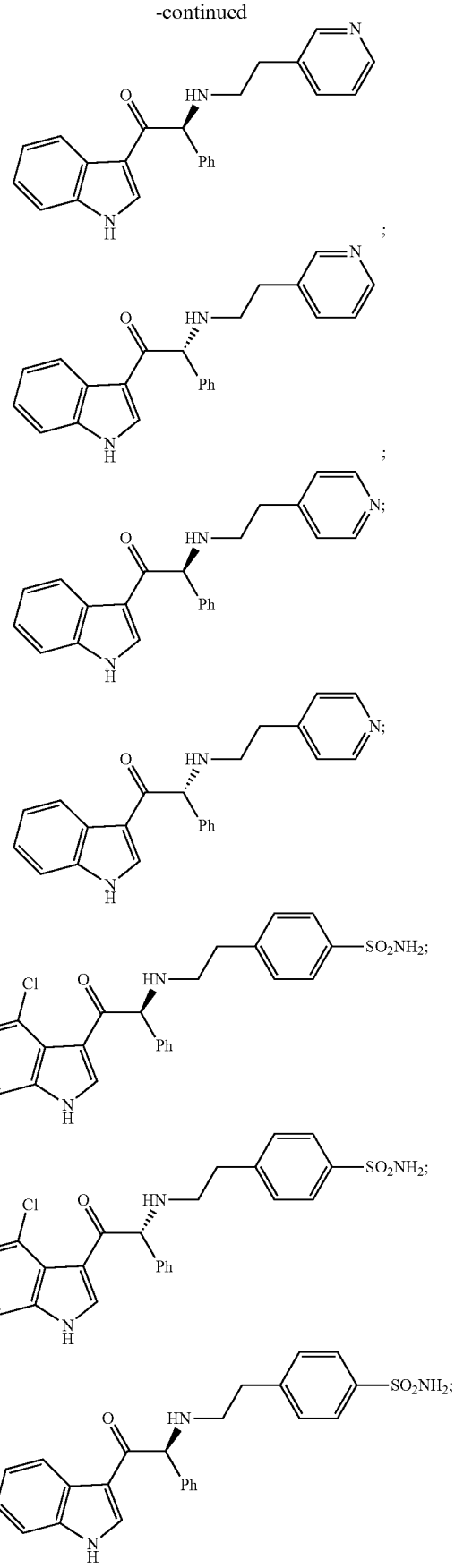

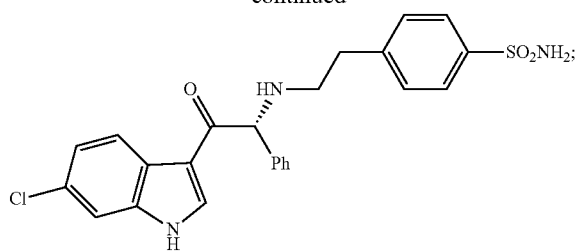
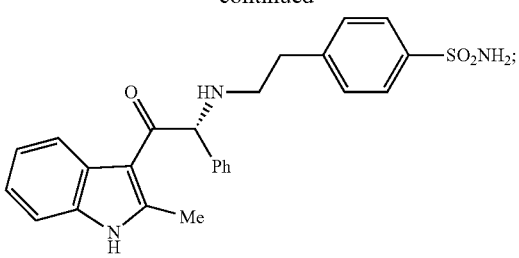
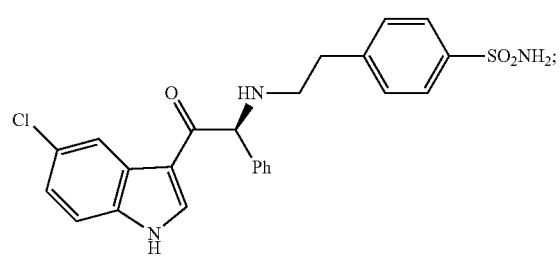
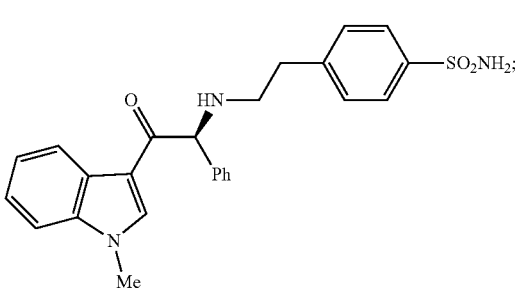
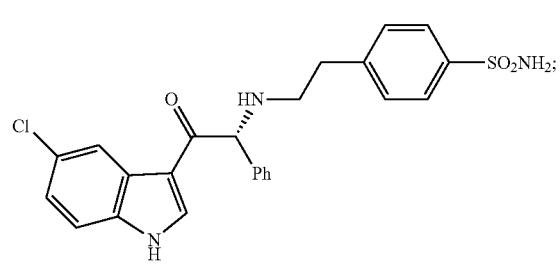
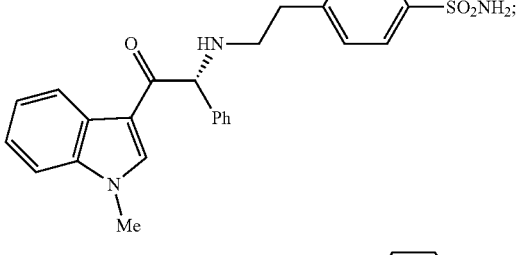
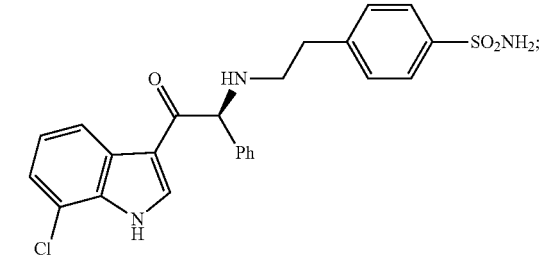
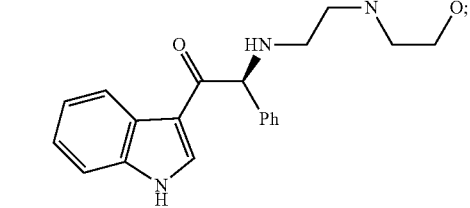
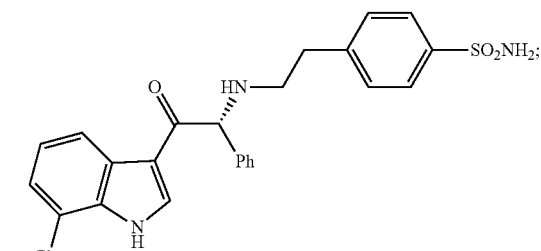
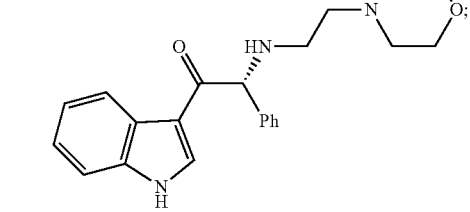
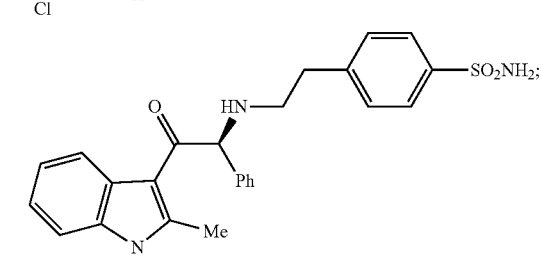
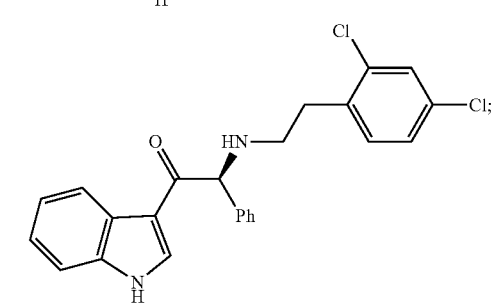

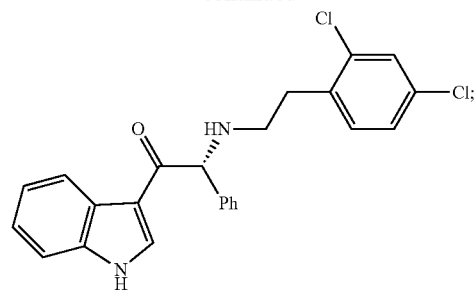
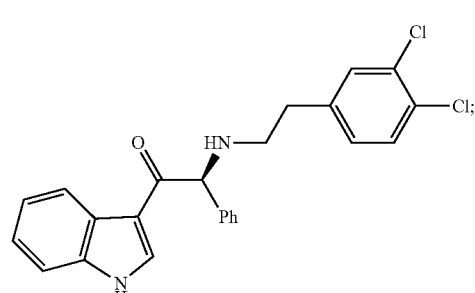
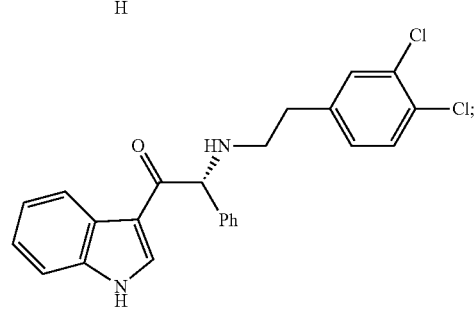
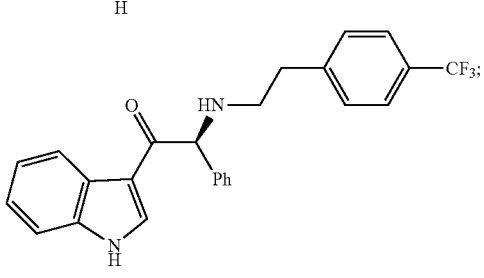
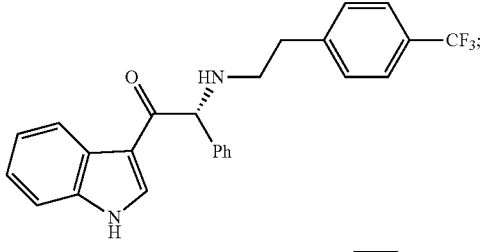
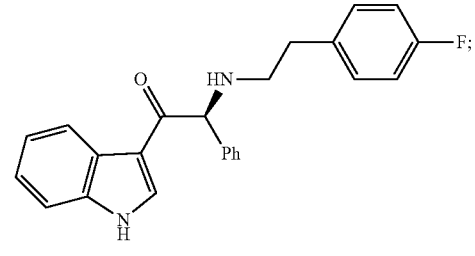
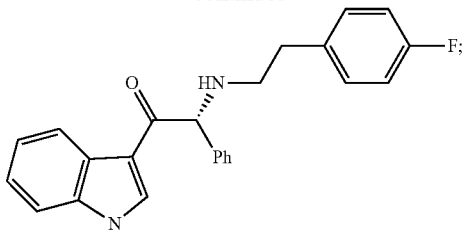
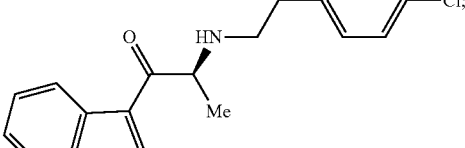
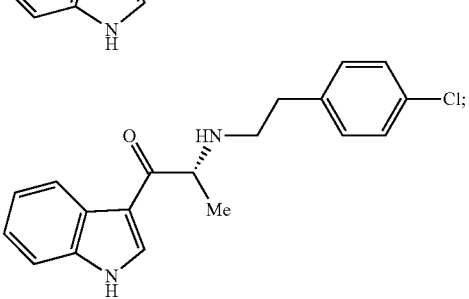
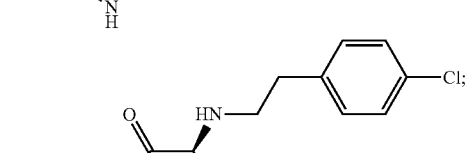
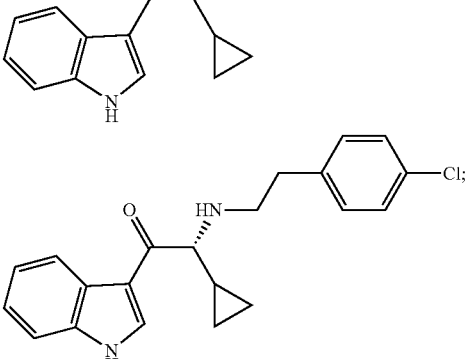
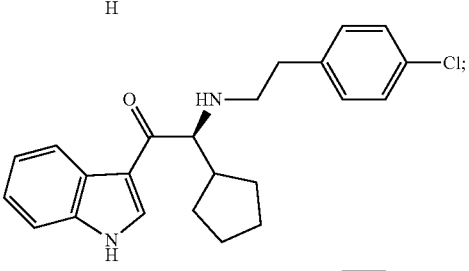
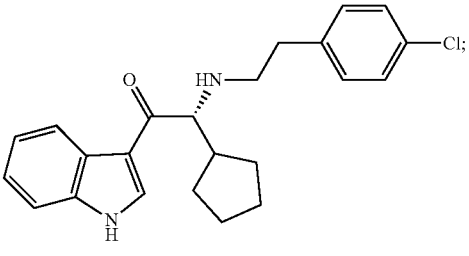

223
-continued
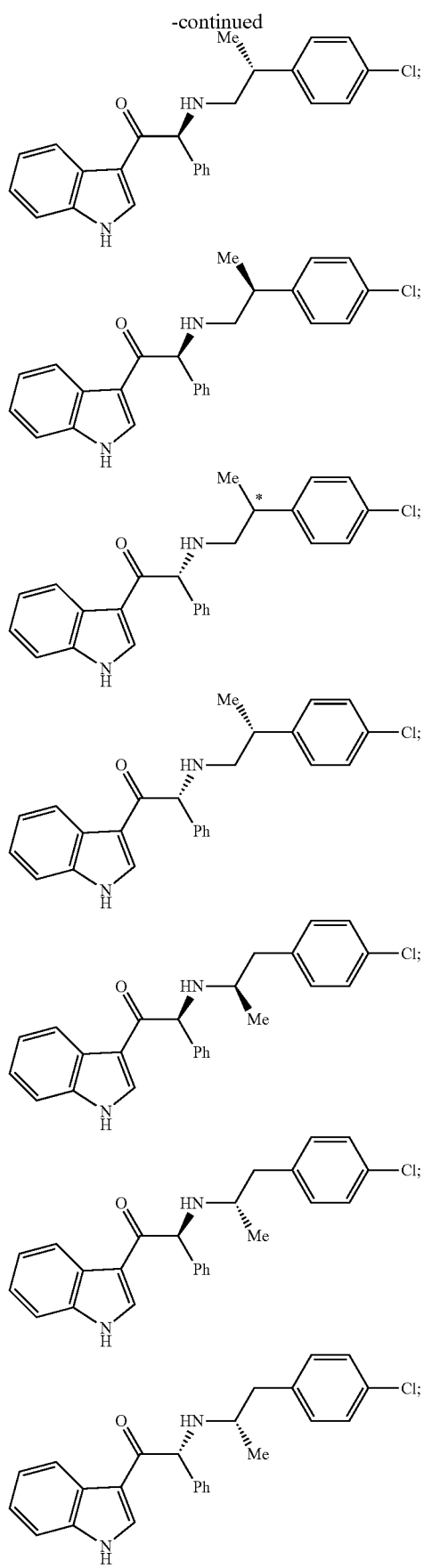
224
-continued
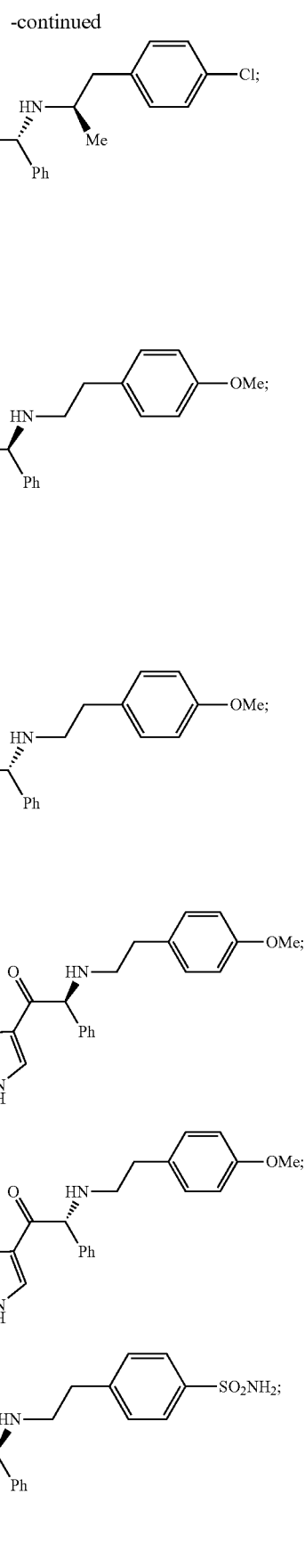

-continued
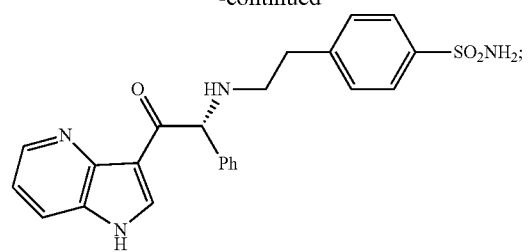
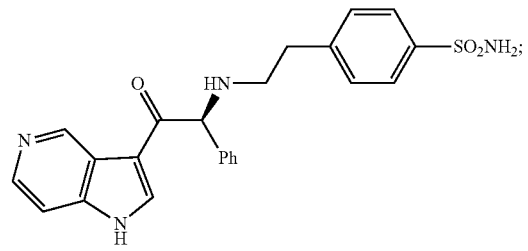
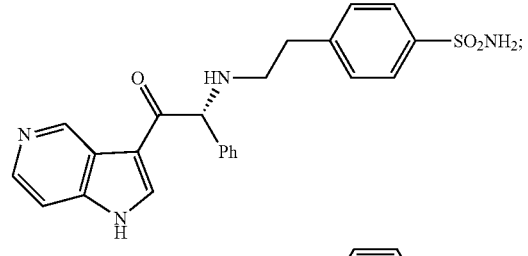
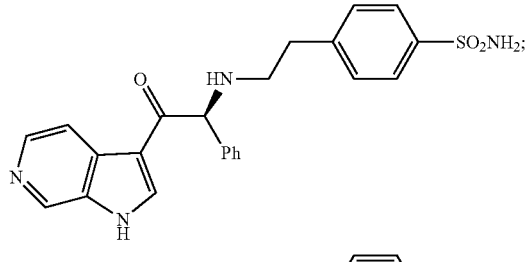
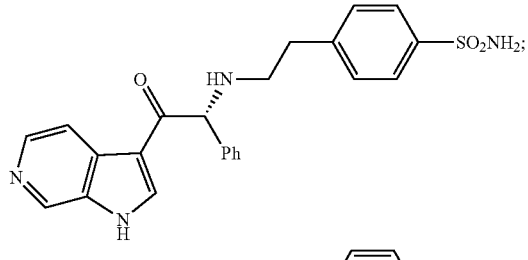
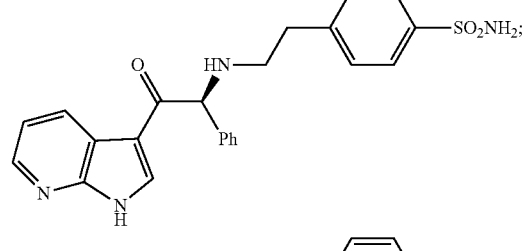
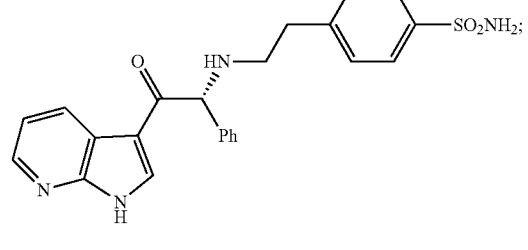
-continued
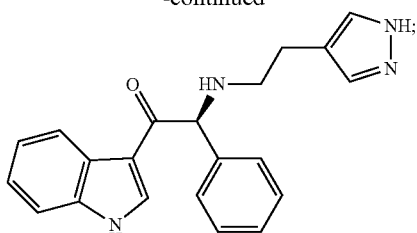
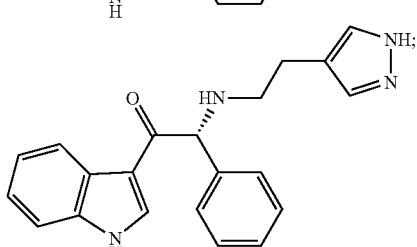
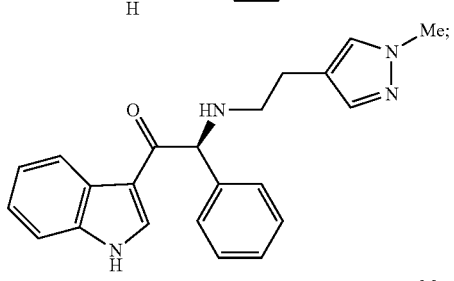
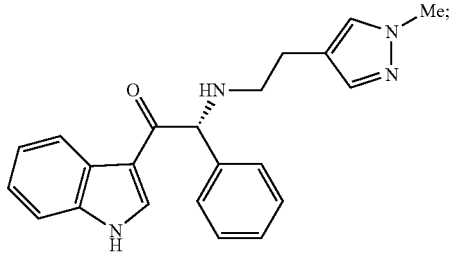
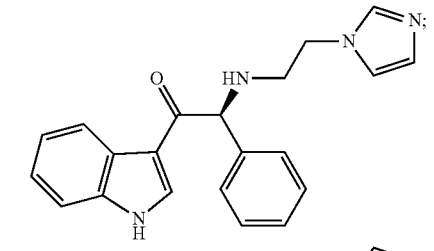
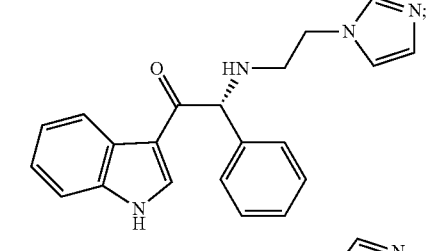
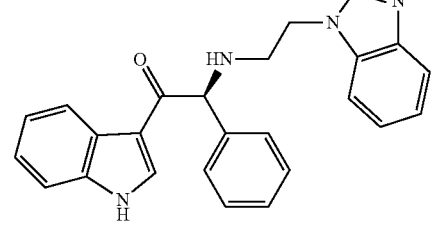

227
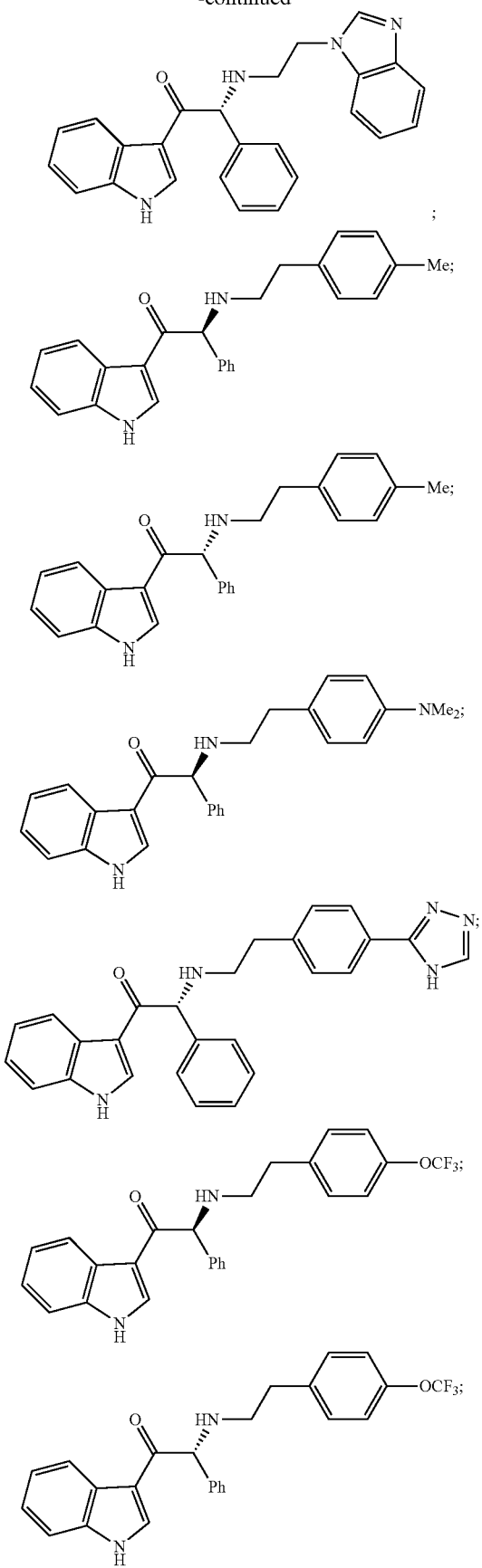
228
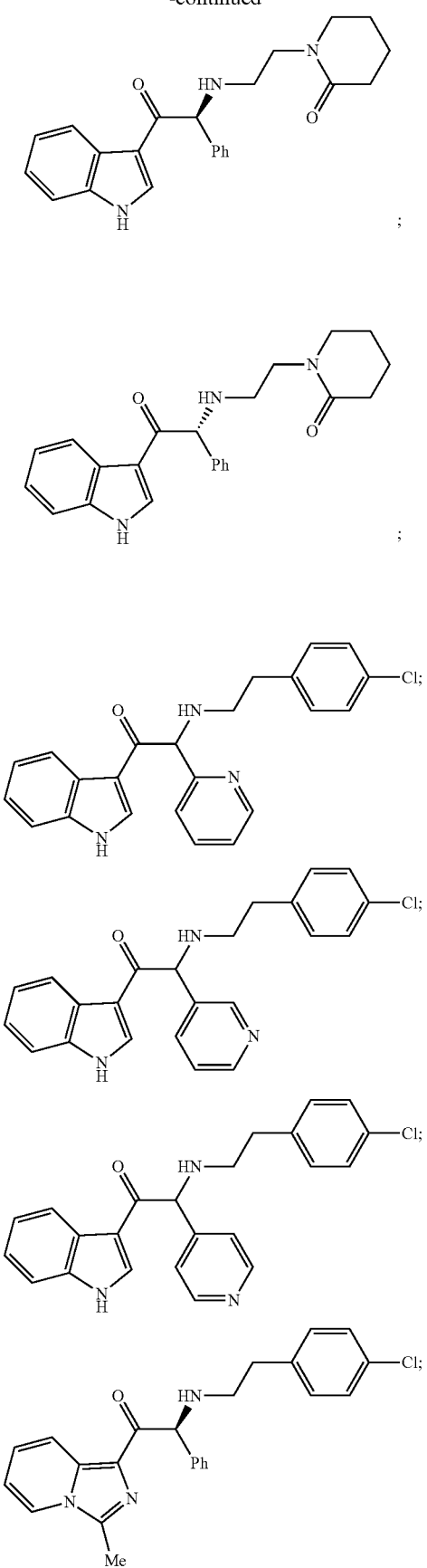

229
-continued
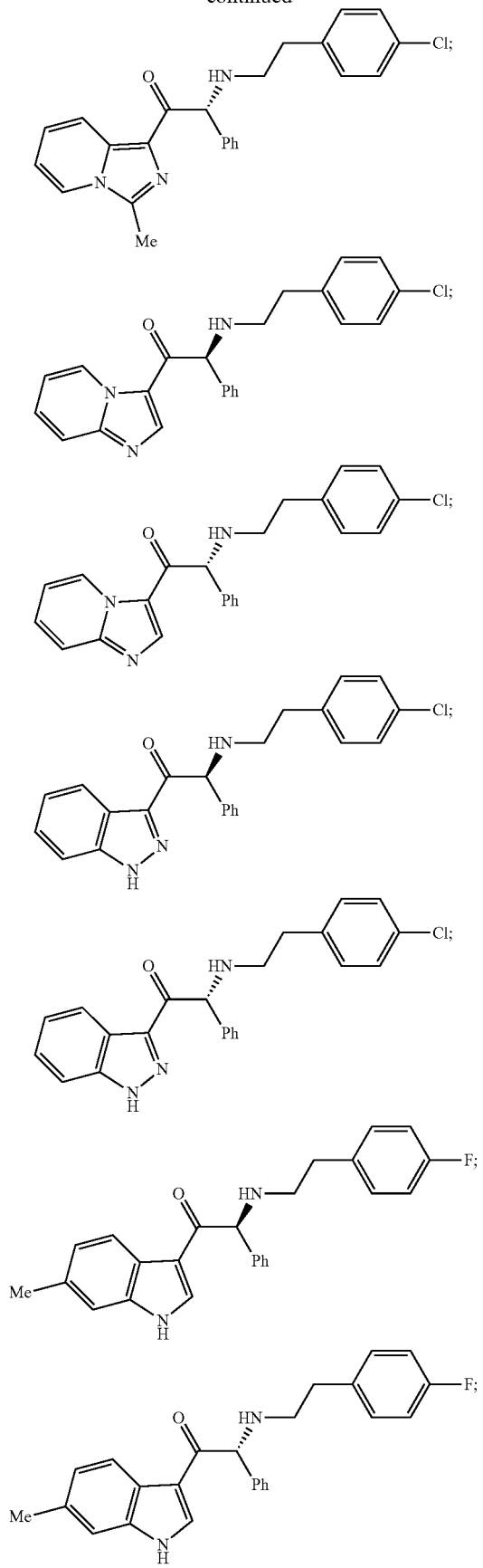
230
-continued
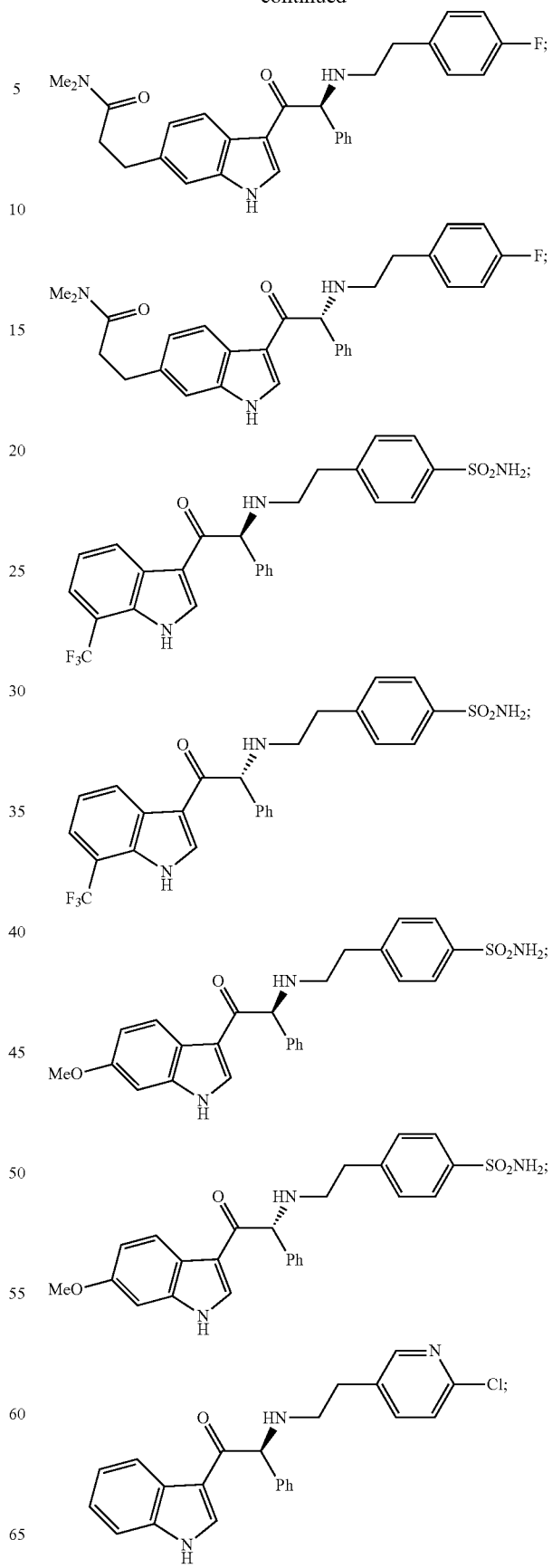

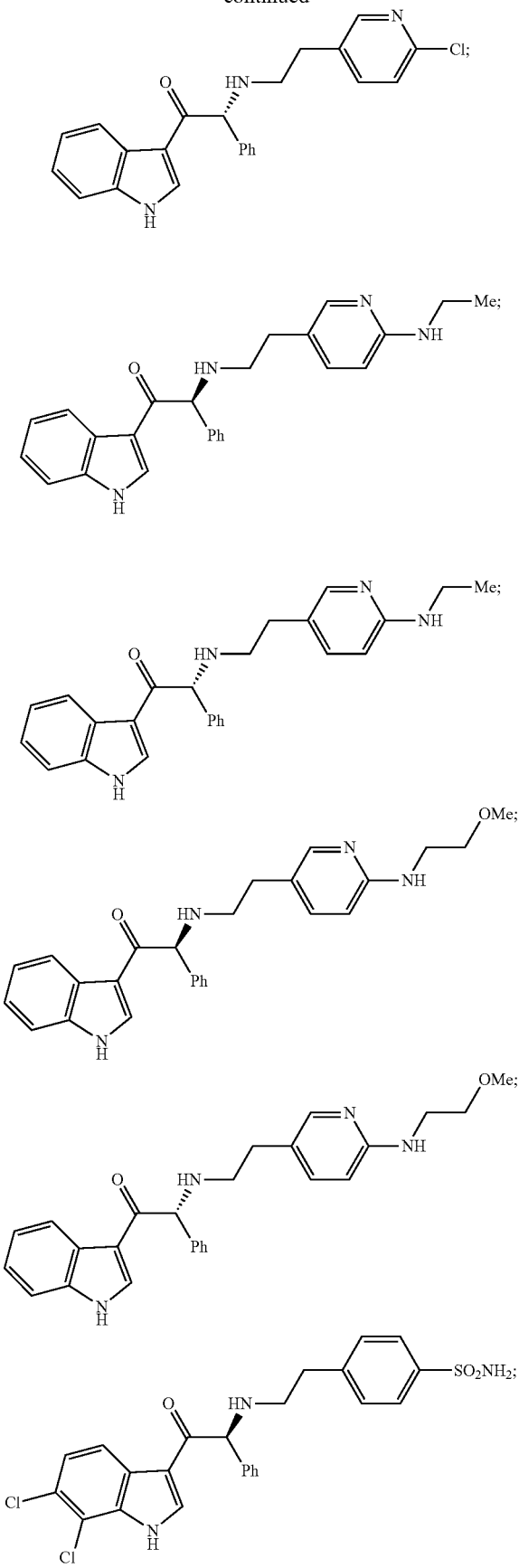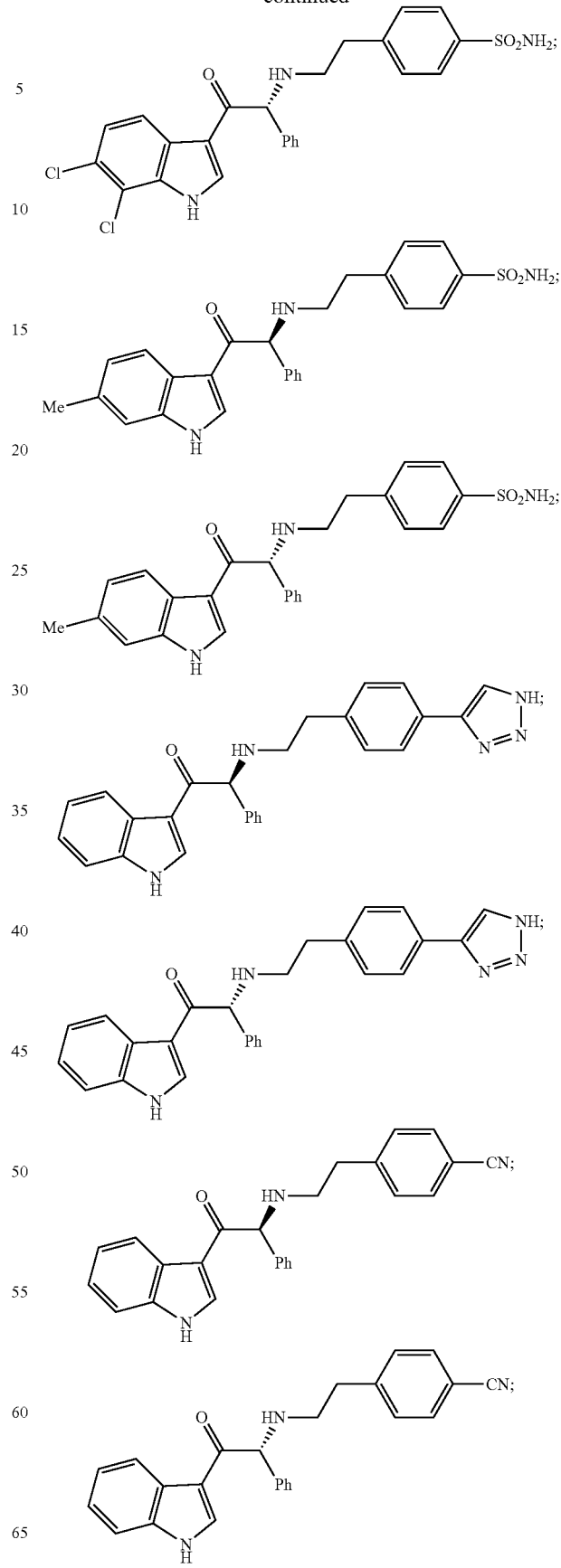

-continued
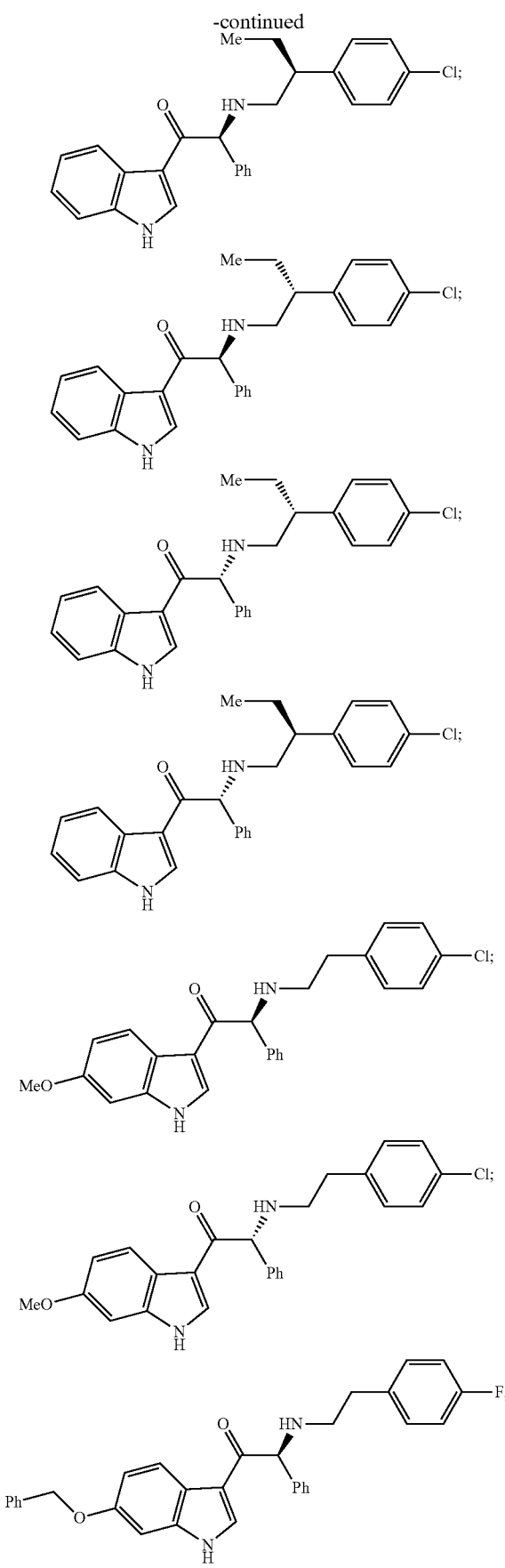
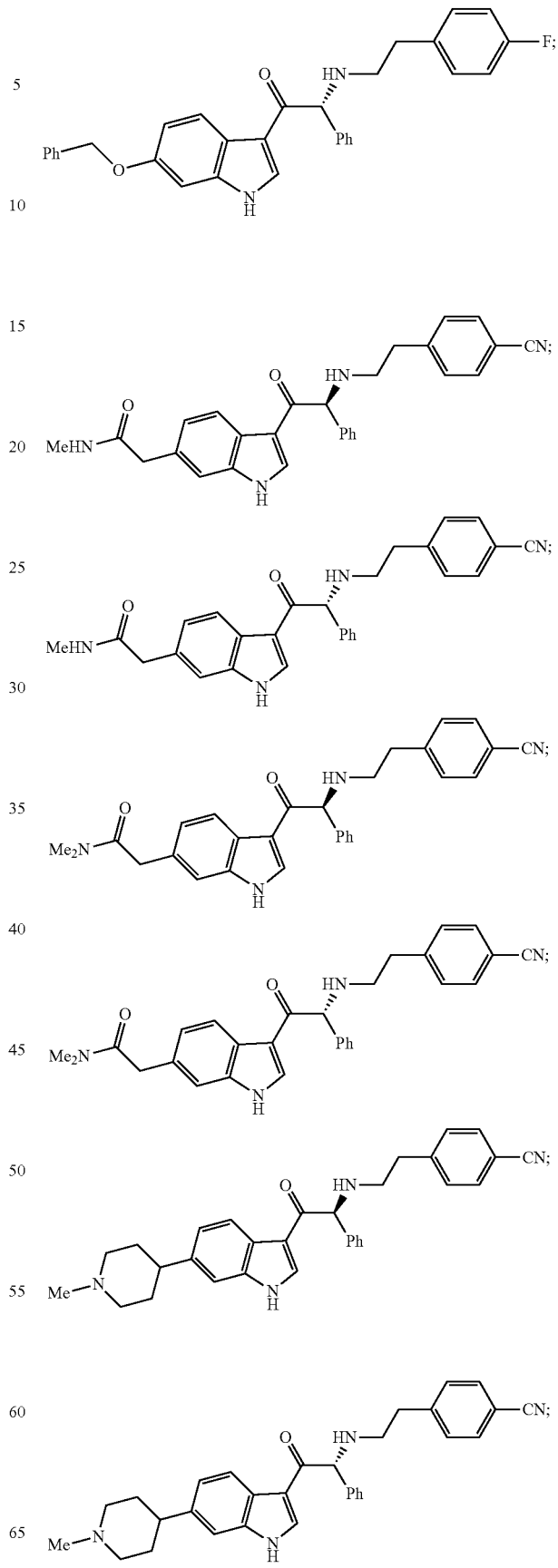

235
-continued
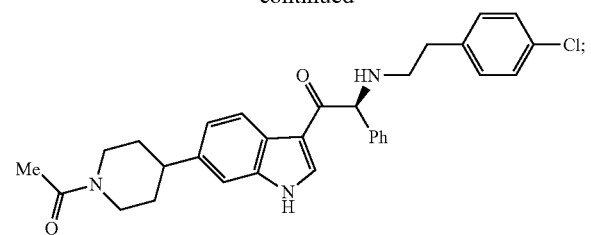
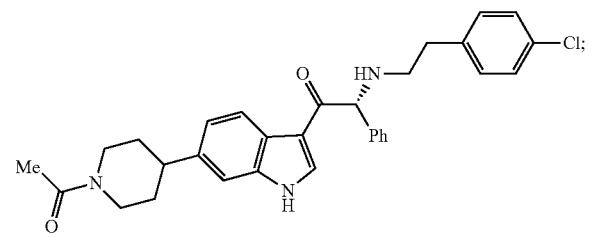
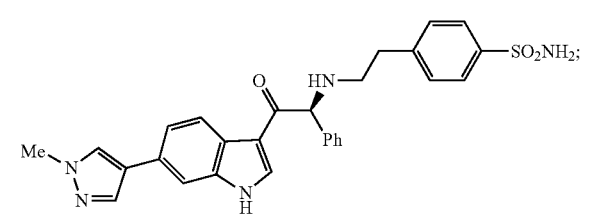
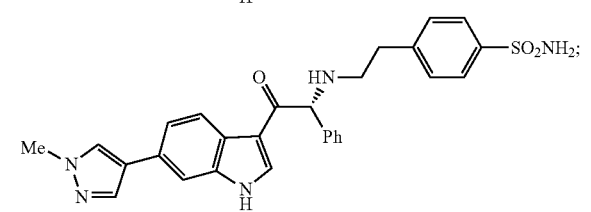
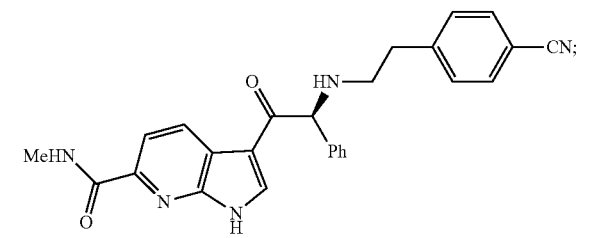 [SMILES: CNC(=O)c1ccc2c(C(=O)C(NCCc3ccc(C#N)cc3)c3ccccc3)c[nH]c2c1]
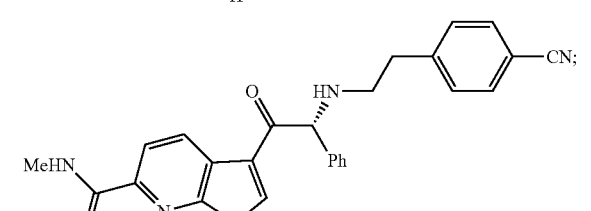
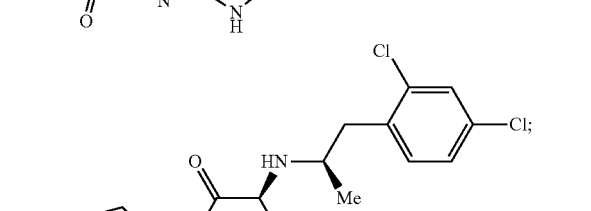
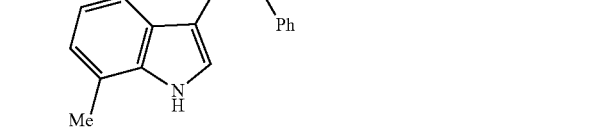
236
-continued
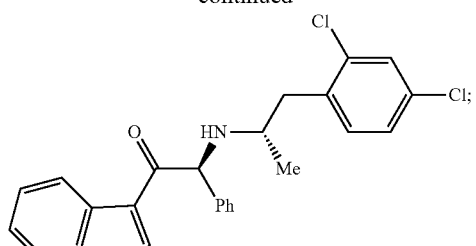
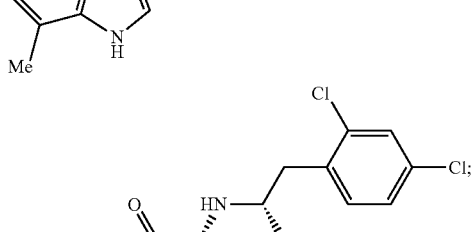
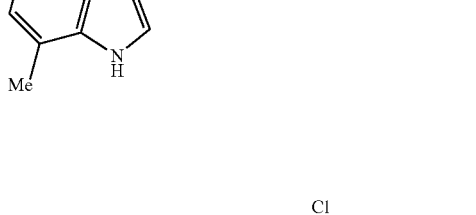
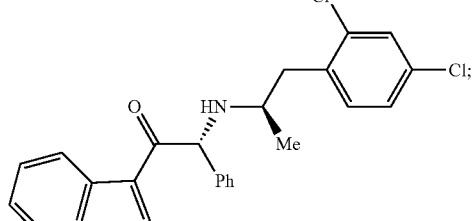
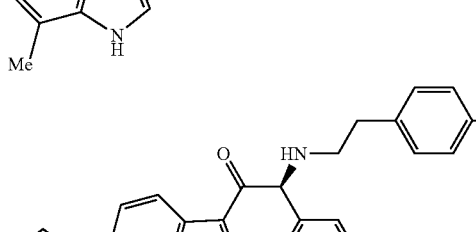
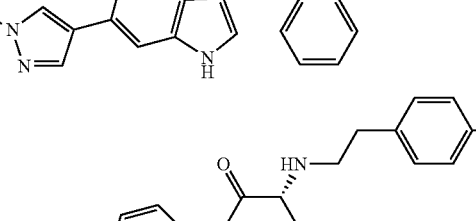
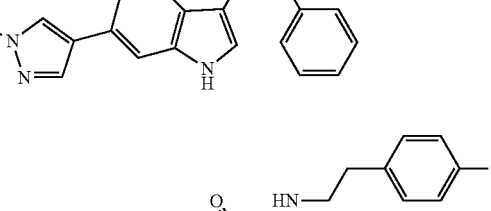
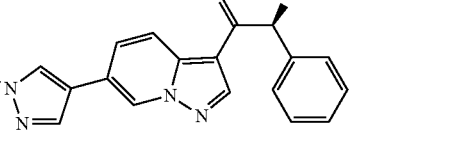

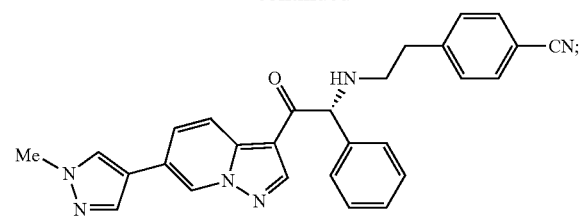
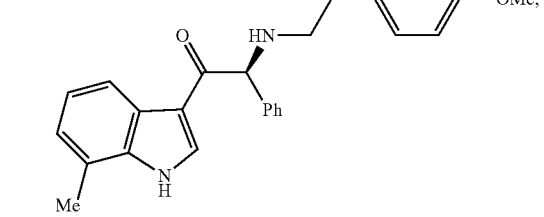
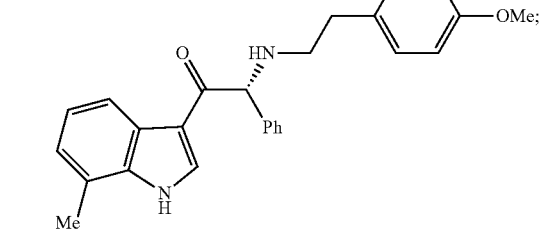
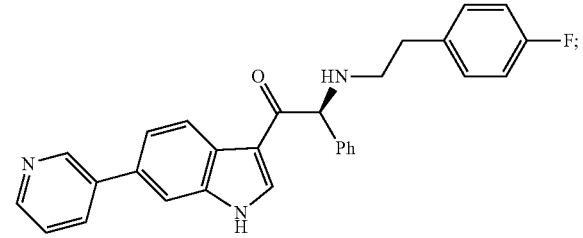
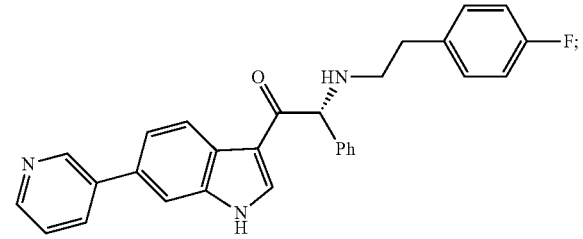
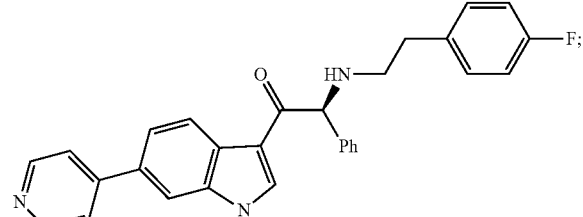
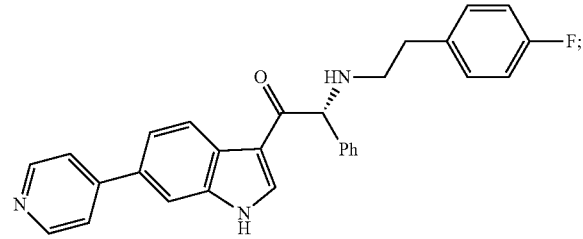
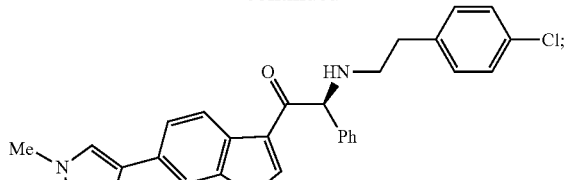
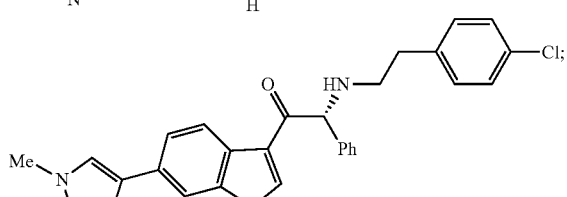
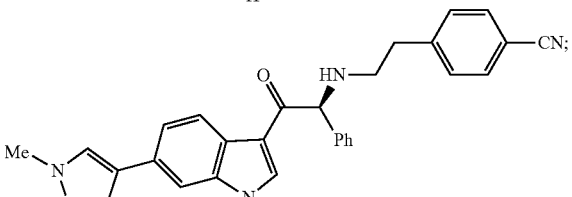
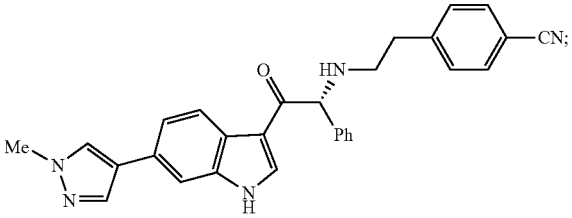
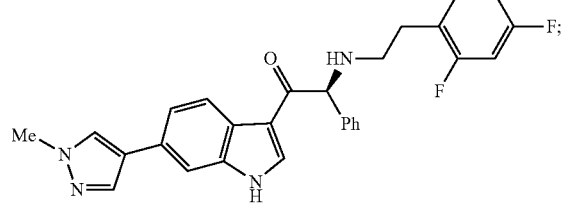
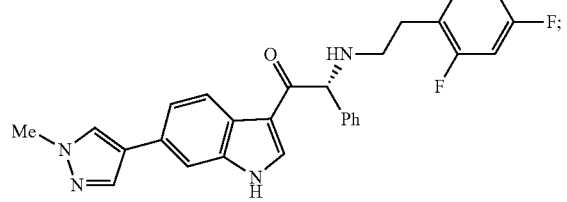
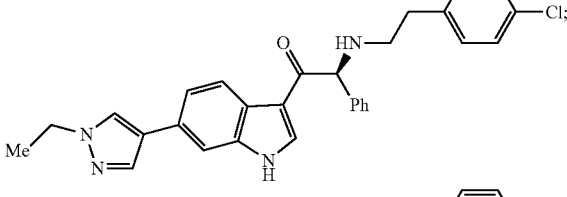
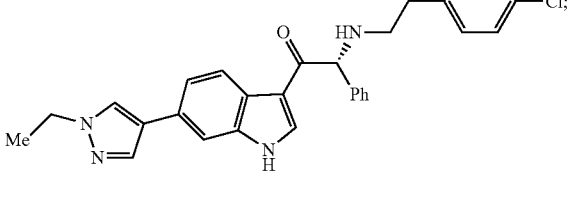

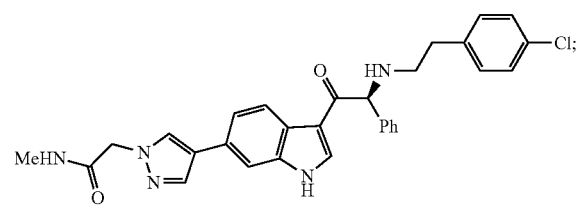
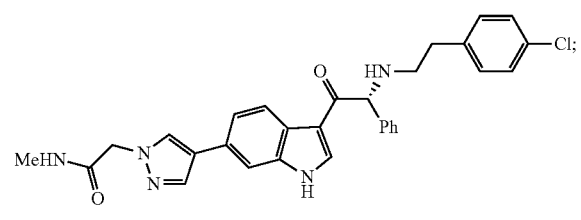
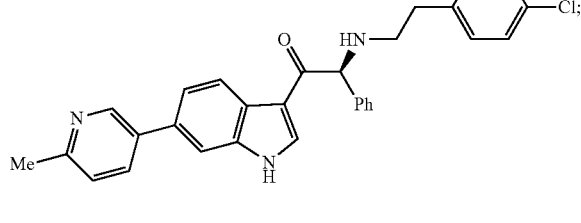
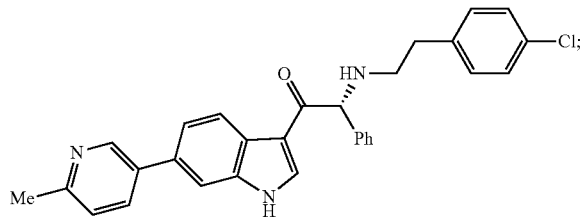
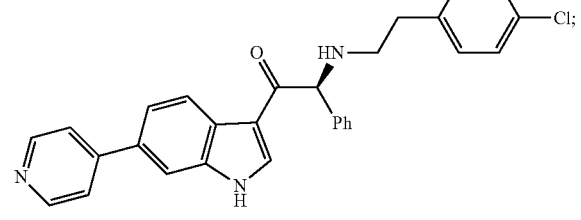
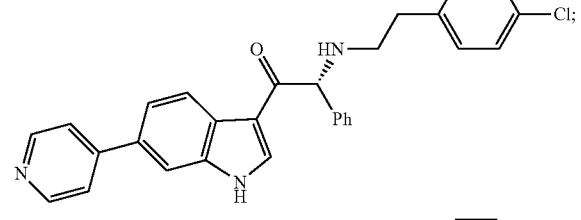
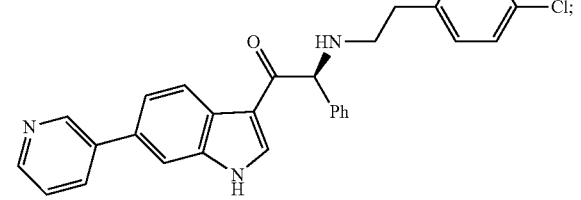
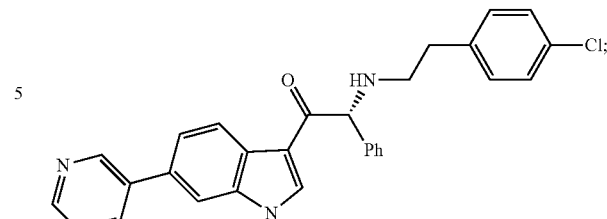
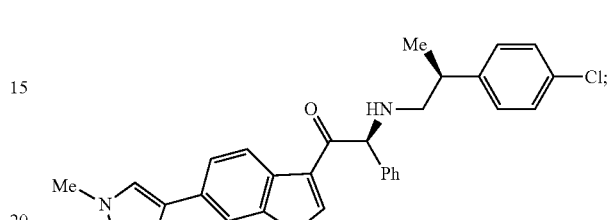
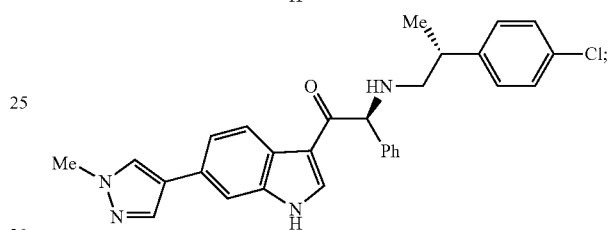
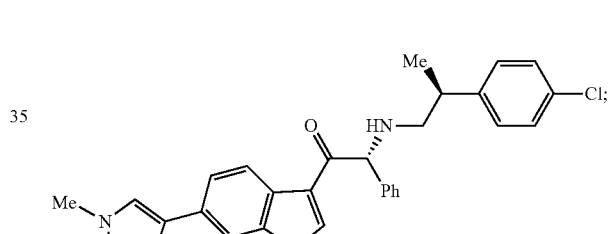
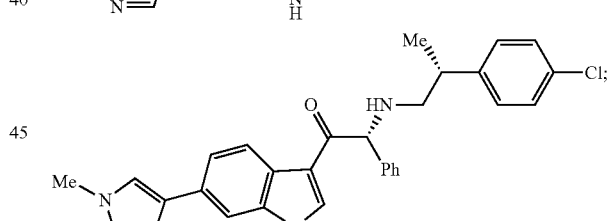
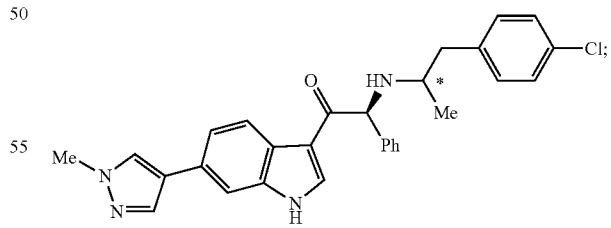
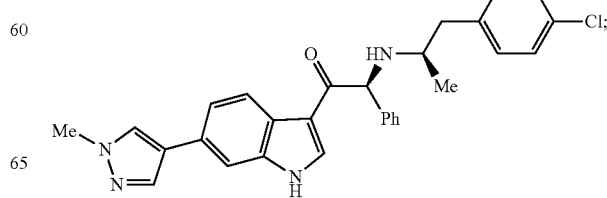

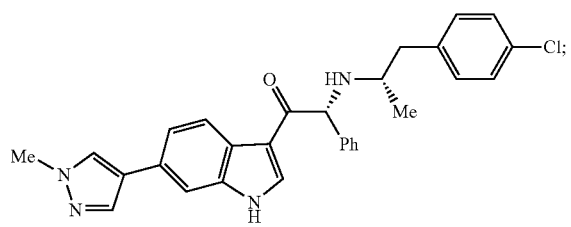
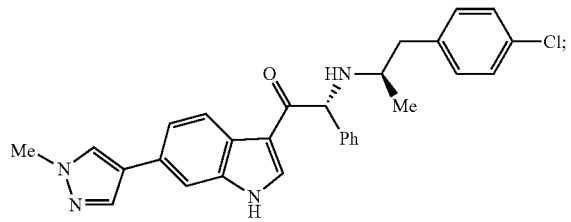
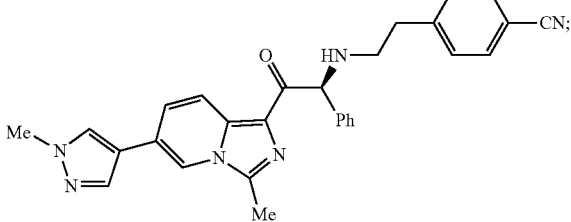
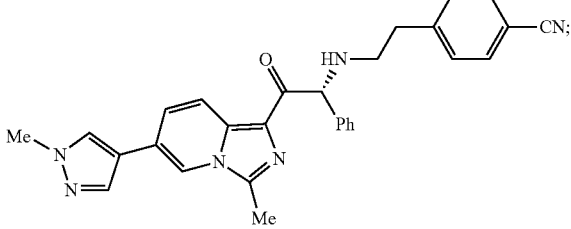
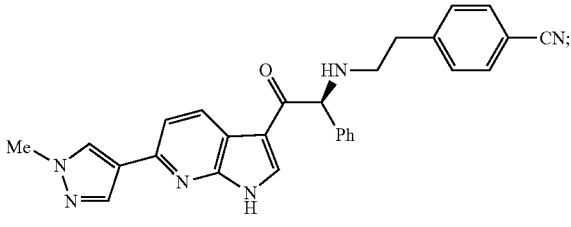
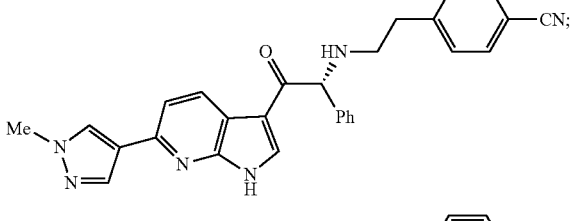
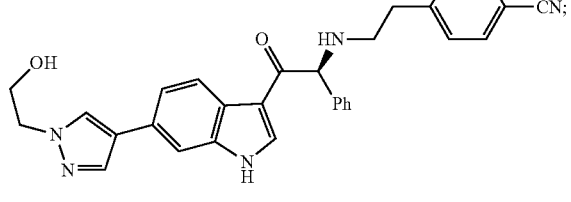
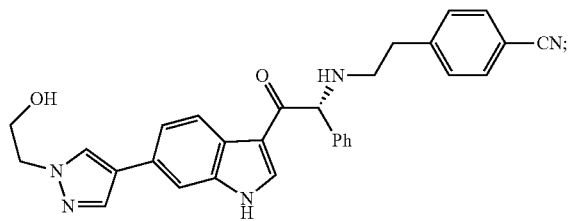
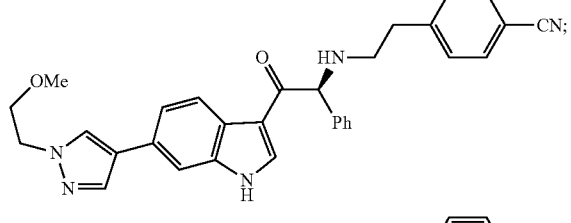
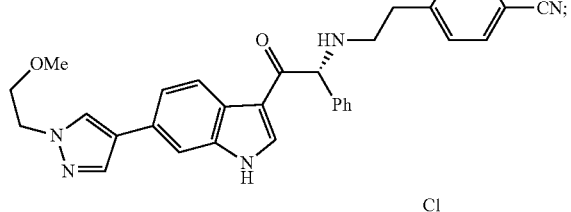
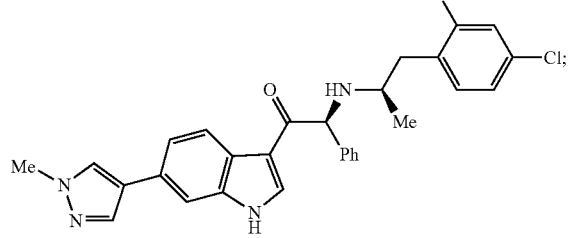
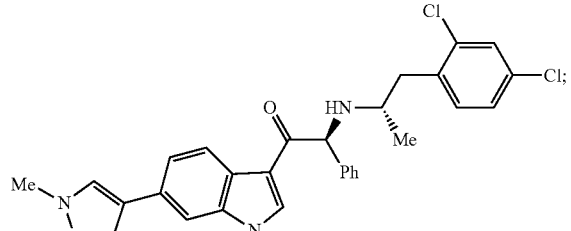
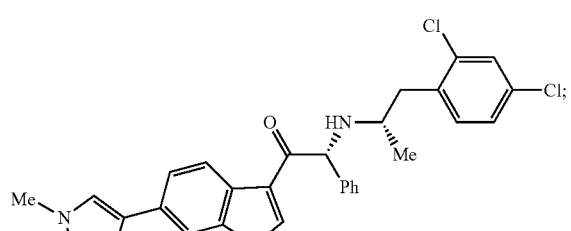
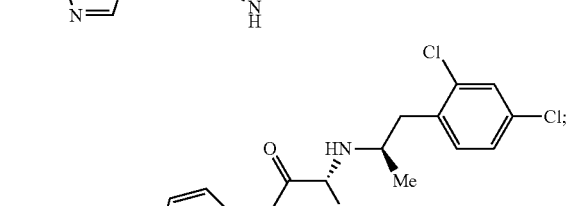
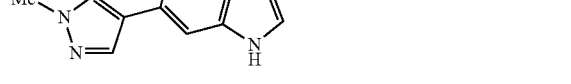

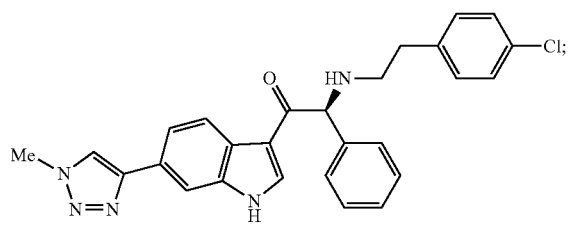
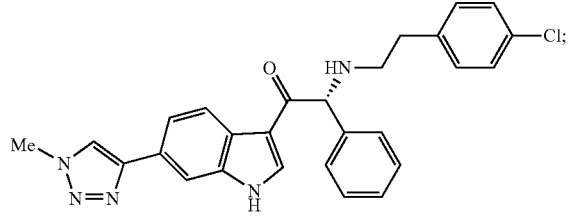
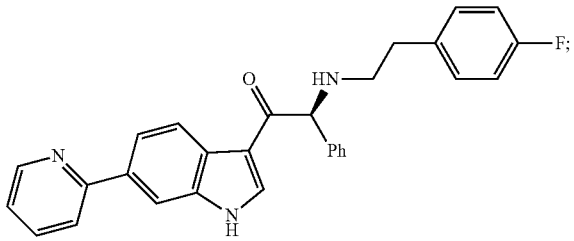
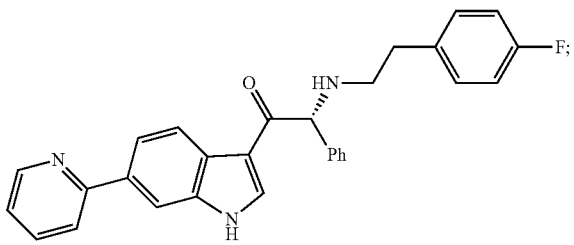
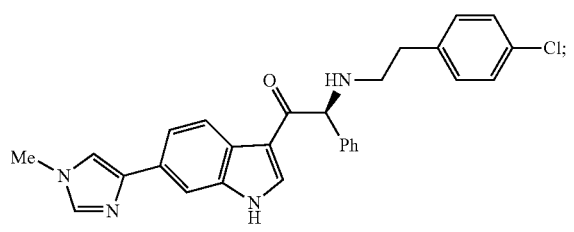
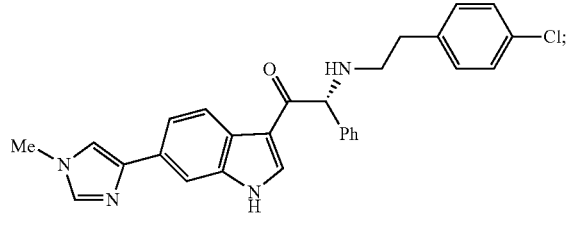
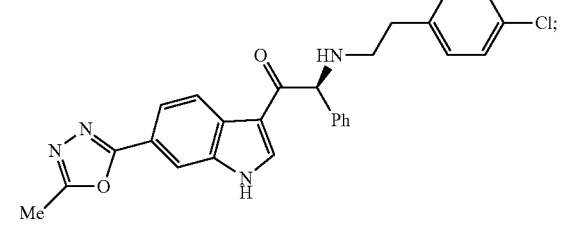
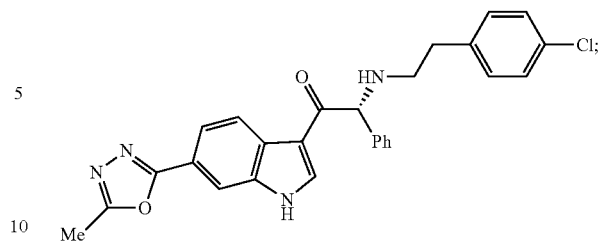
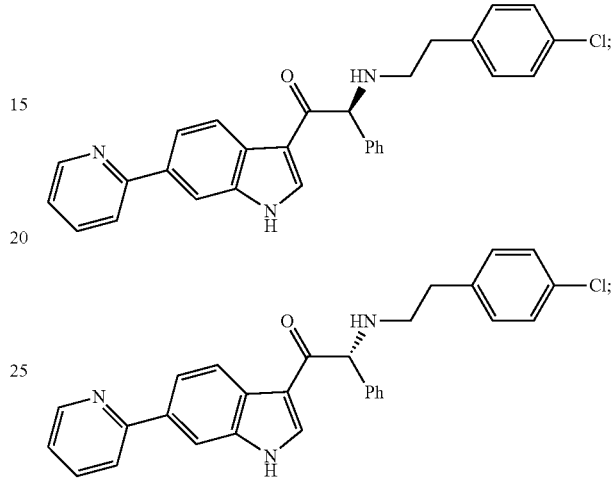
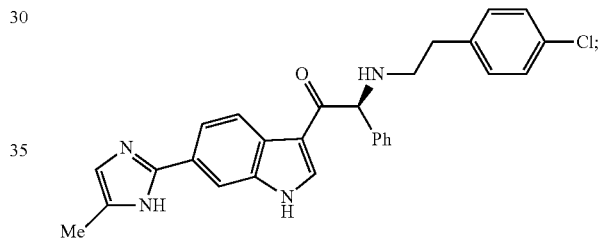
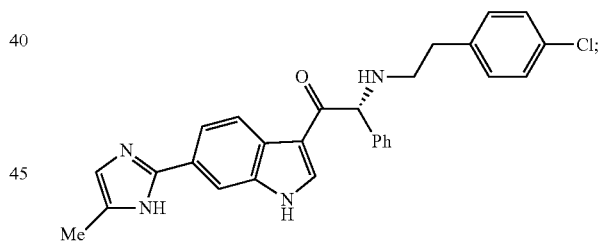
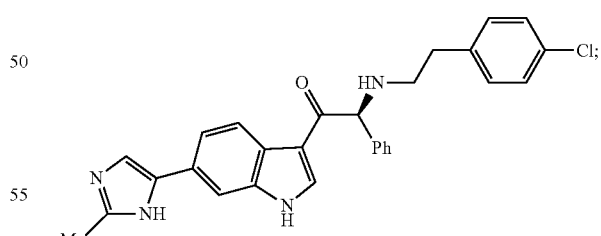
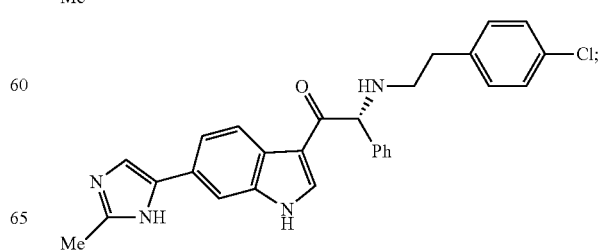

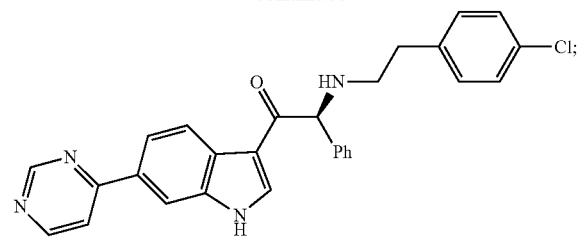
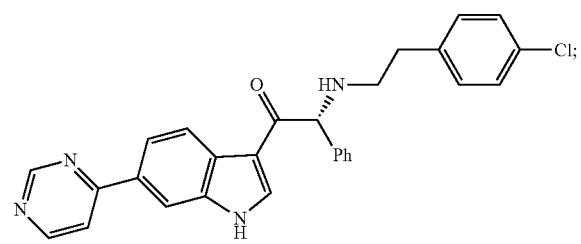
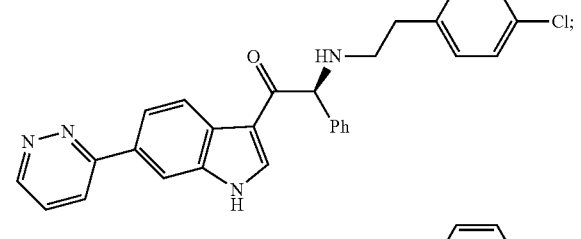
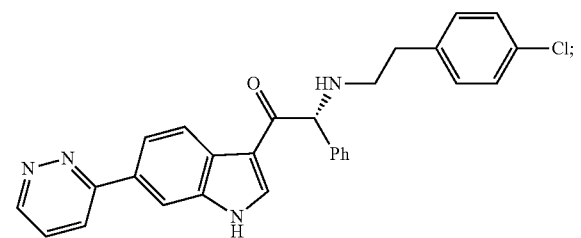
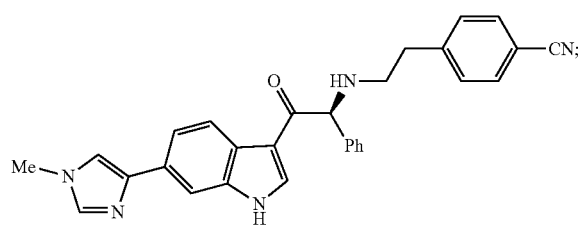
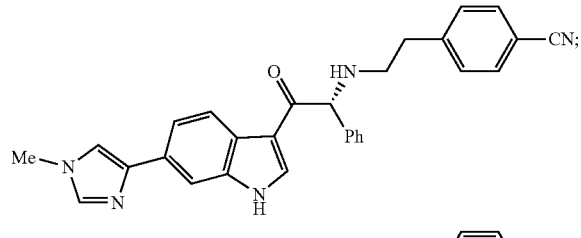
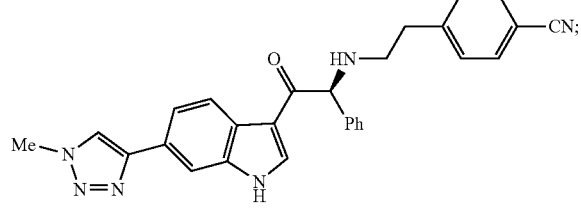
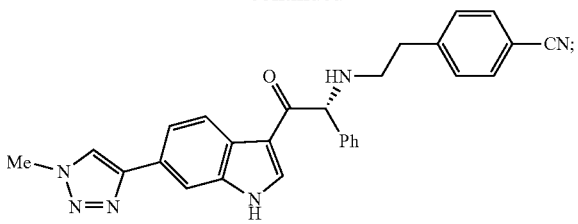
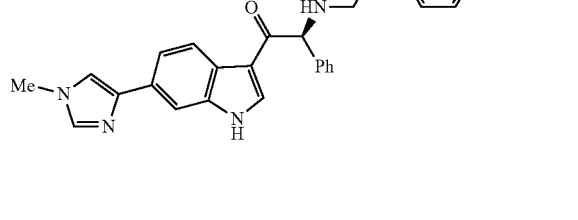
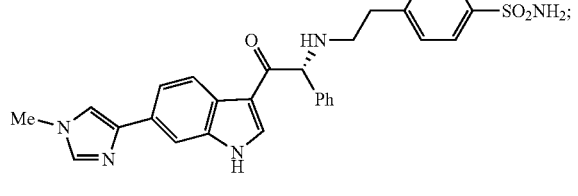
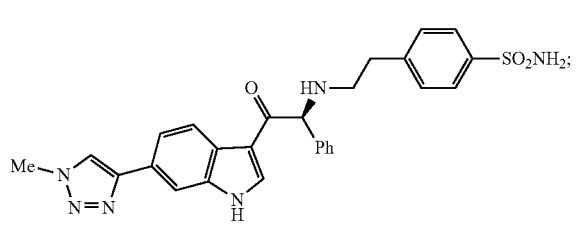
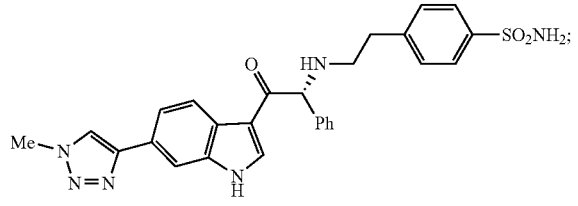
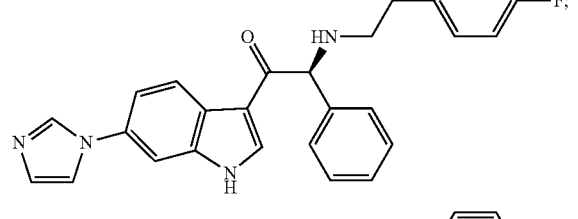
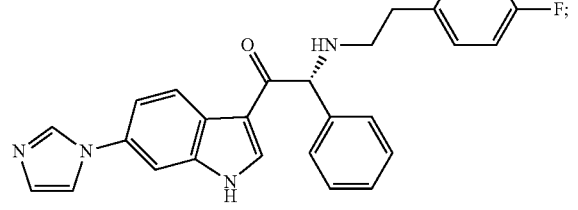

-continued
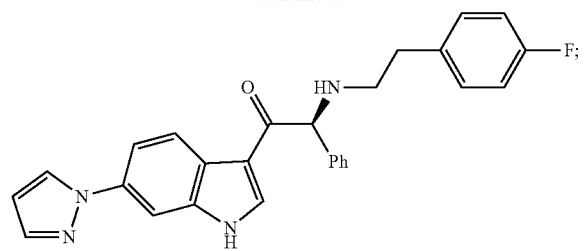
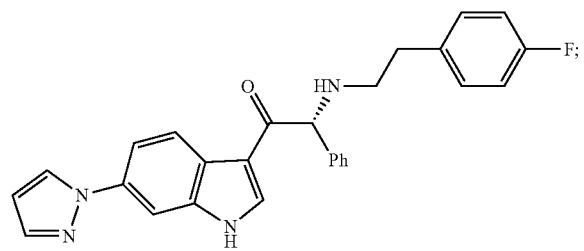
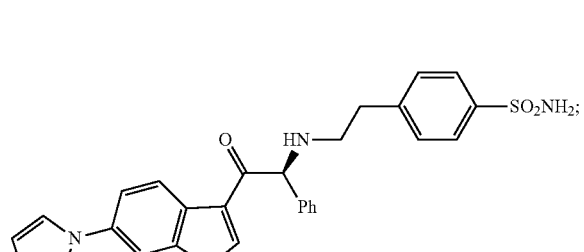
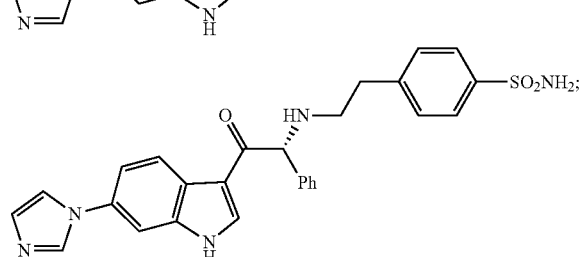
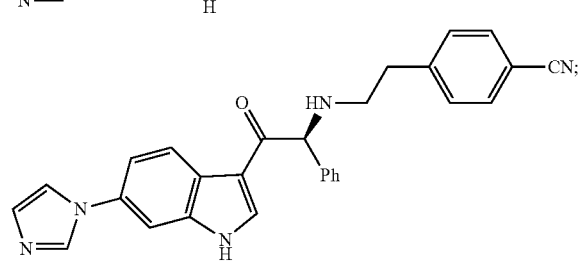
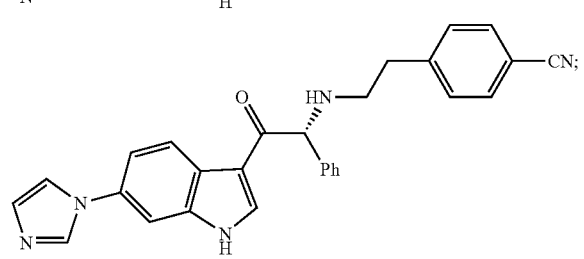
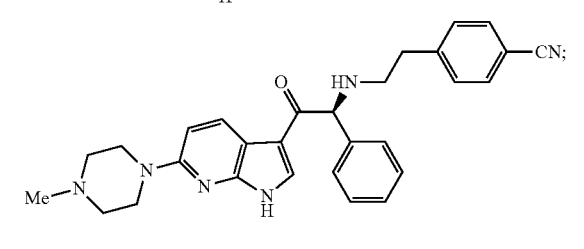
-continued
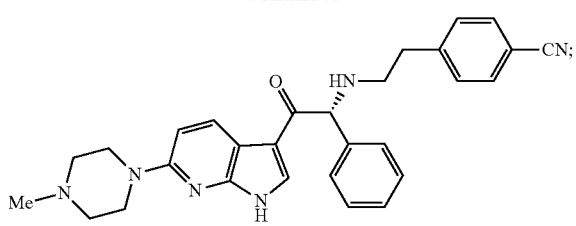
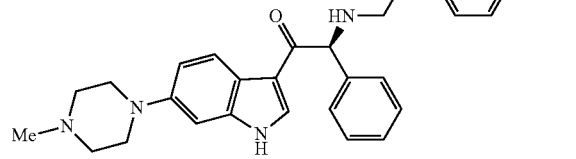
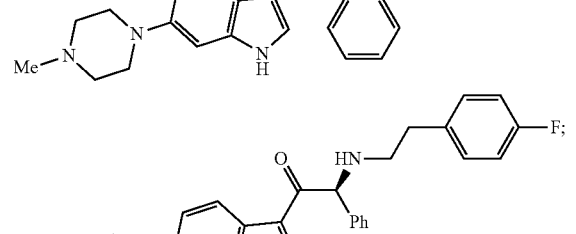
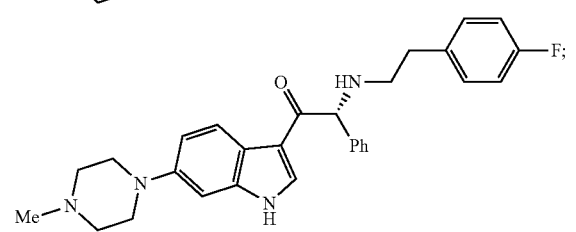
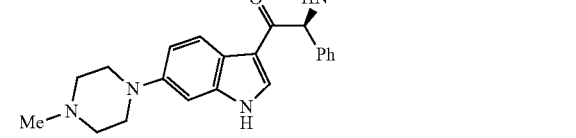
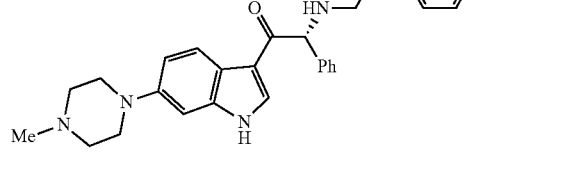
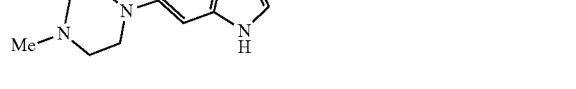

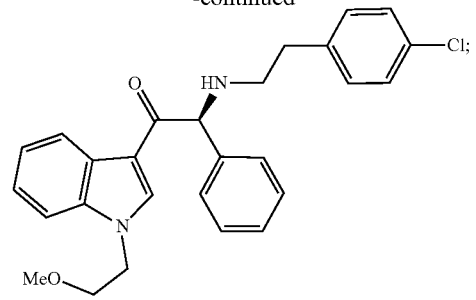
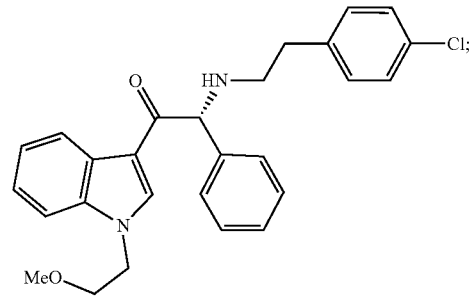
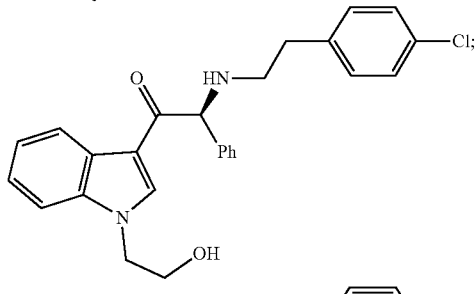
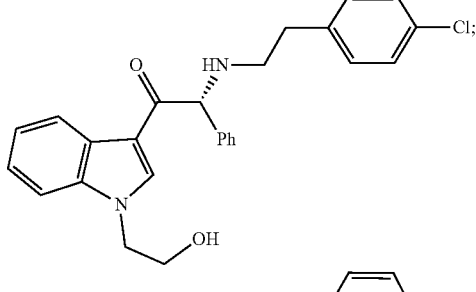
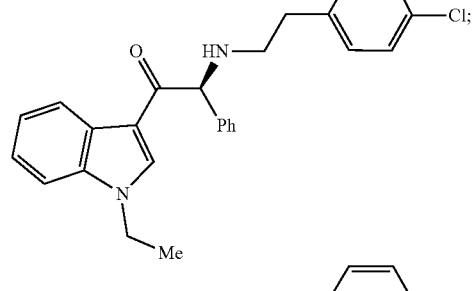
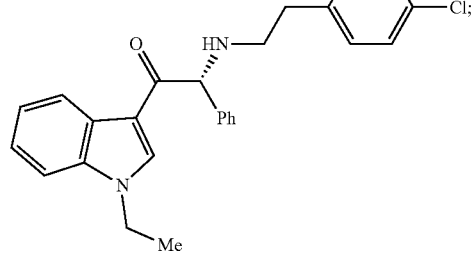
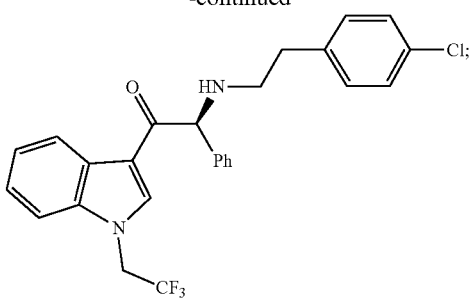
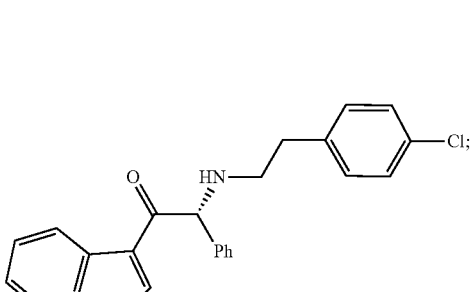
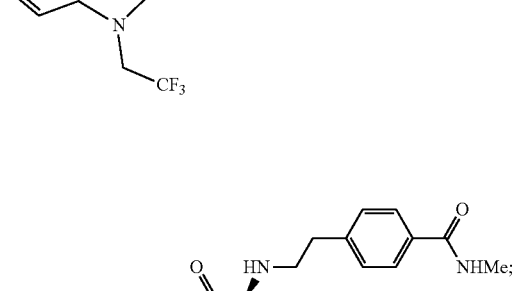
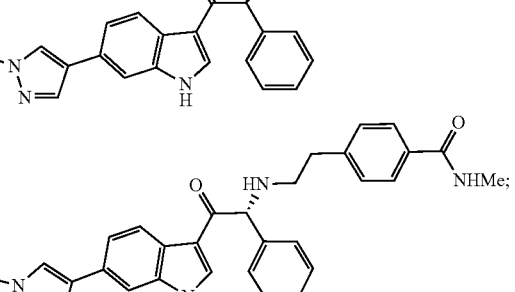
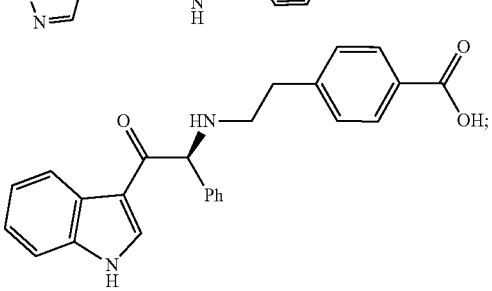
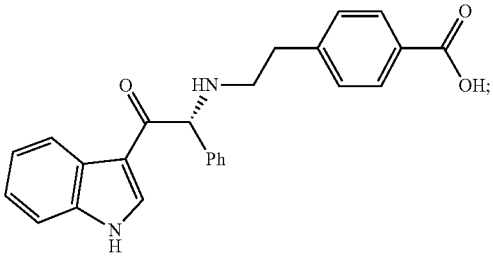

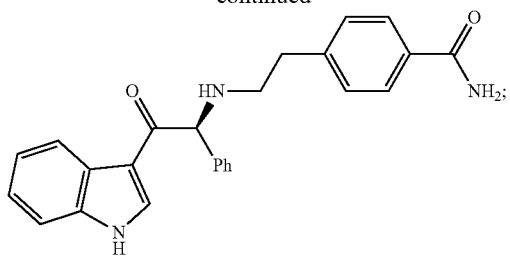
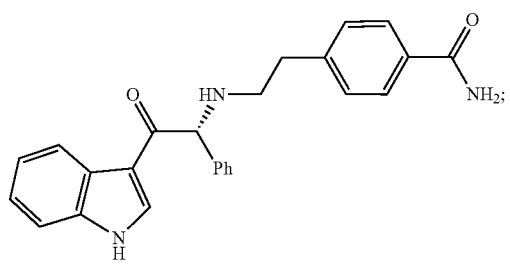
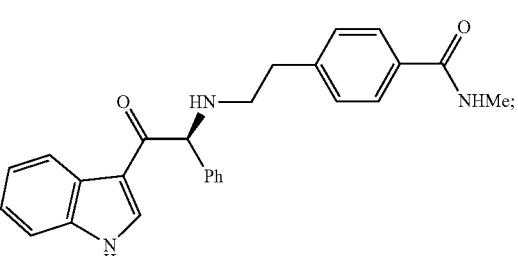
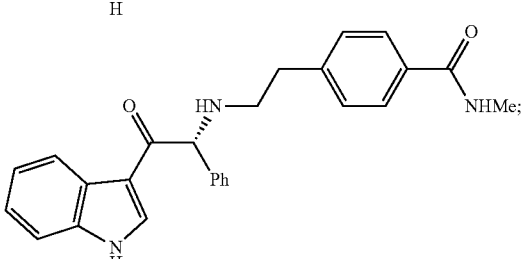
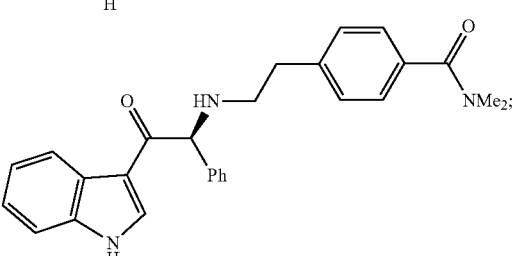
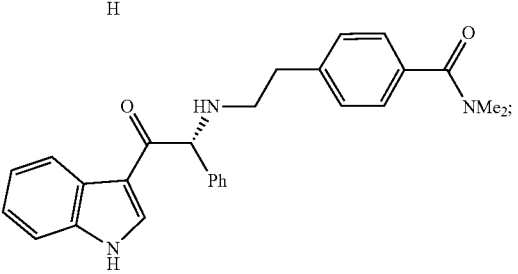
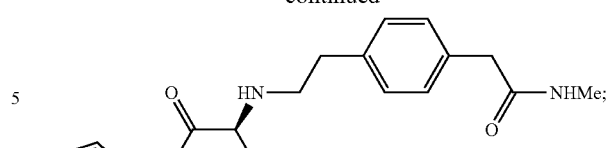
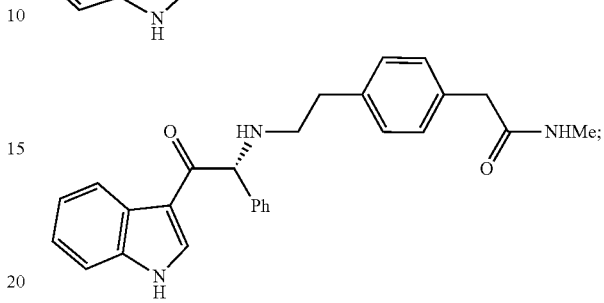
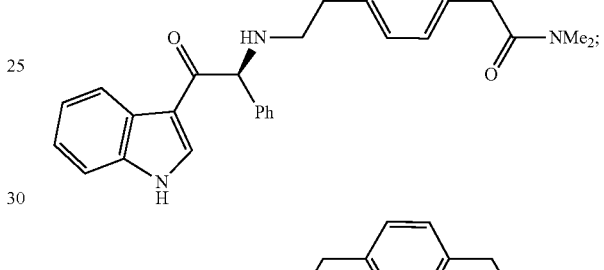
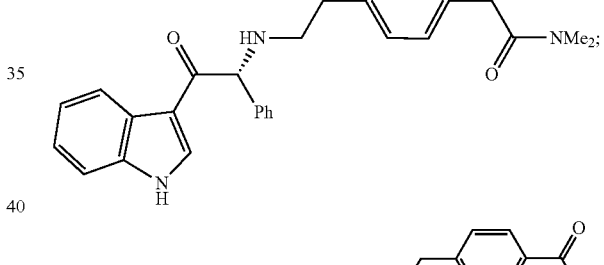
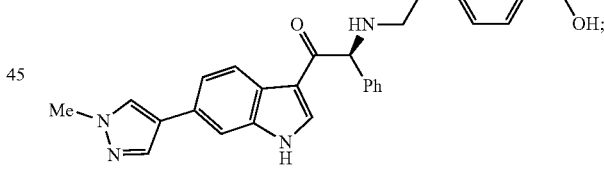
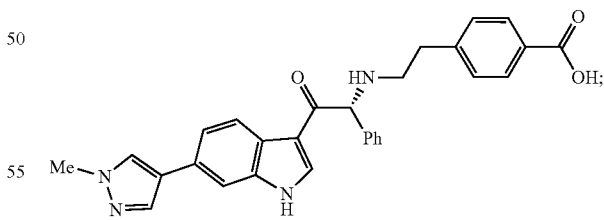
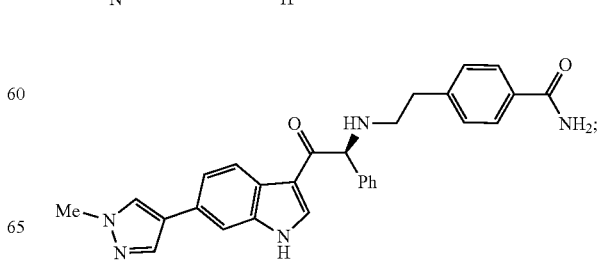

253
-continued
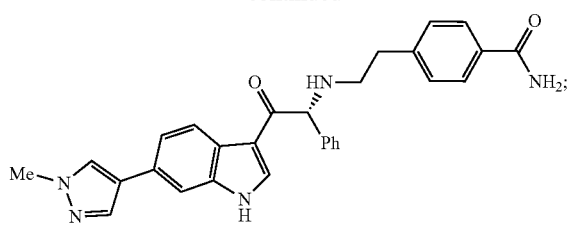
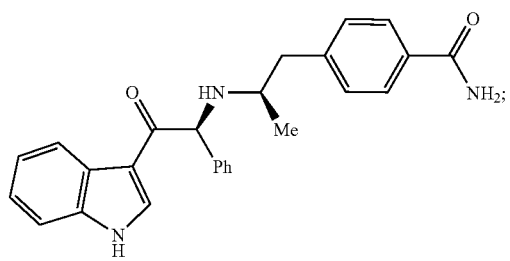
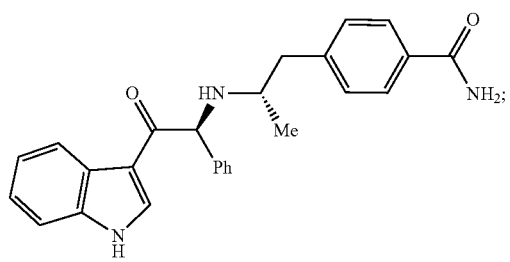
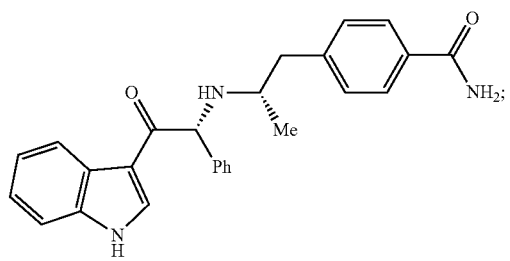
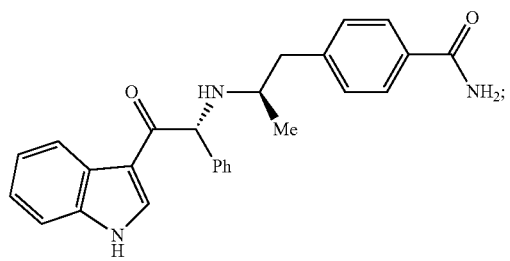
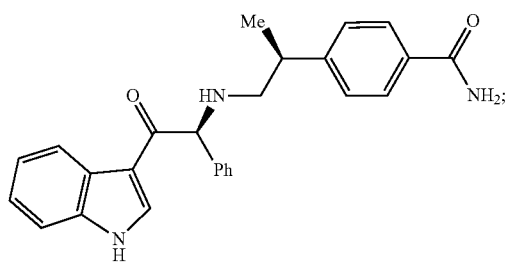
254
-continued
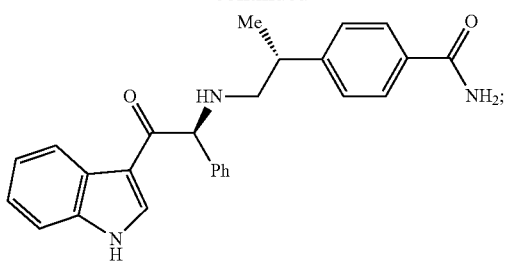
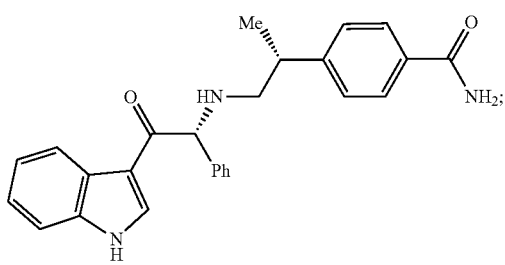
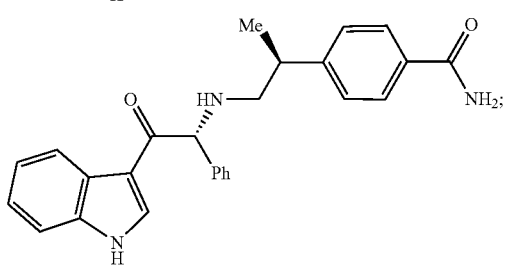
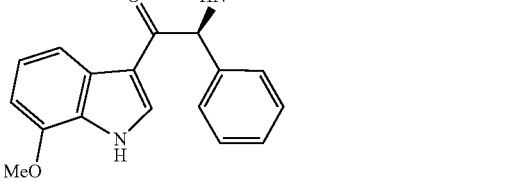
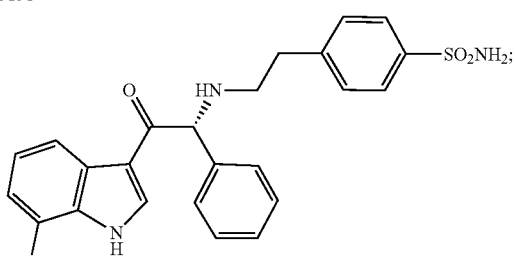
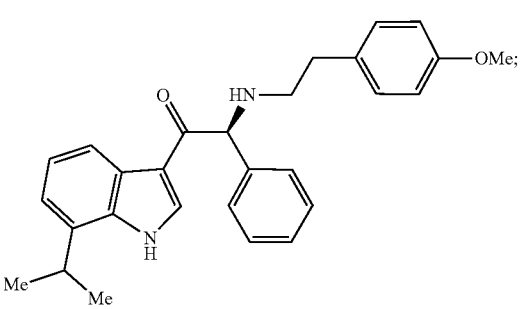

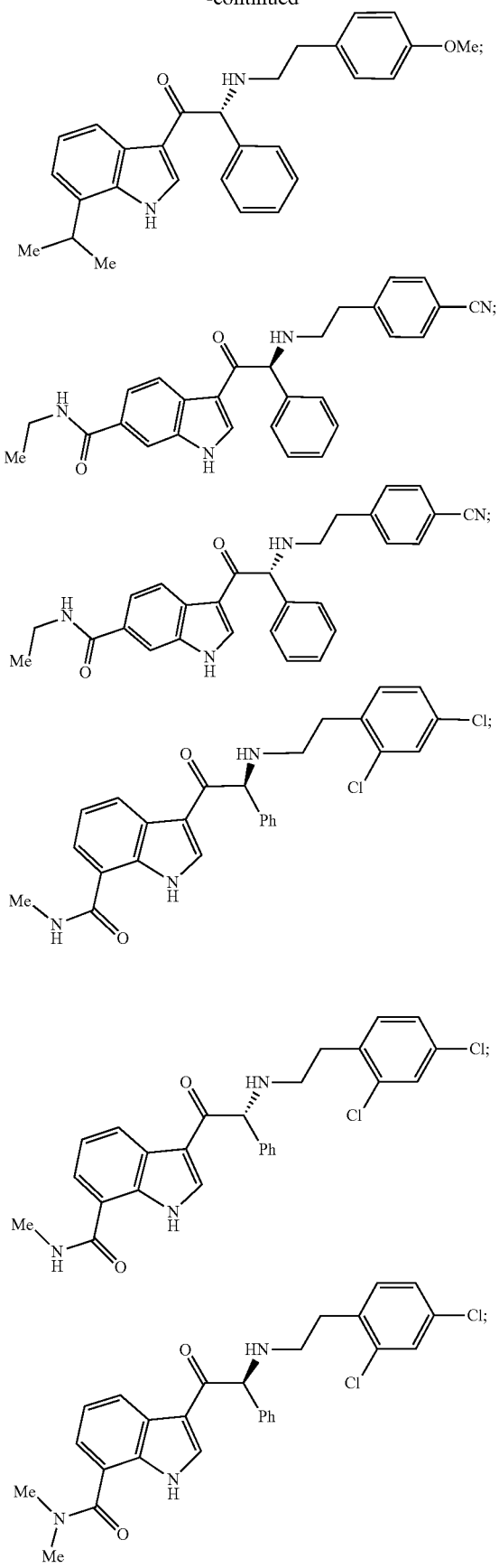
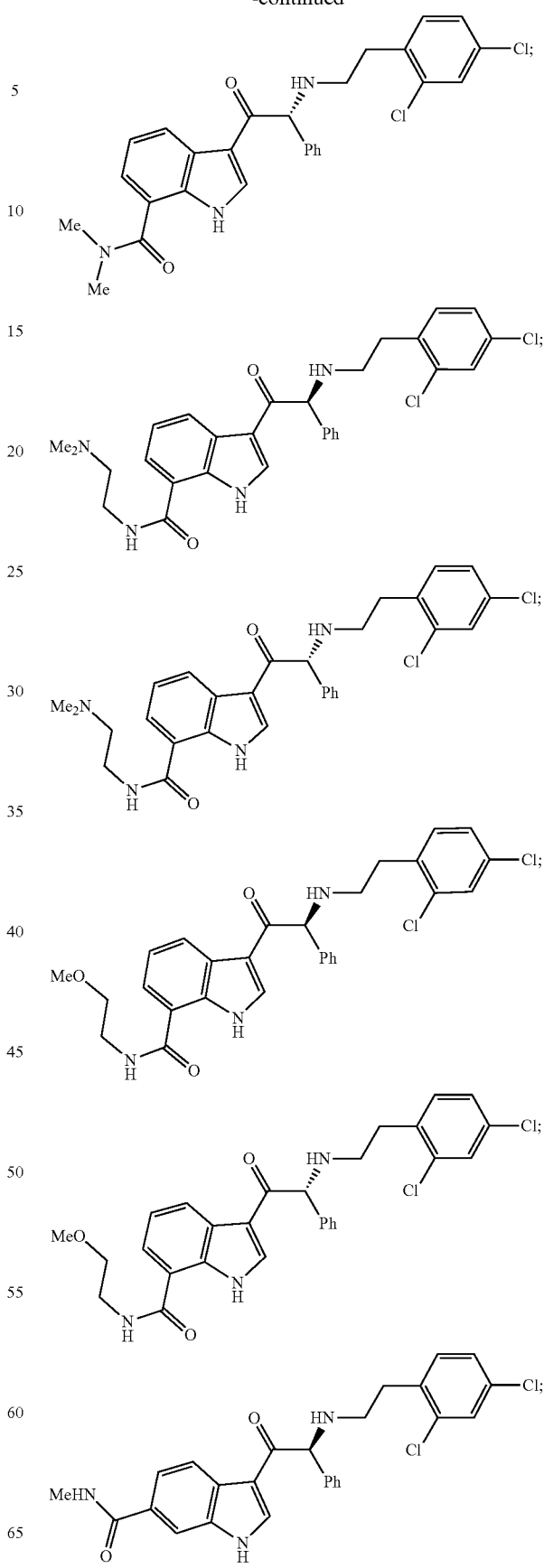

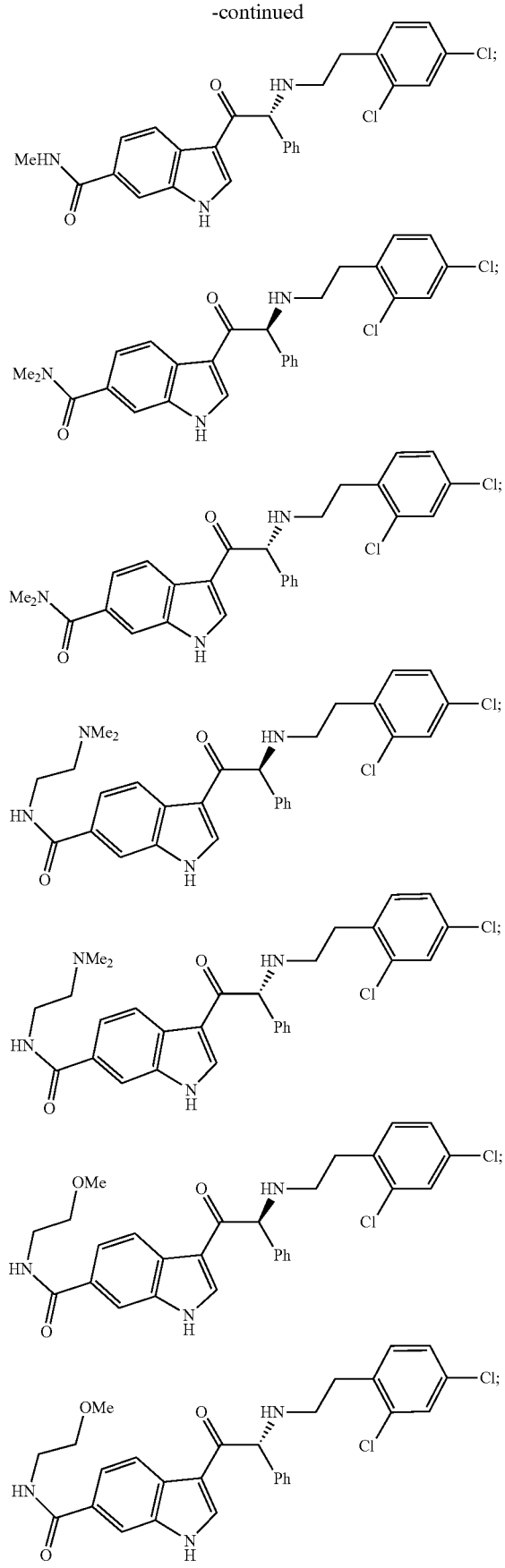
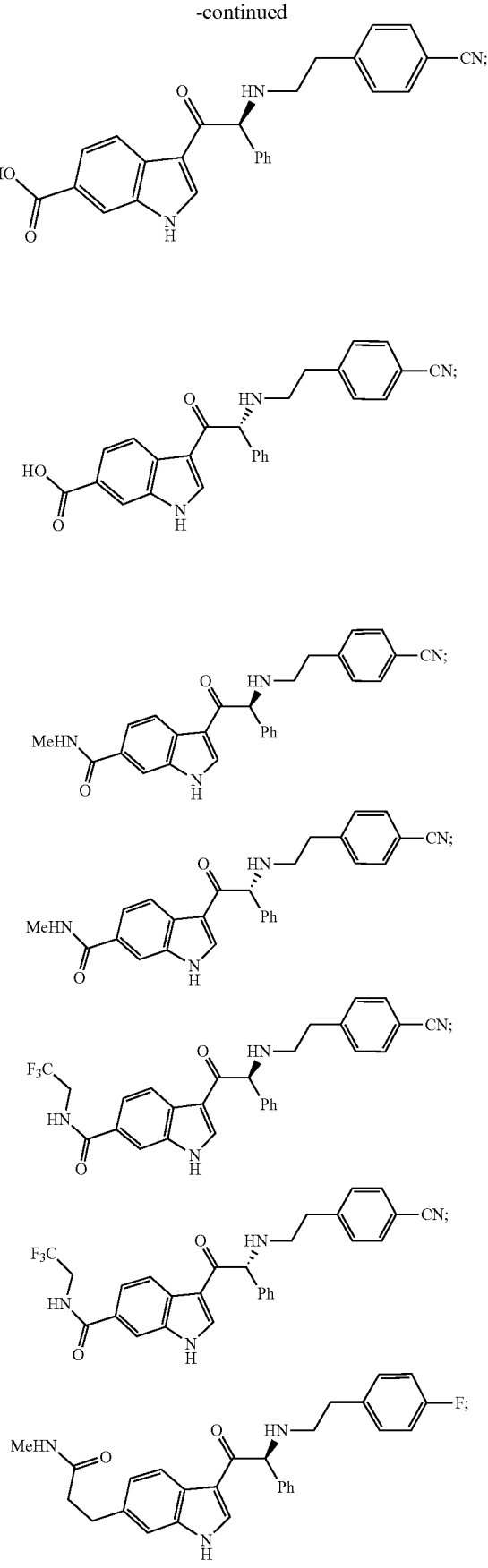

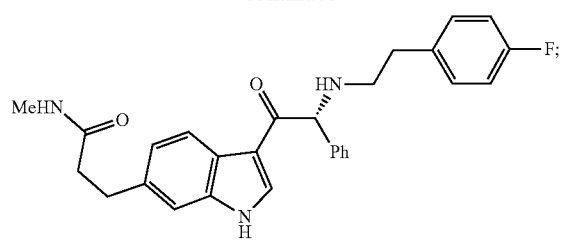
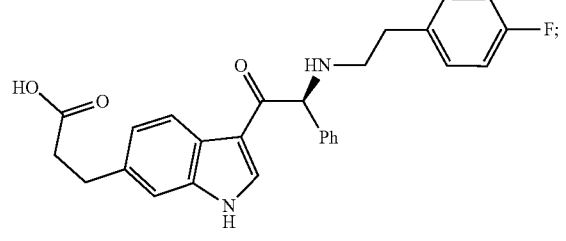
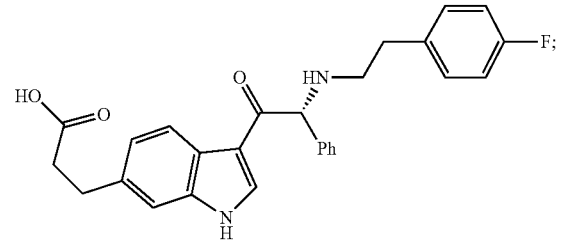
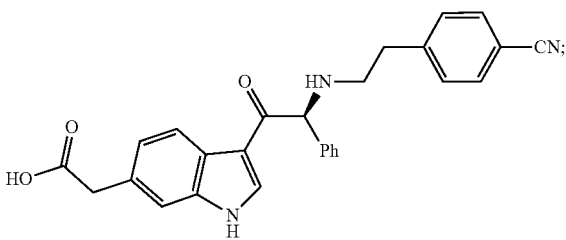
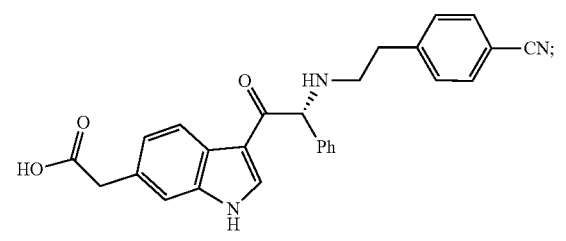
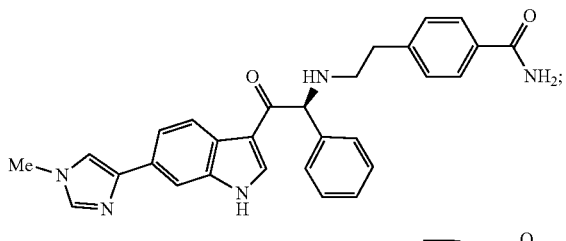
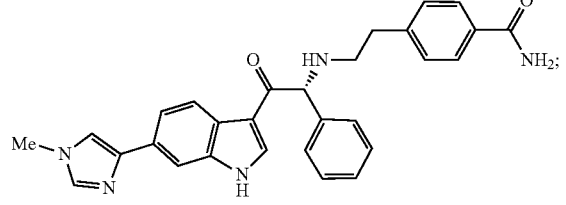
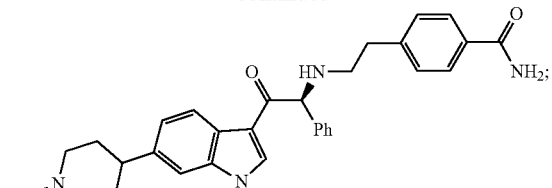
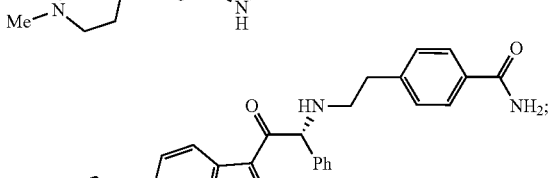
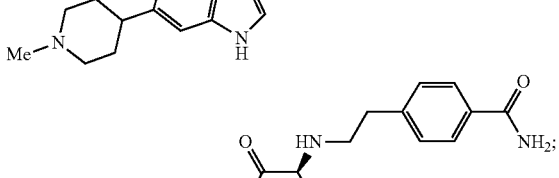
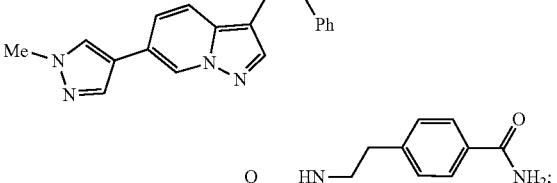
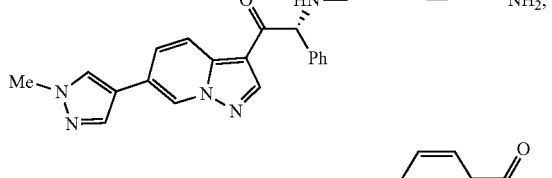
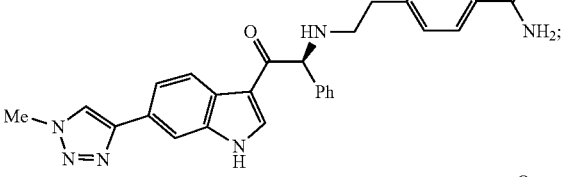
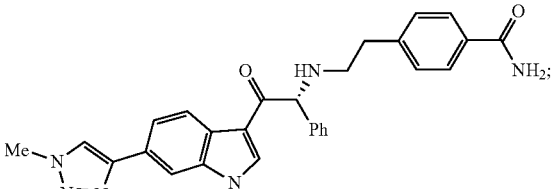
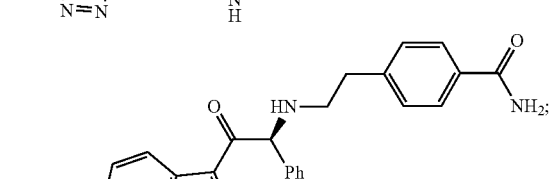
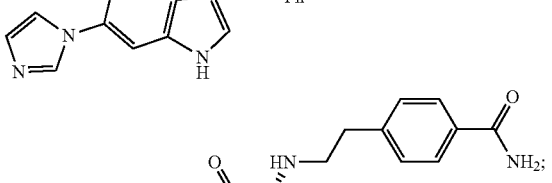
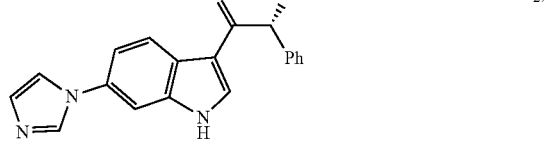

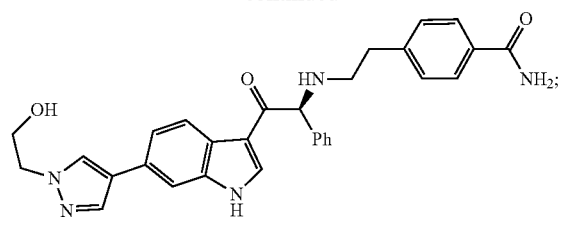
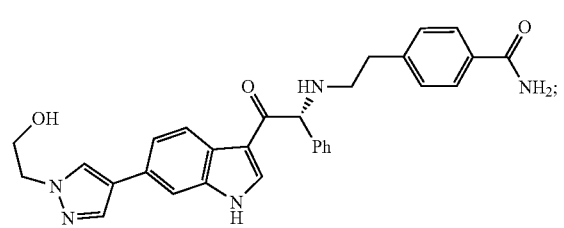
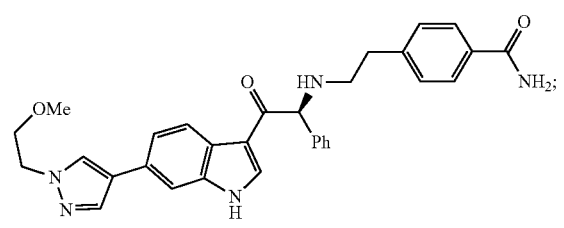
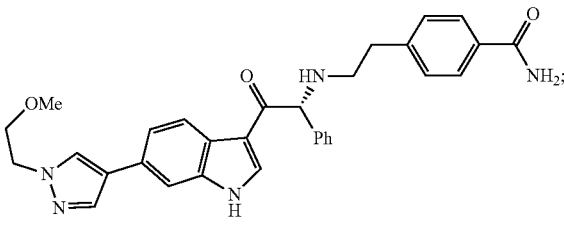
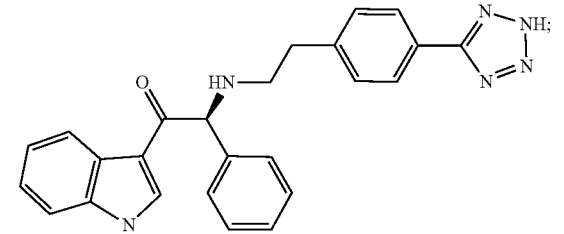
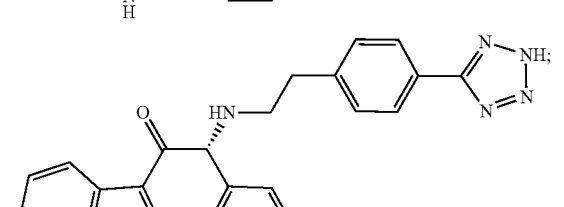
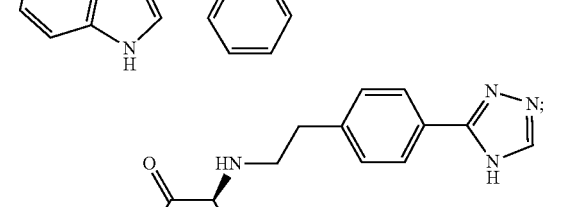
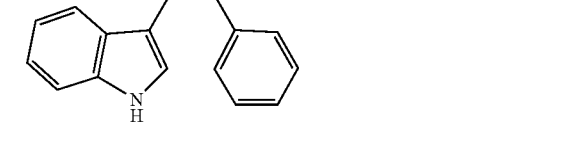
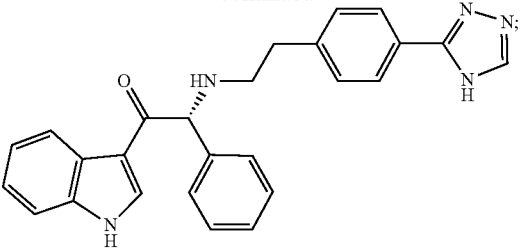
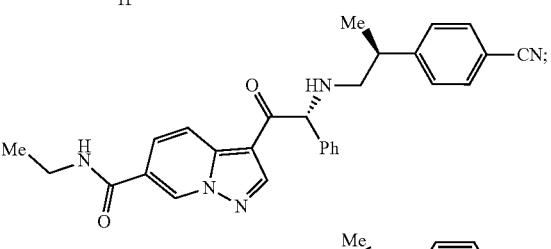
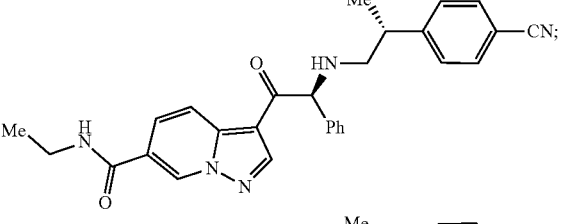
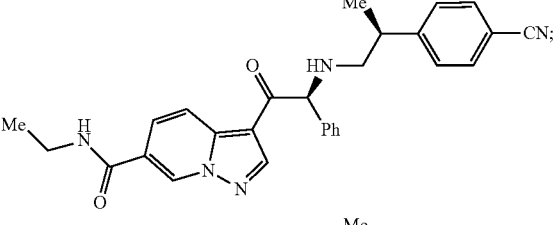
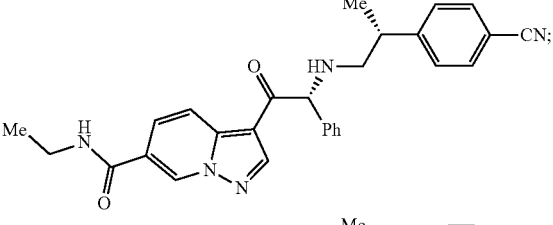
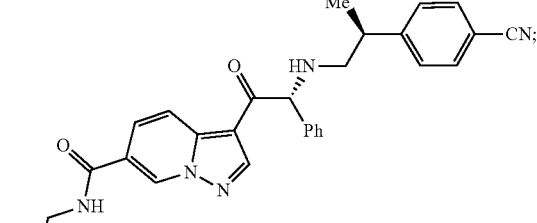
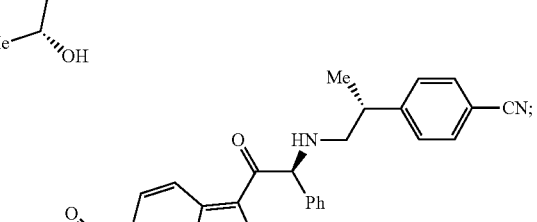

263
-continued
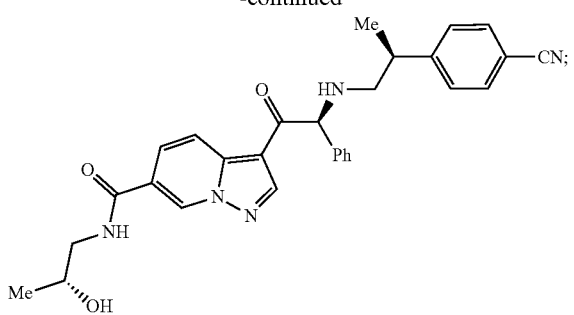
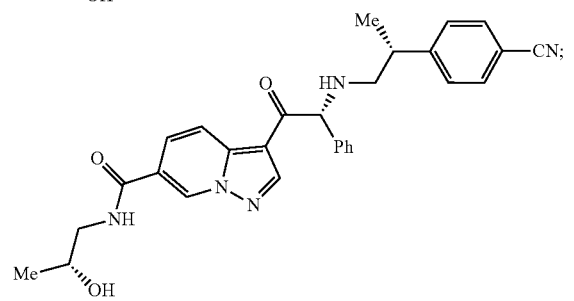
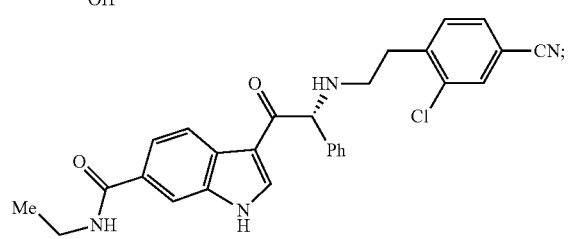
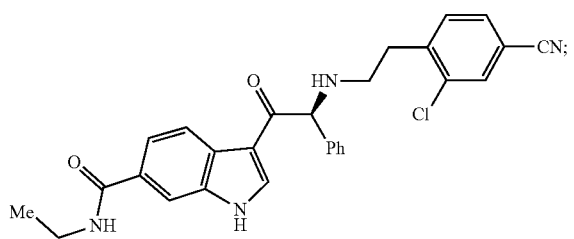
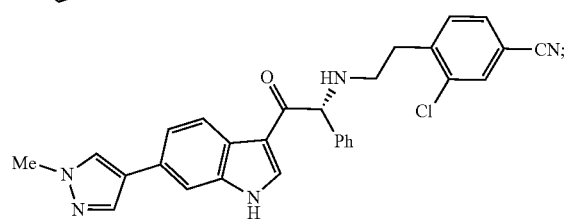
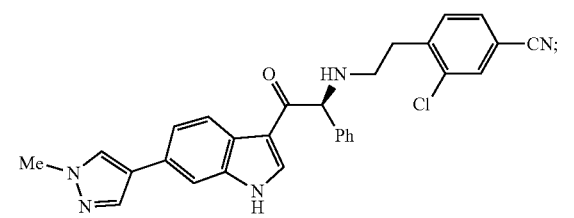
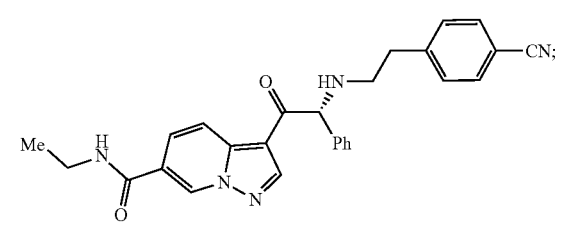
264
-continued
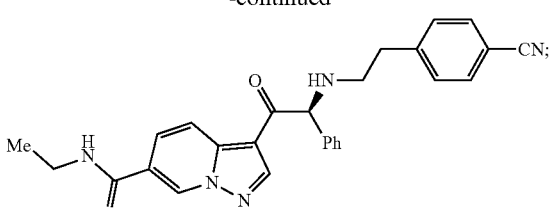
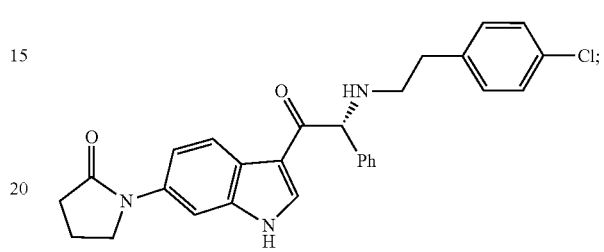
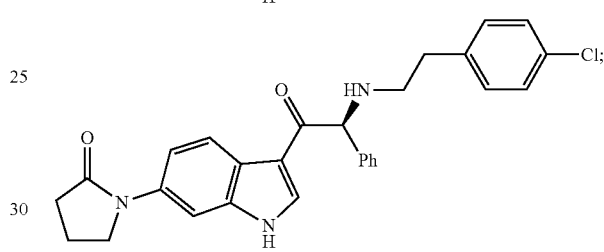
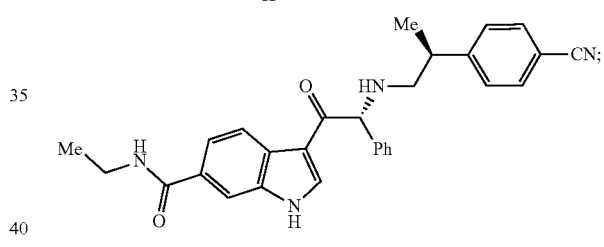
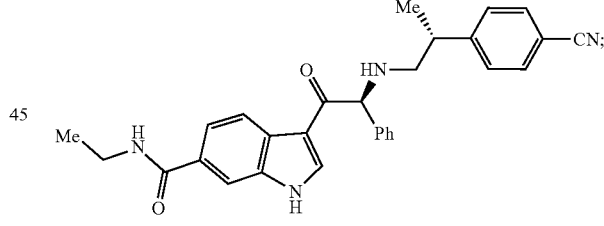
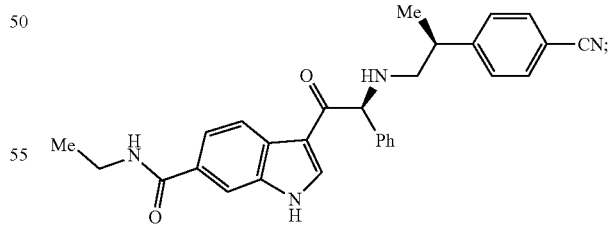
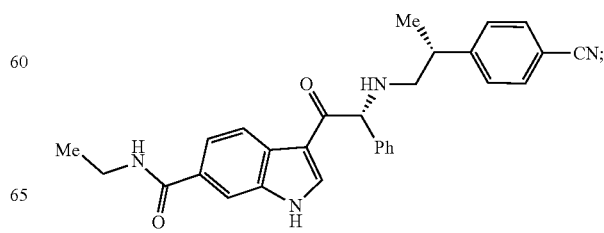

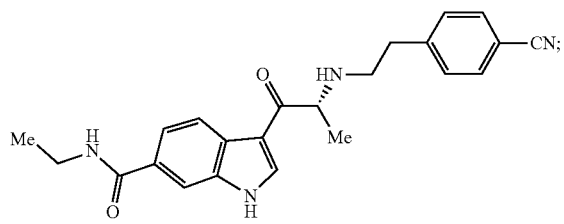
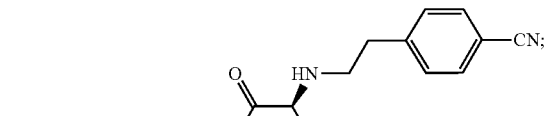
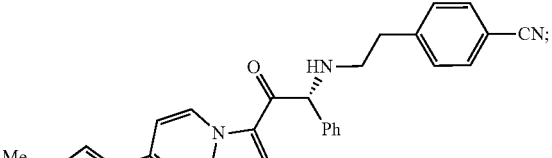
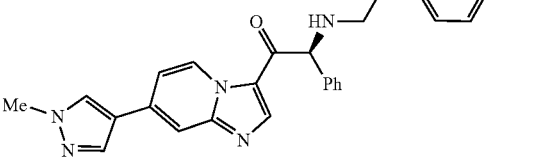
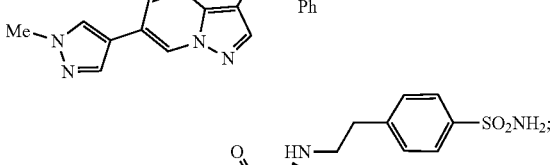
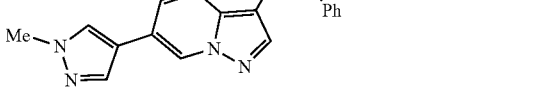
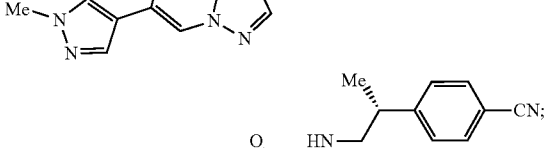

267
-continued
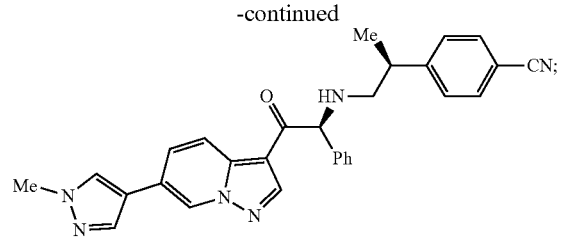
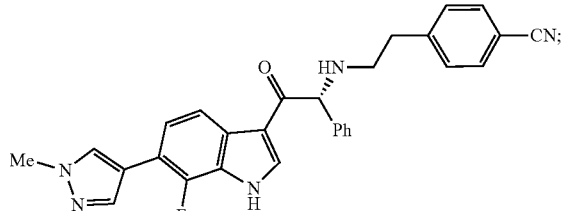
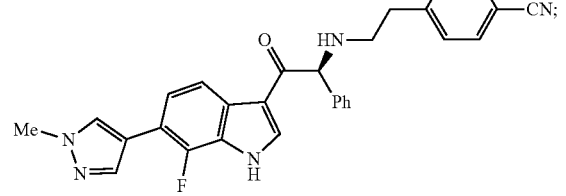
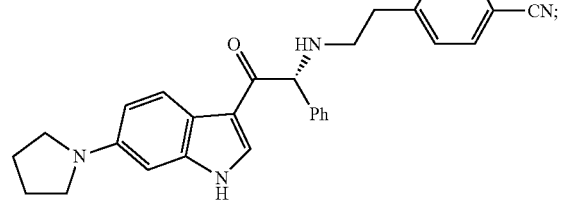
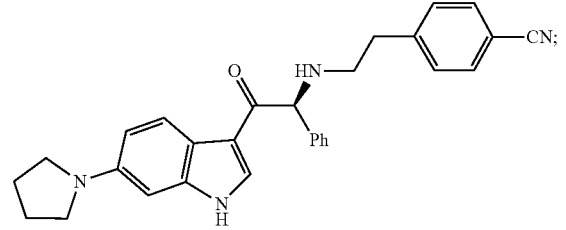
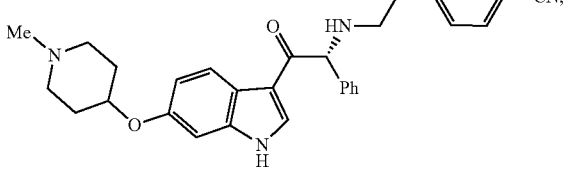
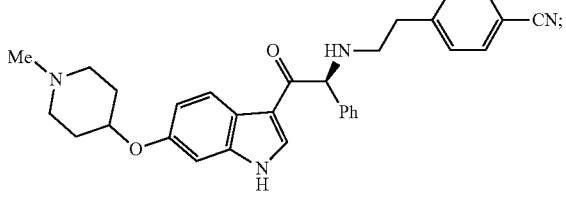
268
-continued
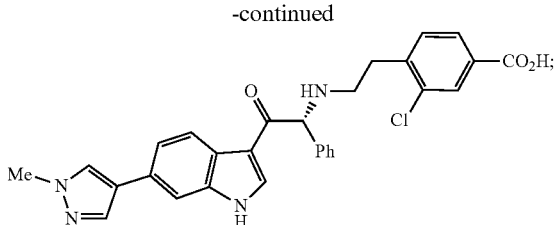
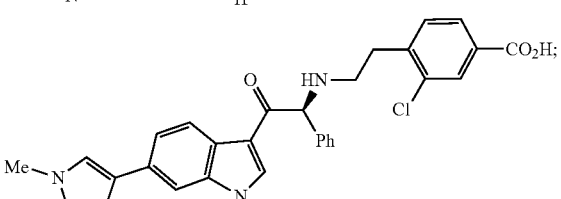
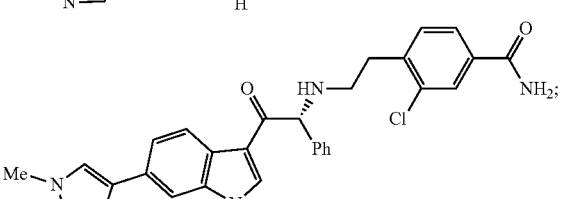
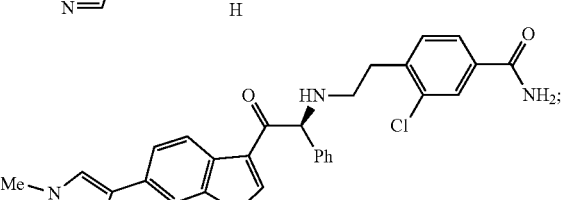
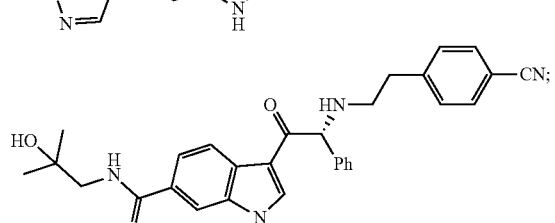
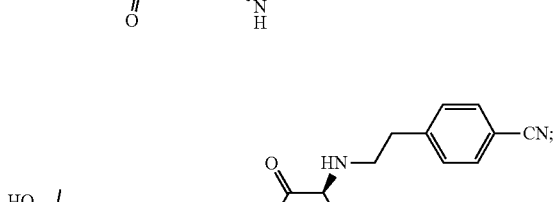
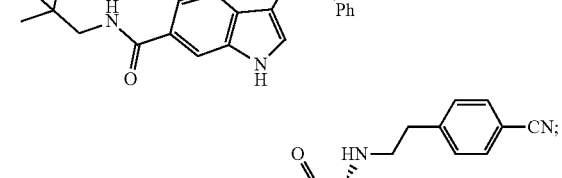
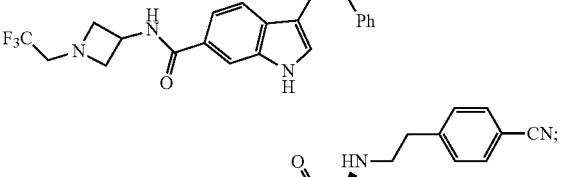
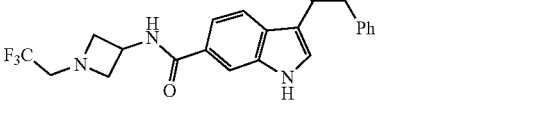

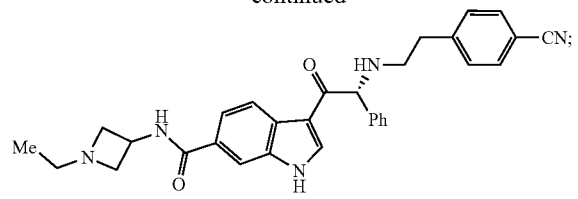
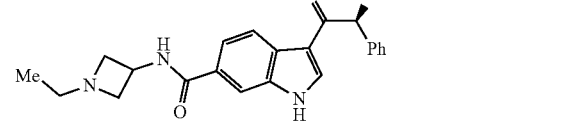
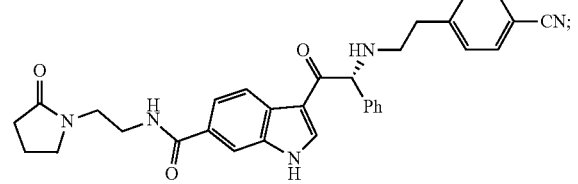
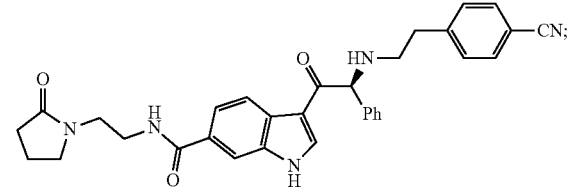
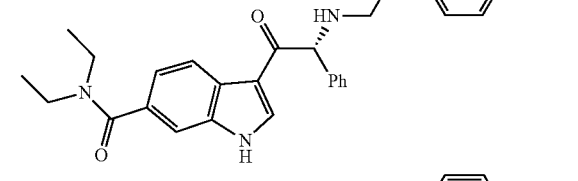
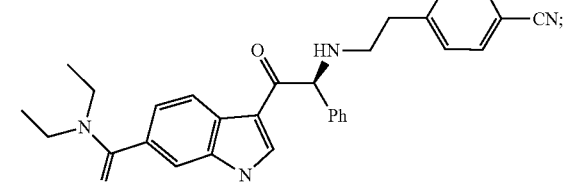
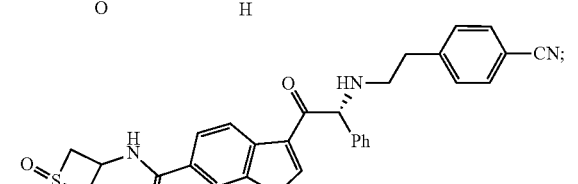
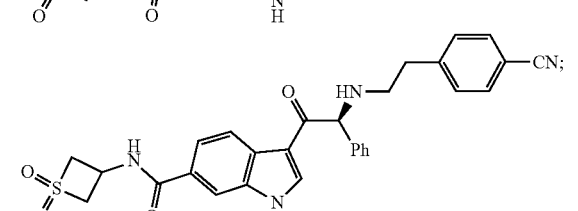
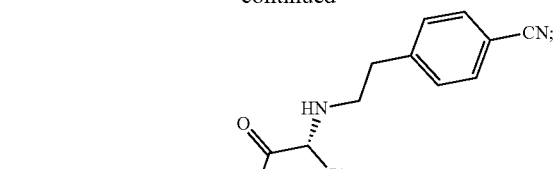
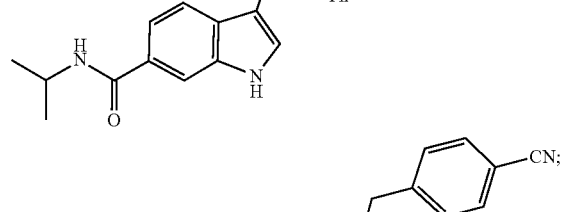
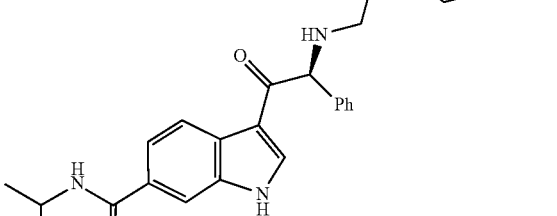
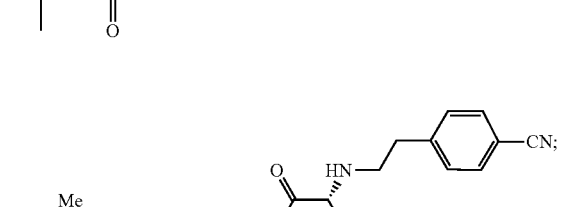
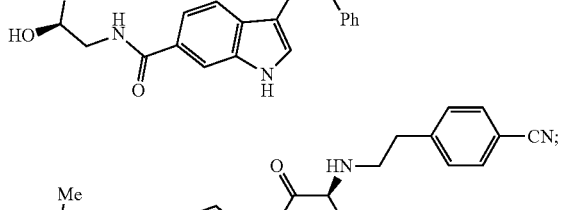
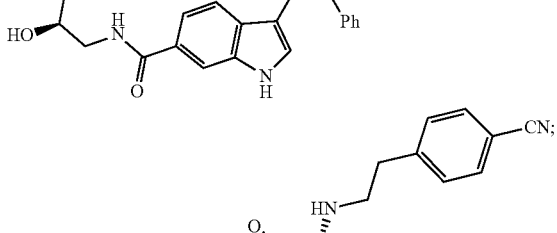
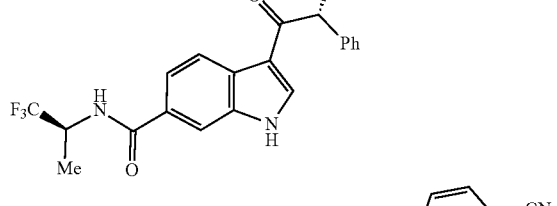

271
-continued
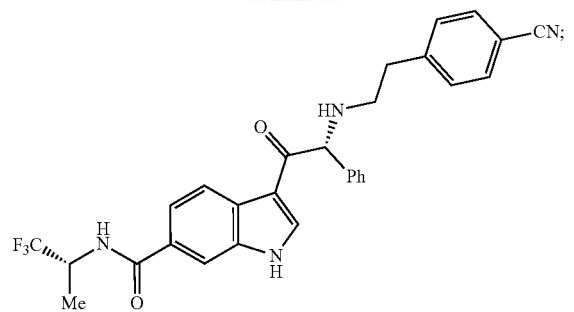
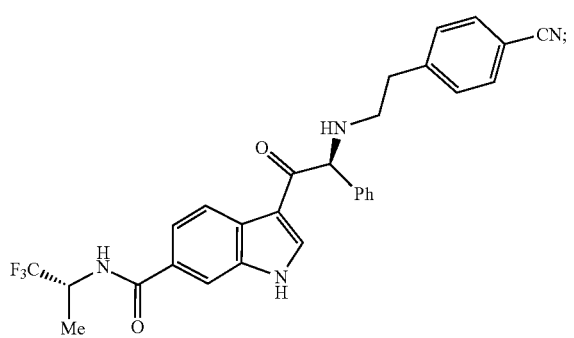
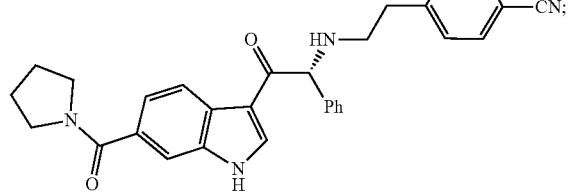
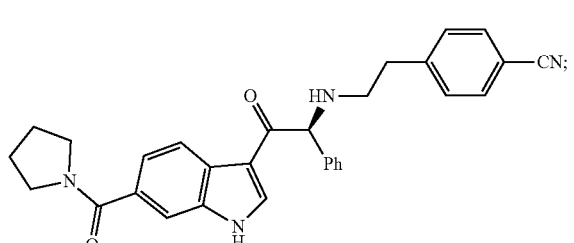
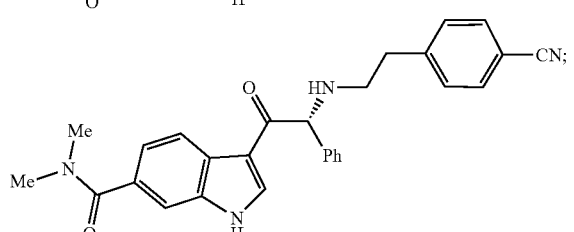
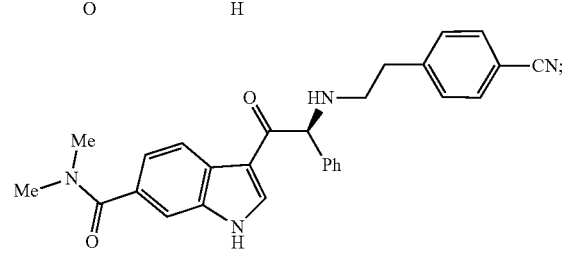
272
-continued
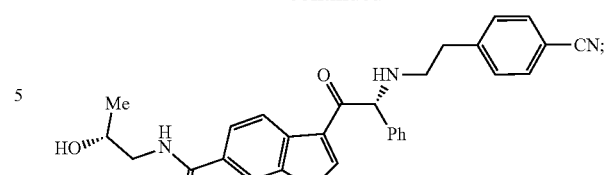
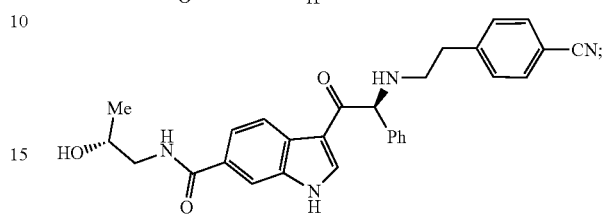
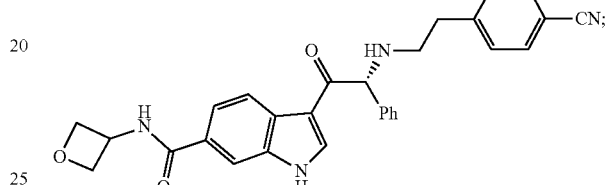
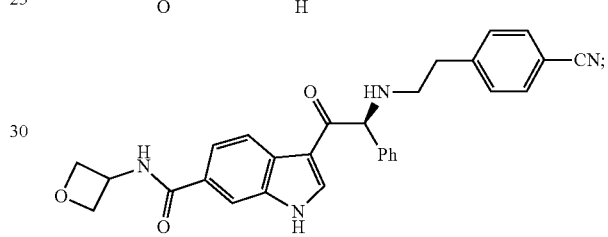
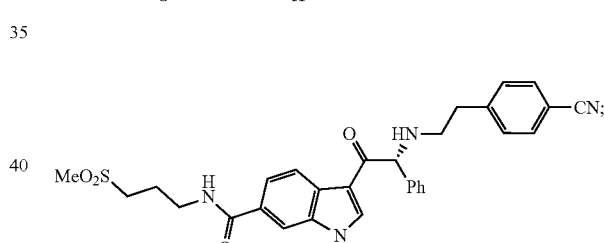
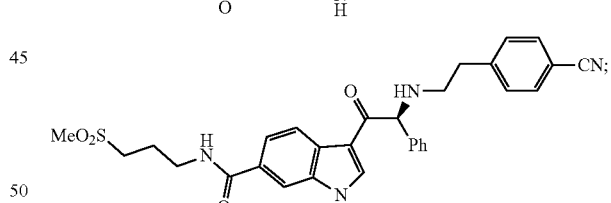
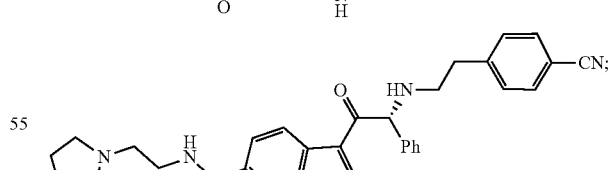
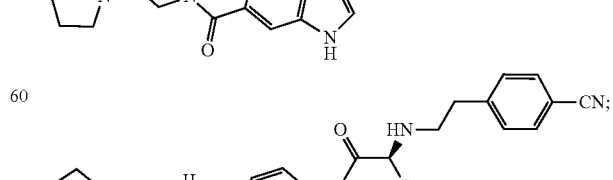
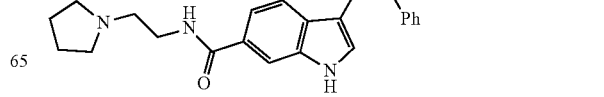

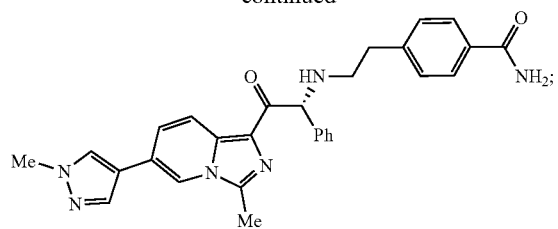
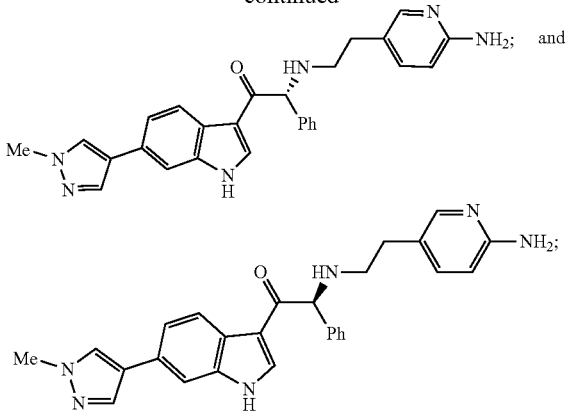
or a pharmaceutically acceptable salt thereof of any of the foregoing.